US010633707B2

(12) United States Patent
Lambrechts

(10) Patent No.: US 10,633,707 B2
(45) Date of Patent: *Apr. 28, 2020

(54) MARKERS FOR DETECTING MICROSATELLITE INSTABILITY IN CANCER AND DETERMINING SYNTHETIC LETHALITY WITH INHIBITION OF THE DNA BASE EXCISION REPAIR PATHWAY

(71) Applicants: VIB VZW, Ghent (BE); Life Sciences Research Partners VZW, Leuven (BE)

(72) Inventor: Diether Lambrechts, Kessel-Lo (BE)

(73) Assignees: VIB VZW, Ghent (BE); Life Sciences Research Partners VZW, Leuven (BE)

( * ) Notice: Subject to any disclaimer, the term of this patent is extended or adjusted under 35 U.S.C. 154(b) by 26 days.

This patent is subject to a terminal disclaimer.

(21) Appl. No.: 14/506,565

(22) Filed: Oct. 3, 2014

(65) Prior Publication Data

US 2015/0045369 A1    Feb. 12, 2015

Related U.S. Application Data

(63) Continuation of application No. PCT/EP2013/057516, filed on Apr. 10, 2013.

(60) Provisional application No. 61/622,383, filed on Apr. 10, 2012, provisional application No. 61/638,955, filed on Apr. 26, 2012.

(30) Foreign Application Priority Data

Mar. 27, 2013 (EP) .................................. 13161395

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
CPC ............ C12Q 1/6886; C12Q 2600/106; C12Q 2600/156
See application file for complete search history.

(56) References Cited

U.S. PATENT DOCUMENTS

| | | | |
|---|---|---|---|
| 4,851,331 A | 7/1989 | Vary et al. | |
| 5,137,806 A | 8/1992 | Lemaistre et al. | |
| 5,210,015 A | 5/1993 | Gelfand et al. | |
| 5,310,893 A | 5/1994 | Erlich et al. | |
| 5,451,512 A | 9/1995 | Apple et al. | |
| 5,468,613 A | 11/1995 | Erlich et al. | |
| 5,487,972 A | 1/1996 | Gelfand et al. | |
| 5,491,063 A | 2/1996 | Fisher et al. | |
| 5,571,673 A | 11/1996 | Picone et al. | |
| 5,595,890 A | 1/1997 | Newton et al. | |
| 5,604,099 A | 2/1997 | Erlich et al. | |
| 5,639,611 A | 6/1997 | Wallace et al. | |
| 5,804,375 A | 9/1998 | Gelfand et al. | |
| 5,994,056 A | 11/1999 | Higuchi et al. | |
| 6,664,064 B1 | 12/2003 | Dietmaier | |
| 10,294,529 B2 * | 5/2019 | Lambrechts | ......... C12Q 1/6886 |
| 2001/0053519 A1 | 12/2001 | Fodor et al. | |
| 2013/0267426 A1 | 10/2013 | Lambrechts | |
| 2015/0045369 A1 | 2/2015 | Lambrechts | |

FOREIGN PATENT DOCUMENTS

| | | |
|---|---|---|
| CN | 102230004 | 11/2011 |
| EP | 235726 A2 | 5/1993 |
| EP | 487218 A1 | 12/1997 |
| EP | 512334 A2 | 9/1999 |
| WO | 8911548 | 11/1989 |
| WO | 9322456 A1 | 11/1993 |
| WO | 2012166151 A1 | 12/2012 |
| WO | 2013153130 A1 | 10/2013 |

OTHER PUBLICATIONS

Suraweera N. et al. Oncogene (2001) 20, 7472-7477.*
Ruggiero T. et al. Nucleic Acids Research, 2003, vol. 31, No. 22 6561-6569 (Year: 2003).*
Suraweera, N. et al. Gastroenterology, 2002;123:1804-1811. (Year: 2002).*
Wilding, J. et al. PNAS Dec. 7, 2010, vol. 107, No. 49, pp. 21058-20163 and Suppoting Information. (Year: 2010).*
Subramanian et al., "Genome-wide analysis of microsatellite repeats in humans: their abundance and density in specific genomic regions," Genome Biology 2003, 4:R13.
Bentley et al., "Accurate whole human genome sequencing using reversible terminator chemistry," Nature 2008, 456:53-59.
Umar et al., Revised Bethesda Guidelines for Hereditary Nonpolyposis Colorectal Cancer (Lunch Syndrome) and Microsatellite Instability, JNCI Journal of the National Cancer Institute, Feb. 18, 2004, pp. 261-268, vol. 96, No. 4.
Morandi et al., T-[20] repeat in the 3'-untranslated region of the MT1X gene: a marker with high sensitivity and specificity to detect microsatellite instability in colorectal cancer, International Journal of Colorectal Disease, Nov. 23, 2011, pp. 647-656, vol. 27, No. 5.
Mao et al., Evidence that a mutation in the MLH1 3'-untranslated region confers a mutator phenotype and mismatch repair deficiency in patients with relapsed leukemia, Journal of Biological Chemistry, Feb. 2008, pp. 3211-3216, vol. 283, No. 6.

(Continued)

*Primary Examiner* — Stephen T Kapushoc
(74) *Attorney, Agent, or Firm* — Patent Law Works LLP

(57) ABSTRACT

Described are mismatch repair (MMR-)deficient tumors. Markers are presented herein having a high sensitivity to detect whether a tumor is mismatch repair deficient or not. The markers are particularly mutations in microsatellite regions. Accordingly, methods and materials are provided for diagnosing microsatellite instability of a tumor. Such a method comprises determining the presence of these markers. Further, kits are provided to detect the presence of these markers (or subsets thereof) in a sample.

10 Claims, 10 Drawing Sheets

(10 of 10 Drawing Sheet(s) Filed in Color)

(56) References Cited

OTHER PUBLICATIONS

Gaymes et al., Microsatellite Instability (MSI) in High Risk Myelodysplastic Syndrome (MDS) and Acute Myeloid Leukaemia (AML) Cells Promotes Frameshift Mutations in DNA Repair Genes: Indications for PARP Inhibitor Therapy, Blood, Nov. 1, 2010, pp. 513, vol. 116, No. 21.

Gu et al., Down-regulation of MLH1 in a relapsed leukemia patient is associated with a three-nucleotide deletion in the MLH1 3' untranslated region, FASEB Journal, Apr. 2008, vol. 22, No. 776, (2 pages).

Ruggiero et al., Deletion in a (T)8 microsatellite abrogates expression regulation by 3'-UTR, Nucleic Acids Research, Nov. 15, 2003, pp. 6561-6569, vol. 31, No. 22.

Yuan et al., An A13 Repeat within the 3'-Untranslated Region of Epidermal Growth Factor Receptor (EGFR) Is Frequently Mutated in Microsatellite Instability Colon Cancers and Is Associated with Increased EGFR Expression, Cancer Research, Oct. 2009, pp. 7811-7818, vol. 69, No. 19.

Ahmed et al., Molecular markers that predict response to colon cancer therapy, Expert Review of Molecular Diagnostics, May 1, 2005, pp. 353-375, vol. 5, No. 3.

PCT International Search Report, PCT/EP2013/057516, dated Jun. 6, 2013.

Final Office Action for co-pending U.S. Appl. No. 13/860,422 with the same inventor dated Apr. 27, 2017.

Boland, et al. "A National Cancer Institute Workshop on Microsatellite Instability for Cancer Detection and Familial Predisposition: Development of International Criteria for the Determination of Microsatellite Instability in Colorectal Cancer." Cancer Research. 58.22 (1998): 5248-5257.

Serrano, et al. "Bethesda Criteria for Microsatellite Instability Testing: Impact on the Detection of New Cases of Lynch Syndrome." Familial Cancer. 11.4 (2012): 571-578.

Vilar E, Bartnik CM, Stenzel SL, Raskin L, Ahn J, Moreno V, Mukherjee B, Iniesta MD, Morgan MA, Renner G, Gruber SB. MRE11 deficiency increases sensitivity to poly(ADP-ribose) polymerase inhibition in microsatellite unstable colorectal cancers. Cancer Research. Apr. 1, 2011;71(7):2632-42. doi: 10.1158/0008-5472.CAN-10-1120. Epub Feb. 7, 2011. PubMed PMID: 21300766; PubMed Central PMCID: PMC3407272.

\* cited by examiner

MARKERS FOR DETECTING MICROSATELLITE INSTABILITY IN CANCER AND DETERMINING SYNTHETIC LETHALITY WITH INHIBITION OF THE DNA BASE EXCISION REPAIR PATHWAY

CROSS-REFERENCE TO RELATED APPLICATIONS

This application is a continuation of International Patent Application PCT/EP2013/057516, filed Apr. 10, 2013, designating the United States of America and published in English as International Patent Publication WO 2013/153130 A1 on Oct. 17, 2013, which claims the benefit under Article 8 of the Patent Cooperation Treaty and under 35 U.S.C. § 119(e) to European Patent Application Serial No. 13161395.2, filed Mar. 27, 2013, to U.S. Provisional Patent Application Ser. No. 61/638,955, filed Apr. 26, 2012, and to U.S. Provisional Patent Application Ser. No. 61/622,383, filed Apr. 10, 2012, the disclosure of each of which is hereby incorporated herein in its entirety by this reference.

TECHNICAL FIELD

The application relates to the field of medicine and cancer, particularly to mismatch repair (MMR-)deficient tumors. New markers are presented herein that have a high sensitivity to detect whether a tumor is mismatch repair deficient or not. The markers are particularly mutations in microsatellite regions. Accordingly, methods are provided for diagnosing microsatellite instability of a tumor, comprising determining the presence of these markers. Further, kits are provided to detect the presence of these markers (or subsets thereof) in a sample.

Interestingly, mutations preferentially affect the double-strand break (DSB) repair by homologous recombination (HR) pathway, and DSB repair is functionally impaired in MMR-deficient tumors. It is shown herein that these tumors are sensitive to induction of single strand breaks by pharmacological inhibition of the enzyme poly ADP ribose polymerase (PARP inhibition). Accordingly, novel treatment modalities for MMR-deficient tumors are provided, based on the synthetic lethal interaction between MMR and PARP.

STATEMENT ACCORDING TO 37 C.F.R. § 1.52(e) TABLES SUBMITTED AS ASCII TEXT FILES

Pursuant to 37 C.F.R. § 1.52(e), files containing tables have been submitted concomitant with this application, the contents of which are hereby incorporated herein in their entirety by this reference.

BACKGROUND

The form of genomic instability associated with defective DNA mismatch repair in tumors is called microsatellite instability (MSI). Microsatellite instability (MSI) is a clonal change in the number of repeated DNA nucleotide units in microsatellites. It typically arises in tumors with defective mismatch repair (MMR) genes: failure of the DNA MMR system to repair errors that occur during the replication of DNA results in accelerated accumulation of single nucleotide mutations and alterations in the length of simple, repetitive microsatellite sequences that occur ubiquitously throughout the genome.

MMR-deficiency represents a well-established cause of Lynch syndrome, which is an autosomal dominant inherited disorder of cancer susceptibility that is responsible for 2% to 5% of endometrial (EM) or colorectal (CRC) cancers. Lynch syndrome is caused by mutations or deletions in the MMR pathway genes (MLH1, MSH2, MSH3, MSH6 or PMS2) (Jiricny, 2006). Additionally, epigenetic silencing of MLH1, often referred to as "sporadic" Lynch syndrome, contributes to another 15% of these tumors (Kuismanen et al., 2002). MMR-deficiency has also been described in a minority of ovarian, pancreatic, gastric, leukemic, as well as several other cancers.

Deficiency of the MMR machinery leads to DNA replication errors in the tumor tissue, but not in the normal surrounding tissue. In particular, somatic errors accumulate as insertion/deletion mutations in mono- and dinucleotide repeats—a phenomenon referred to as microsatellite instability (MSI) (Pinol et al., 2005).

MMR-deficient tumors exhibit a different prognosis and therapeutic outcome after standard chemotherapy (de la Chapelle and Hampel, 2010), such as 5-fluoracil and the alkylating agents such as temozolomide. Untreated CRC patients with MMR-deficient tumors have a modestly better prognosis, but do not seem to benefit from 5-fluorouracil-based adjuvant chemotherapy, which is the first-choice chemotherapy for CRC. In particular, in MMR-deficient tumors mismatches induced by 5-fluorouracil are tolerated, leading to failure to induce cell death (Hewish et al., 2010). MMR-deficient tumors are also resistant to cisplatin and carboplatin, which are frequently used chemotherapies in EM (Hewish et al., 2010). Furthermore, MMR-deficient tumors can be resistant to targeted therapies, including anti-EGFR and anti-VEGF therapies, because they acquire secondary mutations in genes that activate alternative or downstream signaling pathways. For instance, MMR– tumors can acquire mutations in double-strand break repair genes (e.g., MRE11, ATR and RAD50), known oncogenes or tumor suppressors (e.g., PIK3CA or PTEN). Another possibility is that epigenetic silencing of MLH1 coincides with particular mutations, such as the BRAF V600E mutation (Ogino et al., 2012), which represents an established negative predictor of response to targeted anti-EGFR therapies in advanced CRC (De Roock et al., 2010).

Efforts to individualize the treatment of MMR-deficient tumors have focused on identifying synthetic lethal interactions with the MMR pathway. In particular, studies revealed that increased oxidative damage (by methotrexate exposure or PINK1 silencing (Martin et al., 2011)) and interference with the base excision repair (BER) pathway (by DNA polymerase γ or β inhibition (Martin et al., 2010)) sensitize MMR-deficient tumors. In particular, in MMR– tumors, oxidative damage induces 8-oxoguanine (8-oxoG) DNA lesions, which fail to be sufficiently repaired either by the BER or MMR pathway, generating mainly GC to TA dinucleotide transversions at the DNA level, leading to cell death. Additionally, it has been hypothesized that there is a maximum mutation frequency that a tumor can tolerate, above which a further increase in mutations would be detrimental. It has therefore been proposed to additionally treat MMR-tumors with mutagenic nucleoside analogues until a critical level of mutations is obtained resulting in error catastrophe-like ablation of the tumor. Until now, these efforts failed, however, to translate into clinically effective treatment options. Alternatively, secondary mutations occurring as a result of MMR-deficiency can also be targeted (Dorard et al., 2011). However, studies characterizing the secondary mutation spectra of MMR-deficient tumors have been limited to observations at one or a few reporter loci, or have focused exclusively on mutations at known hotspot sequences. Although they were able to establish that mutations most frequently affect mono- and di-nucleotide repeats, the spectrum of somatic mutations occurring in these tumors remains poorly characterized.

Since presence of MMR-deficiency mainly in colorectal and endometrial tumors represent a familial form of cancer, and since tumors exhibiting mutation spectra characteristic of MMR-deficiency, diagnostic tests assessing MMR-deficiency are commonly used.

By far the most common method to detect MSI is to measure the length of a polymerase chain reaction amplicon containing the entire microsatellite. This requires DNA, a pair of primers of which one is often fluorescently end labeled, a sequencer, and suitable software. Alternatively, if the amplicon is sequenced, one can simply count the number of repeat units. MSI can also be indirectly diagnosed by detecting loss of staining by immunohistochemistry (IHC) of one of the mismatch repair genes, since this also points to an abnormality in mismatch repair. Immunohistochemical and genetic methods are both characterized by a considerable number of false-negatives, and for this reason combined assessments at the immunohistochemical and genetic level are performed in a routine diagnostic setting.

There are at least 500,000 microsatellites in the human genome, and because defective MMR does not affect all microsatellites in a given tumor, it is important to study more than one microsatellite and to study microsatellites that are frequently affected by instability. As microsatellite markers were originally quite randomly picked by researchers, based on their own experiments, a conference was held in Bethesda, Md., to discuss the issues and make suggestions to promote consistency across studies. This resulted in a recommendation for a "golden standard" marker panel, known as the Bethesda panel.[9] This panel consists of three dinucleotide repeats (D2S123, D5S346, D17S250) and two mononucleotide repeats (BAT26, BAT25) and is still the standard test for MSI. It was proposed to consider a tumor MSI-positive if 40% or more of the markers tested were unstable (also referred to as MSI-high or MSI-H). When using the five-marker panel, this means that MSI is called when at least two of them are positive; however, often four or all five are positive in tumors with MSI. Tumors that test negative for all five markers are termed microsatellite stable (MSS). For tumors that tested positive on 1 tumor marker (or on <30% of tumor markers), the term MSI-L was proposed.[9]

Although the Bethesda panel is still considered the standard, it is known to have a fairly low sensitivity (also depending on which MMR gene is mutated). For instance, for patients with MLH1 mutations, sensitivity is 80%, but for patients with MSH6 mutations, it is only 55%.[10] This can be improved by adding further markers,[10] but still actual MSI-H patients may present as MSI-L or MSS. This is not without significance, as MSI status is important in prognosis (typically better for MSI-H patients[11]), treatment (MSI-H tumors do not respond to fluoro-uracil (FU)-based adjuvant therapy, as an intact MMR system is needed to induce apoptosis of cells with FU-modified DNA[11-13]), and diagnosis of several cancers (e.g., those of the Lynch syndrome), and newly diagnosed colorectal cancer (CRC) patients are routinely screened for MSI status.

Another significant disadvantage is that the Bethesda panel is only recommended for colon cancer, even though other cancers displaying MSI are known.[9] It seems that this is due to the fact that the five markers were rather randomly identified as being mutated in microsatellite unstable colon cancer, but there is no biological mechanism known.

A further disadvantage is of a technical nature. The Bethesda marker panel contains quite long repeats (e.g., the BAT26 marker contains a 26 nucleotide A repeat), and the typical PCR products used to determine MSI status are well over 100 bp. To accurately sequence these fragments and determine the exact length of the repeat, Sanger based sequencing methods in conjunction with multicapillary gel electrophoresis are typically used. However, more and more labs use so called "next generation" sequencing which employ massively parallel sequencing techniques. While cheaper, these technologies make use of shorter reads and cannot be used to detect microsatellite instability on the Bethesda marker panel. As a consequence, labs need to maintain two sequencers: one for Bethesda marker panel screening, and one for other experiments. It would be far more convenient if no special sequencer was required for determining MSI status and this determination could be done on commonly used equipment.

Thus, it would be advantageous to find markers for microsatellite instability that are more sensitive than the currently used Bethesda panel, while retaining specificity for MSI. Ideally, these markers are found using unbiased detection methods (i.e., looking across the whole genome rather than checking specific regions that are supposed to be altered in disease setting). A further advantage would be the identification of markers that are indicative of MSI as such. That is to say, they are a general marker for microsatellite instability, and not just for microsatellite instability in colon cancer (as is the case for the Bethesda panel). This would indeed obviate the need to find new markers for each cancer where MSI can be present. An additional advantage would be the identification of markers whose status can be determined independently of technology. More particularly, markers that can be identified using next generation sequencing technologies (instead of only being identified using Sanger sequencing). This way, labs need not to hold on to an apparatus they only use for checking the Bethesda panel markers.

SUMMARY OF THE DISCLOSURE

Provided are better markers for determining MSI status of a particular cancer. To make sure detection was unbiased, it is here reported, for the first time, next-generation sequencing of mismatch-repair deficient tumors. The markers are chosen not to be in long microsatellites such that their detection is not dependent on Sanger sequencing methodology. Further, to expand applicability of markers, markers were evaluated in different tumor types such that they represent markers of microsatellite instability across various cancers, and not cancer type-specific markers. Finally, markers were selected to occur recurrently in the tumors. Interestingly, many of the recurrent (hot-spot) mutations clustered in genes affecting the DNA double strand break repair pathway, and it could be shown that this pathway is also functionally affected. As a result, it could be demonstrated that tumors positive for these markers are sensitive to inhibition with inhibitors of DNA base excision repair enzymes, such as PARP inhibitors: this results in a synthetic lethal interaction.

As will be expanded upon in the Examples section, next-generation sequencing allowed the identification of a new panel of markers that can be used to detect MMR-deficiency and that was in agreement with these conditions.

The identified markers can be divided in two classes: indels present in microsatellite regions in coding regions (i.e., exons) and indels present in non-coding regions (most particularly 5' and 3' UTR regions) of specific genes.

Accordingly, methods are provided herein of diagnosing MSI status of a tumor, comprising determining the presence of an indel in at least two microsatellite regions in a sample of the tumor DNA, wherein the at least two microsatellite regions are at least two microsatellite regions present in 5' UTR or 3' UTR regions from the genes listed in Table 1, or at least three microsatellite regions selected from those present in the exons of the genes listed in Table 2 and/or present in 5' UTR or 3' UTR regions from the genes listed in Table 1, wherein the presence of at least one indel is indicative of MSI.

According to further particular embodiments, the microsatellite regions are homopolymer regions. According to yet further particular embodiments, the microsatellite regions are identical to the microsatellite regions identified in Table 1 or 2 (i.e., the at least two microsatellite regions are selected from the list of microsatellite regions listed in Table 1 or 2).

According to specific embodiments, microsatellite regions present in UTRs can be selected from Table 4 instead of Table 1. According to other specific embodiments, these microsatellite regions can be selected from Table 6 instead of Table 1.

According to alternative but non-exclusive specific embodiments, microsatellite regions present in exons of genes can be selected from Table 5 instead of Table 2. According to other specific embodiments, the regions can be selected from Table 7 instead of Table 2.

According to very particular embodiments, the microsatellite regions can be selected from the genes listed in Table 8.

According to particular embodiments, the cancer or tumor for which the MSI status is diagnosed is selected from the group of: colorectal cancer, endometrial cancer, ovarian cancer, gastric cancer, leukemia, and a tumor of the Lynch syndrome.

As indels in microsatellites in non-coding regions (such as the 5' and 3' UTR regions) are subjected to less selection pressure than indels in coding regions (whereby the latter cause frame shift mutations resulting in a completely different translation from the original), it could be demonstrated that indels in microsatellites from non-coding regions are more reliable markers of MSI across cancer types. In fact, over 50% of the non-coding markers identified herein score positive when tested on MMR-deficient tumors with proven MSI. For the exonic markers, still well over ⅓ scored positive when tested on these tumors. This explains why it is envisaged to use at least three markers when at least part of the markers is in exonic regions.

It is also particularly envisaged to use combinations of markers in exonic regions and markers in non-coding regions. For instance, according to particular embodiments, the at least two microsatellite regions wherein the presence of an indel is determined are at least two microsatellite regions selected from those present in 5' UTR or 3' UTR regions from the genes listed in Table 1 and at least two microsatellite regions selected from those present in the exons of the genes listed in Table 2.

According to specific embodiments, it is envisaged to use more markers than at least two or three. Using more markers will typically yield a more accurate diagnosis (although this benefit should be off-set to the increased cost. Also, once above a certain threshold of markers, the relative value of adding another marker is limited, as it does not necessarily add information). Thus, according to particular embodiments, at least four, five, six, seven or eight markers are used (i.e., indels in microsatellite regions selected from those present in the exons of the genes listed in Table 2 and/or present in 5' UTR or 3' UTR regions from the genes listed in Table 1). According to further particular embodiments, the presence of at least 8, 9, 10, 11 or 12 indels in microsatellite regions selected from those present in the exons of the genes listed in Table 2 and/or present in 5' UTR or 3' UTR regions from the genes listed in Table 1 are used to determine the MSI status. According to even further particular embodiments, yet even more markers are used, e.g., at least 15, at least 20, at least 25, at least 30, at least 35, at least 40 markers, or at least 50 markers.

According to specific embodiments, at least one marker used is an exonic marker in a gene not previously associated with cancer, or in a gene not previously known to be affected in MMR deficient tumors. Thus, it is envisaged that the microsatellite(s) selected from those present in the exons of the genes listed in Table 2 comprises at least one microsatellite present in a gene selected from the list of: SETD1B, RBMXL1, CCDC150, OR7E24, C15orf40, KIAA2018, LTN1, SLC22A9, CDH26, DDX27, EXOSC9, FAM111B, KIAA0182, KIAA1919, MIS18BP1, PRRT2, TMEM60, AQP7, ARV1, CCDC168, ELAVL3, F8, FETUB, HPS1, NBEAL1, P4HTM, PIGB, RBM43, RG9MTD1, SRPR, and TMEM97. According to yet even more specific embodiments, at least one microsatellite is present in a gene selected from the list of: SETD1B, TMEM60, DDX27, EXOSC9, FAM111B, and KIAA1919. According to alternative embodiments, SEC31A, CNOT2, RNF145, RNPC3, SLC35F5, TMBIM4, CD3G, DOCK5, MYO10 and PRRG1 can also be used in these lists.

According to alternative specific embodiments, at least one marker used is an indel in a homopolymer of between 10 and 15 repeat bases situated in a 5' or 3' UTR region.

A particularly envisaged marker panel are the microsatellites in the genes shown in Table 3. Thus, according to these embodiments, methods are provided wherein the presence of an indel in at least two microsatellite regions in a sample of the tumor DNA is determined, wherein the at least two microsatellite regions are microsatellite regions from the 56 genes shown in Table 3.

According to particular embodiments, MSI status can be further characterized as follows: if 17% or more of the studied microsatellite regions contains an indel, the tumor is MSI-H, if between 2% and 17% of the microsatellite regions contains an indel, the tumor is MSI-L, and if less than 2% of the microsatellite regions contains an indel, the tumor is microsatellite stable (MSS). By way of example, for a panel of 56 markers, if 0 or 1 markers are positive, the tumor is classified as MSS, for 2 to 9 positive markers, the tumor is MSI-L, and for 10 or more positive markers, the tumor is classified as MSI-H. Alternatively, the range from the Bethesda panel can be extrapolated (0 of 10 positive markers is MSS, 1 or 2 out of 10 positive markers is MSI-L, 3 or more positive markers is MSI-H; which corresponds to boundaries of between 1 and 9% of positive markers for the distinction between MSS and MSI-L and of more than 20% positive markers for classification as MSI-H).

According to a specific aspect, the microsatellite indel markers provided herein can be detected independent of the technology used. However, it is particularly envisaged that determining the presence of an indel is not done through a method based on Sanger sequencing. This because the process of detecting microsatellite instability using the Bethesda marker panel is typically done through Sanger sequencing, a protocol that proves quite cumbersome. According to further embodiments, it is particularly envisaged to determine the presence of an indel through single base pair extension methods (such as a Sequenom MassArray), DNA hybridization technologies (e.g., TAQMAN®), melting curve analysis (including HRM) or a similar technology.

According to another aspect, a biomarker panel is provided for determining MSI in a tumor sample. Such biomarker panel comprises at least eight microsatellite regions selected from those present in 5' UTR or 3' UTR regions from the genes listed in Table 1 and those present in the exons of the genes listed in Table 2. According to very particular embodiments, the biomarker panel comprises at least half of the microsatellite regions listed in Table 3. According to yet even further particular embodiments, the biomarker panel is represented by the 56 microsatellite regions listed in Table 3.

It is particularly envisaged that this biomarker panel can be used to detect MSI status in cancer. Accordingly, the use of this biomarker panel is provided in the diagnosis of microsatellite instability in cancer.

Accordingly, biomarker panels as described herein are provided for use as a medicament. More particularly, biomarker panels as described herein are provided for use as a diagnostic. Even more particularly, biomarker panels as described herein are provided for use in diagnosis of microsatellite instability in cancer.

According to yet other embodiments, a kit is provided for determining MSI in a tumor sample, comprising the tools to genotype the biomarker panel (i.e., the at least eight microsatellite regions selected from those present in 5' UTR or 3' UTR regions from the genes listed in Table 1 and those present in the exons of the genes listed in Table 2). Most particularly, the kit will be adapted to the particularly envisaged biomarker panel(s). According to specific embodiments, the kit may also contain the tools to genotype the Bethesda panel of markers, or the extended Bethesda panel of markers. Such kits are particularly suited to do a side-by-side comparison of the markers with the Bethesda panel.

As shown in the Example section, the indel markers provided herein are enriched in genes involved in DNA double-strand break repair pathways, and affect their functionality. As a consequence, cells in which these markers are present are sensitive to synthetic lethality by inhibition of DNA base excision repair. This offers new therapeutic opportunities, as MSI positive tumors are often resistant to standard chemotherapies used.

Accordingly, in a further aspect, methods are provided of screening sensitivity of cancer cells to treatment with an inhibitor of a DNA base excision repair enzyme, comprising determining MSI status in the cancer cells. According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome. Although these methods can in principle be performed in vivo, ex vivo and in vitro, it is particularly envisaged that they are performed in vitro.

According to particular embodiments, the presence of MSI is indicative of sensitivity of the cancer cells to treatment with an inhibitor of a DNA base excision repair enzyme; i.e., the cancer cells will die, stop growing or proliferate less when treated with such inhibitor.

According to specific embodiments, the cancer cells are cells obtained from a subject, and the screening of sensitivity to treatment with an inhibitor of a DNA base excision repair enzyme is used in guiding the treatment of the subject. According to alternative embodiments, the screening of sensitivity is used in stratifying or classifying the subject for a clinical trial.

According to particular embodiments, the presence of MSI is established by a method described herein, i.e., a method comprising determining the presence of an indel in at least two microsatellite regions in a sample of the tumor DNA, wherein the at least two microsatellite regions are
  at least two microsatellite regions present in 5' UTR or 3' UTR regions from the genes listed in Table 1, or
  at least three microsatellite regions selected from those present in the exons of the genes listed in Table 2 and/or present in 5' UTR or 3' UTR regions from the genes listed in Table 1,
  wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2.

Thus, not only methods of screening sensitivity of cancer cells are provided, but also methods of diagnosing sensitivity of a subject with cancer to treatment with an inhibitor of a DNA base excision repair enzyme, comprising the steps of:
  determining the MSI status in a sample of cancer cells obtained from the subject;
  correlating the MSI status to sensitivity to treatment with an inhibitor of a DNA base excision repair enzyme, wherein the presence of MSI is indicative for sensitivity to the treatment.

Optionally, these methods contain an additional step of obtaining a sample of cancer cells from the subject (prior to the determining step). Determining the MSI status is then typically done in the cells of the obtained sample. It is particularly envisaged that determining the MSI status in a sample of cancer cells is performed in vitro.

According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome (or any other tumor of the Lynch syndrome spectrum). According to particular embodiments, the presence of MSI is established by a method described herein, i.e., a method comprising determining the presence of an indel in at least two microsatellite regions in a sample of the tumor DNA, wherein the at least two microsatellite regions are
  at least two microsatellite regions present in 5' UTR or 3' UTR regions from the genes listed in Table 1, or
  at least three microsatellite regions selected from those present in the exons of the genes listed in Table 2 and/or present in 5' UTR or 3' UTR regions from the genes listed in Table 1,
  wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2.

It is also envisaged that methods according to this aspect may contain a further step of treating the subject with an inhibitor of a DNA base excision repair enzyme (if the subject is sensitive to such treatment, as determined by the MSI status).

Thus, also methods are provided for treating a cancer with MSI in a subject in need thereof, comprising:
establishing the presence of MSI in the cancer;
administration of an inhibitor of a DNA base excision repair enzyme to the subject.

It is envisaged that the cancer is treated by administering the inhibitor to the subject. The methods may optionally have an additional step of obtaining a sample of cancer cells from the subject (prior to the step of determining MSI, and establishing the presence of MSI).

According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome. According to particular embodiments, the presence of MSI is established by a method described herein, i.e., a method comprising determining the presence of an indel in at least two microsatellite regions in a sample of the tumor DNA, wherein the at least two microsatellite regions are
at least two microsatellite regions present in 5' UTR or 3' UTR regions from the genes listed in Table 1, or
at least three microsatellite regions selected from those present in the exons of the genes listed in Table 2 and/or present in 5' UTR or 3' UTR regions from the genes listed in Table 1,
wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2.

BRIEF DESCRIPTION OF THE FIGURES

The patent or application file contains at least one drawing executed in color. Copies of this patent or patent application publication with color drawing(s) will be provided by the Office upon request and payment of the necessary fee.

BRIEF DESCRIPTION OF THE TABLES

Figure 1:
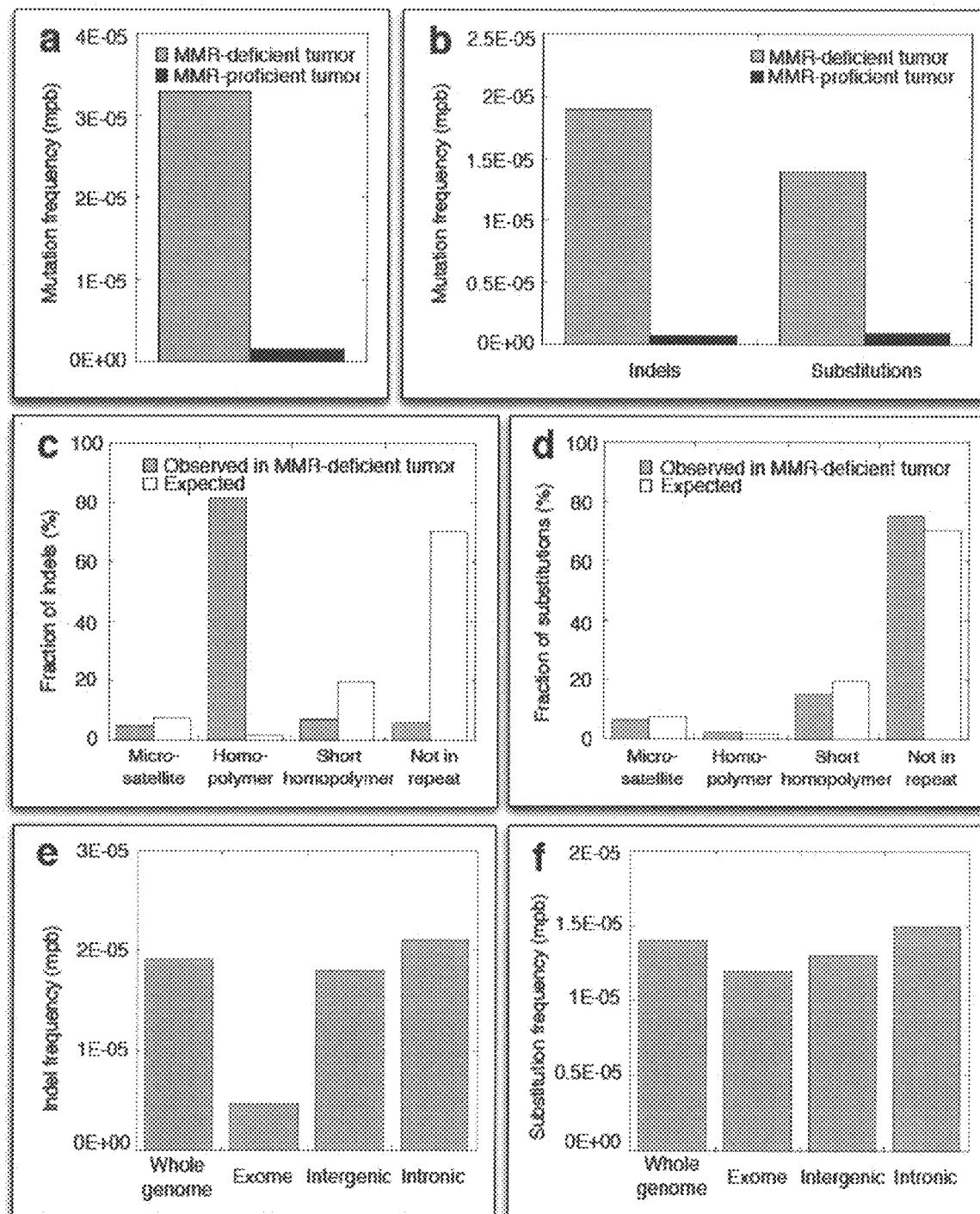
FIG. 1. Somatic substitutions and indels in the MSH6-deficient hypermutator. (a) The average mutation frequencies (number of mutations per base, mpb) in the MMR-deficient tumor and two MMR-proficient tumors. (b) Mutation frequency stratified for indels and substitutions. (c-d) The fraction of indels (c) and substitutions (d) observed in microsatellites, homopolymers (length over 5 bp), short homopolymers (length of 3 to 5 bp) and "not in repeat regions" compared to their expected fraction in these regions. (e-f) Frequencies of indels (e) and substitutions (f) in the MMR-deficient tumor stratified into exonic, intergenic and intronic regions.

Table 1. Most common recurrent indels in 5' and 3' UTR regions for 16 MMR-deficient tumor samples (present in at least 4 of 16 tumor samples). The latter two columns indicate how often the homopolymer is affected with an insertion or deletion, respectively.

Table 2. Most common recurrent indels in exons for 16 MMR-deficient tumor samples. The latter two columns indicate how often the homopolymer is affected with an insertion or deletion, respectively.

Table 3. Panel of 56 markers.

Table 4. Most common recurrent indels in 5' and 3' UTR regions for 16 MMR-deficient tumor samples, after additional filter step.

Table 5. Most common recurrent indels in exonic regions for 16 MMR-deficient tumor samples, after additional filter step.

Table 6. Most common recurrent indels in 5' and 3' UTR regions for 11 MMR-deficient tumor samples.

Table 7. Most common recurrent indels in exons for 11 MMR-deficient tumor samples. The latter three columns indicate whether the gene is a cancer census gene, whether it has previously been reported to be affected in MMR deficient tumors, and whether mutations in the gene are known to be associated with other cancers.

Table 8. Recurrent indels in 5' and 3' UTR regions and in exons for MMR-deficient tumor samples.

Table 9. Standard diagnostic tests to assess MMR-deficiency.

Table 10. Data on the extended Bethesda panel for the three endometrial tumors

Table 11. Tumor samples and clinical information. The table lists detailed information for the three selected tumor samples. All tumors were primary, chemo-naïve tumors from patients without family history of inherited cancers.

Table 12. Results from the calldiff methods applied on the tumor-normal pairs (MMR−1, MMR+1 and MMR+2).

Table 13. Clinical information for additional tumor samples.

Table 14. Standard diagnostic tests to assess MMR-deficiency.

Table 15. Data on the extended Bethesda panel.

Table 16. Overall mutation data after quality filtering and validation.

Table 17. Filtering of false positives from hotspot mutations.

Table 18. List of homopolymers with indels in exonic regions in 11 MMR-deficient tumors.

Table 19. Homopolymer distribution in function of length of the homopolymer.

Table 20. Enrichment in the number of indels occurring in homopolymers of length 8-11 in exomes.

Table 21. Expected and observed indels in homopolymers recurring in 3 of 11 tumors Table 22. Expected and observed indels in homopolymers recurring in 4 of 11 tumors Table 23. Genes affected by indels in at least 3 out of 11 MMR-deficient exomes.

Table 24. Distribution of homopolymers in function of their length.

Table 25. Gene expression in normal endometrium.

Table 26. Analysis of genes specific for colorectal cancers with MSI.

Table 27. Clinical information for ovarian and leukemia tumors.

Table 28. Mutation status of MMR genes in ovarian and leukemia tumors.

Table 29. Pathway analysis of genes carrying hotspot mutations.

Table 30. Genes involved in DSB repair by HR pathway.

Table 31. Primary tumor cell cultures.

Table 32. Cell lines, type, subtype and status are identified.

TABLES

The patent contains table(s) that have been included at the end of the specification.

DETAILED DESCRIPTION

Definitions

The disclosure will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an," "the," this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the disclosure. Practitioners are particularly directed to Sambrook et al., *Molecular Cloning: A Laboratory Manual*, $2^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

The term "microsatellite" or "microsatellite regions" as used herein refers to mono-, di-, tri-, tetra-, penta- or hexanucleotide repeats in a nucleotide sequence, consisting of at least two repeat units and with a minimal length of six bases. A particular subclass of microsatellites includes the homopolymers. "Homopolymer" as used herein refers to a microsatellite region that is a mononucleotide repeat of at least six bases; in other words a stretch of at least six consecutive A, C, T or G residues if looking at the DNA level. Most particularly, when determining microsatellites, one looks at genomic DNA of a subject (or of genomic DNA of a cancer present in the subject).

The term "MSI status" as used in the application refers to the presence of microsatellite instability (MSI), a clonal or somatic change in the number of repeated DNA nucleotide units in microsatellites. MSI status can be one of three discrete classes: MSI-H, also referred to as MSI-high, MSI positive or MSI, MSI-L, also referred to as MSI-low, or microsatellite stable (MSS), also referred to as absence of MSI. Typically, to be classified as MSI-H, at least 20% of the markers used to classify MSI status need to score positive, while for the MSS classification, less than 2.5% score positive. If an intermediate number of markers scores positive, the tumor is classified as MSI-L. Note that, as these initial boundaries are derived from the extended Bethesda marker panel (which consists of only ten markers), as typically fewer than 100 markers will be assessed, and the number of positive markers is a whole number, the percentages are approximate. The difference between MSS and MSI-L will typically be somewhere between 1 and 9% of markers that score positive (when ten markers are assessed, this means that one positive marker results in a MSI-L classification), whereas the difference between MSI-L and MSI-H will typically be between 15 and 25% positive markers (i.e., above that threshold, a tumor is MSI-H, below it is MSI-L). Alternatively, instead of making the distinction in three classes, only the difference between presence and absence of microsatellite instability is assessed, in which case the status is either presence of MSI or absence of MSI (=MSS). Considering the correlation between the absence of an intact mismatch repair (MMR) system and the presence of MSI, diagnosing the presence of MSI (or diagnosing MSI status) can be interpreted as diagnosing MMR deficiency. Note however that MMR can be functional or deficient, there is no intermediate class. Thus, MSI-L also corresponds to MMR deficiency—this situation is equivalent to assessing only the presence or absence of MSI.

"Diagnosing the MSI status of a tumor" or "diagnosing the MSI status of a tumor in a subject" or "diagnosing the MSI status of a subject" or "determining the MSI status of a tumor (or subject)" are all considered synonyms herein. Determining (or diagnosing) the MSI status typically implies drawing the conclusion of MSI based on detecting the presence of one or more indels in the microsatellite regions under investigation, or the conclusion of absence of microsatellite instability based on not detecting indels in the microsatellite regions under investigation. Accordingly, "determining the presence of an indel" in a microsatellite region means assessing or detecting the presence or absence of an indel in said microsatellite region. Likewise, determining the presence of an indel in at least two microsatellite regions means assessing or detecting the presence or absence of an indel in each of said at least two microsatellite regions. The presence of at least one indel is indicative of MSI (as explained in the application, the exact number of positive markers required to establish MSI will depend on the number of markers used).

An "indel" as used herein refers to a mutation class that includes both insertions, deletions, and the combination thereof. An indel in a microsatellite region results in a net gain or loss of nucleotides. The presence of an indel can be established by comparing it to DNA in which the indel is not present (e.g., comparing DNA from a tumor sample to germline DNA from the subject with the tumor), or, especially in case of monomorphic microsatellites or homopolymers, by comparing it to the known length of the microsatellite, particularly by counting the number of repeated units. According to specific embodiments, particularly envisaged indels have a length of between one and five nucleotides (i.e., the length of the microsatellite or homopolymer is one to five nucleotides longer or shorter than the normal known length of the microsatellite or homopolymer). According to further specific embodiments, the indels have a length of one to four nucleotides, one to three nucleotides, or one or two nucleotides. Note that, as indels can be a combination of a insertion and a deletion, the altered nucleic acid sequence may be larger than the length difference (e.g., a deletion of five nucleotides combined with an insertion of three nucleotides leads to an altered length of two, but the sequence of the microsatellite may have changed as well). Most typically however, an indel will be either an insertion or a deletion, typically of one or two nucleotides.

A "monomorphic microsatellite" is one in which all individuals, particularly all individuals of a given population, share the same number of repeat units. This in contrast to a "polymorphic microsatellite," which is used to refer to microsatellites in which more than 1% of a given population display heterozygosity for the number of repeat units. By way of example, the BAT26 marker is comprised of 26 adenines in more than 99% of ethnic Europeans, whereas alleles with different numbers of adenines at this location (e.g., 15, 20, 22, 23) are seen in up to 25% of ethnic Africans, including African Americans.[17] Thus, BAT26 is a monomorphic microsatellite in Europeans and a polymorphic microsatellite in Africans.[16]

A "sample of tumor DNA" refers to any sample that can be used as basis for sequencing, wherein DNA from a cancer is present. The team "cancer" as used herein, refers to different diseases involving unregulated cell growth, also referred to as malignant neoplasm. The term "tumor" is used as a synonym in the application. It is envisaged that this term covers all solid tumor types (carcinoma, sarcoma, blastoma), but it also explicitly encompasses non-solid cancer types such as leukemia, lymphoma or myeloma. Thus, a "sample of tumor DNA" can also be a blood sample from a person with leukemia. Typically, a sample of tumor DNA has at one point been isolated from a subject, particularly a subject with cancer. Optionally, it has undergone one or more forms of pre-treatment (e.g., lysis, fractionation, separation, purification) in order for the DNA to be sequenced, although it is also envisaged that DNA from an untreated sample is sequenced. As used herein, the noun "subject" refers to an individual vertebrate, more particularly an individual mammal, most particularly an individual human being. A "subject" as used herein is typically a human, but can also be a mammal, particularly domestic animals such as cats, dogs, rabbits, guinea pigs, ferrets, rats, mice, and the like, or farm animals like horses, cows, pigs, goat, sheep, llamas, and the like. A subject can also be a non-mammalian vertebrate, like a fish, reptile, amphibian or bird; in essence any animal which can develop cancer fulfills the definition.

The term "colorectal cancer" as used herein is meant to include malignant neoplasms of colon (C18 in ICD-10), malignant neoplasms of rectosigmoid junction (C19 in ICD-10), malignant neoplasms of rectum (C20 in ICD-10) and malignant neoplasms of anus and anal canal (C21 in ICD-10).

The term "Lynch syndrome" as used herein refers to an autosomal dominant genetic condition which has a high risk of colon or colorectal cancer as well as other cancers including endometrium, ovary, stomach, small intestine, hepatobiliary tract, upper urinary tract, brain, and skin cancer. The increased risk for these cancers is due to inherited mutations that impair DNA mismatch repair. The old name for the condition is HNPCC.

An "inhibitor of a DNA base excision repair enzyme" as used herein refers to a substance that can interfere with the base excision repair function of the gene product, either at the DNA level (by inhibiting the formation of the relevant gene product, i.e., by preventing or interfering with transcription), at the RNA level (by neutralizing or destabilizing mRNA to prevent or interfere with translation) or at the protein level (by neutralizing or inhibiting the protein involved in BER). It is particularly envisaged that the inhibitor is a PARP inhibitor, as such inhibitors are well characterized. Most particularly envisaged are inhibitors of PARP-1 and/or of PARP-2, as these enzymes are the PARPs most actively involved in BER. However, inhibitors of other PARPs may be useful as well. In this regard, recent publications suggest that the PARP inhibitor iniparib, which is explicitly envisaged for use, inhibits other PARPs than PARP-1 and 2, particularly PARP-5 and 6 (J. Ji, M. P. Lee, M. Kadota, et al., "Pharmacodynamic and pathway analysis of three presumed inhibitors of poly (ADP-ribose) polymerase: ABT-888, AZD 2281, and BSI201," Proceedings of the 102nd Annual Meeting of the American Association for Cancer Research; 2011 Apr. 2-6; Orlando, Fla. AACR. 2011. Abstract nr 4527; K. A. Maegley, P. Bingham, J. H. Tatlock, et al., "All PARP inhibitors are not equal: an in vitro mechanistic comparison of PF-01367338 to iniparib," J. Clin. Oncol. 2011; 29 (suppl; abstr e13576); R. A. Nagourney, K. R. Kenyon, F. R. Francisco, et al., "Functional analysis of PARP inhibitors AZD 2281 and BSI-201 in human tumor primary cultures: a comparison of activity and examination of synergy with cytotoxic drugs," J. Clin. Oncol. 2011; 29 (suppl; abstr e13599)).

Examples of PARP inhibitors include, but are not limited to: iniparib, olaparib, rucaparib, veliparib, CEP 9722, MK 4827, BMN-673, and 3-aminobenzamide.

Description

DNA replication errors occurring in mismatch repair (MMR) deficient cells persist as mismatch mutations and predispose to a range of tumors. Here, the first genomes from MMR-deficient tumors were sequenced, allowing the unbiased assessment of DNA replication errors. It was observed that mutation rates were drastically increased relative to MMR-proficient tumors. Insertion or deletion (indel) mutations occurred most frequently and were largely confined to homopolymer stretches, whereas single base pair substitutions mainly consisted of A:T>G:C and G:C>A:T transitions and were more often located nearby indels. As the rates of substitutions were higher nearby somatic indels, this suggests that indel mutations act as mutagenic sites during DNA replication. Due to negative clonal selection, somatic mutation rates were lower in the exome than the rest of the genome, whereas due to positive selection, some exonic mutations occurred in several MMR-deficient tumors. These recurrent mutations specifically affected genes expressed in the normal matched tissue, suggesting that they represent drivers of MMR-deficient tumor progression.

Intriguingly, indels were mainly located in homopolymers, in particular in homopolymers of increased length. These observations also have an immediate clinical implication. The extended Bethesda panel, currently used for the diagnostic classification of MSI tumors[9, 14, 15] has only limited sensitivity, i.e., 80%, 84% and 55% for MLH1-, MSH2- and MSH6-deficient tumors,[16] presumably because this panel consists of 8 microsatellite and only 2 homopolymer markers, respectively with a length of 25 and 26 nucleotides. By applying a panel of 56 recurrent indels to 114 endometrial tumors, it could be demonstrated that up to 43% of tumors exhibited a variable degree of MSI. This was significantly higher than previously reported, most likely because these indels were not randomly selected, but were identified through an unbiased assessment of mutations recurrently affecting the exome, 5' and 3' UTRs. It was also observed that recurrent indels in endometrial tumors were located in MMR tumors of other cancer types. Since indels in 3' UTRs are only determined by the length of the affected homopolymer, whereas in the exome they need to be positively selected in genes expressed by the tissue of origin, most indels shared among various cancer types were located in 5' and 3' UTRs. Therefore, recurrent mutations in 5' and 3' UTRs or other non-coding sequences seem to be particularly suitable to detect MSI across various cancer types. Interestingly, a selective panel of the most recurrent mutations was highly sensitive to detect microsatellite instability (MSI) in various cancer types. In 114 primary endometrial tumors, a continuous spectrum of MSI was observed in almost half of the tumors, suggesting that MSI occurs more frequently than anticipated.

As will be detailed in the Examples section, particularly in Example 5, there are particular homopolymers in 5' UTR and 3' UTR regions that are more frequently affected by indels in MMR-deficient tumors. A list of the most frequent recurrently mutated genes is provided in Table 1.

Of note, some of the genes listed in Table 1 have more than one recurrent indel in the UTR regions (e.g., CALN1, EIF4G3, KDM5A), which increases the likelihood that these genomic regions are not randomly affected, but underwent positive selection.

Importantly, also homopolymers in exonic regions are more frequently affected by indels in MMR-deficient tumors. As explained in, e.g., Example 4, this is not based on sequence length, but due to positive clonal selection. So although typically less frequently recurrently mutated, these mutations might be drivers of tumor progression. A list of the 31 genes most frequently affected with indels in their exonic regions is provided in Table 2.

As detailed in the Examples section, over 50% of markers taken from Table 1 score positive in a random set of MMR-deficient tumors, while this is also the case for over a third of the exonic markers listed in Table 2. This allows to correctly classify the MMR deficient tumor as MSI positive with high accuracy and certainty.

Accordingly, methods are provided of diagnosing MSI status of a tumor, comprising determining the presence of an indel in at least two microsatellite regions in a sample of the tumor DNA, wherein the at least two microsatellite regions are

- at least two microsatellite regions present in 5' UTR or 3' UTR regions from the genes listed in Table 1, or
- at least three microsatellite regions selected from those present in the exons of the genes listed in Table 2 and/or present in 5' UTR or 3' UTR regions from the genes listed in Table 1, wherein the presence of at least one indel is indicative of MSI.

Particularly, the microsatellite regions are homopolymer regions. They are most particularly identical to the homopolymer regions listed in Table 1 or 2.

It is particularly envisaged to use several markers, as this increases the power of MSI classification and increases sensitivity. Particularly, a mix of UTR markers from Table 1 and exonic markers from Table 2 is used. Several markers may be at least two from each list, but the total number of markers particularly is at least five, at least eight, at least ten, at least twelve, at least fifteen, at least twenty.

Alternatively, instead of Table 1, the markers can be chosen from Table 4, or from Table 6 or Table 8. Instead of Table 2, the markers can be selected from Table 5, or from Table 7 or Table 8.

According to specific embodiments, at least one marker used is an exonic marker in a gene not previously associated with cancer, or in a gene not previously known to be affected in MMR deficient tumors. Thus, it is envisaged that the microsatellite(s) selected from those present in the exons of the genes listed in Table 2 comprises at least one microsatellite present in a gene selected from the list of: SETD1B, RBMXL1, CCDC150, OR7E24, C15orf40, KIAA2018, LTN1, SLC22A9, CDH26, DDX27, EXOSC9, FAM111B, KIAA0182, KIAA1919, MIS18BP1, PRRT2, TMEM60, AQP7, AR V1, CCDC168, ELAVL3, F8, FETUB, HPS1, NBEAL1, P4HTM, PIGB, RBM43, RG9MTD1, SRPR, and TMEM97. According to yet even more specific embodiments, at least one microsatellite is present in a gene selected from the list of: SETD1B, TMEM60, DDX27, EXOSC9, FAM111B, and KIAA1919. According to alternative embodiments, SEC31A, CNOT2, RNF145, RNPC3, SLC35F5, TMBIM4, CD3G, DOCK8, MYO10 and PRRG1 can also be used in these lists.

According to alternative specific embodiments, at least one marker used is an indel in a homopolymer of between 10 and 15 repeat bases situated in a 5' or 3' UTR region. Particular examples of such homopolymers include, but are not limited to homopolymers in the 3' UTR regions of the following list of genes: WIPF2, NARG2, AHCYL1, C17orf63, CD5L, CEP170, COL5A2, CSNK1G3, DIDO1, EIF4G3, GSK3B, KCNMB4, MAPK1IP1L, NPR3, PI15, PRTG, RASGRP1, SH3KBP1, SHROOM3, SLC5A3, UBE2Z, ZBTB33, ZNF275, AGPAT3, APH1B, BCL11A, BMPR1B, CALN1, CASK, CBFB, CBX5, CCDC85C, CNOT7, CYP1B1, DRAM2, EDA2R, EDEM3, EGR1, EIF4G3, FAM20B, FCHSD2, FLT1, FMO2, G3BP2, HELZ, HRNR, IER3IP1, KCNG1, KCNK1, KLF3, LHX9, LRRC8D, LYRM1, MED13, MYO5B, NCEH1, PPP1R12A, PPPIR3D, RAB11FIP1, RAB6C, SAMD12, SEMA6A, SLAIN2, SMAD4, TMED7, TMEM57, TMEM65, TNPO1, TOR1AIP2, TRAK2, TRIP11, UST, VEGFA, ZBTB7A, ZKSCAN1, ZNF12, and ZNF169.

A biomarker panel consisting of a selection of 56 markers taken from Tables 1 and 2 was designed (see Examples section). According to particular embodiments, these markers are used for diagnosing MSI status. These 56 markers are listed in Table 3.

Markers from this panel that are particularly envisaged to be used (as they are particularly sensitive to recurrent occurrence of indels) include one or more from the list of MYL1, DIDO1, UBE2Z, RYR3, TMEM65, BTBD7, KDM5A, ABAT4, PPM1A, UBA6 and ZNF185. Also additionally envisaged are ARL10, GRIA2, and TMC7, particularly when assessing MSI status of colorectal tumors. These are both sensitive and specific (i.e., detect little false positive MSI cases).

According to very specific embodiments, the 56 marker panel can be supplemented with microsatellites from MSH6 (exonic indel) and/or SULF2 (3' UTR deletion).

According to alternative embodiments, no indels in MSH6 are evaluated, since this is a known MMR deficiency gene. Although MSH3 is also known as a MMR deficiency gene, deficiency of this gene is typically not associated with MSI.[27] Nevertheless, according to particular embodiments, no indels in MSH3 are used as marker.

As detailed in the Examples section, an additional filtering step can be applied to the markers of Table 1, excluding markers present as variants in germline of a proprietary genome database. Note that these are all rare variants, since they are not present in dbSNP or in the 1000 Genomes database. This marker list is shown in Table 4 (minimum recurrence in four of sixteen tumor samples).

The same additional filtering has been applied to markers of Table 2; results are listed in Table 5.

According to particular embodiments, genes wherein more than one recurrent indel is present in the UTR regions are particularly suited as marker. In these embodiments, at least one of the genes is selected from the list of ARHGEF11, CBLN2, DIO2, MBNL1 (all 5' UTR markers), ACVR1C, ANKIB1, ATXN1, BCL11A, BCL11B, BCL7A, BOD1L, BTBD7, C11orf58, C14orf101, CACNB4, CALN1, CANX, CASK, CBFB, CBL, CBX5, CCND1, CCND2, CLCN5, CRTC1, CSNK1E, CYP1B1, DCUN1D5, DDHD1, DLGAP2, DSTYK, DTNA, DUT, DYRK2, EBF1, EFNA5, EIF4G3, ELAVL3, EPS15, ERBB2IP, ERBB4, EVI5, FAM116A, FAM126B, FAM20B, FAM46A, FBN2, FBXO27, FGF9, FGFR1OP2, FOXN2, FOXN3, FOXP1, GABRB2, GDAP2, GNAI2, GSK3B, HAS2, HDAC4, HELZ, HIPK2, HNRNPA3, HNRNPK, HUWE1, IGFBP5, INSR, KDM5A, KIAA0825, KIAA1324, KIF1B, KLHL4, LARP4B, LIN7C, LMO4, LPHN3, LYRM7, MAPIB, MAPK1IP1L, MDM2, MED1, MED13, MED28, MESDC1, MEX3A, MGAT4A, MKLN1, MLL2, NARG2, NCEH1, NPNT, NPR3, NR2F2, NUFIP2, OPA3, OTUD4, OXR1, PALM2, PAPD5, PDGFA, PIGM, PLAGL2, PPP2R3A, PRPF40A, PRTG, RAB11FIP2, RAB8B, RBM12B, RBMS3, RC3H1, RORA, RPRD2, RUNDC3B, SAMD12, SAR1A, SATB2, SDC4, SENP1, SENP5, SH3KBP1, SH3RF1, SIPA1L3, SLAIN2, SLC7A11, SMAD3, SMAD4, SMAD5, SORL1, SOST, SOX4, SPCS3, SRRM4, ST7L, SYNJ2BP, TACC1, TFAP2B, TLCD2, TMEM57, TMTC3, TNRC6B, TNRC6C, TRIM66, TRPS1, UBN2, USP43, VEZF1, WDR82, XKR6, XYLT1, ZBTB7A, ZNF238, ZNF737, ZNF740 (all 3' UTR markers), CPLX4, DDX3X, GABRG2, PIK3R1, PTP4A2, SATB1, SEMA6A, and STK11 (affected in 5' and 3' UTR).

Note, however, that genes wherein only one homopolymer is recurrently affected in the UTR regions can be equally good as a marker, e.g., because there is only one homopolymer region in the UTR, or because there is a clear preference for the occurrence of indels in one homopolymer over the other. The latter is for instance seen in UTRs of genes such as CACNB4, EIF4G3, FAM20B, LPHN3 or PRTG, wherein more than one homopolymer is recurrently affected, but one homopolymer is more often affected than the other(s), even though homopolymer length and composition are comparable.

Also genes with exonic regions that are recurrently affected by more than one indel are particularly envisaged as marker. Thus, according to specific embodiments, CASP5, MIAT, TROVE2 and TSIX are particularly envisaged as exonic marker; most particularly CASP5 and TSIX are envisaged.

Another particular list of UTR markers envisaged are those that were identified in the first eleven solid MMR-deficient tumors. This list is provided in Table 6, common recurrent indels are defined as occurring in at least three out of eleven samples.

Likewise, another particular list of exonic markers envisaged are those that were identified in the first eleven solid MMR-deficient tumors. This list is provided in Table 7, common recurrent indels are defined as occurring in at least three out of eleven samples.

A further particular envisaged list from which markers can be selected is listed in Table 8. According to specific embodiments, the at least two UTR microsatellite regions or at least three microsatellite regions (as described above) are regions selected from those listed in Table 8. According to alternative, very specific embodiments however, the markers are selected from Tables 1 and/or 2 and do not contain a marker listed in Table 8. Exemplary markers in this case include, but are not limited to, LLRC8D, SAMD12, SEPT7, CASK, FAM20B, HELZ, KCNK1, LHX9, LYRM1, TMEM26, TRIP11, ZBTB7A, ZKSCAN1, ZNF217, WIPF2, COL5A2, ZBTB33, AGPAT3, BMPR1B, CNOT7, EDEM3, G3BP2, HRNR, KLF3, TNPO1, TRAK2, ZNF169, BDNF, OIT3, CNOT2, LTN1, MBD4, SLC22A9, ATR, CDH26, KIAA2018, RNF145, TGFBR2, and TMBIM4.

According to particular embodiments, the length of the homopolymers used as markers will not exceed 20 nucleotides, or will not exceed 15 nucleotides (e.g., to allow more efficient detection of the presence of an indel). Thus, according to particular embodiments, the markers are selected from, e.g., any of Tables 1 to 8, but only from markers that are shorter than 20 nucleotides, or shorter than 15 nucleotides. This shorter length is particularly advantageous compared to the prior art markers (e.g., the BAT25 and BAT26 marker).

Particularly, in some embodiments the length of the homopolymers used as markers does not exceed 15 nucleotides, 14 nucleotides, 13 nucleotides, 12 nucleotides or even 11 nucleotides. On the other hand, according to particular embodiments, the envisaged homopolymers are at least six nucleotides, at least seven nucleotides, at least eight nucleotides, at least nine nucleotides or even at least ten nucleotides in length. According to particular specific embodiments, it is envisaged that the marker length of at least one marker (and up to all markers used) is between 7 and 15 nucleotides, between 8 and 15 nucleotides, between 8 and 14 nucleotides, between 8 and 13 nucleotides, between 9 and 13 nucleotides, between 10 and 13 nucleotides, between 8 and 12 nucleotides, between 9 and 12 nucleotides, between 8 and 11 nucleotides or between 9 and 11 nucleotides.

Importantly, the above described markers can be used for determining MSI status independent of cancer type. Thus, in principle, diagnosing MSI status can be done with the markers provided herein for every type of cancer. However, since MSI is most often present in cancers with a deficiency in mismatch repair genes, it is particularly envisaged to diagnose MSI status in a tumor sample of tumors where MMR deficiency occurs more frequently than in other types. Accordingly, the cancer sample is typically a sample selected from a cancer of colorectal cancer, endometrial cancer, ovarian cancer, gastric cancer, leukemia, and a tumor of the Lynch syndrome spectrum.

Diagnosing MSI status typically implies drawing the conclusion of detecting the presence of MSI or not (this is equivalent as detecting the absence of MSI). Typically, detecting the presence of MSI will be based on detection of one or more indels in the microsatellite regions under investigation. The more marker genes presented in Tables 1-3 herein that have an indel in a microsatellite region, the higher the chance that the tumor is characterized by microsatellite instability.

Typically, MSI can be classified as MSI-H, MSI-L and MSS. According to particular embodiments, if 20% (or 25%) or more of the microsatellite regions used to diagnose MSI status contains an indel, the tumor is MSI-H, if between 2.5% and 20% (25%) of the microsatellite regions contains an indel, the tumor is MSI-L, and if less than 2.5% of the microsatellite regions contains an indel, the tumor is microsatellite stable. According to alternative embodiments, MSI can be classified as MSI-H if 17% or more of the microsatellite regions used to diagnose MSI status contains an indel; if between 2% (or 2.5%) and 17% of the microsatellite regions contains an indel, the tumor is MSI-L, and if less than 2% (or 2.5%) of the microsatellite regions contains an indel, the tumor is microsatellite stable. The latter classification is particularly preferred when a high number (e.g., 25 or more) of markers are used. Percentages are used rather than absolute numbers, as the number of markers can be varied by a skilled person. As a general guideline, the percentages should more or less correspond to the percentages applied in the well-recognized Bethesda panel. For instance, if eight markers are used, the tumor will be MSS only if none of the microsatellite markers contains an indel; it will be MSI-H if two or more markers are positive, while it will be MSI-L if only one marker contains an indel. Since it is apparent from this example that one positive marker more or less can affect the diagnosis if a limited number of markers is used, it is particularly envisaged to use more markers. This is particularly helpful to reliably classify tumors as MSI-L. For instance, with the 2-17% classification, if the preferred marker panel of 56 markers is used, a tumor is MSS if zero or one marker scores positive, MSI-L if two to nine markers score positive and MSI-H if ten or more markers score positive.

Published work also suggests that MMR− tumors have a distinct response to standard treatments and emerging targeted therapies. Preclinical investigations suggest, for instance, that MMR-deficient tumors show resistance to 5-fluorouracil, anti-EGFR and VEGF therapies.[25, 26] The precise reason for this heterogeneity is unknown, but presence or absence of secondary (recurrent) mutations as a consequence of MMR-deficiency might determine treatment outcome. For instance, it was observed that a recurrent mutation in KRAS, which acts as an established negative response predictor of anti-EGFR therapies. Interestingly, most recurrent mutations in endometrial tumors also specifically affect genes expressed in the normal endometrium and were differentially expressed in MMR− versus MMR+ tumors, suggesting positive clonal selection of these mutations. The identification of recurrent mutations also reveals several novel therapeutic targets for the treatment of MMR-deficient tumors.

Thus, according to some particular embodiments, the methods of diagnosing MSI status of a tumor, as presented herein, may further comprise a step of choosing the treatment regimen based on the MSI status (i.e., based on whether the tumor was found to be MSI-H, MSI-L or MSS).

The present methods all rely on the detection of indels in microsatellite regions of the genome. Frequently used methodologies for analysis of nucleic acid samples to detect indels will be briefly described. However, any method known in the art can be used in the invention to detect the presence of indels.

a. Allele-Specific Hybridization

This technique, also commonly referred to as allele specific oligonucleotide hybridization (ASO) (e.g., Stoneking et al., Am. J. Hum. Genet. 48:70-382, 1991; Saiki et al., Nature 324, 163-166, 1986; EP 235,726; and WO 89/11548), relies on distinguishing between two DNA molecules differing by one base by hybridizing an oligonucleotide probe that is specific for one of the variants to an amplified product obtained from amplifying the nucleic acid sample. This method typically employs short oligonucleotides, e.g., 15-20 bases in length. The probes are designed to differentially hybridize to one variant versus another. Principles and guidance for designing such probe is available in the art, e.g., in the references cited herein. Hybridization conditions should be sufficiently stringent that there is a significant difference in hybridization intensity between alleles, and producing an essentially binary response, whereby a probe hybridizes to only one of the alleles. Some probes are designed to hybridize to a segment of target DNA such that the polymorphic site aligns with a central position (e.g., in a 15-base oligonucleotide at the 7 position; in a 16-based oligonucleotide at either the 8 or 9 position) of the probe, but this design is not required.

The amount and/or presence of an allele is determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing sequences with different microsatellite length. After stringent hybridization and washing conditions, fluorescence intensity is measured for each microsatellite oligonucleotide.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A reverse line-blot detection assay is described in the example.

b. Allele-Specific Primers

Indels can also be detected using allele-specific amplification or primer extension methods. These reactions typically involve use of primers that are designed to specifically target a polymorphism via a mismatch at the 3'-end of a primer. The presence of a mismatch effects the ability of a polymerase to extend a primer when the polymerase lacks error-correcting activity. For example, to detect an allele sequence using an allele-specific amplification- or extension-based method, a primer complementary to the normal allele of a microsatellite (i.e., without indel) is designed such that the 3'-terminal nucleotide hybridizes with the sequence containing the right number of repeats. The presence of the particular allele can be determined by the ability of the primer to initiate extension. If the 3'-terminus is mismatched, the extension is impeded.

In some embodiments, the primer is used in conjunction with a second primer in an amplification reaction. The second primer hybridizes at a site unrelated to the microsatellite. Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and 4,851,331.

Using allele-specific amplification-based genotyping, identification of the alleles requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, allele-specific amplification methods can be performed in reactions that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified using a single amplification by gel analysis of the amplification product.

As in the case of allele-specific probes, an allele-specific oligonucleotide primer may be exactly complementary to one of the polymorphic alleles in the hybridizing region or may have some mismatches at positions other than the 3'-terminus of the oligonucleotide, which mismatches occur at non-polymorphic sites in both allele sequences.

c. Detectable Probes i) 5'-Nuclease Assay Probes

Genotyping can also be performed using a "TAQMAN®" or "5'-nuclease assay," as described in U.S. Pat. Nos. 5,210,015; 5,487,972; and 5,804,375; and Holland et al., 1988, *Proc. Natl. Acad. Sci. USA* 88:7276-7280. In the TAQMAN® assay, labeled detection probes that hybridize within the amplified region are added during the amplification reaction. The probes are modified so as to prevent the probes from acting as primers for DNA synthesis. The amplification is performed using a DNA polymerase having 5'- to 3'-exonuclease activity. During each synthesis step of the amplification, any probe which hybridizes to the target nucleic acid downstream from the primer being extended is degraded by the 5'- to 3'-exonuclease activity of the DNA polymerase. Thus, the synthesis of a new target strand also results in the degradation of a probe, and the accumulation of degradation product provides a measure of the synthesis of target sequences.

The hybridization probe can be an allele-specific probe that discriminates between the alleles with and without indels. Alternatively, the method can be performed using an allele-specific primer and a labeled probe that binds to amplified product.

Any method suitable for detecting degradation product can be used in a 5'-nuclease assay. Often, the detection probe is labeled with two fluorescent dyes, one of which is capable of quenching the fluorescence of the other dye. The dyes are attached to the probe, usually one attached to the 5'-terminus and the other is attached to an internal site, such that quenching occurs when the probe is in an unhybridized state and such that cleavage of the probe by the 5'- to 3'-exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

ii) Secondary Structure Probes

Probes detectable upon a secondary structural change are also suitable for detection of a polymorphism, including indels. Exemplified secondary structure or stem-loop structure probes include molecular beacons or SCORPION® primer/probes. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. Molecular beacon probes are, however, highly sensitive to small sequence variation in the probe target (S. Tyagi and F. R. Kramer, *Nature Biotechnology*, Vol. 14, pages 303-308 (1996); Tyagi et al., *Nature Biotechnology*, Vol. 16, pages 49-53(1998); Piatek et al., *Nature Biotechnology*, Vol. 16, pages 359-363 (1998); S. Marras et al., *Genetic Analysis: Biomolecular Engineering*, Vol. 14, pages 151-156 (1999); I. Tpp et al, *BioTechniques*, Vol 28, pages 732-738 (2000)). A SCORPION® primer/probe comprises a stem-loop structure probe covalently linked to a primer.

d. DNA Sequencing and Single Base Extensions

Indels can also be detected by direct sequencing. Methods include, e.g., dideoxy sequencing-based methods and other methods such as Maxam and Gilbert sequence (see, e.g., Sambrook et al., supra).

Other detection methods include PYROSEQUENCING™ of oligonucleotide-length products. Such methods often employ amplification techniques such as PCR. For example, in pyrosequencing, a sequencing primer is hybridized to a single stranded, PCR-amplified, DNA template; and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated. Apyrase, a nucleotide degrading enzyme, continuously degrades unincorporated dNTPs and excess ATP. When degradation is complete, another dNTP is added.

Another similar method for characterizing indels does not require use of a complete PCR, but typically uses only the extension of a primer by a single, fluorescence-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes,* 9:175-182, 1995).

e. Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g., Erlich, ed., *PCR Technology, Principles and Applications for DNA Amplification,* W.H. Freeman and Co, New York, 1992, Chapter 7).

Distinguishing of microsatellite polymorphisms can be done using capillary electrophoresis. Capillary electrophoresis conveniently allows identification of the number of repeats in a particular microsatellite allele. The application of capillary electrophoresis to the analysis of DNA polymorphisms is well known to those in the art (see, for example, Szantai et al., *J. Chromatogr. A.* (2005) 1079(1-2):41-9; Bjorheim and Ekstrom, *Electrophoresis* (2005) 26(13):2520-30; and Mitchelson, *Mol. Biotechnol.* (2003) 24(1):41-68).

f. Single-Strand Conformation Polymorphism Analysis

Alleles of target sequences can be differentiated using single-strand conformation polymorphism analysis, which identifies base differences by alteration in electrophoretic migration of single stranded PCR products, as described, e.g., in Orita et al., *Proc. Nat. Acad. Sci.* 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target genes.

g. Melting Curve Analysis

Melting curve analysis is an assessment of the dissociation-characteristics of double-stranded DNA during heating. As the temperature is raised, the double strand begins to dissociate leading to a rise in the absorbance intensity, hyperchromicity. The temperature at which 50% of DNA is denatured is known as the melting point (not to be confused with the term melting point used in physics). The energy required to break the base-base hydrogen bonding between two strands of DNA is dependent on their length, GC content and their complementarity. Due to the fact that G-C base pairings have three hydrogen bonds between them while A-T base pairs have only two, DNA with a higher G-C content will have a higher melting temperature than DNA with a higher A-T content. By heating a reaction-mixture that contains double-stranded DNA sequences and measuring dissociation against temperature, the presence and identity of single-nucleotide polymorphisms (SNP) can be determined.

Originally, strand dissociation was observed using UV absorbance measurements, but techniques based on fluorescence measurements are now the most common approach. The temperature-dependent dissociation between two DNA-strands can be measured using a DNA-intercalating fluorophore such as SYBR green, EvaGreen or fluorophore-labelled DNA probes.

A variant technique is the High Resolution Melt (HRM) analysis. Many dyes and high resolution instruments are commercially available to perform melting curve analysis or HRM; including most qPCR machines.

Indel detection methods often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., 32P, electron-dense reagents, enzyme, such as peroxidase or alkaline phosphatase, biotin, or haptens and proteins for which antisera or monoclonal antibodies are available. Labeling techniques are well known in the art (see, e.g., Sambrook et al., supra).

The microsatellite indel markers provided herein can be detected using any of these technologies, or others—the marker panel is independent of the technology used. However, it is particularly envisaged that determining the presence of an indel is not done through a method based on Sanger sequencing. This because the process of detecting microsatellite instability using the Bethesda marker panel is typically done through Sanger sequencing, a protocol that proves quite cumbersome. According to further embodiments, it is particularly envisaged to determine the presence of an indel through single base pair extension methods (such as a Sequenom MassArray), DNA hybridization technologies (e.g., TAQMAN®), melting curve analysis, or a similar technology.

According to another aspect, the biomarker panel as described herein is provided for use as a medicament. Particularly, the biomarker panel as described herein is provided for use as a diagnostic. It is particularly envisaged that this biomarker panel can be used to detect MSI status in cancer, or for determining MSI in a tumor sample. Accordingly, the use of this biomarker panel is provided in the diagnosis of microsatellite instability (or of MSI status) in cancer.

Although the use of fewer markers is also explicitly envisaged, particularly suited biomarker panels for determining MSI in a tumor sample are biomarker panels comprising at least eight markers (microsatellite regions). Such biomarker panel comprises at least eight microsatellite regions selected from those present in 5' UTR or 3' UTR regions from the genes listed in Table 1 and those present in the exons of the genes listed in Table 2. The at least eight markers may be at least 10 markers, at least 12 markers, at least 16 markers, at least 20 markers, at least 25 markers or even more. According to very particular embodiments, the biomarker panel comprises at least half of the microsatellite regions listed in Table 3. According to yet even further particular embodiments, the biomarker panel is represented by the 56 microsatellite regions listed in Table 3.

According to particular embodiments, the markers are selected from those that are most recurrent, i.e., markers occurring in at least a third or at least half of the MMR-deficient tumors. Accordingly, markers are selected from the markers occurring at least 5 times out of 16 (e.g., in Tables 1 and 2, or in Tables 4 and 5), 6 times out of 16, 7 times out of 16 or at least 8 times out of 16 tumors. Or they occur at least 4 times out of 11 (e.g., in Tables 6 and 7), at least 5 times out of 11, at least 6 times out of 11 tumors.

According to yet other embodiments, a kit is provided for determining MSI in a tumor sample, comprising the tools to genotype the biomarker panel (i.e., the at least eight microsatellite regions selected from those present in 5' UTR or 3' UTR regions from the genes listed in Table 1 and those present in the exons of the genes listed in Table 2). Most particularly, the kit will be adapted to the particularly envisaged biomarker panel(s). According to specific embodiments, the kit may also contain the tools to genotype the Bethesda panel of markers, or the extended Bethesda panel of markers. Such kits are particularly suited to do a side-by-side comparison of the markers with the Bethesda panel. It is also envisaged that a kit only takes a subset of the Bethesda panel of markers (e.g., one to five markers instead of all ten). In such case, the BAT25 and BAT26 markers are explicitly envisaged to be included, since these are generally considered most reliable. Needless to say, this also means that methods of diagnosing MSI described herein may also further contain a step of determining the status of one or more markers of the extended Bethesda marker panel (in addition to the use of the markers described herein).

As shown in the Examples section (particularly Examples 8 and 9), the indel markers provided herein are enriched in genes involved in DNA double-strand break repair pathways, and affect their functionality. As a consequence, cells in which these markers are present are sensitive to synthetic lethality by inhibition of DNA base excision repair. This offers new therapeutic opportunities, as MSI positive tumors are often resistant to standard chemotherapies used.

Accordingly, in a further aspect, methods are provided of screening sensitivity of cancer cells to treatment with an inhibitor of a DNA base excision repair enzyme, comprising determining MSI status in the cancer cells. According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome. According to further specific embodiments, the cancer cells are from a cancer resistant to a standard therapy. It is particularly envisaged that such standard therapy is selected from 5-FU (5-fluorouracil, Efudex), carboplatin, cisplatin, or targeted therapy (particularly targeted therapy directed against EGFR (e.g., gefitinib, erlotinib, cetuximab, panitumumab), or against Braf. Although these methods can in principle be performed in vivo, ex vivo and in vitro, it is particularly envisaged that they are performed in vitro.

According to particular embodiments, the presence of MSI is indicative of sensitivity of the cancer cells to treatment with an inhibitor of a DNA base excision repair enzyme; i.e., the cancer cells will die, stop growing or proliferate less when treated with such inhibitor.

According to specific embodiments, the cancer cells are cells obtained from a subject, and the screening of sensitivity to treatment with an inhibitor of a DNA base excision repair enzyme is used in guiding the treatment of the subject. According to alternative embodiments, the screening of sensitivity is used in stratifying or classifying the subject for a clinical trial.

According to particular embodiments, the presence of MSI is established by a method described herein, i.e., a method comprising determining the presence of an indel in at least two microsatellite regions in a sample of the tumor DNA, wherein the at least two microsatellite regions are:
 at least two microsatellite regions present in 5' UTR or 3' UTR regions from the genes listed in Table 1, or
 at least three microsatellite regions selected from those present in the exons of the genes listed in Table 2 and/or present in 5' UTR or 3' UTR regions from the genes listed in Table 1,
 wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2. According to even further specific embodiments, the biomarker panel comprises at least eight microsatellite regions selected from those listed in Table 3.

According to very specific embodiments, the methods may also comprise a step of sequencing genes involved in the homologous recombination pathway.

Thus, not only methods of screening sensitivity of cancer cells are provided, but also methods of diagnosing sensitivity of a subject with cancer to treatment with an inhibitor of a DNA base excision repair enzyme, comprising the steps of:
 determining the MSI status in a sample of cancer cells obtained from the subject;
 correlating the MSI status to sensitivity to treatment with an inhibitor of a DNA base excision repair enzyme, wherein the presence of MSI is indicative for sensitivity to the treatment.

Optionally, these methods contain an additional step of obtaining a sample of cancer cells from the subject (prior to the determining step). Determining the MSI status is then typically done in the cells of the obtained sample. It is particularly envisaged that determining the MSI status in a sample of cancer cells is performed in vitro.

According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome (or any other tumor of the Lynch syndrome spectrum). According to particular embodiments, the presence of MSI is established by a method described herein, i.e., a method comprising determining the presence of an indel in at least two microsatellite regions in a sample of the tumor DNA, wherein the at least two microsatellite regions are:
 at least two microsatellite regions present in 5' UTR or 3' UTR regions from the genes listed in Table 1, or
 at least three microsatellite regions selected from those present in the exons of the genes listed in Table 2 and/or present in 5' UTR or 3' UTR regions from the genes listed in Table 1,
 wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2.

It is also envisaged that methods according to this aspect may contain a further step of treating the subject with an inhibitor of a DNA base excision repair enzyme (if the subject is sensitive to such treatment, as determined by the MSI status).

Thus, also methods are provided for treating a cancer with MSI (or, equivalently, MMR deficiency) in a subject in need thereof, comprising:
  establishing the presence of MSI in the cancer;
  administration of an inhibitor of a DNA base excision repair enzyme to the subject.

For methods relating to diagnosing sensitivity of a subject with cancer to treatment with an inhibitor of a DNA base excision repair enzyme, or to treating a subject having cancer with MSI, it is particularly envisaged that this cancer is resistant to at least one standard therapy, particularly a standard therapy selected from 5-FU (5-fluorouracil, Efudex), carboplatin, cisplatin, or targeted therapy (particularly targeted therapy directed against EGFR (e.g., gefitinib, erlotinib, cetuximab, panitumumab), or against Braf.

It is envisaged that the cancer is treated by administering the inhibitor to the subject. The methods may optionally have an additional step of obtaining a sample of cancer cells from the subject (prior to the step of determining MSI, and establishing the presence of MSI).

According to particular embodiments, the inhibitor of a DNA base excision repair enzyme is a PARP inhibitor. According to specific embodiments, the cancer cells are from a cancer selected from the list of: colorectal cancer, endometrial cancer, ovarian cancer, gastric cancer, leukemia, and a tumor of the Lynch syndrome. According to particular embodiments, the presence of MSI is established by a method described herein, i.e., a method comprising determining the presence of an indel in at least two microsatellite regions in a sample of the tumor DNA, wherein the at least two microsatellite regions are:
  at least two microsatellite regions present in 5' UTR or 3' UTR regions from the genes listed in Table 1, or
  at least three microsatellite regions selected from those present in the exons of the genes listed in Table 2 and/or present in 5' UTR or 3' UTR regions from the genes listed in Table 1,
  wherein the presence of at least one indel is indicative of MSI.

According to further particular embodiments, the presence of MSI is established using a biomarker panel as described herein, i.e., a biomarker panel comprising at least eight microsatellite regions selected from those present in 5' UTR or 3' UTR regions from the genes listed in Table 1 and those present in the exons of the genes listed in Table 2.

It is to be understood that although particular embodiments, specific configurations as well as materials and/or molecules, have been discussed herein for cells and methods according to the disclosure, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

Whole-genome Sequencing of an Endometrial Tumor with MMR-deficiency

To select MMR-deficient tumors for whole-genome sequencing, standard diagnostic tests were used, including immunohistochemistry of MMR proteins (MLH1, MSH2 and MSH6), assessment of microsatellite instability (MSI) using the extended Bethesda panel (Pinol et al., 2005) and methylation profiling of the MLH1 promoter. Results for immunohistochemistry and MLH1 promoter hypermethylation are shown as the top three lines in Table 9. Microsatellite instability (MSI) status was analyzed at ten different loci containing mono- or dinucleotide repeat sequences (respectively, two and eight markers), using the panel recommended by the international guidelines for evaluation of MSI, i.e., the revised Bethesda panel (Boland et al., 1998; Dietmaier et al., 1997). PCR amplifications were performed in two pentaplexes: Multiplex A (BAT25, BAT26, D5S346, D17S250, D2S123) and multiplex B (BAT40, D17S787, D18S58, D18S69, TGFβ-RII). The forward primers were labeled with 6-FAM, HEX, VIC or TET. The amplicons from tumor and normal DNA of the same patient were analyzed on an ABI 3130 Genetic Analyzer (Applied Biosystems). Tumor 1 was strongly positive for 7 out of 8 successful markers, whereas the two other tumors were negative. This confirms that Tumor 1 is MMR-deficient. Results are summarized in Table 10. More information on the tumor samples is included in Table 11.

One MMR-deficient EM tumor, exhibiting a positive MSI status and absence of MSH6 expression (Table 9), and two MMR-proficient EM tumors were selected. Using COMPLETE GENOMICS® (CG) technology, high coverage sequencing data of the tumor and matched normal samples (on average 95.2× and 77.1×, respectively) was obtained, which were subsequently analyzed using a previously developed annotation and filtering pipeline (Reumers et al., 2011). The MMR-deficient tumor exhibited a clear hypermutator phenotype, containing significantly more novel somatic mutations than the other tumors using the verified CGA-TOOLS™ calldiff method (http://cgatools.sourceforge.net) (Table 12, somatic mutations using calldiff). This algorithm is designed to find differences between two genomes from the same individual, such as a tumor-normal pair.

Next, a quality score threshold was applied based on the independent validation of randomly selected mutations, resulting in an overall accuracy of mutation calling estimated at 94.6%. This confirmed that the mutation load of the MMR-deficient tumor was 20.3-fold higher (FIG. 1a and Table 12). Detailed inspection of somatic variants in the hypermutator sample revealed a somatic frame shift insertion in exon 5 of MSH6 (F1088fs; Note S2) that was consistent with absence of MSH6 expression. No mutations were found in DNA polymerases, such as POLE. In fact, of the 34 known DNA polymerases only REV3L was somatically mutated in the hypermutator. However, since REV3L is involved in translesion DNA synthesis, it is unlikely that a mutation in REV3L causes a hypermutator phenotype. Further, copy number analysis was performed using the ASCAT algorithm (Van Loo et al., 2010). ASCAT is specifically designed to detect copy number aberrations in tumor samples. It accurately determines allele-specific copy numbers in solid tumors by estimating and adjusting for overall tumor ploidy and the effective tumor fraction in the sample. Unlike MMR-proficient tumors, the hypermutator is a chromosomal stable tumor (data not shown).

Table 9. Standard Diagnostic Tests to Assess MMR-deficiency

All tumors were sequenced using either Complete Genomics (CG) whole-genome sequencing technology or Truseq exome enrichment combined with Illumina sequencing technology. For each tumor, microsatellite instability (MSI) using the extended Bethesda panel, standard immunohistochemistry of MMR proteins (MLH1, MSH2 and MSH6), and methylation status of the MLH1 promoter are shown. Asterisks (*) indicate the presence of a weak positive nuclear staining in the minority of the tumor cells.

Example 2

Somatic Mutation Patterns in the MSH6-deficient Hypermutator

Studies in model organisms and cell lines revealed that somatic mutations arising due to MMR-deficiency mostly involve insertion/deletions (indels) that affect microsatellite sequences (di- to hexa-nucleotide repeats with a minimal length of six bases and at least two repeat units) and homopolymers (mononucleotide repeats with a minimal length of six bases) (Ellegren, 2004). In order to test this hypothesis, the genome was stratified into four different classes using the following definitions:

Microsatellite regions: di-, tri-, tetra, penta- or hexanucleotide repeats consisting of at least two repeat units and with a minimal length of six bases.

Homopolymer regions: mononucleotide repeats with a minimal length of six bases.

Short homopolymer regions: mononucleotide repeats of three, four or five bases in length.

Non-repeat regions: the remainder of the genome, i.e., every base that is not part of a simple repeat sequence.

The genomic regions following these definitions were determined by scanning the sequence files (in FASTA format) using the "grepseq" tool (http://code.google.com/p/grepseq/). At the whole genome level, the overall repeat composition was as follows: microsatellites (7.9%), homopolymers (1.9%), short homopolymers (19.8%), and not in repeat regions (70.4%).

In a hypermutator, it was observed that somatic mutations are more frequently located in homopolymers than expected based on their genome-wide occurrence (not shown). It was observed that somatic mutations accumulate more frequently in homopolymers (47.7%) compared to their genome-wide occurrence (1.9%). 35.5%, 10.7% and 6.2% of the somatic mutations were located in non-repeat regions, short homopolymers and microsatellites, respectively. Compared to the genome-wide occurrence of these regions (i.e., 70.4%, 19.8% and 7.9% for non-repeat, short homopolymers and microsatellites, respectively), somatic mutations were less frequently affected in these regions than expected.

Further, it was observed that indels were indeed more frequent than single base pair substitutions (57.4% indels versus 42.6% substitutions; FIG. 1b), but predominantly affected homopolymers (81.3%) and not microsatellites (FIG. 1c). Substitutions did not preferentially affect homopolymers or microsatellites (FIG. 1d). Mutations occurred as frequently in introns as in the rest of the genome, but clearly less in exons (excluding 5' and 3' untranslated regions (UTRs)). For indels, this decrease was more pronounced than for substitutions (74.7% versus 14.3%; FIGS. 1e, 1f). Correction for the number of homopolymers or the length of homopolymers in exonic, intergenic and intronic regions confirmed that this reduction could not be ascribed to fewer or shorter homopolymers. Most exonic indels resulted in heterozygous frame shift mutations (160 frame shift versus three non-frame shift indels), suggesting that they are loss-of-function mutations undergoing negative clonal selection.

Somatic Substitutions in the MSH6-deficient Hypermutator

Figure 2:
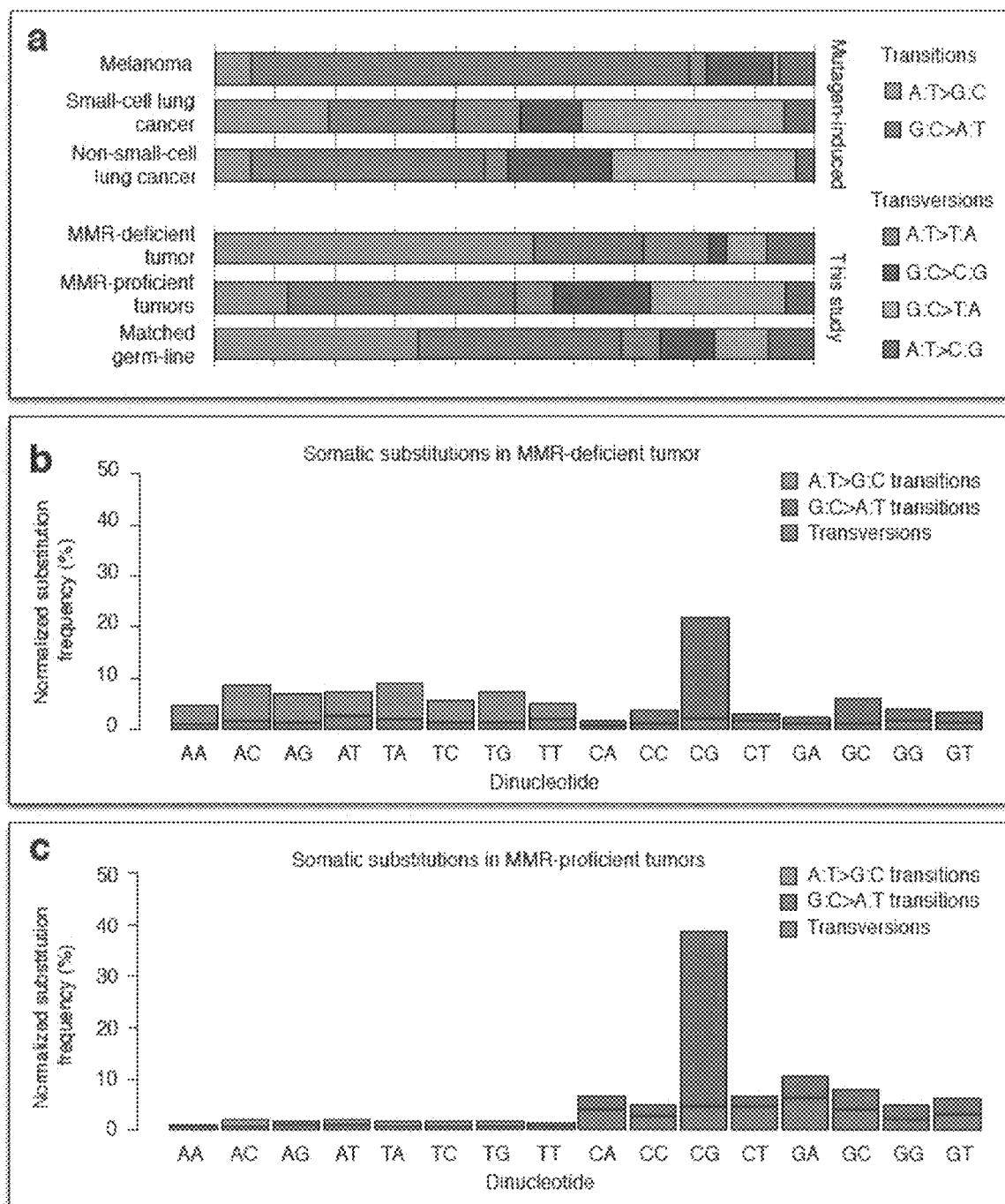
FIG. 2. Somatic substitution and indel patterns in the MSH6-deficient hypermutator. (a) Somatic substitution patterns in whole-genome sequences of melanoma, small-cell lung cancer, non-small-cell lung cancer, the MMR-deficient endometrial tumor, two MMR-proficient endometrial tumors and matched germ-line DNA (peripheral white blood cell) from the endometrial tumor patient. (b-c) Stratification of somatic substitution frequency in the MMR-deficient (b) and MMR-proficient (c) tumors per dinucleotide, with the first nucleotide being mutated. Normalized substitution frequencies reflect the number of affected dinucleotides divided by the genome-wide number of those dinucleotides, expressed as percentage of the total substitution frequencies. (d) Multivariate linear regression modeling of genome features predicting substitutions frequencies in the MMR-deficient tumor. Displayed are heat maps of the genome feature data ordered according to the number of substitutions visualizing the correlations between substitution frequencies and genome features. T-values resulting from the linear model are displayed for each genome feature in the bar plots on the right of the heat maps, and indicate significance (shaded grey equals P>0.01) and direction of the correlation. To accommodate the different scales of each feature in a single heat map, genome feature data are displayed distributed per centile, with white and red respectively indicating low and high centiles. G:C>A:T transitions in CpG sites were binned in 10 Mb windows as numbers were insufficient for modeling per 1 Mb window. (e) Frequency of substitutions, transitions (excluding G:C>A:T in CG) and transversions in the hypermutator per 1 Mb window, versus the replication time of that window binned per decile. Frequencies are displayed relative to windows replicating earliest. Error bars indicate standard error of mean (P<0.01 for substitutions and transitions at replication times over 0.2). (f) Frequency of substitutions, transitions (excluding G:C>A:T in CG) and transversions in and outside of CpG islands, relative to their genome-wide frequency in the hypermutator. (g) Multivariate linear regression modeling of genome features predicting indel frequency in the MMR-deficient tumor. The heat map and bar plot are as described for panel (d). (h) Fraction of homopolymers affected by an indel stratified per nucleotide in the MMR-deficient tumor compared to the genome-wide fraction of homopolymers with that nucleotide content. (i) Fraction of all indels inserting or deleting the indicated number of bases. (j-k) The distance between a somatic substitution and the nearest somatic indel (j) or substitution (k) in the hypermutator, and the expected distance based on 200 random models.
Figure 2:
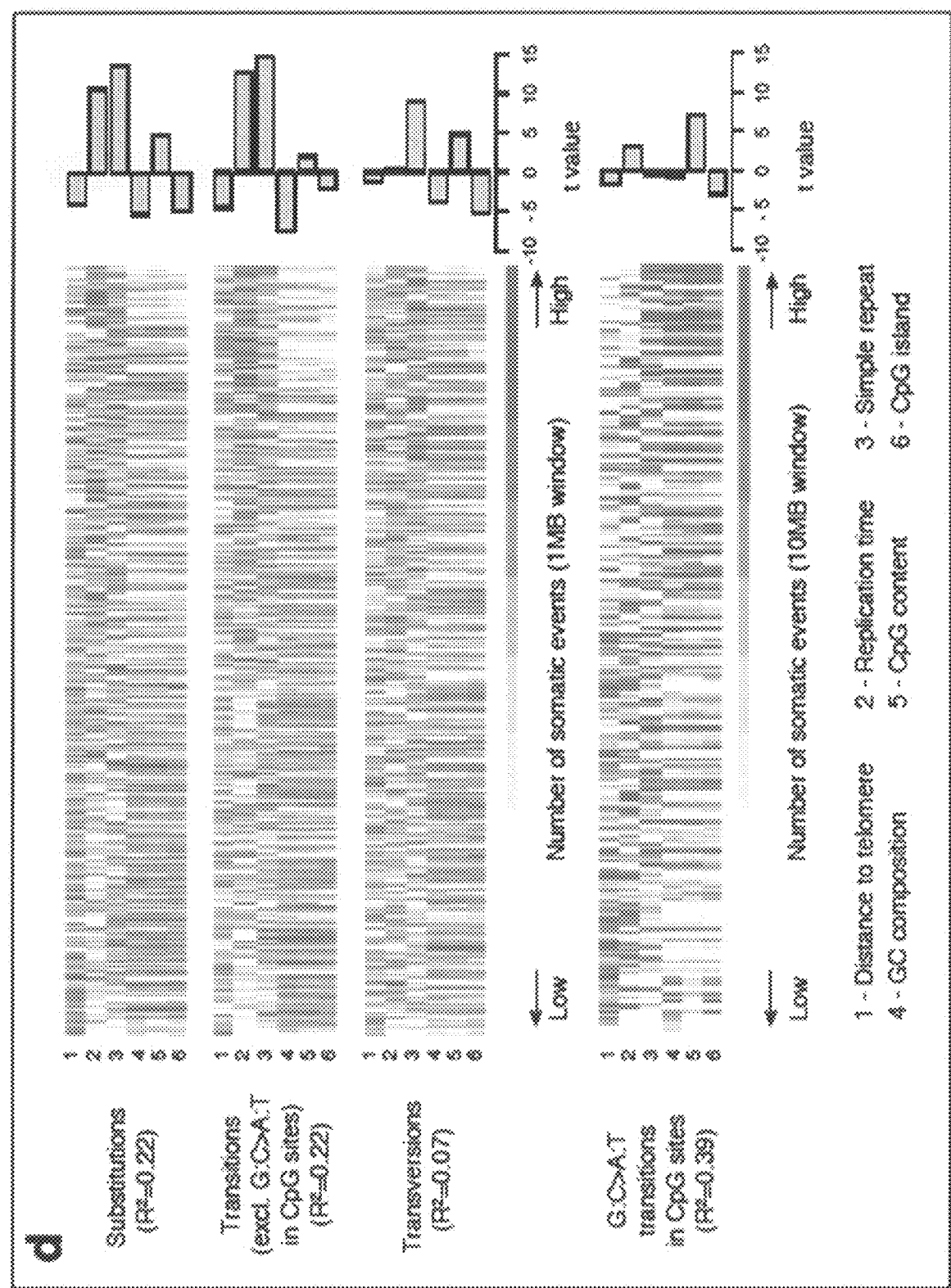
Figure 2:
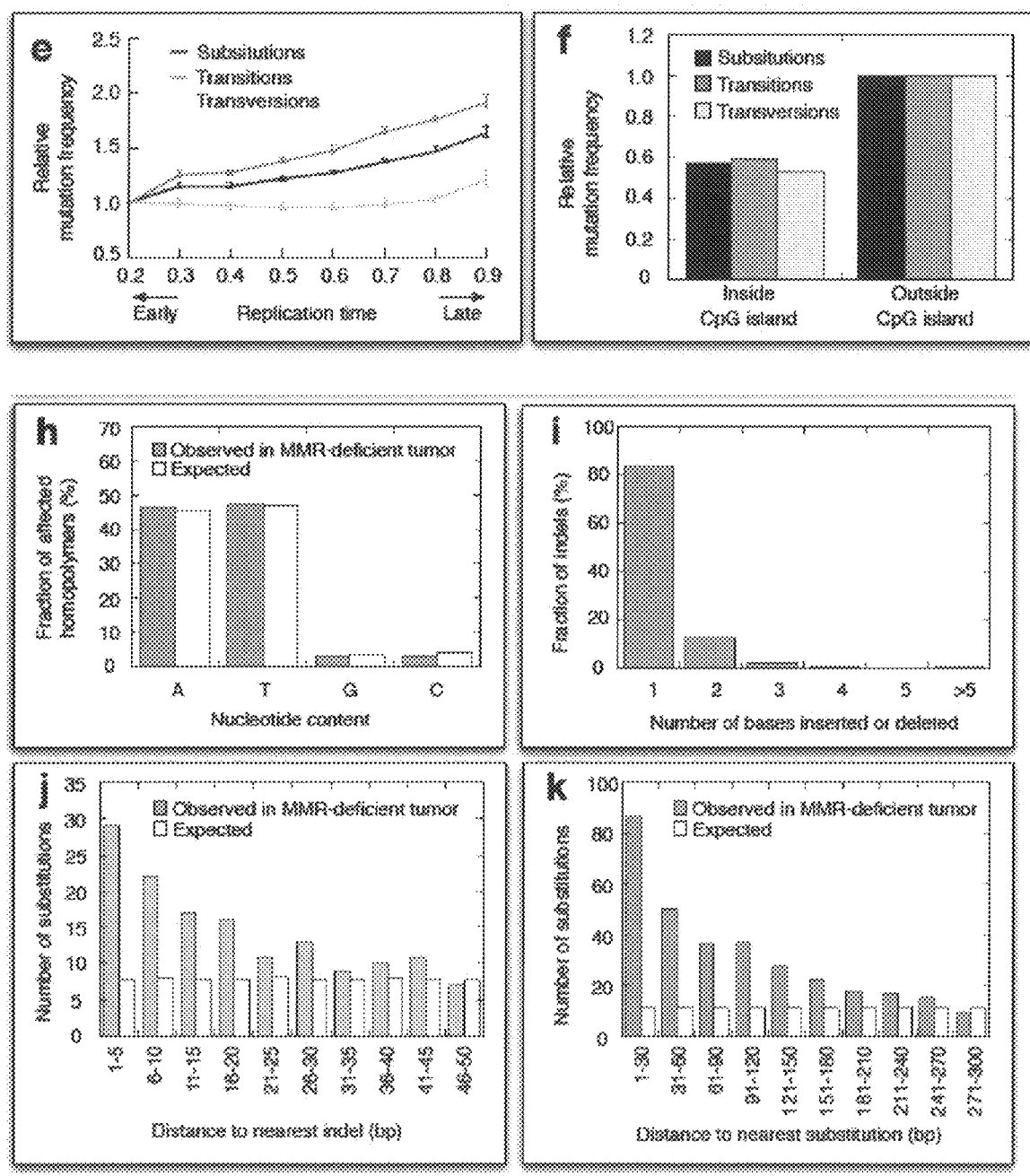
Figure 2:
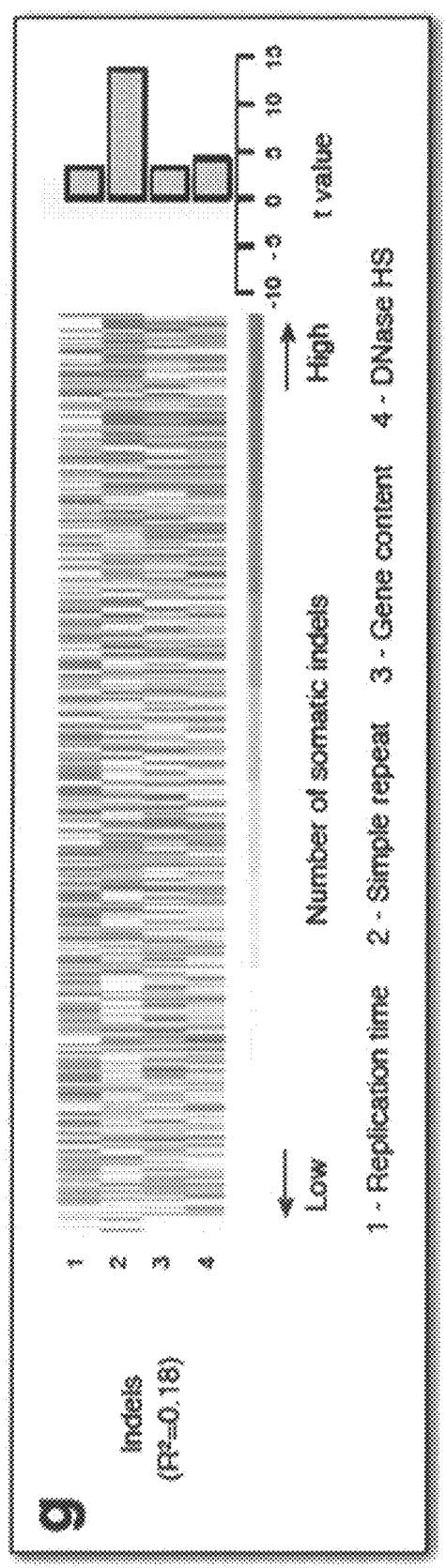

Studies assessing somatic substitutions in UV-light-induced melanoma (Pleasance et al., 2010a) and tobacco smoke-induced lung adenocarcinoma (Pleasance et al., 2010b) revealed that, respectively, G:C>A:T transitions and G:C>T:A transversions, occur frequently in these tumors. When assessing somatic substitutions in a hypermutator, a clearly distinct pattern, in which 71.5% of all substitutions represented A:T>G:C and G:C>A:T transitions compared to only 50.1% in MMR-proficient tumors, was observed (FIG. 2a). Remarkably, in the hypermutator, G:C>A:T transitions most frequently occurred in the context of a CG dinucleotide (where C is undergoing the substitution and G represents the following nucleotide), whereas A:T>G:C transitions occurred independently of the dinucleotide context and more frequently than in MMR-proficient tumors (FIGS. 2b, 2c).

Next, to identify those features that provide a best fit to the hypermutator mutation pattern, linear regression was used to correlate the various types of substitutions with nine genomic features previously implicated in explaining genetic variability in the human population (Hodgkinson and Eyre-Walker, 2011) (FIG. 2d; the nine features are distance to telomere, replication time, simple repeats, GC composition, CpG content, CpG island, Gene content, DNase hypersensitivity, and Nuclear lamina binding sites). Although a correlation with gene content was not observed, DNAse hypersensitivity or lamina-associated domains (not shown), the distance to telomere, replication time, simple repeat content, GC composition (GC %), CpG frequency and CpG island fraction represented significant and independent predictors. Overall, it was observed a better predictive model for transitions than transversions ($R^2$=0.22 versus 0.07, respectively; FIG. 2d), whereas at the individual level, the following relevant correlations were observed. First of all, a positive correlation between replication time and transitions, but not transversions (FIG. 2e) was found, indicating that reduced fidelity of DNA replication in late S phase increases transition mutations but not transversions, suggesting that the previously observed increase in late S phase transversions (Koren et al., 2012) can be attributed to a reduced MMR activity at that time, as the lack of an MMR machinery constitutes the major difference between the current and the previously investigated data sets. Secondly, for simple repeats, a 42% increase in substitutions at bases immediately flanking homopolymers was observed. This was true both for transitions and transversions, and most probably relates to DNA polymerase stalling within repetitive DNA sequences leading to error-prone replication (Hodgkinson and Eyre-Walker, 2011). Thirdly, GC % inversely correlated with transition and transversion frequencies. This was described previously in numerous organisms, and although a dominant model to explain this correlation is yet to emerge, the data indicate that differential MMR activity does not contribute to this effect. Fourthly, G:C>A:T transitions in CpG sites strongly depend on CpG content, but are inversely correlated with the fraction of CpG islands (FIG. 2d). Because most CpGs in the genome, except for those in CpG islands, are methylated, this indicates a link with cytosine methylation similar to deamination-driven mutations, whereby CG>TG transitions arise through the spontaneous, replication-independent process of cytosine deamination. As MMR is canonically considered replication-associated, the much larger increase in CG>TG transitions observed in MMR-deficient compared to MMR-proficient tumors (3042 versus 452 mutations) demonstrates that replication-independent, non-canonical MMR, which was recently described at the molecular level (Hombauer et al., 2011; Liu et al., 2008; Pena-Diaz et al., 2012), is important for genome integrity. Finally, CpG island frequencies were inversely related to overall mutation frequencies. Indeed, bases outside CpG islands were nearly two times more likely to undergo mutation than those inside CpG islands (FIG. 2f). Negative selection is unlikely to explain this decrease, since exonic substitutions are not decreased to the same extent. DNA methylation offers an alternative explanation through the polymerase stalling that it can induce (Song et al., 2012), although another possibility is through deamination repair, which can be catalyzed by error-prone polymerases.

Overall, most genomic features that correlate with mutation frequency in the general population also correlate with somatic substitutions in the MMR-deficient tumor, suggesting that a considerable portion of human genetic diversity arises due to mismatches that escape MMR. In support of this notion, it was observed very similar mutation frequencies in somatic and germ-line DNA of the hypermutator, in the 1000 Genomes Project and the mouse dbSNP databases (respectively 71.5%, 68.3%, 66.9% and 67.1% of all substitutions represented transitions). In particular, the somatic substitution frequency per chromosomal unit (100 kb) in the hypermutator was strongly correlated with the number of matched germ-line ($R^2$=0.90 and 1000 Genomes Project SNPs ($R^2$=0.90) in the same unit, but not with the somatic substitution frequency in the lung adenocarcinoma or melanoma genomes ($R^2$=0.53 and 0.37).

Somatic Indels in the MSH6-deficient Hypermutator

Next, the somatic indel pattern in the hypermutator was evaluated. As expected, since the majority of indels was located in homopolymers, a strong correlation between simple repeats and indel frequency was observed (FIG. 2g). Almost all indels affected A or T homopolymers (94.0%; FIG. 2h), but since 92.2% of homopolymers consist of A or T bases, C or G homopolymers seem equally prone to accumulate indels. Additionally, up to 96.4% of indels consisted of 1 or 2 bp frame shifts (FIG. 2i), thereby confirming that MSH6 is mainly involved in the repair of 1 or 2 bp indels. Deletions were slightly less frequent than insertions (47.7% versus 52.3%; P<10E-6). When calculating for every somatic substitution the distance to the closest somatic indel, it was observed that substitutions were, respectively, 3.8 and 3.4 times more frequently located within a distance <5 or <10 bp than expected based on a random distribution of substitutions and indels (FIG. 2j). Similarly, although there was no evidence of kataegis (somatic storms) (Nik-Zainal et al., 2012), somatic substitutions clustered 7.6 times more frequently than predicted by random modeling (FIG. 2k). The same clustering of substitutions was observed in the MMR-proficient tumors (not shown), albeit at a lower overall frequency, suggesting that the occurrence of these clusters is suppressed by MMR. Remarkably, these observations are similar to eukaryotic genomes, in which the number of substitutions is elevated near other substitutions and indels (McDonald et al., 2011; Tian et al., 2008).

Example 3

Exome Sequencing of Mismatch Repair Deficient and Proficient Tumors and their Matched Normal Samples Ten additional MMR-deficient EM and CRC tumors were selected characterized by the absence of either MLH1, MSH2 or MSH6, as well as 4 MMR-proficient tumors (Table 9, Table 13). Thus, in total, fourteen tumor-normal pairs were collected for exome sequencing, including eleven endometrial tumors (EM) and their matched germ-line samples and three colorectal tumors (CRC) and their matched germ-line pairs. All tumors were primary, chemo-naïve tumors. Tumor DNA was derived from fresh frozen tumor tissue, while matched germ-line DNA for these samples was extracted from peripheral white blood cells. Detailed clinical information for all these samples is listed in Table 13. Additionally, five primary endometrial tumor cell lines that are MMR-deficient were included in the analysis, so that a total of sixteen MMR-deficient tumor samples is reached.

3.1 Standard Diagnostics Tests

Tables 14 and 15 below describe the results of standard diagnostic tests in MSI determination (immunohistochemistry of MMR genes MLH1, MSH2 and MSH6; hypermethylation status of the MLH1 promoter regions; microsatellite instability using the extended Bethesda panel of eight dinucleotide and two mononucleotide repeat markers) performed on the sequenced endometrial and colon tumors. In the immunohistochemistry experiments, an asterisk (*) indicates weak positive nuclear staining in a minority of the tumor cells. Classification of MMR-deficiency status was performed using immunohistochemistry of the major MMR proteins (MLH1, MSH2 and MSH6). When either of these proteins were absent in the nucleus of tumor cells, the tumor was classified as MMR-deficient (MMR-), otherwise as MMR-proficient (MMR+).

For the microsatellite instability test, detailed results for all markers included in the extended Bethesda panel are listed below.

Remarkably, the MMR-4, 7 and 8 tumors were negative for either MLH1, MSH2 or MSH6 as assessed by immunohistochemistry, but failed to be identified as MSI-positive tumors using the Bethesda panel. This observation most likely illustrates that the current Bethesda panel for the diagnosis of MSI fails to recognize a number of MSI-positive tumors. However, using an improved panel of 56 markers (Table 3, and Example 7), these MMR-deficient tumors were confirmed to be MSI-positive.

Figure 3:
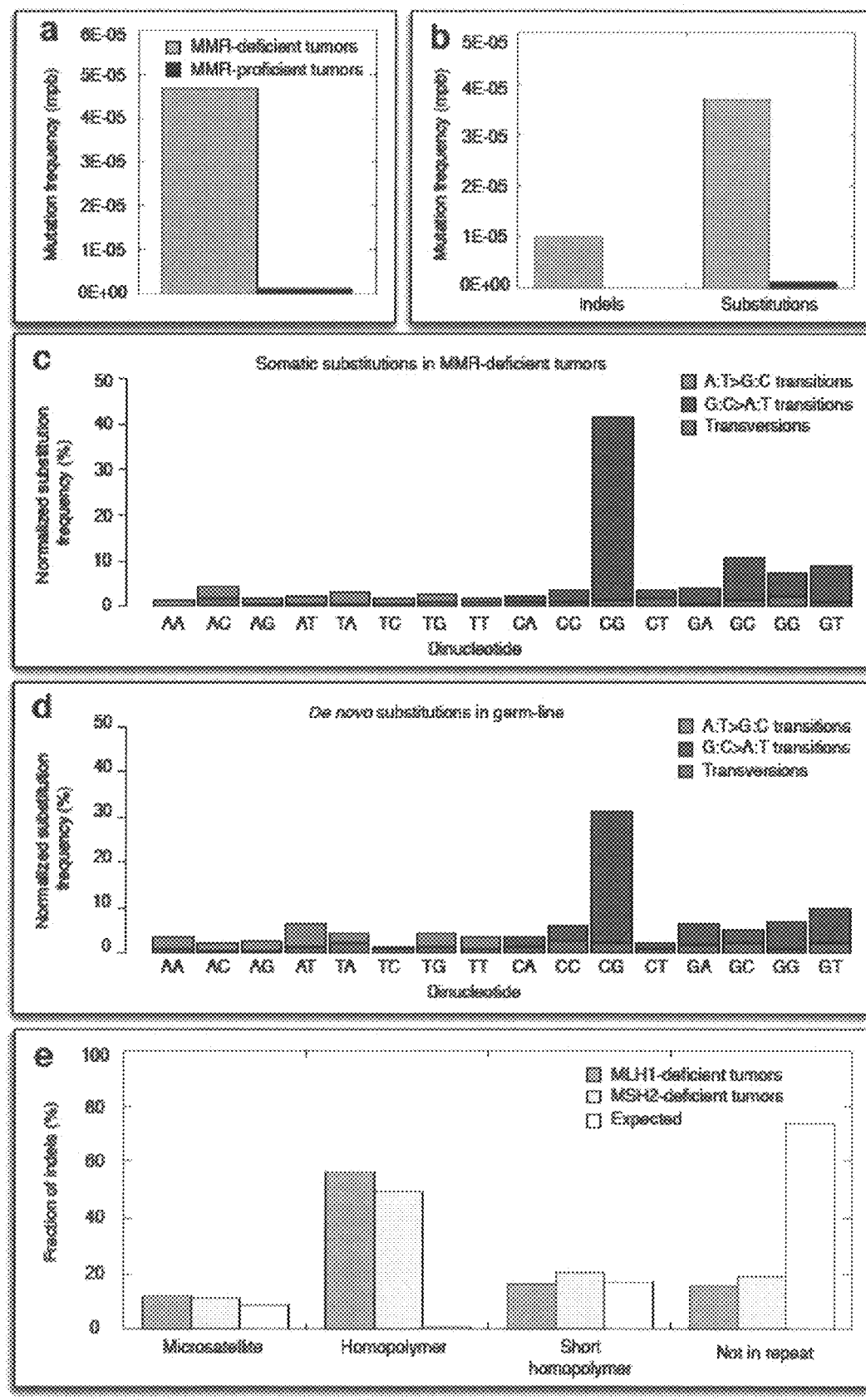
FIG. 3. Somatic mutation patterns of 10 MMR-deficient exomes. (a) The average mutation frequencies in the coding exons of 10 MMR-deficient tumors and 4 MMR-proficient tumors. (b) The average mutation frequency in the coding exons of 10 MMR-deficient versus 4 MMR-proficient tumors stratified for indels and substitutions. (c-d) Stratification of substitution frequencies per dinucleotide (with the first nucleotide being mutated) in MMR-deficient exons (c) and a set of published germ-line de novo substitutions (d). The normalized substitution frequencies plotted reflect the number of affected dinucleotides divided by the genome-wide number of those dinucleotides and expressed as percentage of the total somatic substitution frequencies. (e) The fraction of indels observed in microsatellites, homopolymers, short homopolymers and not in repeat regions in MLH1-deficient and MSH2-deficient tumors compared to the genome-wide fraction of these regions.

3.2 Sequencing, Mapping and Variant Calling for Exomes Sequenced with Illumina's HiSeq2000 Technology Exome-sequencing of tumor and matched germ-line DNA using an independent sequencing technology (ILLUMINA®) revealed that each MMR-deficient tumor on average contained 1,497 somatic events versus 39 for MMR-proficient tumors (38.9-fold increase; FIG. 3a). In MMR-deficient tumors, a large majority of these (78.4%) represented substitutions (FIG. 3b), most of which were A:T>G:C and G:C>A:T transitions (81.5%). The remaining mutations represented somatic indels, which were highly enriched in homopolymers (55.9%).

Briefly, exomes were captured using Illumina's TruSeq Exome Enrichment Kit (8 rxns), after enrichment, the enriched libraries were subjected to Illumina sequencing (HiSeq 2000). Paired-end sequencing (2×75 bp) was performed with TruSeq SBS kits. BWA was used to align the raw reads from each sequencing lane (in fastq format) to the human reference genome (NCBI37/hg19) using default parameters. Aligned reads were processed and sorted with SAMtools (v.0.1.13) and PCR duplicates were removed with Picard MarkDuplicates (http://picard.sourceforge.net, v1.32). Base recalibration, local realignment around indels and single nucleotide variant calling were performed using the GenomeAnalysisToolKit (GATK v1.0.4487). Additionally, all the common variants were filtered from the somatic mutation lists. This was done using various data tracks, which were applied to the variant lists using the intersected command of BEDTools (Quinlan and Hall, 2010). Somatic substitutions and indels were validated using Sequenom MassARRAY genotyping. Overall mutation data after quality filtering and validation are given in Table 16.

Context-dependent effects revealed a strong CG effect for G:C>A:T transitions (FIG. 3c). Intriguingly, germ-line de novo substitutions identified by exome-sequencing showed similar context-dependent effects, confirming the notion that mutations underlying human genetic variation and disease often arise due to mismatches that escape MMR (FIG. 3d). Furthermore, although the number of somatic events was slightly higher in CRC than EM tumors (on average, 2,278 versus 1,161 events), clear differences in the mutation pattern were not observed between both cancer types (not shown).

Likewise, stratification of mutation patterns according to MLH1- or MSH2-deficiency failed to reveal obvious differences. In particular, although it was observed that indels were slightly more common in microsatellites (12.0% and 11.2% versus 5.4% in the hypermutator exome), homopolymers were still most frequently affected (FIG. 3e), confirming that indels in MLH1 or MSH2-deficient tumors preferentially affect homopolymers, rather than microsatellites.

Example 4

Positive Clonal Selection and Recurrent Mutations in MMR-deficient Tumors 4.1 Analysis of Recurrently Affected Homopolymers (Hotspot Mutations)

Whereas the mutation frequency observed in the exomes of MMR-deficient tumors revealed evidence of negative selection, some mutations may also be subject to positive selection. Such mutations are more likely to appear as hotspot (recurrent) mutations. Thus, it was assessed how many homopolymers were recurrently affected in MMR-deficient tumors. The ten MMR-deficient exomes, together with the exome extracted from the hypermutator whole-genome, were therefore analyzed for the occurrence of recurrent substitutions and indels. Two sets of recurrent mutations were generated: data for substitutions or indels recurring in at least three, or at least four out of eleven tumors.

Hotspot mutations were detected in eleven MMR-deficient tumors. Variant lists for mutations recurring in three (four) or more samples were generated. It was first sought to exclude the fact that these hotspot mutations represent sequencing errors. The chance that hotspot mutations are false-positive exists, as they can be generated either by systematic false-positive variant calls in the tumors or by systematic false-negative calls in the normal samples. An additional filtering step was performed. In particular, all variants identified in each of the eleven endometrial normal exomes and three colorectal normal exomes were collected. Each hotspot mutation that was also present as a germ-line variant in at least one of these exomes was considered a systematic error and was removed from the dataset. This resulted in a large reduction in recurrent substitutions, while the effect on recurring indels was very limited (Table 17).

The five hotspot substitutions in three or more tumors were subjected to Sequenom validation. Of these substitutions, only one was confirmed. In addition, all indels recurring in four or more samples were attempted to be verified. Of these 44 recurrent indels, 26 indels could be successfully genotyped and were all confirmed using Sequenom genotyping (100% validation rate). Given the high validation rate of recurrent and non-recurrent somatic indels, further validations for the remaining indels (n=18) were not pursued, but considered all recurrent indels as true positive indels.

Since in MMR-deficient tumors, indels were mainly confined to homopolymers, the analyses were limited to indels recurrently affecting homopolymer regions. All 30,111 Illumina TruSeq-captured exonic homopolymers were screened in each of the eleven MMR-deficient tumors. Table 18 lists the number of homopolymers that were recurrently affected in MMR-deficient tumors.

In total, 1,493 homopolymers were affected at least once, 255 were affected at least twice, 82 were affected three times and 44 were recurrently affected in at least 4 out of 11 tumors. These 82 affected homopolymers were considered as hotspot mutations. 4 out of 82 hotspot mutations were located in known cancer census genes (RPL22, MSH6, MLL3, and BRAF). 41 out of 82 hotspot mutations were located in genes previously implicated in MMR-deficient tumors or other cancer types. The list of these mutations is given in Table 7. The analysis was extended by additionally analyzing five primary tumor cell lines. This led to a total of 149 exonic homopolymers recurrently affected in at least four out of sixteen MMR-deficient tumors. Details of these hotspot mutations can be found in Table 2. When an additional filtering step was applied, excluding not only the common variants present in the 1000 Genomes database and dbSNP database, but also variants in a proprietary database of over 100 individuals, this led to 103 recurrently affected exonic homopolymers, listed in Table 5.

Out of the 44 homopolymers affected in at least 4 out of 11 tumors, 21, 18, 1 and 4 consisted of A, T, G or C stretches, respectively. For the 82 homopolymers affected in at least 3 out of 11 tumors, respectively 34, 31, 7 and 10 consisted of A, T, G or C stretches (not shown). The length of recurrently affected homopolymers varied from seven nucleotides to 25 nucleotides. However, a strong bias towards homopolymer with length 7-11 nucleotides affected in at least 3 out of 11 times can be observed (not shown).

4.2 Expected Versus Observed Frequency of Recurrent Indels

To assess whether recurrent indels occur as a consequence of positive selection or occur randomly as a result of an increased indel frequency in the MMR-deficient tumors, the expected number of recurrent indels were calculated based on the observed genome-wide indel frequency in the hypermutator. Since polymerase slippage during replication is more likely to occur in long homopolymers, it is expected that indel mutations more easily affect homopolymers of increased length. The expected frequency ($f_{e,genome}$) were calculated for each homopolymer length between 6 and 11 bases, as these represent the majority of exonic homopolymers (99.7%, FIG. 4a).

As mentioned, the observed frequency in the hypermutator ($f_{e,genome}$) was used to calculate the expected number of affected homopolymers in the exome (by multiplying the expected number of indels per homopolymer by the number of homopolymers of this length in the exome). The number of homopolymers of a given length that are affected in the eleven MMR-deficient tumors were calculated. This number is averaged over the eleven MMR-deficient exomes and is referred to as the observed frequency ($f_{o,exome}$) of a homopolymer of a given length to be affected. The fold enrichment relative to the expected number of indels in homopolymers of this length is then calculated as the ratio of the observed and expected frequencies. There was a weak enrichment in the number of indels occurring in homopolymers of length 8-11 in these exomes (see Table 20).

Assuming that every homopolymer of the same length has an equally high chance of being affected, the probability of homopolymers being affected in two or three independent tumors can be calculated as the product of the probability of a homopolymer being affected in one tumor (i.e., the observed genome-wide frequency $f_{genome}$).

As such, the expected frequency of a homopolymer being affected in three tumors was calculated as follows:

$$f_{e,recurrent\ in\ 3} = (f_{e,genome})^3$$

and for an indel to be affected in four tumors:

$$f_{e,current\ in\ 4} = (f_{e,genome})^4$$

To calculate the expected number of recurrent indels in three, respectively four tumors, the expected frequencies were multiplied with the number of homopolymers in the exome, and with the number of ways 3 can be drawn, resp. 4, samples out of eleven samples (i.e., the number of combinations C(3,11) and C(4,11)). Thus, the number of expected recurrent indels in eleven tumors is calculated as follows:

$$N_{recurrent\ in\ 3} = C(3,11) * N_{homopolymers} * f_{e,recurrent\ in\ 3}$$

$$N_{recurrent\ in\ 4} = C(4,11) * N_{homopolymers} * f_{e,recurrent\ in\ 4}$$

For indels recurring in three tumors, the data are as shown in Table 21.

Although an enrichment of indels was already seen recurring in three samples, the enrichment of indels recurring in four or more samples is much stronger as shown in Table 22.

In summary, although the majority of homopolymers in the exome consist of 6 nucleotides, most recurrently affected homopolymers exhibited a length of 8-11 nucleotides. The possibility that these homopolymers were recurrently affected due to their increased length was assessed. The genome-wide probability that a homopolymer of a specific length was affected by an indel in the hypermutator was calculated and it was found that the number of observed mutations in the exome was higher than expected for every homopolymer length. The genome-wide probability to observe recurrent indels in homopolymers of a specific length was also calculated and it was found that the observed number of exonic recurrent mutations in >2 or >3 tumors was much higher than expected for each homopolymer length, thus indicating that exonic homopolymers were not recurrently affected due to increased length. This indicates that these indels in these homopolymers are positively selected in these cancers.

Conclusion

Overall, 1,238 out of 30,111 homopolymers were affected once, whereas 173 homopolymers were affected twice. Furthermore, 82 homopolymers were affected by the same indel in at least 3 tumors. Of those, 27 and 8 homopolymers were present in 4 or 5 tumors, and 5 were present in 6 tumors (Table 7 and Table 23). In contrast, only a single substitution (G13D in KRAS) was identified in more than one MMR-deficient tumor.

Example 5

Recurrent Indels in 3' and 5' UTRs Affect Long Homopolymers

Since 5' and 3' UTRs are critical in determining gene expression, mutations in these regions were also assessed. In particular, using exome data from MMR-deficient tumors, up to 83.9% and 91.9% of these regions were reliably assessed.

5.1 Recurrent Indels in Regulatory Regions

To assess whether any of 5' UTR and 3' UTR regions were affected by recurrent mutations, 5,367 and 59,259 homopolymers located in the exome-captured 5' UTRs and 3' UTRs of 10 MMR-deficient tumors were screened, respectively. These homopolymers were also screened in the 5' UTRs and 3' UTRs of the whole-genome sequenced hypermutator sample such that the total number of tumors in which the 5' and 3' UTRs was able to be screened was eleven MMR-deficient tumors. Each hotspot mutation that was also present as a germ-line variant in at least one of eleven MMR-deficient samples was removed.

Recurrent indels in homopolymers were much more frequent in 5' and 3' UTR regions than expected from the observations in the exome: in the 3' UTR regions it was observed 1,142 recurrent indels in at least four out of eleven tumors and 1,812 in at least three out of eleven tumors, while in the 5' UTR it was observed 50 recurrent indels in at least four out of eleven tumors and 89 in at least three out of eleven tumors. These recurrent indels are shown in Table 6. When the five additional MMR-deficient samples were taken into account, this resulted in 2648 recurrent indels in four out of sixteen tumors for the 3' UTR regions and 155 indels recurrent in four out of sixteen tumors for the 5' UTR regions. This list of frequent recurrent indels in homopolymers in UTR regions (present in at least four out of sixteen MMR-deficient tumors) is shown in Table 1. Here also, an additional filtering step, excluding not only the common variants present in the 1000 Genomes database and dbSNP database, but also variants in a proprietary database of over 100 individuals, reduced the number of recurrently affected homopolymers in UTR regions to 1314 recurrent indels in four out of sixteen tumors for the 3' UTR regions and 88 indels recurrent in four out of sixteen tumors for the 5' UTR regions, listed in Table 4.

In contrast, recurrent substitutions were very rare: three recurrent substitutions were found in at least four out of eleven tumors, and eighteen in at least three out of eleven tumors, while in the 5' UTR regions one recurrent substitution was observed in three samples, and no substitution was encountered in four or more samples.

5.1.1. Homopolymer Length and Recurrence of Somatic Mutation in Exonic Regions, 5' UTRs and 3' UTRs In order to assess whether recurrent indels in 5' and 3' UTR regions also result from positive clonal selection or simply occur due to homopolymer content, the length distribution of homopolymers in function of their location in exons, 5' UTRs and 3' UTRs was assessed. It was observed that there are much more homopolymers in 3' UTRs and much less homopolymers in 5' UTRs. Homopolymers in the 3' UTR were also longer than in the exome. For instance, the exome contains 29,733 (98.7%) homopolymers of length <9 nucleotides, whereas 5' UTRs and 3' UTRs contain 4,857 (90.5%) and 49,769 (84.0%) homopolymers of length <9 nucleotides, respectively. Despite the higher number of homopolymers of short length (6 or 7) in the 3' UTR than in the exome (not shown), the number of affected homopolymers in the 3' UTR and exome was more or less equal (not shown). In the 3' UTR, a lot of indels were located in the long homopolymers, i.e., homopolymers with a length of 9, 10, 11, >=12 base pairs.

When assessing recurrent indels in 5' and 3' UTRs and the exome, it was observed that also the number of recurrent indels was much higher in the 3' UTR than in the 5' UTR or exome. Recurrent indels in 3' UTRs mainly affected homopolymers with a length >9 base pairs. Remarkably, despite the higher number of homopolymers of length 7 or 8 in the 3' UTR than in the exome and despite the higher number of indels in homopolymers of length 7 or 8 in the 3' UTR than in the exome, there were more recurrent indels that affected homopolymers of length 7 or 8 in the exome than in the 3' UTR. Recurrent indels in the 3' UTR mainly affected homopolymers of length 11 and >=12.

To verify that the increased fraction of recurrently affected homopolymers with a length <9 in the exome is not due to overall differences in length distributions for homopolymers in the different regions, the indel frequency (i.e., the fraction of affected homopolymers) in homopolymers of length <9 for the overall occurrence of these homopolymers in the different regions was corrected. The corrected fraction was calculated as follows:

$$\text{Corrected fraction} = \frac{\text{Fraction}}{\left(\frac{\text{Number of homopolymer with length} < 9 \text{ in a given region}}{\text{Average number of homopolymer with length} < 9 \text{ in three regions}}\right)}$$

This corrected mutation frequency was then calculated for the three different regions (exome, 5' UTR and 3' UTR). After this correction, the enrichment for shorter recurrent homopolymers in the exome was still observed (39.2% with length <9) compared to in 5' (19.5%) and 3' UTRs (2.2%). These data clearly indicate that homopolymer length critically determines which homopolymers are recurrently affected in 5' and 3' UTR regions, whereas in the exome, homopolymer length as well as the effect of the mutation on clonal growth advantage determine which homopolymers are recurrently affected. Table 24 shows an overview of the data described in the previous paragraphs.

Figure 4:
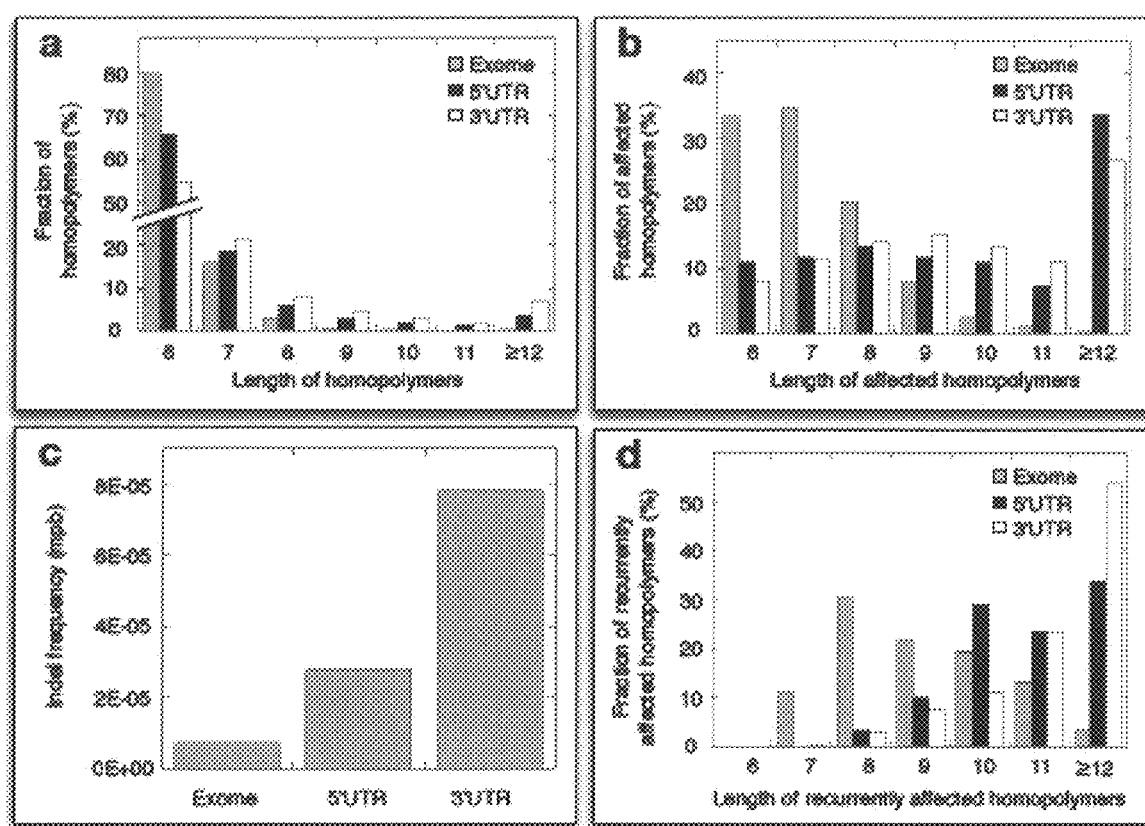
FIG. 4. Hotspot mutations in the exome, 5' and 3' UTR of MMR-deficient tumors. (a) Fraction of homopolymers in function of their length in coding regions, 5' and 3' UTRs. (b) Fraction of homopolymers affected by an indel in function of the homopolymer length for coding regions, 5' and 3' UTRs. (c) Average somatic indel frequencies in the coding regions, 5' and 3' UTR of MMR-deficient tumors. (d) The fraction of homopolymers recurrently affected by an indel in function of the homopolymer length for coding regions, 5' and 3' UTRs.

Thus, in summary, in 5' and 3' UTRs, homopolymers are longer than in coding regions (FIG. 4a); longer homopolymers in UTRs moreover have an increased propensity to accumulate indels (FIG. 4b). Together, this leads to a higher indel frequency in 5' and 3' UTRs than in coding regions (3.8 and 10.7-fold increase, respectively; FIG. 4c). In UTRs, hotspot mutations are however depleted in long homopolymers. For instance, only 3 (out of 89; 3.4%) and 71 (out of 1,812; 3.9%) hotspot mutations in 5' and 3' UTRs affected homopolymers <9 bp in length (Table 24), whereas in coding regions, up to 34 (out of 82; 41.5%) such hotspot mutations were present (FIG. 4d). Overall, this suggests that homopolymer length critically determines which homopolymers are frequently affected in 5' and 3' UTR regions, whereas in coding regions, the impact of the mutation on clonal growth advantage co-determines which homopolymer is most frequently affected.

Example 6

Gene Expression Profiles of Recurrently Mutated Genes

Since it is hypothesized that recurrent mutations are linked with positive selection due to growth advantage for the tumor, the genes affected by these recurrent mutations should at least be expressed in normal endometrial tissue. It is also expected that at least a subset of these genes may be found in other mismatch repair deficient tumors, and that hotspot mutations will change expression of the affected gene. Therefore, the expression profiles of genes affected by recurrent mutations both in the context of endometrium-specific expression and in the context of genes differentially expressed in colorectal MMR-deficient tumors was analyzed.

6.1 Gene Expression in Normal Endometrium

Expression data for genes in normal endometrium tissue were downloaded from the Gene Expression Atlas[23] (http://www.ebi.ac.uk/gxa/) using the query "all genes over/under/non-differentially expressed in *Homo sapiens*, endometrium." This query resulted in 14,664 genes, of which 9,021 were overexpressed in the normal endometrium, 463 were underexpressed, and 5,180 showed no differential expression. Since the over- and underexpression was calculated with respect to general gene expression profiles throughout different tissue types, it is difficult to assess whether underexpressed genes are effectively absent (not expressed) or merely expressed at a lower level. However, for genes significantly overexpressed in endometrial tissue it is safely argued that they at least play a role within the normal endometrium. Therefore, this analysis was limited to genes overexpressed in normal endometrium.

Mutations from different datasets were compared with the derived expression data: all genes mutated in MMR-proficient tumors (MMR+ genes), all genes mutated in MMR-deficient tumors (MMR- genes), all genes recurrently affected in MMR-deficient tumors (defined as three out of eleven samples, Recurrent Genes), and finally all recurrent indels in exonic regions (Recurrent Exonic). This analysis indicated that the recurrent (hotspot) mutations were overrepresented in genes that were overexpressed in normal endometrium tissue. Full data for these analyses are shown in Table 25.

Analysis in Genes Specific for Microsatellite Instable Colorectal Cancers

Genes differentially expressed between microsatellite instable (MSI-H) and microsatellite stable (MSS) colorectal cancers were derived from a study by Banerjea et al.[22] In this study, 133 colorectal tumors were analyzed of which 29 (22%) tumors were identified as MSI-H. Gene expression data were derived from Affymetrix HG-U133A chips. The derived dataset contains 4,874 genes differentially expressed between microsatellite instable and stable cancers (P<0.05, Benjamini and Hochberg False Discovery Rate).

Mutations from different datasets were compared with the derived expression data: all genes mutated in MMR-proficient tumors (MMR+ genes), all genes mutated in MMR-deficient tumors (MMR- genes), all genes recurrently affected in MMR-deficient tumors (defined as three out of eleven samples, Recurrent Genes), and finally all recurrent indels in exonic regions (Recurrent Exonic). This analysis revealed that hotspot mutations were enriched among the set genes differentially expressed in microsatellite instable tumors.

Summary

Using publicly available expression data from the Gene Expression Atlas (Kapushesky et al., 2010), it was assessed whether genes affected by the same mutation in at least three MMR-deficient tumors (hereafter referred to as hotspot mutations) were expressed in normal EM tissue. Of all genes mutated in MMR-proficient and MMR-deficient tumors, 58% and 64% were expressed in EM tissue compared to 88% of genes affected by hotspot mutations (Table 25). Similar data were obtained for normal mucosa tissue (not shown). Furthermore, when assessing expression differences between MMR-deficient versus MMR-proficient tumors (Banerjea et al., 2004), it was observed that 20% of genes affected by non-hotspot mutations versus 32% of genes affected by hotspot mutations was differentially expressed.

Thus, hotspot mutations preferentially affect genes that are expressed in normal tissue and alter their expression, indicating that they result from positive clonal selection in the tumor.

Example 7

Recurrent Mutations Reliably Detect MSI in Various Tumor Types

The extended Bethesda panel, which consists of 8 microsatellite markers and two homopolymer markers is currently used to diagnostically assess MSI as a marker of MMR-deficiency.[9, 15] Since these markers were not selected based on the relative frequency by which they affect MMR-tumors, this panel sometimes fails to detect MMR− tumors.[24] It was therefore assessed whether recurrent mutations could improve detection of MSI.

7.1 Construction of a Diagnostic Panel

There are two criteria by which it is believed possible to improve the diagnostic panel currently used for detecting microsatellite instability. First of all, recurrent mutations in MMR-deficient tumors were determined in an unbiased way: by performing whole-genome and exome sequencing experiments and simply observing which positions were recurrently affected. The detection in an unbiased way suggests that the most frequent hotspot mutations will be most sensitive to detect MSI. Second, the majority of the recurrent indels identified were located in the 3' UTR. Recurrent indels in 5' and 3' UTRs do not undergo stringent positive selection, but are mainly determined by the length of the affected homopolymer, and it is unlikely that tissue-specific enrichments occur. These two criteria ensure that the i) chosen markers, which without a priori knowledge about their function, are recurrently affected in multiple tumor samples and ii) there are a number of markers that are likely to be cancer-type independent. For the latter, indels selected from 5' and 3' UTRs may be most useful.

To obtain the highest sensitivity, mutations occurring in four or more samples were only used. For the 5' and 3' UTR recurrent indels, priority was given to indels affecting five or more samples. The resulting 44 recurrent exonic indels, 1,142 recurrent 3' UTR indels and 50 recurrent 5' UTR indels were used to design a Sequenom-based panel to detect MMR-deficiency. Since the recurrent indels were located in homopolymer regions, the primer design of a Sequenom multiplex PCR was complex. After extensive optimization experiments, six assays genotyping 56 hotspot mutations were successfully generated. Of the 56 hotspot mutations, 11 were located in exons, 40 in the 3' UTR and 5 in the 5' UTR, respectively. Reference is made to this panel as the 56-marker panel. The full details of these 56 mutations can be found in Table 3.

7.2 Diagnostic Assessment of MSI in Endometrial Tumors

Figure 5:
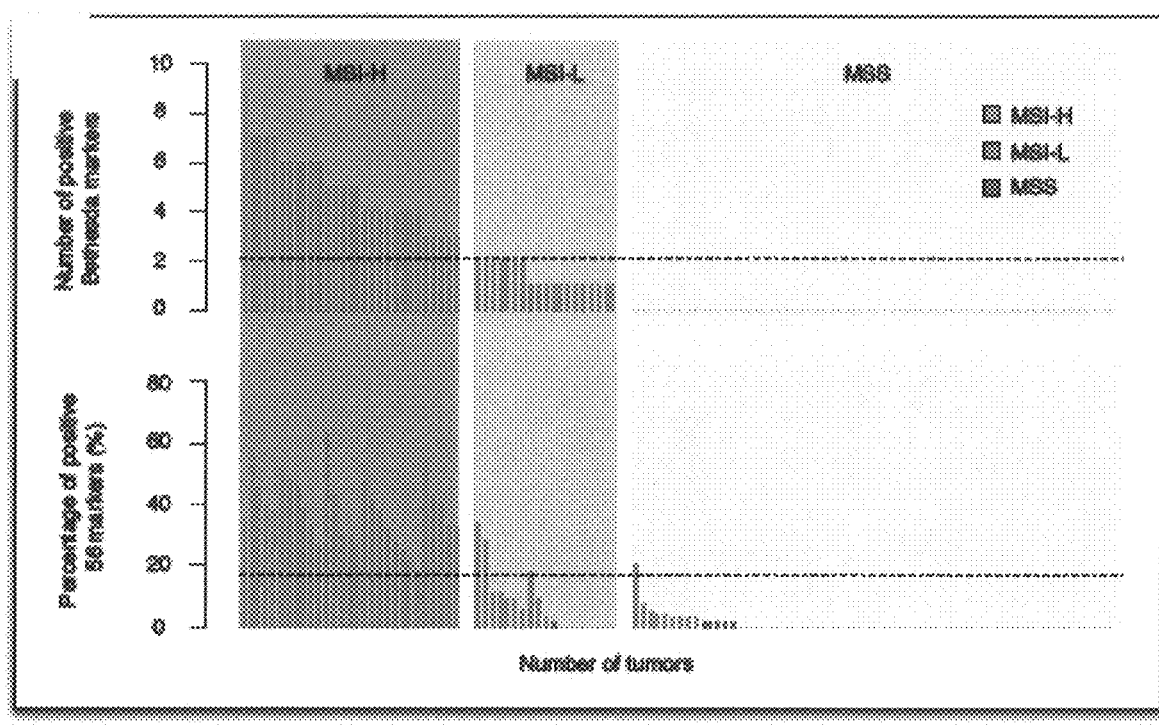
FIG. 5. The Bethesda and 56-marker hotspot mutation panel to assess MSI. The extended Bethesda panel and a panel of 56 hotspot mutations in exons, 5' and 3' UTRs identified by exome-sequencing were analyzed in an independent series of 114 unselected primary endometrial tumors. Results were color-coded according to high microsatellite instability (MSI-H), low microsatellite instability (MSI-L) or microsatellite stable (MSS) status based on the extended Bethesda panel.

Next, the 56-marker panel was applied to an additional series of 114 unselected surgically resected endometrial tumors, consisting of seven clear cell, 69 endometrioid, 18 mixed serousendometrioid, 10 serous and 10 unclassified endometrial carcinomas. All tumors were primary chemo-naïve endometrial tumors. Fresh-frozen tissue was available for each of these tumors. The genotyping success rate of the selected markers was high (on average 98.7%). The number of positive markers for one sample varied between 0 and 33, with an overall average of 6.5 positive markers per sample. Analogously with the Bethesda panel, three categories of microsatellite instability were defined: microsatellite stable (MSS, 0 out of 10 markers in Bethesda, 0 or 1 out of 56 markers in 56-marker panel), low microsatellite instability (MSI-L, 1-2 out of 10 markers in Bethesda panel, between 2 and 9 markers in 56-marker panel) and high microsatellite instability (MSI-H, 3 or more out of 10 markers in Bethesda, 10 or more out of 56 in 56-marker panel). Based on these categories for 56-marker panel, 65 tumors (57.0%) are defined as MSS. 33 tumors (29.0%) and 16 tumors (14.0%) are defined as MSI-H and MSI-L respectively. Out of these 33 MSI-H tumors, Bethesda identified 29 tumors as MSI-H (>2 markers positive), 3 tumors as MSI-L and one tumor as MSS. Vice versa, Bethesda did not identify any MSI-H tumor that was not identified by a panel of hotspot mutations (as shown in FIG. 5). This result shows that 56-marker panel outperformed Bethesda panel for this series of endometrial tumors. Data in colorectal tumors are comparable (not shown).

7.3 Mutation Signatures in Other Tumor Types.

56-marker panel was also applied to other tumor types (ovarian tumors and leukemia). Four MSI-H samples were selected, including one ovarian tumor and three leukemia cell lines samples (DND41, CCRF-CEM and SUPT1). In order to assess whether these observations in MMR-deficient endometrial/colorectal tumors were extendable to other tumor types, the MSI-H ovarian tumor, two ovarian tumors that were detected as MSS and their matched normal samples, as well as three MSI-H leukemia cell lines and a MSS leukemia cell line (RPMI-8402) were sequenced.

The three ovarian tumor-normal pairs were primary, chemo-naïve tumors collected during surgery. The MMR-deficient ovarian tumor (MMR− Ovarian 1) together with its matched normal DNA was exome-sequenced using Illumina's TruSeq capture. The same analysis pipeline that was described above was used for the analysis of these exome data. The exome data of two MMR+ ovarian tumors (MMR+Ovarian 1 and 2), together with their matched normal samples were extracted from existing whole-genome data. In particular, both MMR-proficient tumor-normal pairs were already available from another project and were sequenced using Complete Genomics. Whole-genome sequence data have been deposited at the European Genome-Phenome Archive with accession number EGAS00001000158. The same analyses as described in the earlier Examples herein were used for these genomes.

In addition, 4 leukemia cell lines were exome-sequenced using Nimblegen capture. The exomes were captured using Nimblegen SeqCap EZ Human Exome Library v2.0. Pre-enrichment DNA libraries were constructed according to standard protocol from Illumina's paired-end DNA Sample Preparation Guide. Exome enrichment was performed according to the manufacturer's instructions. One round (72 hours) of biotinylated bait-based hybridizations was performed, followed by Streptavidin Magnetic Beads binding, a washing step and an elution step. An 18-cycle PCR enrichment was performed after the elution and the enriched libraries were subjected to Illumina sequencing (HiSeq 2000). Paired-end sequencing (2×51 bp) was performed with TruSeq SBS kits. One lane was used for one exome. Detailed clinical information for all samples is listed in Table 27. Table 28 lists all mutations found in MMR genes in all ovarian and leukemia samples.

In the MMR-deficient ovarian tumor (MMR− Ovarian 1), 2,045 novel somatic substitutions and 280 novel somatic indels were detected. Because the validation rate in the other MMR-deficient tumors was very high in both the whole-genome and exome-sequenced tumors (see above), no further validation was performed for this tumor. In the two MMR-proficient ovarian tumors, respectively 32 and 42 novel somatic substitutions, and 12 and 18 novel somatic indels were detected. Due to the low validation rate in MMR-proficient tumors in general, all somatic mutations in the two MMR-proficient ovarian tumors were validated using Sequenom MassARRAY. Respectively, 16 and 20 substitutions were confirmed as true substitutions in the two MMR-proficient ovarian tumors. No indel was confirmed in either tumor. For these somatic mutations, it was observed the same patterns as observed in EM/CRC tumors (data not shown).

The exomes of four leukemia cell lines were sequenced using Illumina HiSeq technology, as described above. Since there was no matched normal DNA samples available for these cell lines, somatic or germ-line mutations could not be distinguished. However, using the common variant filtering pipeline described earlier, the most frequently occurring variants could be eliminated. As previously observed in MMR-deficient tumors, indels were mainly located in the homopolymers of the MMR-deficient leukemia samples. On the other hand, the MMR-proficient sample did not exhibit this pattern (not shown).

For substitutions, the patterns in MMR-deficient and MMR-proficient samples were very similar (not shown). In particular, these patterns revealed that the majority of substitutions were located not in repeat regions. As in the endometrial/colorectal MMR-deficient tumors, substitutions in MMR-deficient samples were mainly composed of transitions (73.0% versus 27.0% transversions, respectively).

Summary 56 of the most frequent hotspot mutations were selected identified by exome-sequencing: 45 were in UTRs, which are less prone to clonal selection and could therefore detect MSI in tumors of different tissue types, and 11 were in coding regions. Genotyping of 114 surgically resected EM tumors for these 56 mutations revealed that 33 (29.0%) tumors were positive for >10 markers (MSI-high or MSI-H) and 16 (14.0%) tumors for 2 to 9 markers (MSI-low or MSI-L). The remaining 65 (57.0%) tumors were positive for <2 markers and were microsatellite stable (MSS) tumors (FIG. 5). Out of 33 MSI-H tumors, Bethesda identified only 29 tumors as MSI-H (>2 markers positive). The 4 discordant tumors contained a frame shift mutation in MSH6 or were deficient for MSH6 on histopathology, thereby confirming that they were MSI-H. Vice versa, Bethesda did not identify any MSI-H tumor that was not identified by a panel of hotspot mutations.

Finally, it was assessed whether hotspot mutations were also present in ovarian tumors and leukemia. First, using a 56-marker panel, one ovarian tumor and three leukemia cell lines (DND41, CCRF-CEM and SUPT1) that were positive for 20, 25, 23 and 21 markers respectively were selected, as well as two ovarian tumors and one leukemia cell line (RPM18402) without positive markers. Exome-sequencing of the ovarian tumors and their matched normal samples confirmed that the MSI-H ovarian tumor contained substantially more somatic events than the two corresponding MSS tumors, including a frame shift deletion in MSH6. Although somatic or germ-line mutations in the leukemia cell lines could not be distinguished since matched germ-line DNA was not available, substitutions and indels were also more frequent in the MSI-H cell lines (Note S9). Two loss-of-function mutations in MLH1 and a frame shift deletion in MSH6 were observed, confirming that the MSI-H cell lines were MMR-deficient. When assessing whether recurrent mutations identified in endometrial tumors were also present in the ovarian and leukemia genomes, it was noticed that out of 384 recurrent mutations in endometrial MMR− tumors, 60, 25, 8 and 1 were present in respectively 1, 2, 3 or 4 MMR− tumors (not shown). A more pronounced enrichment was seen when limiting the recurrent mutations to those that were present in at least 3 endometrial tumors. Finally, since recurrent indels in the exome are positively selected by the tumor tissue whereas recurrent indels in 5' and 3' UTRs largely depend on the length of the homopolymer, indels in UTRs might represent better markers of MSI.

Example 8

Mutation Patterns of MMR-deficient Tumors Affect DNA Double-strand Break Repair

In order to explore the biological relevance of the hotspot mutations in MMR-deficient tumors, pathway analyses were performed with two different tools, namely IPA® and GenomeMuSiC. These two tools use four different pathway databases, i.e., the IPA, KEGG, BioCarta and Reactome databases. The use of multiple tools and databases allowed for obtaining of detailed impression of the pathways affected.

8.1. Pathway Analyses Using IPA® and GenomeMuSiC

Ingenuity Pathway Analysis (IPA®, http://www.ingenuity.com/) enables the identification of biological pathways most relevant to the genes of interest. Pathway analysis of all genes with somatic indels (3,022 indels in 2,231 genes, excluding the indels in MMR genes, due to secondary mutations resulting from MMR-deficiency) using IPA® revealed that 24 pathways are significantly enriched (P<0.05) (not shown). "Role of BRCA1 in DNA damage response" and "DNA double-strand break (DSB) repair by Homologous Recombination (HR)" were ranked top 1 and 3 respectively. If restricting the gene list of interest to the genes carrying the hotspot mutations only (1,382 indels in 452 genes), 13 significantly enriched pathways were revealed as shown in Table 29. The "Role of BRCA1 in DNA damage response" and "G2/M DNA checkpoint regulation" pathways were ranked top 1 and 2, respectively.

In summary, IPA® revealed "Role of BRCA1 in DNA damage response" as the top enriched pathway using two different sets of genes of interest, namely all genes carrying somatic indels and all genes with hotspot mutations. "G2/M DNA checkpoint regulation" and "DNA double-strand break (DSB) repair by Homologous Recombination (HR)" were also highly significant.

A similar analysis was done using GenomeMuSiC (http://gmt.genome.wustl.edu/genome-music/0.3/index.html), using all somatic indels (excluding all indels on MMR genes) as an input. Pathway analyses of all somatic indels (3,022 indels in 2,231 genes, indels in MMR genes were excluded) in MMR-deficient tumors using GenomeMuSiC revealed 51 significantly mutated pathways (FDR <0.05). The "DNA repair," "Base-excision repair," and "G2/M DNA damage checkpoint" pathways were ranked highest, thereby confirming the results from IPA® analyses.

8.2 Pathway Analysis of Indels in Exon/Intron Boundaries

Furthermore, as it is known that genes are also inactivated by indels affecting homopolymers located in exon/intron boundaries, mutation calling was extended to indels occurring in the 25 base pair sequences up and down-stream of every exon. The same mutation calling and filtering pipeline was performed as earlier described. 1,700 additional indels in exon/intron boundaries were detected, including a deletion in the homopolymer of intron 7 of ATM, a deletion in the homopolymer of intron 4 of MRE11 and an insertion in the homopolymer of intron 5 of FANCD2. These three indels affect 7, 5 and 1 samples respectively. Together with the 3,022 indels in exonic regions, GenomeMuSiC analysis of all 4,722 mutations revealed 54 significantly mutated pathways (FDR <0.05). Inclusion of indels in the exon/intron boundaries yielded an even stronger signal for DNA DSB repair as the top enriched pathway.

Considering all the analyses, there are 11 genes involved in the DSB repair by HR pathway. Table 30 below lists these genes and the MMR-deficient tumors carrying mutations in these genes.

Summary

Figure 6:
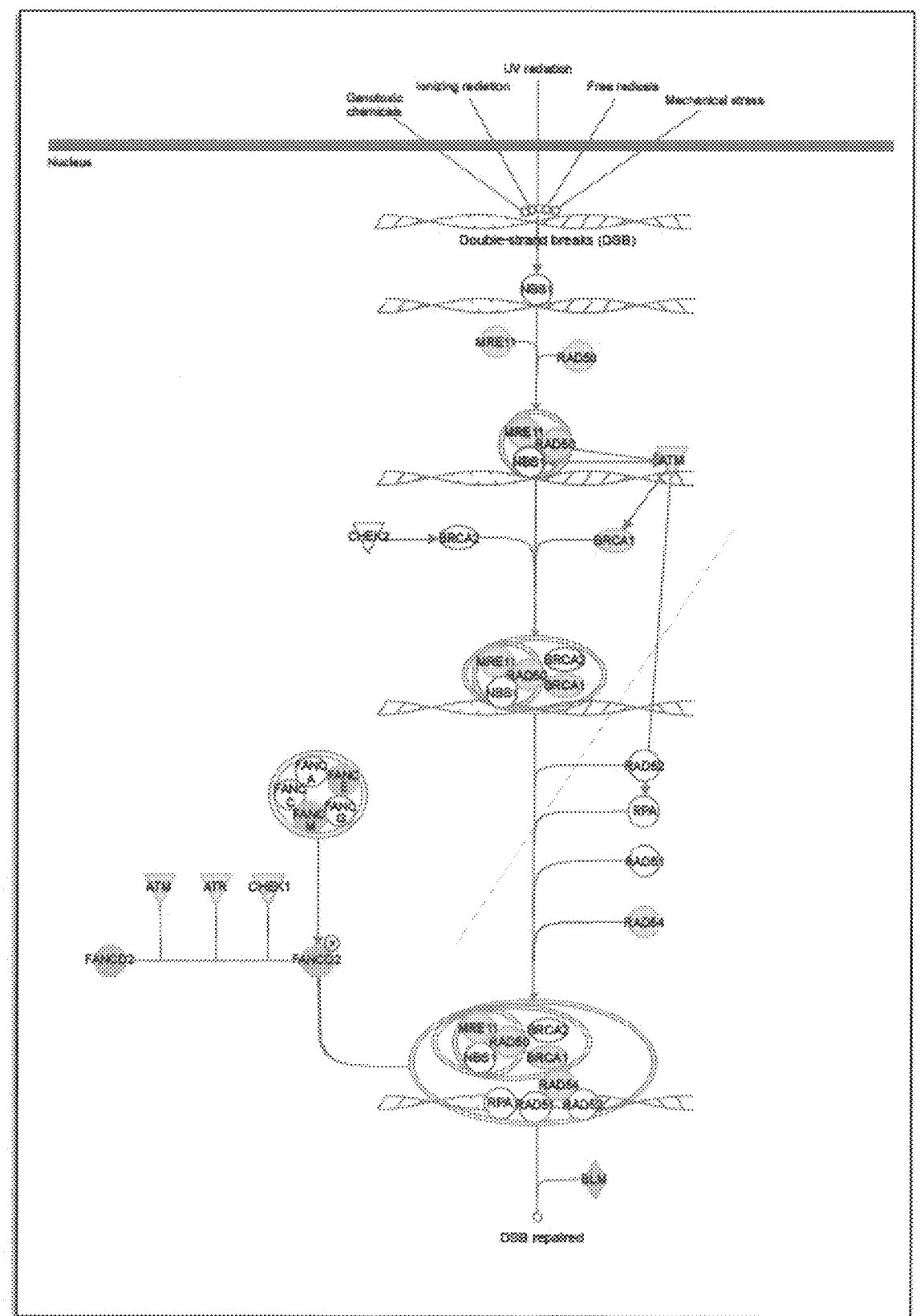
FIG. 6. Somatic mutations affecting the DNA DSB repair by HR pathway. Diagram of the DSB repair by HR pathway (adapted from the IPA homologous recombination pathway diagram). Genes marked in orange (with grey background) carry somatic mutations either in a set of MMR-deficient tumors or in MSI-H tumors from the publically available TCGA dataset.

Since indels in MMR-deficient tumors can be subject to positive or negative clonal selection, it was assessed whether specific pathways are enriched for these mutations. On average, each MMR-deficient tumor contained 309 indels, 30 of which were hotspot mutations. Pathway analyses of all genes affected by a somatic indel (except for MMR genes because indels in these genes are causing MMR-deficiency) using IPA® revealed that the "Role of BRCA1 in DNA damage response" and "DNA double-strand break (DSB) repair by Homologous Recombination (HR)" were the top enriched pathways (P=6.5E-03 and P=1.1E-02, respectively). IPA® analysis of all hotspot mutations revealed that in addition to the "Role of BRCA1 in DNA damage response" (P=2.0E-03), the "G2/M DNA damage checkpoint regulation" pathway was also enriched (P=3.1E-03). Genes most frequently mutated in these pathways included, amongst several others, ATR, BLM, BRCA1, CHEK1 and FANCM (4, 2, 2, 2 and 2 mutations, respectively; Table 30). Pathway analyses of all indels in MMR-deficient tumors using GenomeMuSiC, which calculates the pathways that are specifically mutated based on KEGG, BioCarta or Reactome databases, while correcting for the background mutation rate, revealed that respectively, the "DNA repair," "Base-excision repair" and "G2/M DNA damage checkpoint" pathways were ranked highest (P=6.3E-05,P=3.1E-04 and P=9.8E-04, respectively). Furthermore, since DSB repair genes can also be affected by loss-of-function indels in homopolymers located in the exon/intron boundaries (Ham et al., 2006), mutation calling was extended to indels occurring in the 25 bp sequences up and down-stream of every exon. GenomeMuSiC analysis of all mutations (1,700 exon/intron boundary indels and 3,022 exonic indels) yielded an even stronger signal for DNA DSB repair as the top enriched pathway (e.g., P=6.8E-07 for "ATR/BRCA" pathway in BioCarta and P=3.0E-05 for the "G2/M DNA damage checkpoint" pathway in Reactome). Overall, each MMR-deficient tumor contained on average 3.0±0.5 indels in the DSB repair by HR pathway (FIG. 6).

In an attempt to replicate these findings, exome data of 27 CRC MSI-H tumors sequenced were analyzed in the context of The Cancer Genome Atlas network (TCGA, 2012). Although these tumors were sequenced with an average coverage depth of only 20x, which is quite low to reliably detect indels in homopolymers (Reumers et al., 2011), each of the 1,426 frame shift indels (in 1,284 genes, not including the MMR genes) that were reported for these tumors were selected, but additionally also selected 19 indels identified by TCGA based on a separate assessment of 29 homopolymers selected by a candidate gene approach. Remarkably, IPA analysis of the 1,303 genes affected with indels confirmed that the "Role of BRCA1 in DNA damage response" was again the top enriched pathway (P=0.0148). Genes mutated in this pathway included, amongst several others, RAD50, ATR, BLM and CHEK1 (7, 5, 2 and 1 mutations, respectively; FIG. 6).

8.3 Inactivation of the DSB Repair by HR Pathway in MMR-deficient Cells

To investigate whether the DSB repair by HR pathway is functionally inactivated in MMR-deficient tumors, it was assessed the DSB repair activity in eight MMR-deficient and four MMR-proficient primary tumor cultures and cancer cell lines. The MMR status of these cells was analyzed using the 56-marker panel and confirmed by the Bethesda Panel.

Nine primary endometrial and ovarian tumor cell cultures were established from patients undergoing surgery at the Division of Gynecologic Oncology, University Hospitals Gasthuisberg, Leuven (Belgium). Only after providing informed consent, patients were included in the study. The following protocol was used to generate primary tumor cultures. First, tumor samples were placed into sterile RPMI medium supplemented with Penicillin/Streptomycin (1000 U/ml) and Fungizone (0.5 µg/ml) (all from Life Technologies) for transport from the surgery room to the cell culture laboratory. Tumor tissue was subsequently washed with PBS supplemented with Penicillin/Streptomycin and Fungizone, and tissue was minced with sterile blades. Tumor tissue was digested with collagenases type IV (1 mg/ml; Roche) in RPMI medium (Life Technologies) supplemented with Penicillin/Streptomycin and Fungizone. Also DNase I (0.1 mg/ml; Roche) was added to the digestion medium. Digestion was performed while shaking for 3 hours at 37° C. Thereafter, single cell suspension was prepared by filtration through a 70 µm filter and red blood cells were lysed using Ammonium Chloride solution (Stem Cell Technologies). Single cells were finally plated into a 25 $cm^2$ culture flask and medium was changed the day after. After one to three weeks, when cells reached 60-70% confluency, fibroblasts were removed using mouse anti-human CD90 (Clone AS02; Dianova) and negative selection with Mouse Pan IgG Dynabeads (Life Technologies). Cell cultures were subsequently passaged at 70-90% confluency and cell cultures were stored in a cell bank at different passages. Table 31 lists the various primary tumor cultures that were generated according to this protocol.

Primary tumor cell cultures were grown in RPMI Medium 1640 (Gibco) supplemented with 20% fetal bovine serum, 2 mM L-Glutamine, 100 U/ml of penicillin, 100 µg/ml of streptomycin, 1 µg/ml of fungizone and 10 µg/ml of gentamicin up to 20 passages. All cell cultures were performed in a humidified atmosphere containing 5% CO2 at 37° C. They were also routinely monitored for *Mycoplasma* contamination and no *Mycoplasma* growth has been detected.

HEC-1-A, MDA-MB-231 and MCF7 cells were all obtained from American Type Culture Collections (ATCC, Manassas, Va., USA). HEC-1-A cells were cultured in McCoy's 5A Medium (Gibco-BRL, Life technologies), MDA-MB-231 and MCF7 cells in Dulbecco's Modified Eagle's Medium (DMEM, Gibco-BRL) all supplemented with 10% Fetal Bovine Serum (FBS, Gibco-BRL), 2 mM LGlutamine, 100 U/ml of penicillin and 100 µg/ml of streptomycin (all from Life Technologies). All human cells were maintained in a humidified 5% CO2-containing atmosphere at 37° C. The cell lines are listed in Table 32.

Summary

Figure 7:
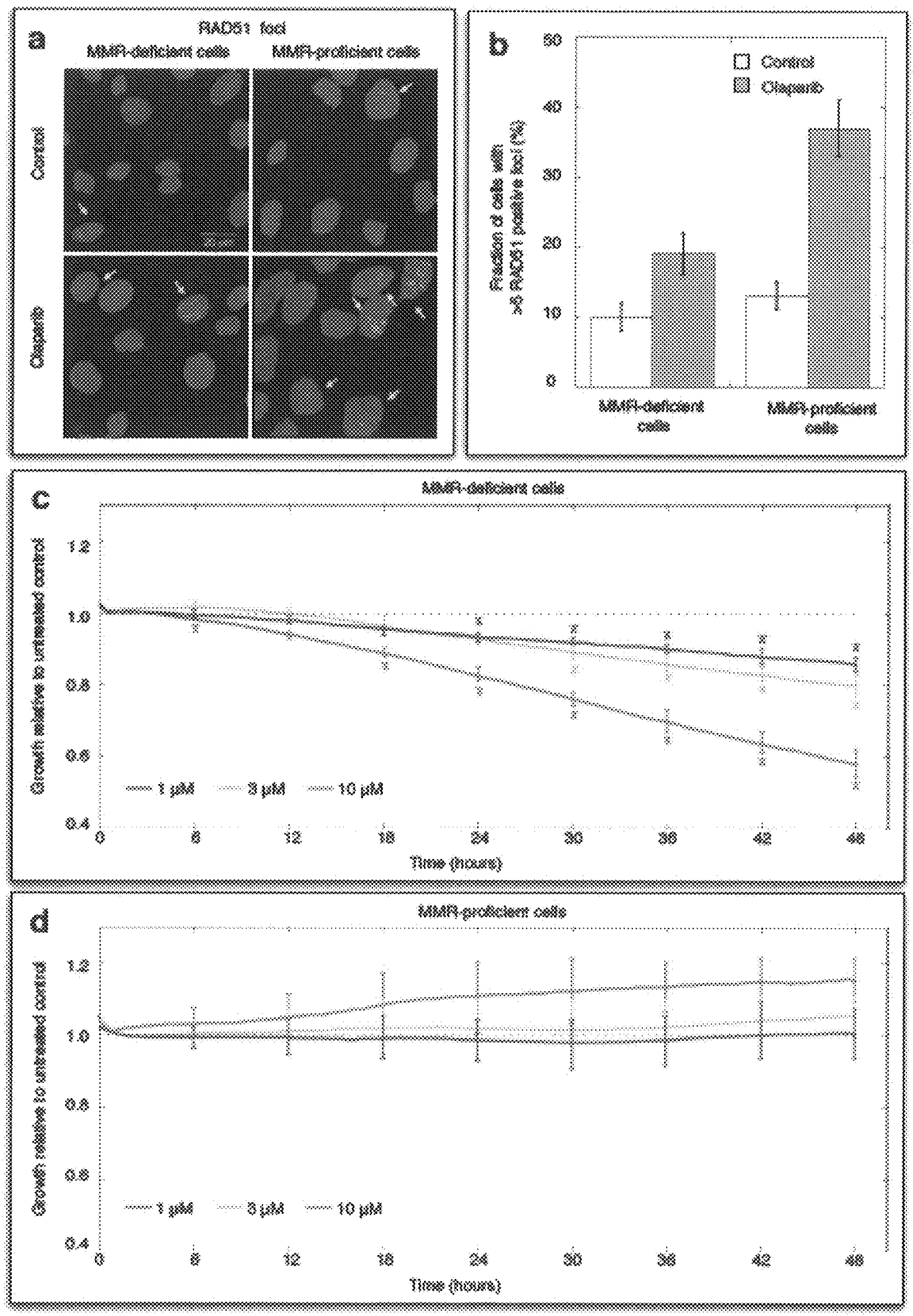
FIG. 7. MMR-deficient cells are sensitive to PARP inhibition. (a) Representative confocal images of MMR-deficient and MMR-proficient primary tumor cells exposed to 0 or 10 µM olaparib stained for the DNA repair marker RAD51 (green) and counterstained with DAPI (blue). Arrows (yellow) indicate RAD51-positive cells containing over 5 green nuclear foci. (b) Quantification of cells containing >5 RAD51 foci. Averages are shown for cultures of 8 different MMR-deficient and 4 different MMR-proficient cells at 24 hours after treatment with olaparib (10 µM) or carrier control. (c-d) The average cell proliferation of 8 MMR-deficient cells (c) and 4 MMR-proficient cells (d) with increasing concentrations of olaparib (1 µM, 3 µM, 10 µM). Real-time cell proliferation was measured using xCELLigence RTCA DP system (Roche Applied Science) until 48 hours after treatment. Values are normalized to the mock-treated control (0 µM olaparib). Error bars represent standard error of means. An asterisk indicates statistically significant difference between treated versus mock-treated cells at the indicated time point (P<0.05). In summary, MMR-deficient cells were characterized by a dose-dependent decrease in proliferation, whereas MMR-proficient cells did not respond to olaparib (P=2.0E-7 by repeated measurement; see also FIG. 7c).

Having established that MMR-deficient tumors are enriched in loss-of-function mutations affecting the DSB repair by HR pathway, whether this pathway is also functionally inactivated was investigated. This is relevant as these mutations represent heterozygous indels, whose loss-of-function effects may be compensated by the unaffected allele. Since during DNA replication single-strand breaks (SSB) are converted into DSBs, thereby activating DSB repair by HR, eight MMR-deficient and four MMR-proficient tumors (nine primary tumor cultures and three cancer cell lines) were exposed to the PARP inhibitor olaparib, which inhibits SSB repair, and subsequently quantified the relative number of cells with γH2AX- and RAD51-positive foci as a measure of DNA damage and active HR, respectively. Since none of the tumors were subjected to exome-sequencing, thus representing an independent set of MMR-deficient tumors, MMR status was determined using a 56-marker panel and confirmed using the Bethesda panel. Although a difference in RAD51 foci formation between MMR-deficient and MMR-proficient tumor cultures in the absence of olaparib (10±2% of cells versus 13±2% showed RAD51 foci formation, P=0.74; FIGS. 7a, 7b) was not observed, exposure to 10 μM olaparib triggered significantly less RAD51 foci formation in MMR-deficient than MMR-proficient cells (19±3% versus 37±4%; P=0.02; FIGS. 7a, 7b). In contrast, when investigating the degree of unrepaired DNA damage by H2AX immunofluorescence, olaparib drastically increased the number of γH2AX foci in all cells regardless of their MMR status (not shown), thus indicating that the extent of DNA damage was similar between both cultures. Since in BRCA1 or BRCA2-deficient cells, RAD51 foci formation is completely absent upon PARP inhibition (Farmer et al., 2005), these data suggest that in MMR-deficient cells the DSB repair by HR pathway is only partially inactivated.

Example 9

The PARP Inhibitor Olaparib Sensitizes MMR-deficient Tumors

As MMR-deficient tumors are characterized by reduced activity of the DSB repair by HR pathway, it was hypothesized that these tumors, similar to BRCA1-deficient tumors (Farmer et al., 2005), can be selectively targeted by PARP inhibition. All eight MMR-deficient and four MMR-proficient cultures were dose-dependently (1, 3 and 10 μM) exposed to olaparib and effects on proliferation were assessed. Individual MMR-deficient cultures, including each of the six MMR-deficient primary tumor cultures, exhibited a dose-dependent decrease in proliferation upon exposure to olaparib, whereas none of the MMR-proficient cells was characterized by a similar response. On average, 1, 3 and 10 μM of olaparib decreased proliferation of MMR-deficient cells by respectively 15%, 20% and 42% (P=0.02, P<0.001 and P<0.001, respectively versus untreated cells; FIG. 7c), whereas no effect was seen in MMR-proficient tumors at 48 hours (P=NS for all concentrations of olaparib; FIG. 7d). Overall, proliferation also differed highly significantly between MMR-deficient and -proficient tumors (P<0.001 by repeated measurement). Since BRCA1 and BRCA2-deficient cells exposed to respectively, 3 μM and 10 μM of olaparib, are characterized by a 78% and 91% decrease in viability (Farmer et al., 2005; Patel et al., 2012), these ex vivo data confirm that MMR-deficient cells, consistent with their partial inactivation of the DSB repair by HR pathway, are sensitized by PARP inhibition.

Cell Proliferation with xCELLigence System

Real-Time Cell Analyzer (RTCA) xCELLigence System (Roche Applied Science, Mannheim, Germany) was used to dynamically monitor cell proliferation rates. The system measures electrical impedance across microelectrodes on the bottom of tissue culture E-plates. The impedance measurement provides quantitative information about cell number, viability, morphology and adhesion. 5,000 cells/well were seeded on E-plate 16 (Roche) in 200 μl medium. 24 hours post-seeding, cells were treated with olaparib to the desired final concentration (1, 3, 10 μM olaparib). The final DMSO percent in all wells was 0.1%. Each treatment condition was measured in triplicate. Dynamic cell index values were monitored in five-minute intervals for 48 hours after treatments. Cell index values were normalized to the vehicle-treated control for each cell. The figure below shows cell proliferation rates for each of the cell cultures (MMR-deficient cells are shown in blue and MMR-proficient cells are shown in red). In summary, MMR-deficient cells were characterized by a dose-dependent decrease in proliferation, whereas MMR-proficient cells did not respond to olaparib (P=2.0E-7 by repeated measurement; FIG. 7c).

Discussion

Here, the first whole-genome of an MMR-deficient tumor was sequenced. It was observed that the majority of somatic substitutions consisted of nucleotide transitions and that adjacent nucleotides had an important context-dependent effect on determining which nucleotides were affected. Remarkably, these substitution patterns were also observed in the germ-line DNA and other eukaryotic organisms, and in these genomes correlated with important genome features in a similar manner (Hodgkinson and Eyre-Walker, 2011). In particular, it was observed a higher number of substitutions in methylated CpG sequences, implicating the MMR machinery in the repair of methylated cytosine deamination and demonstrating that the non-canonical MMR is critical to maintain genomic integrity.

Moreover, deamination is one of the most important processes underlying human disease-associated mutations and evolution. From that perspective, it is interesting to note that it was observed a very similar signature in ten additional exomes from MMR-deficient tumors, in de novo germ-line substitutions and in human and mouse SNP databases. Overall, these observations indicate that, similar to bacterial populations (Saint-Ruf and Matic, 2006), incomplete mismatch repair in humans contributes to natural selection through genetic adaptation.

About half of the mutations in the hypermutator represented indels. Importantly, although in high-throughput sequencing indel detection is burdened with very high false-positive rates, 92.7% of indels were validated using orthogonal technologies. Most indels specifically affect homopolymer stretches. This is relevant because the extended Bethesda panel, which is currently used for the diagnostic classification of MSI, has only limited sensitivity (80%, 84% and 55% for MLH1-, MSH2- and MSH6-deficient tumors (de la Chapelle and Hampel, 2010)), presumably because it consists of eight microsatellite and only two homopolymer markers. A 56-marker panel of hotspot mutations identified by exome sequencing was more sensitive in detecting MSI, especially in EM tumors, which are known to be more frequently MSH6- than MLH1 or MSH2-deficient. Furthermore, since 45 out of 56 markers were located in UTRs, which are less likely to drive clonal selection, MSI-H in cancers affecting different tissues were detected. Finally, since most of the 56 markers were located in homopolymers ≤10 bps in length, these markers are compatible with various low- to high-throughput genotyping technologies, such as single base pair extension (Sequenom MassArray), allele-specific hybridization (TAQMAN®) technologies, and melting curve analysis (including HRM). The most sensitive markers in Bethesda (BAT25 and BAT26) are clearly less compatible as they detect indels in homopolymers of 25 and 26 bps.

Intriguingly, it was observed that several indels in the exome, all of which represented loss-of-function mutations, occurred as hotspot mutations. On average, each tumor contained 30 hotspot mutations, which is remarkably high compared to previous cancer sequencing efforts of MMR-proficient tumors (Nik-Zainal et al., 2012; Rausch et al., 2012). Pathway analyses further revealed that the DSB repair by HR pathway was enriched in mutations; on average three mutations affected this pathway in each tumor. Mutations in DSB repair genes, such as MRE11A or RAD50, have previously been reported, but these studies focused on specific mutations in individual genes rather than on pathways, and for this reason could only establish that a fraction of MMR-deficient tumors is mutated in one of these genes (Miguel et al., 2007). Furthermore, although it is well established that BRCA1 and BRCA2-deficient cells, as well as cells deficient in Fanconi anemia- or other HR-related genes, are selectively hypersensitive to PARP inhibitors (Murai et al., 2012), data demonstrating the selectivity of MMR-deficient cell lines to PARP inhibition have not been conclusive. The most promising study, so far, observed a weak but significant correlation between expression levels of MRE11 and cytotoxicity to the PARP inhibitor ABT-888, but subsequent knockdown of MRE11 in a MSS cell line only modestly changed proliferation at high concentrations of the inhibitor (Vilar et al., 2011). In contrast, a hypothesis-free discovery that DSB repair by HR is the top pathway affected by loss-of-function mutations in MMR-deficient EM and CRC tumors, both a dataset and in the public TCGA dataset, suggests that mutations in several genes in the pathway cooperate to inactivate DSB repair by HR in MMR-deficient tumors. The finding that each MMR-deficient primary tumor culture, also those without MRE11 mutations, exhibited a dose-response effect upon challenge with olaparib functionally confirms the cumulated effect of these heterozygous mutations.

Several PARP inhibitors, such as olaparib (AZD2281), veliparib (ABT-888) and niraparib (MK-4827), have been developed. Initial studies with these inhibitors revealed a remarkable clinical benefit in breast or ovarian cancer patients carrying BRCA1 and BRCA2 mutations, without causing excess toxicity (Tutt et al., 2010). Despite these encouraging results, PARP inhibitors have not yet been approved (Maxwell and Domchek, 2012). One of the main hurdles is the lack of a cost-effective FDA-approved diagnostic test. Diagnostic tests for BRCA1 and BRCA2 mutation testing are not FDA-approved and associated costs are exceedingly high. As a result, pharmaceutical companies have been hesitant to start-up phase 3 clinical studies with PARP inhibitors (Maxwell and Domchek, 2012). These observations that MMR-deficient tumors are sensitive to PARP inhibition are very interesting in this regard. First of all, this study identifies a second subgroup of tumors that might be sensitive to PARP inhibition. Although it may be perceived that MSI tumors represent only a small proportion of CRC and EM tumors, the absolute patient population with MSI tumors that could benefit is as large, if not larger, than that with BRCA1 or BRCA2 mutations or even other targeted agents. Secondly, companion diagnostic testing for MSI tumors is already available, either using traditional methods, such as the Bethesda panel, or through profiling of frequent hotspot mutations. Translation of these observations into the clinical setting might thus go more rapid than for BRCA1 or BRCA2 mutation carriers, and could be further accelerated through a more sensitive and automatable/scalable marker panel. Thirdly, there is a great clinical need for targeted treatment options in MSI tumors. In particular, although stage II or III CRC tumors with MSI are characterized by a modestly improved prognosis, MSI tumors in the advanced setting are associated with more peritoneal metastasis and a worse overall survival independent of the chemotherapy regimen (Smith et al., 2013).

Additionally, whereas clinical resistance to PARP inhibition has been ascribed to secondary mutations restoring full-length BRCA1 or 2 proteins, thus re-establishing their function in tumor cells (Barber et al., 2012), such a mechanism is less likely to occur for each of the DSB repair genes affected by somatic mutations. This suggests that MMR-deficient tumors are less likely to develop resistance against PARP inhibitors, rendering them therapeutically more valuable in the long term.

Materials and Methods

Detection of mismatch repair deficiency: To assess MLH1, MSH2 and MSH6 expression in tumor and matched germ-line samples, immunohistochemistry was performed using the following monoclonal antibodies: clone ES05 for MLH1 (DAKO), clone G219-1129 for MSH2 (BD Pharmagen) and clone EP49 for MSH6 (Epitomics). The hypermethylation status of the MLH1 promoter regions was determined using the SALSA MS-MLPA KIT (MRC-Holland). MSI status was detected by the extended Bethesda panel.

Sample selection and preparation: fourteen endometrial, three colorectal and three ovarian tumor-normal pairs were selected for sequencing. Tumor DNA was derived from fresh frozen tumor tissue. All samples represented primary chemo-naïve tumors. Matched normal DNA for these 20 samples was extracted from peripheral white blood cells. Informed consent was obtained from all patients. In addition, four commercial T-cell acute lymphoblastic leukemia cell lines (DND41, CCRF-CEM, SUPT1 and RPMI-8402, obtained from DSMZ, http://www.dsmz.de/) were sequenced. DNA was extracted using the Qiagen DNAeasy kit for all samples.

Whole genome sequencing: five tumor-normal pairs, including three EM pairs and two ovarian pairs were selected for whole-genome sequencing. Paired-end sequencing was performed using the COMPLETE GENOMICS® service, which includes primary data analysis (image analysis, base calling, alignment and variant calling). The calldiff method of CGAtools (http://cgatools.sourceforge.net) was used to select somatic mutations. For each somatic mutation, CGAtools reports a somatic score, reflecting the confidence of the called somatic mutation. Higher scores indicate increased confidence. Using validation data generated by Sequenom MassARRAY, it was determined the optimal cut-off for selecting true somatic mutations and eliminating false-positive sequencing errors. Somatic score cut-off were applied to all somatic mutations lists and for further analyses only mutations with a score higher than these thresholds were used.

Exome sequencing of MMR-deficient tumors: Exomes of 15 endometrial, colorectal and ovarian tumor-normal pairs were captured using the TruSeq Exome Enrichment Kit (Illumina). Paired-end sequencing was performed with TruSeq SBS kits on the HiSeq2000 (2×75 bp for EM and ovarian samples, 2×100 bp for CRC samples). Exomes of four leukemia genomes were captured using Nimblegen SeqCap EZ Human Exome Library v2.0. Pairedend sequencing (2×50 bp) was performed with TruSeq SBS kits on the HiSeq2000. For all exomes, BWA was used to align the raw reads from each sequencing lane to the human reference genome using default parameters. Aligned reads were processed and sorted with SAMtools (v.0.1.13) and PCR duplicates were removed with Picard MarkDuplicates.

Base recalibration, local realignment around indels and single nucleotide variant calling were performed using the GenomeAnalysisToolKit (McKenna et al., 2010) (GATK v1.0.4487). Substitutions were called using the GATK Unified Genotyper, while indels were detected using Dindel (Albers et al., 2011) (v1.01). Initial quality filtering on substitutions was performed based on the quality score provided by the GATK variant caller. Mutations were retained only if the quality score was larger than Q30 in the tumor and matched normal sample.

Annotation of whole-genome and -exome data: Whole-genome sequence data were annotated using ANNOVAR and the UCSC RefGene hg18 annotation track (Wang et al., 2010). Repeat regions were determined using "grepseq" (http://code.google.com/p/grepseq/). Microsatellites were defined as di-, tri-, tetra-, penta- and hexanucleotide repeats consisting of at least two repeat units and with a minimal length of six bases, homopolymers as mononucleotide repeats with a minimal length of six bases, short homopolymers as mononucleotide repeats of three, four or five bases long. Annotation of repeat regions was performed using the intersectBed command of BEDtools.

Availability of whole-genome and exome data: The unfiltered variant files of all whole genome and exome data have been deposited at the European Genotype Phenotype Archive (http://www.ebi.ac.uk/ega) under restricted access, with accession number EGAS00001000182 and EGAS00001000158.

Primary tumor cultures and immunofluorescence: Nine primary endometrial and ovarian tumor cell cultures were established from tumors of the patients undergoing surgery. Primary tumor cell cultures were grown in RPMI1640 medium (GIBCO) supplemented with 20% FBS, 2 mM L-Glutamine, 100 U/ml penicillin, 100 µg/ml streptomycin, 1 µg/ml fungizone and 10 µg/ml gentamicin up to 20 passages. 25,000 cells/well were seeded on eight-well slides (Nunc) in 400 µl medium and grown for 24 hours. Following exposure to 0 or 10 µM olaparib, slides were rinsed in PBS, fixed in paraformaldehyde at 37° C., permeabilized with 0.1% Triton X-100 and blocked with BSA. Cells were stained with mouse anti-phospho-Histone H2A.X monoclonal antibody (Millipore clone JBW301, 1:100) or rabbit anti-Rad51 (H-92) polyclonal antibody (Santa Cruz H-92, 1:1000) and washed in 0.1% Triton X-100 in PBS. Alexa Fluor 488 (Invitrogen) was used and slides were mounted in Prolong Gold Antifade reagent containing DAPI (Molecular Probes). The percentage of foci positive cells (>5 foci per nucleus) was determined on a Zeiss LSM 510 inverted confocal microscope using Plan-Neofluar 40x/1.3 oil immersion objective. For each experiment, at least 100 nuclei were analyzed.

Cell Proliferation: Real-Time Cell Analyzer (RTCA) xCELLigence System (Roche) was used to dynamically monitor cell proliferation rates. 5,000 cells/well were seeded on E-plate 16 (Roche) in 200 µl medium. Olaparib (AZD-2281, JS Research Chemicals Trading) was dissolved in DMSO. 24 hours post-seeding, cells were treated with olaparib (1, 3, 10 olaparib). Each condition was measured in triplicate and all experiments were done in duplicate at different time points. Dynamic cell index values were monitored for 48 hours after treatment.

Materials

Mouse anti-phospho-Histone H2A.X (Ser139) monoclonal antibody (clone JBW301) was from Millipore Corporation, Billerica, Mass., USA. Rabbit anti-Rad51 (H-92) polyclonal antibody was from Santa Cruz Biotechnology, Santa Cruz, Calif., USA. Olaparib (AZD-2281, batch 3-8/10) was purchased from JS Research Chemicals Trading, Schleswig Holstein, Germany and was prepared as stock solution in DMSO and 10 aliquots were stored at −20° C. until use. Olaparib was further diluted 1:50 in respective media before being dilutes 1:20 in the well of the plate.

γH2AX Immunostaining

The degree of unrepaired DNA damage upon olaparib treatment was measured with γH2AX immunofluorescence. When there is a double strand break in DNA, H2AX is phosphorylated on Serine 139 and is referred to as γH2AX. For γH2AX immunostaining 25,000 cells/well were seeded on eight-well Lab-tek Permanox Chamber slides (Nunc) in 400 µl medium and incubated for 24 hours at 37° C., 5% $CO_2$. Subsequently, after 24 hours incubation, cells were exposed to 0 or 10 µM olaparib, slides were rinsed in phosphate-buffered saline (PBS) and fixed in 4% paraformaldehyde for 10 minutes at 37° C., permeabilized with 0.1% Triton X-100 for 5 minutes and blocked with 5% bovine serum albumin (BSA) for 10 minutes, both at room temperature. Cells were stained with a 1:100 dilution of mouse anti-phospho-Histone H2A.X (Ser139) monoclonal antibody (clone JBW301, Millipore). The primary antibody was visualized with Alexa Fluor-488 goat anti-mouse IgG (Alexa) and mounted in Prolong Gold Antifade reagent with DAPI (Molecular Probes). 10 µM Olaparib treatment increased the number of γH2AX foci 4-6 fold as compared to the baseline in all cells regardless of their MMR status, indicating that the extent of DSB DNA damage was similar between both cultures.

Rad51 Immunostaining

RAD51 protein plays a major role in the DSB repair by HR pathway and the formation of RAD51-positive foci is used as a marker of ongoing DSB repair by HR. To perform RAD51 immunostaining, 25,000 cells/well were seeded on eight-well Lab-tek Peimanox Chamber slides (Nunc) in 400 µl medium and incubated for 24 hours at 37° C., 5% $CO_2$ until olaparib treatment. After 24 hours incubation post-exposure to 0 or 10 µM olaparib, cells were washed with PBS at room temperature and fixed in 3% paraformaldehyde with 0.1% Triton X-100 in PBS for 20 minutes at 37° C. Slides were incubated with a 1:1000 dilution of rabbit anti-Rad51 (H-92) polyclonal antibody (Santa Cruz) for 16 hours at 4° C., then washed four times for 15 minutes with 0.1% Triton X-100 in PBS. The primary antibody was visualized with Alexa Fluor-488 goat anti-rabbit IgG (Alexa) and mounted in Prolong Gold Antifade reagent with DAPI (Molecular Probes).

Confocal Microscopy

γH2AX and RAD51 foci were visualized with Zeiss LSM 510 inverted confocal microscope using Plan-Neofluar 40x/1.3 oil immersion objective and excitation wavelengths of 488 and 750 nm (Chameleon coherent two-photon laser). Through focus maximum projection, images were acquired from optical sections 1.20 µm apart and with a section thickness of 0.5 nm. Images were processed using LSM510 software. Nuclei with >5 foci were scored positive, and at least 100 nuclei were counted per culture and per condition.

REFERENCES

1. Stratton, M. R., Campbell, P. J. & Futreal, P. A. The cancer genome. *Nature* 458, 719-724 (2009).
2. Futreal, P. A. et al. A census of human cancer genes. Nat. Rev. Cancer 4, 177-183 (2004).
3. Loeb, L. A., Loeb, K. R. & Anderson, J. P. Multiple mutations and cancer. *Proc. Natl. Acad. Sci. U.S.A.* 100, 776-781 (2003).

4. Loeb, L. A., Springgate, C. F. & Battula, N. Errors in DNA replication as a basis of malignant changes. *Cancer Res.* 34, 2311-2321 (1974).
5. Loeb, L. A. Human cancers express mutator phenotypes: origin, consequences and targeting. *Nat. Rev. Cancer* 11, 450-457 (2011).
6. Poulogiannis, G., Frayling, I. M. & Arends, M. J. DNA mismatch repair deficiency in sporadic colorectal cancer and Lynch syndrome. *Histopathology* 56, 167-179 (2010).
7. Beckman, R. A. & Loeb, L. A. Negative clonal selection in tumor evolution. *Genetics* 171, 2123-2131 (2005).
8. Jones, S. et al. Frequent mutations of chromatin remodeling gene ARID1A in ovarian clear cell carcinoma. *Science* 330, 228-231 (2010).
9. Boland C R, Thibodeau S N, Hamilton S R, et al: A National Cancer Institute Workshop on Microsatellite Instability for cancer detection and familial predisposition: Development of international criteria for the determination of microsatellite instability in colorectal cancer. *Cancer Res.* 58:5248-5257, 1998.
10. Palomaki G E, McClain M R, Melillo S, et al: EGAPP supplementary evidence review: DNA testing strategies aimed at reducing morbidity and mortality from Lynch syndrome. *Genetics in Medicine* 11:42-65, 2009.
11. Popat S, Hubner R, Houlston R S: Systematic review of microsatellite instability and colorectal cancer prognosis. *J. Clinl. Oncol.* 23:609-617, 2005.
12. Ribic C M, Sargent D J, Moore M J, et al: Tumor microsatellite-instability status as a predictor of benefit from Fluorouracil-based adjuvant chemotherapy for colon cancer. *N. Engl. J. Med.* 349:247-257, 2003.
13. Des Guetz G, Schischmanoff O, Nocalas P, et al: Does microsatellite instability predict the efficacy of adjuvant chemotherapy in colorectal cancer? A systematic review with meta-analysis. *Euro. J. Cancer* 45:1890-1896, 2009.
14. Dietmaier, W. et al. Diagnostic microsatellite instability: definition and correlation with mismatch repair protein expression. *Cancer Res.* 57, 4749-4756 (1997).
15. Umar, A. et al. Revised Bethesda Guidelines for hereditary nonpolyposis colorectal cancer (Lynch syndrome) and microsatellite instability. *J. Natl. Cancer Inst.* 96, 261-268 (2004).
16. de la Chapelle, A. & Hampel, H. Clinical relevance of microsatellite instability in colorectal cancer. *J. Clin. Oncol.* 28, 3380-3387 (2010).
17. Pyatt R, Chadwick R B, Johnson C K, et al: Polymorphic variation at the BAT-25 and BAT-26 loci in individuals of African origin: Implications for microsatellite instability testing. *Am. J. Pathol.* 155:349-353, 1999.
18. Lindor, N. M. et al. Immunohistochemistry versus microsatellite instability testing in phenotyping colorectal tumors. *J. Clin. Oncol.* 20, 1043-1048 (2002).
19. Simpkins, S. B. et al. MLH1 promoter methylation and gene silencing is the primary cause of microsatellite instability in sporadic endometrial cancers. *Hum. Mol. Genet.* 8, 661-666 (1999).
20. Heiman, J. G. et al. Incidence and functional consequences of hMLH1 promoter hypermethylation in colorectal carcinoma. *Proc. Natl. Acad. Sci. U.S.A.* 95, 6870-6875 (1998).
21. Quinlan, A. R. & Hall, I. M. BEDTools: a flexible suite of utilities for comparing genomic features. *Bioinformatics* 26, 841-842 (2010).
22. Banerjea, A. et al. Colorectal cancers with microsatellite instability display mRNA expression signatures characteristic of increased immunogenicity. *Mol. Cancer* 3, 21 (2004).
23. Kapushesky, M. et al. Gene expression atlas at the European bioinformatics institute. *Nucleic Acids Res.* 38, D690-698 (2010).
24. Pinol, V. et al. Accuracy of revised Bethesda guidelines, microsatellite instability, and immunohistochemistry for the identification of patients with hereditary nonpolyposis colorectal cancer. *JAMA* 293, 1986-1994 (2005).
25. Hewish, M., Lord, C. J., Martin, S. A., Cunningham, D. & Ashworth, A. Mismatch repair deficient colorectal cancer in the era of personalized treatment. *Nat. Rev. Clin. Oncol.* 7, 197-208 (2010).
26. Heijink, D. M. et al. Perspectives for tailored chemoprevention and treatment of colorectal cancer in Lynch syndrome. *Crit. Rev. Oncol. Hematol.* (2010).
27. Plaschke, J. et al. Aberrant protein expression and frequent allelic loss of MSH3 in colorectal cancer with low-level microsatellite instability. *Int. J. Colorectal Dis.* 27:911-919 (2012)

TABLE 1

| Nr of affected samples | Gene | Chromosome | Start Position | Affected homopolymer base | Affected homopolymer length | region |
|---|---|---|---|---|---|---|
| 13 | LRRC8D | chr1 | 90401405 | T | 11 | 3' UTR |
| 13 | NPR3 | chr5 | 32787131 | A | 11 | 3' UTR |
| 12 | AHCYL1 | chr1 | 110566210 | A | 14 | 3' UTR |
| 12 | CD5L | chr1 | 157801230 | A | 13 | 3' UTR |
| 12 | CEP170 | chr1 | 243288181 | T | 11 | 3' UTR |
| 12 | SAMD12 | chr8 | 119209320 | A | 11 | 3' UTR |
| 12 | UBE2Z | chr17 | 47005701 | A | 11 | 3' UTR |
| 11 | SEPT7 | chr7 | 35944036 | T | 11 | 3' UTR |
| 11 | CASK | chrX | 41379131 | A | 13 | 3' UTR |
| 11 | DIDO1 | chr20 | 61536691 | A | 11 | 3' UTR |
| 11 | EIF4G3 | chr1 | 21133286 | A | 13 | 3' UTR |
| 11 | FAM20B | chr1 | 179044906 | A | 12 | 3' UTR |
| 11 | GSK3B | chr3 | 119542766 | A | 11 | 3' UTR |
| 11 | HELZ | chr17 | 65070976 | A | 14 | 3' UTR |
| 11 | KCNK1 | chr1 | 233807667 | A | 11 | 3' UTR |
| 11 | KCNMB4 | chr12 | 70824838 | A | 14 | 3' UTR |
| 11 | LHX9 | chr1 | 197898395 | T | 12 | 3' UTR |
| 11 | LYRM1 | chr16 | 20935842 | T | 11 | 3' UTR |
| 11 | MYO5B | chr18 | 47351784 | A | 12 | 3' UTR |
| 11 | NARG2 | chr15 | 60712503 | T | 13 | 3' UTR |
| 11 | PPP1R12A | chr12 | 80169697 | T | 13 | 3' UTR |

TABLE 1-continued

| Nr of affected samples | Gene | Chromosome | Start Position | Affected homopolymer base | Affected homopolymer length | region |
|---|---|---|---|---|---|---|
| 11 | PRTG | chr15 | 55903921 | A | 11 | 3' UTR |
| 11 | RAB11FIP1 | chr8 | 37718707 | A | 13 | 3' UTR |
| 11 | RASGRP1 | chr15 | 38781450 | T | 13 | 3' UTR |
| 11 | SH3KBP1 | chrX | 19552231 | T | 13 | 3' UTR |
| 11 | SHROOM3 | chr4 | 77701305 | A | 12 | 3' UTR |
| 11 | TMEM26 | chr10 | 63166725 | A | 12 | 3' UTR |
| 11 | TMEM65 | chr8 | 125325217 | A | 11 | 3' UTR |
| 11 | TRIP11 | chr14 | 92435633 | A | 12 | 3' UTR |
| 11 | ZBTB7A | chr19 | 4046571 | T | 11 | 3' UTR |
| 11 | ZKSCAN1 | chr7 | 99633041 | T | 12 | 3' UTR |
| 11 | ZNF217 | chr20 | 52185289 | A | 13 | 3' UTR |
| 11 | ZNF275 | chrX | 152617043 | A | 12 | 3' UTR |
| 10 | ACVR1C | chr2 | 158387581 | T | 14 | 3' UTR |
| 10 | ARAP2 | chr4 | 36068192 | A | 12 | 3' UTR |
| 10 | BCL11A | chr2 | 60685409 | T | 12 | 3' UTR |
| 10 | C14orf101 | chr14 | 57114799 | A | 13 | 3' UTR |
| 10 | C15orf29 | chr15 | 34434105 | T | 12 | 3' UTR |
| 10 | C17orf63 | chr17 | 27083744 | T | 12 | 3' UTR |
| 10 | CBFB | chr16 | 67133068 | T | 11 | 3' UTR |
| 10 | CBX5 | chr12 | 54628041 | T | 13 | 3' UTR |
| 10 | CD36 | chr7 | 80306123 | T | 12 | 3' UTR |
| 10 | EPS15 | chr1 | 51821385 | A | 13 | 3' UTR |
| 10 | ERBB2IP | chr5 | 65375200 | T | 15 | 3' UTR |
| 10 | ERGIC2 | chr12 | 29493722 | T | 11 | 3' UTR |
| 10 | FAM38B | chr18 | 10670849 | T | 14 | 3' UTR |
| 10 | FGF9 | chr13 | 22278024 | T | 13 | 3' UTR |
| 10 | FLRT2 | chr14 | 86090074 | A | 12 | 3' UTR |
| 10 | GABPB1 | chr15 | 50570604 | A | 13 | 3' UTR |
| 10 | GBP1 | chr1 | 89518865 | T | 13 | 3' UTR |
| 10 | HIPK1 | chr1 | 114519857 | T | 14 | 3' UTR |
| 10 | KCNG1 | chr20 | 49620212 | T | 14 | 3' UTR |
| 10 | LPHN3 | chr4 | 62936763 | T | 12 | 3' UTR |
| 10 | MAPK1IP1L | chr14 | 55535728 | T | 13 | 3' UTR |
| 10 | MSR1 | chr8 | 15997800 | A | 11 | 3' UTR |
| 10 | NCEH1 | chr3 | 172348807 | A | 12 | 3' UTR |
| 10 | PEX13 | chr2 | 61276332 | T | 15 | 3' UTR |
| 10 | PTEN | chr10 | 89725293 | T | 11 | 3' UTR |
| 10 | RBMS1 | chr2 | 161128989 | T | 13 | 3' UTR |
| 10 | RSPO2 | chr8 | 108912568 | A | 11 | 3' UTR |
| 10 | SEMA6A | chr5 | 115779928 | A | 13 | 3' UTR |
| 10 | SLAIN2 | chr4 | 48428163 | T | 11 | 3' UTR |
| 10 | SNX31 | chr8 | 101585895 | T | 11 | 3' UTR |
| 10 | TMEM57 | chr1 | 25826052 | T | 12 | 3' UTR |
| 10 | TMTC3 | chr12 | 88591979 | T | 13 | 3' UTR |
| 10 | UST | chr6 | 149398012 | T | 13 | 3' UTR |
| 10 | VEGFA | chr6 | 43754176 | A | 12 | 3' UTR |
| 10 | KLHL4 | chrX | 86922591 | A | 13 | 3' UTR |
| 9 | AEN | chr15 | 89174888 | T | 12 | 3' UTR |
| 9 | ALDH8A1 | chr6 | 135238907 | T | 10 | 3' UTR |
| 9 | ANK2 | chr4 | 114303782 | T | 11 | 3' UTR |
| 9 | ARHGAP17 | chr16 | 24930800 | A | 14 | 3' UTR |
| 9 | ASPN | chr9 | 95218905 | A | 12 | 3' UTR |
| 9 | BCL11B | chr14 | 99637947 | T | 12 | 3' UTR |
| 9 | BCL7A | chr12 | 122498799 | A | 12 | 3' UTR |
| 9 | BRAP | chr12 | 112080129 | T | 12 | 3' UTR |
| 9 | C11orf87 | chr11 | 109296012 | A | 12 | 3' UTR |
| 9 | C15orf2 | chr15 | 24927891 | A | 10 | 3' UTR |
| 9 | CACNB4 | chr2 | 152694131 | T | 11 | 3' UTR |
| 9 | CALN1 | chr7 | 71245682 | A | 12 | 3' UTR |
| 9 | CAMK2A | chr5 | 149600684 | T | 11 | 3' UTR |
| 9 | CBLN4 | chr20 | 54572755 | A | 12 | 3' UTR |
| 9 | CCDC85C | chr14 | 99978765 | A | 12 | 3' UTR |
| 9 | CD1E | chr1 | 158327025 | T | 13 | 3' UTR |
| 9 | CISD1 | chr10 | 60048285 | T | 11 | 3' UTR |
| 9 | CMTM6 | chr3 | 32523862 | A | 12 | 3' UTR |
| 9 | CNR1 | chr6 | 88853530 | A | 11 | 3' UTR |
| 9 | CSNK1E | chr22 | 38686807 | T | 12 | 3' UTR |
| 9 | CYP1B1 | chr2 | 38297055 | T | 12 | 3' UTR |
| 9 | DLGAP2 | chr8 | 1652939 | A | 11 | 3' UTR |
| 9 | DRAM2 | chr1 | 111660181 | A | 11 | 3' UTR |
| 9 | DUSP10 | chr1 | 221875661 | A | 11 | 3' UTR |
| 9 | EHD4 | chr15 | 42191704 | A | 12 | 3' UTR |
| 9 | EPT1 | chr2 | 26617514 | T | 11 | 3' UTR |
| 9 | FAM104A | chr17 | 71204073 | A | 13 | 3' UTR |
| 9 | FAM46A | chr6 | 82458103 | A | 13 | 3' UTR |

TABLE 1-continued

| Nr of affected samples | Gene | Chromosome | Start Position | Affected homopolymer base | Affected homopolymer length | region |
|---|---|---|---|---|---|---|
| 9 | FMO2 | chr1 | 171178335 | A | 11 | 3' UTR |
| 9 | FOXN3 | chr14 | 89622979 | T | 13 | 3' UTR |
| 9 | FRMD4A | chr10 | 13686797 | A | 12 | 3' UTR |
| 9 | FYN | chr6 | 111982555 | T | 12 | 3' UTR |
| 9 | GLI3 | chr7 | 42001569 | A | 11 | 3' UTR |
| 9 | H3F3C | chr12 | 31944217 | T | 12 | 3' UTR |
| 9 | HIPK2 | chr7 | 139249947 | A | 14 | 3' UTR |
| 9 | HNRNPK | chr9 | 86583189 | T | 12 | 3' UTR |
| 9 | IER3IP1 | chr18 | 44682385 | A | 11 | 3' UTR |
| 9 | IFNGR1 | chr6 | 137518966 | A | 14 | 3' UTR |
| 9 | IL33 | chr9 | 6256984 | T | 12 | 3' UTR |
| 9 | KCTD7 | chr7 | 66105589 | T | 11 | 3' UTR |
| 9 | KCTD9 | chr8 | 25286171 | A | 12 | 3' UTR |
| 9 | KIAA1712 | chr4 | 175238738 | T | 13 | 3' UTR |
| 9 | KIAA2018 | chr3 | 113371321 | A | 11 | 3' UTR |
| 9 | KRT8 | chr12 | 53291007 | A | 11 | 3' UTR |
| 9 | LARP4B | chr10 | 856116 | A | 13 | 3' UTR |
| 9 | MED1 | chr17 | 37561712 | T | 13 | 3' UTR |
| 9 | MED28 | chr4 | 17626082 | T | 11 | 3' UTR |
| 9 | METTL9 | chr16 | 21667438 | A | 12 | 3' UTR |
| 9 | MEX3A | chr1 | 156043944 | T | 11 | 3' UTR |
| 9 | MLL2 | chr12 | 49413580 | A | 12 | 3' UTR |
| 9 | NAALAD2 | chr11 | 89925062 | T | 10 | 3' UTR |
| 9 | PCBD2 | chr5 | 134296980 | T | 14 | 3' UTR |
| 9 | PCDH9 | chr13 | 66878392 | A | 26 | 3' UTR |
| 9 | PGK1 | chrX | 77381770 | T | 13 | 3' UTR |
| 9 | PHACTR2 | chr6 | 144151003 | T | 10 | 3' UTR |
| 9 | PI15 | chr8 | 75766071 | T | 10 | 3' UTR |
| 9 | PLEKHA2 | chr8 | 38830288 | T | 13 | 3' UTR |
| 9 | PPP2R3A | chr3 | 135865826 | T | 11 | 3' UTR |
| 9 | PRCC | chr1 | 156770552 | T | 12 | 3' UTR |
| 9 | PRKD3 | chr2 | 37478759 | T | 12 | 3' UTR |
| 9 | PRPF40A | chr2 | 153512044 | T | 15 | 3' UTR |
| 9 | PSEN1 | chr14 | 73688298 | T | 13 | 3' UTR |
| 9 | RCC2 | chr1 | 17735285 | A | 14 | 3' UTR |
| 9 | RELL1 | chr4 | 37613352 | A | 12 | 3' UTR |
| 9 | RGS16 | chr1 | 182569291 | T | 26 | 3' UTR |
| 9 | RUNDC3B | chr7 | 87460421 | T | 12 | 3' UTR |
| 9 | SATB2 | chr2 | 200136194 | T | 12 | 3' UTR |
| 9 | SCML4 | chr6 | 108025850 | T | 13 | 3' UTR |
| 9 | SEC61G | chr7 | 54819993 | A | 11 | 3' UTR |
| 9 | SENP1 | chr12 | 48436768 | T | 11 | 3' UTR |
| 9 | SLC35D1 | chr1 | 67465371 | A | 13 | 3' UTR |
| 9 | SMAD3 | chr15 | 67486032 | T | 13 | 3' UTR |
| 9 | SPIN1 | chr9 | 91090830 | A | 12 | 3' UTR |
| 9 | SRC | chr20 | 36033633 | T | 13 | 3' UTR |
| 9 | TACC1 | chr8 | 38705639 | A | 11 | 3' UTR |
| 9 | TAF4B | chr18 | 23971176 | A | 14 | 3' UTR |
| 9 | TBC1D24 | chr16 | 2553486 | A | 13 | 3' UTR |
| 9 | THAP1 | chr8 | 42692467 | A | 12 | 3' UTR |
| 9 | TMEM106B | chr7 | 12273303 | A | 13 | 3' UTR |
| 9 | TMEM14B | chr6 | 10756863 | A | 11 | 3' UTR |
| 9 | TMEM209 | chr7 | 129805893 | A | 12 | 3' UTR |
| 9 | TMEM33 | chr4 | 41959614 | T | 14 | 3' UTR |
| 9 | TRA2A | chr7 | 23544783 | A | 11 | 3' UTR |
| 9 | TRIM66 | chr11 | 8635430 | A | 9 | 3' UTR |
| 9 | TTBK2 | chr15 | 43037302 | A | 12 | 3' UTR |
| 9 | UBE2M | chr19 | 59067290 | A | 13 | 3' UTR |
| 9 | USP44 | chr12 | 95911789 | A | 11 | 3' UTR |
| 9 | VCPIP1 | chr8 | 67545797 | A | 15 | 3' UTR |
| 9 | VGLL4 | chr3 | 11599949 | T | 13 | 3' UTR |
| 9 | XPO4 | chr13 | 21356029 | A | 10 | 3' UTR |
| 9 | ZBTB3 | chr11 | 62519422 | A | 12 | 3' UTR |
| 9 | ZNF264 | chr19 | 57730525 | A | 14 | 3' UTR |
| 9 | ZNF347 | chr19 | 53643153 | T | 12 | 3' UTR |
| 9 | ZNF704 | chr8 | 81550824 | A | 12 | 3' UTR |
| 9 | ZNF740 | chr12 | 53582896 | T | 11 | 3' UTR |
| 8 | A1CF | chr10 | 52566432 | T | 12 | 3' UTR |
| 8 | ABAT | chr16 | 8876792 | T | 11 | 3' UTR |
| 8 | ABI1 | chr10 | 27037487 | A | 11 | 3' UTR |
| 8 | ACTR2 | chr2 | 65498035 | A | 12 | 3' UTR |
| 8 | AIDA | chr1 | 222841524 | T | 10 | 3' UTR |
| 8 | AKIRIN1 | chr1 | 39471672 | A | 10 | 3' UTR |
| 8 | APH1B | chr15 | 63600287 | T | 12 | 3' UTR |
| 8 | ARHGAP18 | chr6 | 129898731 | A | 11 | 3' UTR |

TABLE 1-continued

| Nr of affected samples | Gene | Chromosome | Start Position | Affected homopolymer base | Affected homopolymer length | region |
|---|---|---|---|---|---|---|
| 8 | ARHGAP5 | chr14 | 32627034 | T | 11 | 3′ UTR |
| 8 | ASB7 | chr15 | 101189293 | T | 10 | 3′ UTR |
| 8 | ATRX | chrX | 76763679 | A | 13 | 3′ UTR |
| 8 | BACE1 | chr11 | 117159733 | T | 11 | 3′ UTR |
| 8 | C4orf49 | chr4 | 140187661 | T | 11 | 3′ UTR |
| 8 | CADPS | chr3 | 62384481 | T | 10 | 3′ UTR |
| 8 | CALML4 | chr15 | 68483096 | A | 12 | 3′ UTR |
| 8 | CAMKK2 | chr12 | 121676365 | A | 11 | 3′ UTR |
| 8 | CANX | chr5 | 179158477 | A | 12 | 3′ UTR |
| 8 | CANX | chr5 | 179155907 | T | 12 | 3′ UTR |
| 8 | CAP2 | chr6 | 17556926 | A | 11 | 3′ UTR |
| 8 | CCDC43 | chr17 | 42754916 | T | 13 | 3′ UTR |
| 8 | CCDC89 | chr11 | 85395559 | T | 10 | 3′ UTR |
| 8 | CD47 | chr3 | 107762288 | A | 11 | 3′ UTR |
| 8 | CDC23 | chr5 | 137524388 | A | 11 | 3′ UTR |
| 8 | CELF2 | chr10 | 11373567 | A | 11 | 3′ UTR |
| 8 | CHM | chrX | 85118100 | T | 13 | 3′ UTR |
| 8 | COPA | chr1 | 160258927 | T | 15 | 3′ UTR |
| 8 | CPEB3 | chr10 | 93809826 | A | 11 | 3′ UTR |
| 8 | CPNE3 | chr8 | 87571865 | T | 11 | 3′ UTR |
| 8 | CRTAP | chr3 | 33187520 | A | 12 | 3′ UTR |
| 8 | CSDA | chr12 | 10851811 | T | 14 | 3′ UTR |
| 8 | CSMD2 | chr1 | 33979967 | T | 12 | 3′ UTR |
| 8 | DCP2 | chr5 | 112351058 | T | 11 | 3′ UTR |
| 8 | DDHD1 | chr14 | 53513439 | A | 12 | 3′ UTR |
| 8 | DIEXF | chr1 | 210026704 | T | 15 | 3′ UTR |
| 8 | DLG3 | chrX | 69722274 | T | 13 | 3′ UTR |
| 8 | DLGAP2 | chr8 | 1653883 | T | 11 | 3′ UTR |
| 8 | DSC3 | chr18 | 28573880 | A | 12 | 3′ UTR |
| 8 | EFNA5 | chr5 | 106714693 | A | 12 | 3′ UTR |
| 8 | EPHA4 | chr2 | 222290623 | T | 11 | 3′ UTR |
| 8 | EXOSC2 | chr9 | 133579920 | A | 11 | 3′ UTR |
| 8 | FAM107B | chr10 | 14561157 | T | 12 | 3′ UTR |
| 8 | FAM116A | chr3 | 57611367 | A | 11 | 3′ UTR |
| 8 | FAM8A1 | chr6 | 17609273 | T | 11 | 3′ UTR |
| 8 | FAM91A1 | chr8 | 124826583 | T | 12 | 3′ UTR |
| 8 | FGFBP3 | chr10 | 93666830 | A | 11 | 3′ UTR |
| 8 | GABRG2 | chr5 | 161581834 | A | 11 | 3′ UTR |
| 8 | GAL | chr11 | 68458592 | T | 12 | 3′ UTR |
| 8 | GLS | chr2 | 191828629 | T | 12 | 3′ UTR |
| 8 | GPAM | chr10 | 113910871 | T | 12 | 3′ UTR |
| 8 | HCRTR2 | chr6 | 55147361 | T | 12 | 3′ UTR |
| 8 | HERPUD2 | chr7 | 35672678 | T | 14 | 3′ UTR |
| 8 | HIP1 | chr7 | 75166838 | A | 11 | 3′ UTR |
| 8 | HIPK2 | chr7 | 139257355 | T | 11 | 3′ UTR |
| 8 | HMGCS1 | chr5 | 43290194 | A | 16 | 3′ UTR |
| 8 | HNRNPUL1 | chr19 | 41812943 | A | 12 | 3′ UTR |
| 8 | HSPA9 | chr5 | 137891047 | A | 13 | 3′ UTR |
| 8 | IFIT2 | chr10 | 91068075 | T | 12 | 3′ UTR |
| 8 | IGF2BP1 | chr17 | 47129195 | T | 12 | 3′ UTR |
| 8 | KLF9 | chr9 | 73002115 | T | 11 | 3′ UTR |
| 8 | LHFPL4 | chr3 | 9543422 | A | 13 | 3′ UTR |
| 8 | LRAT | chr4 | 155673737 | A | 10 | 3′ UTR |
| 8 | LSM14A | chr19 | 34718607 | T | 12 | 3′ UTR |
| 8 | MAP3K5 | chr6 | 136878751 | T | 14 | 3′ UTR |
| 8 | MED13 | chr17 | 60023567 | A | 10 | 3′ UTR |
| 8 | MESDC1 | chr15 | 81296129 | T | 12 | 3′ UTR |
| 8 | METTL21B | chr12 | 58175145 | T | 15 | 3′ UTR |
| 8 | MITF | chr3 | 70014804 | A | 11 | 3′ UTR |
| 8 | MS4A7 | chr11 | 60161438 | A | 12 | 3′ UTR |
| 8 | MTF2 | chr1 | 93602675 | A | 14 | 3′ UTR |
| 8 | NAP1L4 | chr11 | 2966276 | A | 15 | 3′ UTR |
| 8 | NEDD1 | chr12 | 97346987 | A | 13 | 3′ UTR |
| 8 | NEK5 | chr13 | 52639268 | A | 13 | 3′ UTR |
| 8 | OXR1 | chr8 | 107763507 | T | 13 | 3′ UTR |
| 8 | PAPD5 | chr16 | 50264031 | A | 13 | 3′ UTR |
| 8 | PDE9A | chr21 | 44195537 | A | 13 | 3′ UTR |
| 8 | PIGM | chr1 | 159998798 | T | 11 | 3′ UTR |
| 8 | PM20D2 | chr6 | 89874860 | T | 11 | 3′ UTR |
| 8 | POGZ | chr1 | 151377008 | A | 13 | 3′ UTR |
| 8 | POMT2 | chr14 | 77741349 | T | 11 | 3′ UTR |
| 8 | POU2F2 | chr19 | 42595246 | T | 17 | 3′ UTR |
| 8 | RAB11FIP2 | chr10 | 119766958 | A | 12 | 3′ UTR |
| 8 | RAP2A | chr13 | 98118463 | A | 14 | 3′ UTR |
| 8 | RBM25 | chr14 | 73587904 | T | 14 | 3′ UTR |

TABLE 1-continued

| Nr of affected samples | Gene | Chromosome | Start Position | Affected homopolymer base | Affected homopolymer length | region |
|---|---|---|---|---|---|---|
| 8 | RBM33 | chr7 | 155569742 | T | 13 | 3' UTR |
| 8 | RBM45 | chr2 | 178994205 | T | 11 | 3' UTR |
| 8 | RIMKLB | chr12 | 8926680 | T | 11 | 3' UTR |
| 8 | RNF149 | chr2 | 101893233 | A | 10 | 3' UTR |
| 8 | RNLS | chr10 | 90034667 | A | 11 | 3' UTR |
| 8 | RORA | chr15 | 60788653 | A | 12 | 3' UTR |
| 8 | SAMD5 | chr6 | 147887423 | T | 12 | 3' UTR |
| 8 | SAR1A | chr10 | 71911798 | A | 12 | 3' UTR |
| 8 | SEL1L | chr14 | 81942829 | T | 13 | 3' UTR |
| 8 | SEMA4D | chr9 | 91992883 | A | 13 | 3' UTR |
| 8 | SETX | chr9 | 135139195 | T | 11 | 3' UTR |
| 8 | SH3RF1 | chr4 | 170017405 | A | 14 | 3' UTR |
| 8 | SMARCC2 | chr12 | 56556167 | A | 14 | 3' UTR |
| 8 | SNRNP40 | chr1 | 31732677 | A | 11 | 3' UTR |
| 8 | SOX4 | chr6 | 21596500 | A | 12 | 3' UTR |
| 8 | ST7L | chr1 | 113067470 | A | 10 | 3' UTR |
| 8 | STXBP5 | chr6 | 147708451 | A | 10 | 3' UTR |
| 8 | TGIF2 | chr20 | 35220571 | A | 14 | 3' UTR |
| 8 | TLE3 | chr15 | 70340967 | A | 11 | 3' UTR |
| 8 | TMC7 | chr16 | 19073947 | A | 10 | 3' UTR |
| 8 | TMEM57 | chr1 | 25825931 | T | 13 | 3' UTR |
| 8 | TNRC6B | chr22 | 40722031 | A | 10 | 3' UTR |
| 8 | TNRC6B | chr22 | 40720866 | T | 14 | 3' UTR |
| 8 | TNRC6B | chr22 | 40720294 | T | 15 | 3' UTR |
| 8 | TRPS1 | chr8 | 116424407 | A | 12 | 3' UTR |
| 8 | TSGA10 | chr2 | 99614595 | A | 13 | 3' UTR |
| 8 | TSPAN14 | chr10 | 82279557 | T | 14 | 3' UTR |
| 8 | TTL | chr2 | 113289264 | A | 11 | 3' UTR |
| 8 | TTLL5 | chr14 | 76420881 | T | 11 | 3' UTR |
| 8 | UBA6 | chr4 | 68481877 | T | 12 | 3' UTR |
| 8 | UFM1 | chr13 | 38935214 | T | 11 | 3' UTR |
| 8 | VCP | chr9 | 35056078 | T | 12 | 3' UTR |
| 8 | VEZF1 | chr17 | 56049540 | T | 11 | 3' UTR |
| 8 | WHSC1L1 | chr8 | 38175279 | A | 11 | 3' UTR |
| 8 | WSB1 | chr17 | 25640066 | A | 15 | 3' UTR |
| 8 | ZBTB43 | chr9 | 129596297 | A | 11 | 3' UTR |
| 8 | ZNF12 | chr7 | 6730082 | T | 12 | 3' UTR |
| 8 | ZNF238 | chr1 | 244220229 | T | 10 | 3' UTR |
| 8 | ZNF281 | chr1 | 200375822 | T | 12 | 3' UTR |
| 8 | ZNF621 | chr3 | 40575421 | A | 11 | 3' UTR |
| 7 | ADRBK2 | chr22 | 26121915 | A | 11 | 3' UTR |
| 7 | ALG9 | chr11 | 111655441 | A | 11 | 3' UTR |
| 7 | ANKIB1 | chr7 | 92029899 | T | 11 | 3' UTR |
| 7 | ANKRD28 | chr3 | 15709862 | T | 13 | 3' UTR |
| 7 | ARFIP1 | chr4 | 153832102 | T | 11 | 3' UTR |
| 7 | ARID4A | chr14 | 58840119 | T | 10 | 3' UTR |
| 7 | ATP11A | chr13 | 113540850 | T | 12 | 3' UTR |
| 7 | ATP2B1 | chr12 | 89984601 | T | 12 | 3' UTR |
| 7 | ATXN1 | chr6 | 16300902 | T | 11 | 3' UTR |
| 7 | BOD1L | chr4 | 13570453 | A | 11 | 3' UTR |
| 7 | C14orf37 | chr14 | 58471378 | T | 11 | 3' UTR |
| 7 | C2orf29 | chr2 | 101886538 | T | 12 | 3' UTR |
| 7 | C3orf58 | chr3 | 143709141 | T | 11 | 3' UTR |
| 7 | C3orf62 | chr3 | 49308391 | A | 11 | 3' UTR |
| 7 | C3orf72 | chr3 | 138671354 | T | 13 | 3' UTR |
| 7 | C8orf44-SGK3,SGK3 | chr8 | 67772690 | A | 11 | 3' UTR |
| 7 | CALN1 | chr7 | 71249416 | T | 10 | 3' UTR |
| 7 | CASK | chrX | 41377809 | A | 11 | 3' UTR |
| 7 | CD300LB | chr17 | 72518440 | A | 11 | 3' UTR |
| 7 | CDC25A | chr3 | 48199852 | T | 12 | 3' UTR |
| 7 | CDC73 | chr1 | 193220974 | T | 12 | 3' UTR |
| 7 | CDKN2AIPNL | chr5 | 133738313 | A | 11 | 3' UTR |
| 7 | CELSR1 | chr22 | 46756848 | A | 11 | 3' UTR |
| 7 | CMIP | chr16 | 81744987 | A | 10 | 3' UTR |
| 7 | COIL | chr17 | 55016354 | A | 14 | 3' UTR |
| 7 | COPS7B | chr2 | 232673378 | T | 13 | 3' UTR |
| 7 | COX18 | chr4 | 73923142 | A | 12 | 3' UTR |
| 7 | CSNK1E | chr22 | 38686864 | A | 11 | 3' UTR |
| 7 | DCP1A | chr3 | 53321360 | T | 27 | 3' UTR |
| 7 | DNAJC27 | chr2 | 25167221 | T | 14 | 3' UTR |
| 7 | DNMT3B | chr20 | 31395997 | T | 11 | 3' UTR |
| 7 | DTNA | chr18 | 32446839 | T | 12 | 3' UTR |
| 7 | EFNB1 | chrX | 68061978 | A | 12 | 3' UTR |
| 7 | ENTPD1 | chr10 | 97628618 | A | 10 | 3' UTR |
| 7 | ERBB4 | chr2 | 212247967 | A | 18 | 3' UTR |

TABLE 1-continued

| Nr of affected samples | Gene | Chromosome | Start Position | Affected homopolymer base | Affected homopolymer length | region |
|---|---|---|---|---|---|---|
| 7 | EYA1 | chr8 | 72110673 | A | 12 | 3' UTR |
| 7 | FAM118A | chr22 | 45736689 | T | 11 | 3' UTR |
| 7 | FAM126B | chr2 | 201838933 | A | 13 | 3' UTR |
| 7 | FAM13B | chr5 | 137274915 | A | 11 | 3' UTR |
| 7 | FAM169A | chr5 | 74075446 | T | 12 | 3' UTR |
| 7 | FAM60A | chr12 | 31435556 | A | 10 | 3' UTR |
| 7 | FBLN7 | chr2 | 112945284 | T | 11 | 3' UTR |
| 7 | FGF9 | chr13 | 22277774 | T | 10 | 3' UTR |
| 7 | FKBP5 | chr6 | 35554624 | T | 12 | 3' UTR |
| 7 | FOXO3 | chr6 | 109005013 | A | 11 | 3' UTR |
| 7 | FXR1 | chr3 | 180694863 | T | 14 | 3' UTR |
| 7 | GBP6 | chr1 | 89851722 | A | 13 | 3' UTR |
| 7 | GNB1 | chr1 | 1717242 | T | 12 | 3' UTR |
| 7 | GNRHR | chr4 | 68604166 | A | 12 | 3' UTR |
| 7 | GPC3 | chrX | 132670054 | A | 13 | 3' UTR |
| 7 | GRIK2 | chr6 | 102517011 | T | 11 | 3' UTR |
| 7 | H3F3B | chr17 | 73774199 | T | 13 | 3' UTR |
| 7 | HAS2 | chr8 | 122625936 | A | 12 | 3' UTR |
| 7 | HELZ | chr17 | 65073603 | A | 11 | 3' UTR |
| 7 | HIPK2 | chr7 | 139250450 | T | 11 | 3' UTR |
| 7 | HN1 | chr17 | 73132058 | A | 12 | 3' UTR |
| 7 | HNRNPA3 | chr2 | 178088002 | T | 10 | 3' UTR |
| 7 | HNRNPR | chr1 | 23636874 | T | 11 | 3' UTR |
| 7 | HUS1B | chr6 | 656079 | A | 10 | 3' UTR |
| 7 | KDM5A | chr12 | 389523 | T | 11 | 3' UTR |
| 7 | KHNYN | chr14 | 24908391 | T | 11 | 3' UTR |
| 7 | KIF3A | chr5 | 132029672 | A | 14 | 3' UTR |
| 7 | KIF5C | chr2 | 149879665 | T | 10 | 3' UTR |
| 7 | KLHL28 | chr14 | 45398006 | T | 11 | 3' UTR |
| 7 | LRCH1 | chr13 | 47325657 | A | 10 | 3' UTR |
| 7 | LRIG2 | chr1 | 113667282 | T | 11 | 3' UTR |
| 7 | LRP6 | chr12 | 12272288 | A | 12 | 3' UTR |
| 7 | MAGEB3 | chrX | 30255422 | A | 11 | 3' UTR |
| 7 | MAK | chr6 | 10764372 | T | 9 | 3' UTR |
| 7 | MCTS1 | chrX | 119754487 | A | 14 | 3' UTR |
| 7 | MDM2 | chr12 | 69236873 | T | 13 | 3' UTR |
| 7 | MED19 | chr11 | 57471199 | T | 13 | 3' UTR |
| 7 | MESDC1 | chr15 | 81296262 | T | 9 | 3' UTR |
| 7 | MGAT4A | chr2 | 99235842 | A | 11 | 3' UTR |
| 7 | MLL3 | chr7 | 151832596 | T | 11 | 3' UTR |
| 7 | MTMR9 | chr8 | 11185354 | A | 10 | 3' UTR |
| 7 | NAA35 | chr9 | 88637203 | A | 10 | 3' UTR |
| 7 | NAF1 | chr4 | 164049985 | A | 11 | 3' UTR |
| 7 | NHLH1 | chr1 | 160341680 | A | 11 | 3' UTR |
| 7 | NIPAL3 | chr1 | 24799398 | A | 12 | 3' UTR |
| 7 | NPAS3 | chr14 | 34271068 | A | 12 | 3' UTR |
| 7 | NRF1 | chr7 | 129395138 | T | 11 | 3' UTR |
| 7 | NTRK2 | chr9 | 87487518 | T | 11 | 3' UTR |
| 7 | PALM2 | chr9 | 112708967 | A | 25 | 3' UTR |
| 7 | PAPSS2 | chr10 | 89507276 | A | 11 | 3' UTR |
| 7 | PCDH7 | chr4 | 31146675 | T | 12 | 3' UTR |
| 7 | PCSK2 | chr20 | 17463028 | T | 11 | 3' UTR |
| 7 | PHF6 | chrX | 133561520 | T | 10 | 3' UTR |
| 7 | PKP4 | chr2 | 159537312 | T | 10 | 3' UTR |
| 7 | PLXNA4 | chr7 | 131809795 | A | 13 | 3' UTR |
| 7 | POFUT1 | chr20 | 30826323 | A | 11 | 3' UTR |
| 7 | PPP1CB | chr2 | 29024298 | T | 14 | 3' UTR |
| 7 | PPP2R3A | chr3 | 135865709 | A | 14 | 3' UTR |
| 7 | PRPF4 | chr9 | 116054493 | A | 14 | 3' UTR |
| 7 | PRPF40A | chr2 | 153509691 | A | 11 | 3' UTR |
| 7 | PRR23A | chr3 | 138723892 | A | 9 | 3' UTR |
| 7 | PSMD11 | chr17 | 30807996 | A | 11 | 3' UTR |
| 7 | PTAFR | chr1 | 28475836 | T | 27 | 3' UTR |
| 7 | PTPN11 | chr12 | 112944240 | T | 12 | 3' UTR |
| 7 | PTPN18 | chr2 | 131131908 | T | 14 | 3' UTR |
| 7 | PTPRJ | chr11 | 48189153 | T | 13 | 3' UTR |
| 7 | PURB | chr7 | 44920830 | A | 9 | 3' UTR |
| 7 | RB1CC1 | chr8 | 53536112 | A | 11 | 3' UTR |
| 7 | RBM12B | chr8 | 94745437 | A | 11 | 3' UTR |
| 7 | RC3H1 | chr1 | 173901043 | T | 11 | 3' UTR |
| 7 | RDH10 | chr8 | 74236678 | T | 10 | 3' UTR |
| 7 | RECK | chr9 | 36123172 | T | 11 | 3' UTR |
| 7 | RPS6KA2 | chr6 | 166824706 | T | 13 | 3' UTR |
| 7 | RS1 | chrX | 18659977 | A | 13 | 3' UTR |
| 7 | RUNDC3B | chr7 | 87459581 | A | 13 | 3' UTR |

TABLE 1-continued

| Nr of affected samples | Gene | Chromosome | Start Position | Affected homopolymer base | Affected homopolymer length | region |
|---|---|---|---|---|---|---|
| 7 | RXRA | chr9 | 137331937 | A | 12 | 3' UTR |
| 7 | RYBP | chr3 | 72424549 | T | 9 | 3' UTR |
| 7 | RYR3 | chr15 | 34157541 | A | 10 | 3' UTR |
| 7 | SAMD10 | chr20 | 62605493 | T | 12 | 3' UTR |
| 7 | SEC31A | chr4 | 83740163 | T | 11 | 3' UTR |
| 7 | SENP1 | chr12 | 48437910 | T | 11 | 3' UTR |
| 7 | SGCD | chr5 | 156190730 | A | 12 | 3' UTR |
| 7 | SH3BP5 | chr3 | 15297082 | T | 13 | 3' UTR |
| 7 | SH3RF1 | chr4 | 170016066 | A | 11 | 3' UTR |
| 7 | SLC16A7 | chr12 | 60173983 | A | 11 | 3' UTR |
| 7 | SLC2A3 | chr12 | 8072022 | T | 13 | 3' UTR |
| 7 | SLC30A7 | chr1 | 101446221 | T | 11 | 3' UTR |
| 7 | SLC7A11 | chr4 | 139092374 | A | 11 | 3' UTR |
| 7 | SLC9A2 | chr2 | 103326258 | T | 10 | 3' UTR |
| 7 | SMAD4 | chr18 | 48609102 | T | 12 | 3' UTR |
| 7 | SNAPC1 | chr14 | 62262433 | A | 11 | 3' UTR |
| 7 | SNAPC3 | chr9 | 15461137 | A | 13 | 3' UTR |
| 7 | SNX27 | chr1 | 151666826 | T | 11 | 3' UTR |
| 7 | SPCS3 | chr4 | 177250201 | T | 10 | 3' UTR |
| 7 | STARD7 | chr2 | 96851899 | A | 14 | 3' UTR |
| 7 | TBC1D22B | chr6 | 37299299 | T | 12 | 3' UTR |
| 7 | TBL1XR1 | chr3 | 176741889 | A | 13 | 3' UTR |
| 7 | TFAP2C | chr20 | 55213320 | T | 11 | 3' UTR |
| 7 | TIGD6 | chr5 | 149373143 | T | 13 | 3' UTR |
| 7 | TMEM108 | chr3 | 133116233 | A | 14 | 3' UTR |
| 7 | TMEM161B | chr5 | 87491917 | T | 10 | 3' UTR |
| 7 | TMEM47 | chrX | 34646666 | T | 12 | 3' UTR |
| 7 | TMEM64 | chr8 | 91637753 | A | 12 | 3' UTR |
| 7 | TNRC6B | chr22 | 40719790 | A | 14 | 3' UTR |
| 7 | TNRC6C | chr17 | 76101834 | T | 9 | 3' UTR |
| 7 | TOMM20 | chr1 | 235275027 | T | 12 | 3' UTR |
| 7 | TPH1 | chr11 | 18042321 | A | 11 | 3' UTR |
| 7 | UACA | chr15 | 70946988 | A | 12 | 3' UTR |
| 7 | UBXN7 | chr3 | 196080741 | T | 11 | 3' UTR |
| 7 | UGT2B28 | chr4 | 70160632 | A | 11 | 3' UTR |
| 7 | USP28 | chr11 | 113669136 | A | 11 | 3' UTR |
| 7 | WDR82 | chr3 | 52289627 | A | 11 | 3' UTR |
| 7 | ZBTB34 | chr9 | 129646763 | T | 11 | 3' UTR |
| 7 | ZBTB44 | chr11 | 130102910 | A | 11 | 3' UTR |
| 7 | ZDHHC13 | chr11 | 19197719 | A | 10 | 3' UTR |
| 7 | ZNF136 | chr19 | 12299608 | A | 13 | 3' UTR |
| 7 | ZNF238 | chr1 | 244219573 | A | 9 | 3' UTR |
| 7 | ZNF563 | chr19 | 12428823 | T | 15 | 3' UTR |
| 7 | ZNF652 | chr17 | 47369576 | T | 11 | 3' UTR |
| 7 | ZNF716 | chr7 | 57529811 | A | 10 | 3' UTR |
| 7 | ZNF737 | chr19 | 20723566 | A | 11 | 3' UTR |
| 7 | ZNF737 | chr19 | 20722094 | A | 14 | 3' UTR |
| 6 | MARCH1 | chr4 | 164446860 | T | 9 | 3' UTR |
| 6 | ADRA1D | chr20 | 4201344 | T | 10 | 3' UTR |
| 6 | AJAP1 | chr1 | 4843660 | T | 11 | 3' UTR |
| 6 | AK4 | chr1 | 65692499 | T | 11 | 3' UTR |
| 6 | ANKH | chr5 | 14705393 | A | 13 | 3' UTR |
| 6 | ANKRD13C | chr1 | 70727638 | A | 12 | 3' UTR |
| 6 | ANKRD40 | chr17 | 48770711 | A | 10 | 3' UTR |
| 6 | AP1AR | chr4 | 113190822 | A | 11 | 3' UTR |
| 6 | APOL1 | chr22 | 36662141 | T | 12 | 3' UTR |
| 6 | ARHGAP28 | chr18 | 6914974 | A | 10 | 3' UTR |
| 6 | ARID1B | chr6 | 157530262 | A | 14 | 3' UTR |
| 6 | ARIH1 | chr15 | 72877867 | A | 12 | 3' UTR |
| 6 | ARL10 | chr5 | 175800426 | T | 10 | 3' UTR |
| 6 | ATF2 | chr2 | 175939223 | A | 12 | 3' UTR |
| 6 | ATP11C | chrX | 138809822 | A | 10 | 3' UTR |
| 6 | ATXN1 | chr6 | 16301824 | A | 13 | 3' UTR |
| 6 | BCLAF1 | chr6 | 136581674 | T | 11 | 3' UTR |
| 6 | BIN1 | chr2 | 127805622 | T | 10 | 3' UTR |
| 6 | BNIP3L | chr8 | 26268445 | A | 10 | 3' UTR |
| 6 | BOD1L | chr4 | 13571144 | A | 10 | 3' UTR |
| 6 | C1orf9 | chr1 | 172580460 | T | 9 | 3' UTR |
| 6 | C5orf43 | chr5 | 60453908 | A | 9 | 3' UTR |
| 6 | C6orf145 | chr6 | 3723315 | A | 11 | 3' UTR |
| 6 | C9orf167 | chr9 | 140176659 | T | 10 | 3' UTR |
| 6 | CAMLG | chr5 | 134086670 | A | 13 | 3' UTR |
| 6 | CBL | chr11 | 119175340 | T | 14 | 3' UTR |
| 6 | CCND2 | chr12 | 4411110 | T | 12 | 3' UTR |
| 6 | CCNE2 | chr8 | 95892992 | A | 11 | 3' UTR |

TABLE 1-continued

| Nr of affected samples | Gene | Chromosome | Start Position | Affected homopolymer base | Affected homopolymer length | region |
|---|---|---|---|---|---|---|
| 6 | CHD7 | chr8 | 61778758 | T | 11 | 3' UTR |
| 6 | CHP | chr15 | 41572703 | T | 27 | 3' UTR |
| 6 | CIT | chr12 | 120123939 | T | 11 | 3' UTR |
| 6 | CLCN5 | chrX | 49862213 | A | 12 | 3' UTR |
| 6 | CLN8 | chr8 | 1729701 | T | 14 | 3' UTR |
| 6 | CLSPN | chr1 | 36201819 | A | 17 | 3' UTR |
| 6 | CRTC1 | chr19 | 18890267 | T | 14 | 3' UTR |
| 6 | DAG1 | chr3 | 49571620 | T | 11 | 3' UTR |
| 6 | DNAJB7 | chr22 | 41256660 | T | 14 | 3' UTR |
| 6 | DNAJC17 | chr15 | 41060070 | A | 14 | 3' UTR |
| 6 | DSTYK | chr1 | 205112278 | T | 14 | 3' UTR |
| 6 | DYRK2 | chr12 | 68054141 | A | 11 | 3' UTR |
| 6 | EBF1 | chr5 | 158125829 | A | 12 | 3' UTR |
| 6 | ECE1 | chr1 | 21546032 | A | 10 | 3' UTR |
| 6 | EGR3 | chr8 | 22545637 | T | 11 | 3' UTR |
| 6 | EIF4EBP2 | chr10 | 72188037 | A | 11 | 3' UTR |
| 6 | EIF5A2 | chr3 | 170607962 | A | 11 | 3' UTR |
| 6 | ELTD1 | chr1 | 79356149 | T | 11 | 3' UTR |
| 6 | ENTPD4 | chr8 | 23289680 | A | 11 | 3' UTR |
| 6 | EPM2AIP1 | chr3 | 37030780 | T | 11 | 3' UTR |
| 6 | ERBB2IP | chr5 | 65376306 | A | 11 | 3' UTR |
| 6 | ERBB4 | chr2 | 212243952 | T | 11 | 3' UTR |
| 6 | FAM120C | chrX | 54098998 | A | 12 | 3' UTR |
| 6 | FAM122A | chr9 | 71396662 | T | 11 | 3' UTR |
| 6 | FAM168B | chr2 | 131805979 | G | 9 | 3' UTR |
| 6 | FBLIM1 | chr1 | 16112130 | A | 10 | 3' UTR |
| 6 | FBXO21 | chr12 | 117582899 | T | 11 | 3' UTR |
| 6 | FBXO27 | chr19 | 39514872 | T | 12 | 3' UTR |
| 6 | FGFR1OP2 | chr12 | 27118594 | A | 11 | 3' UTR |
| 6 | FOXP1 | chr3 | 71007140 | T | 11 | 3' UTR |
| 6 | G3BP1 | chr5 | 151184779 | T | 11 | 3' UTR |
| 6 | GABRB2 | chr5 | 160717254 | T | 12 | 3' UTR |
| 6 | GDA | chr9 | 74866560 | T | 12 | 3' UTR |
| 6 | GIT1 | chr17 | 27901146 | A | 12 | 3' UTR |
| 6 | GJC1 | chr17 | 42878975 | T | 13 | 3' UTR |
| 6 | GPR4 | chr19 | 46093443 | A | 11 | 3' UTR |
| 6 | GSK3B | chr3 | 119544323 | A | 9 | 3' UTR |
| 6 | GSR | chr8 | 30536666 | A | 19 | 3' UTR |
| 6 | GTF3C1 | chr16 | 27471985 | T | 11 | 3' UTR |
| 6 | HAS2 | chr8 | 122625490 | T | 10 | 3' UTR |
| 6 | HMGN2 | chr1 | 26801737 | T | 15 | 3' UTR |
| 6 | HNRNPA3 | chr2 | 178088125 | A | 12 | 3' UTR |
| 6 | HNRNPH2, RPL36A-HNRNPH2 | chrX | 100668932 | T | 13 | 3' UTR |
| 6 | HNRNPU | chr1 | 245014280 | T | 11 | 3' UTR |
| 6 | HOMEZ | chr14 | 23744114 | A | 14 | 3' UTR |
| 6 | ICA1L | chr2 | 203642599 | T | 22 | 3' UTR |
| 6 | IGF2BP3 | chr7 | 23350733 | T | 12 | 3' UTR |
| 6 | IGFBP5 | chr2 | 217537045 | T | 14 | 3' UTR |
| 6 | ILF3 | chr19 | 10796313 | T | 10 | 3' UTR |
| 6 | INSR | chr19 | 7112347 | A | 9 | 3' UTR |
| 6 | IPCEF1 | chr6 | 154476149 | A | 12 | 3' UTR |
| 6 | KCNJ2 | chr17 | 68175917 | A | 10 | 3' UTR |
| 6 | KDM5A | chr12 | 393489 | T | 12 | 3' UTR |
| 6 | KHSRP | chr19 | 6413651 | T | 10 | 3' UTR |
| 6 | KIAA0825 | chr5 | 93489194 | T | 8 | 3' UTR |
| 6 | KIAA1671 | chr22 | 25592399 | T | 12 | 3' UTR |
| 6 | LANCL1 | chr2 | 211297865 | T | 9 | 3' UTR |
| 6 | LCORL | chr4 | 17882781 | T | 11 | 3' UTR |
| 6 | LIN7C | chr11 | 27517703 | A | 14 | 3' UTR |
| 6 | LMO4 | chr1 | 87813143 | A | 11 | 3' UTR |
| 6 | LRRC4 | chr7 | 127668232 | T | 9 | 3' UTR |
| 6 | LYRM7 | chr5 | 130537006 | A | 12 | 3' UTR |
| 6 | MAGI1 | chr3 | 65340577 | T | 11 | 3' UTR |
| 6 | MAL | chr2 | 95719330 | A | 10 | 3' UTR |
| 6 | MEIS2 | chr15 | 37183446 | T | 10 | 3' UTR |
| 6 | MKL1 | chr22 | 40806781 | C | 9 | 3' UTR |
| 6 | MKLN1 | chr7 | 131175980 | A | 10 | 3' UTR |
| 6 | MTDH | chr8 | 98740104 | A | 10 | 3' UTR |
| 6 | NANP | chr20 | 25595618 | A | 11 | 3' UTR |
| 6 | NAPEPLD | chr7 | 102742595 | A | 10 | 3' UTR |
| 6 | NCEH1 | chr3 | 172349171 | T | 12 | 3' UTR |
| 6 | NCOA5 | chr20 | 44689693 | A | 10 | 3' UTR |
| 6 | NKAIN2 | chr6 | 125146684 | T | 9 | 3' UTR |
| 6 | NPNT | chr4 | 106892254 | T | 13 | 3' UTR |

TABLE 1-continued

| Nr of affected samples | Gene | Chromosome | Start Position | Affected homopolymer base | Affected homopolymer length | region |
|---|---|---|---|---|---|---|
| 6 | NPR3 | chr5 | 32786465 | T | 11 | 3' UTR |
| 6 | NR2F2 | chr15 | 96881216 | T | 10 | 3' UTR |
| 6 | NR3C1 | chr5 | 142657694 | T | 9 | 3' UTR |
| 6 | NUFIP2 | chr17 | 27584536 | T | 12 | 3' UTR |
| 6 | OPA3 | chr19 | 46052745 | T | 12 | 3' UTR |
| 6 | ORAI3 | chr16 | 30965549 | T | 15 | 3' UTR |
| 6 | OTUB2 | chr14 | 94512841 | A | 11 | 3' UTR |
| 6 | OXR1 | chr8 | 107764239 | A | 10 | 3' UTR |
| 6 | PAQR7 | chr1 | 26188503 | A | 31 | 3' UTR |
| 6 | PCDHB3 | chr5 | 140482943 | T | 10 | 3' UTR |
| 6 | PDP2 | chr16 | 66920308 | T | 10 | 3' UTR |
| 6 | PEBP1 | chr12 | 118582973 | A | 21 | 3' UTR |
| 6 | PELI2 | chr14 | 56764487 | T | 13 | 3' UTR |
| 6 | PGPEP1 | chr19 | 18477965 | A | 20 | 3' UTR |
| 6 | PGR | chr11 | 100902321 | T | 15 | 3' UTR |
| 6 | PHLDA1 | chr12 | 76421757 | T | 12 | 3' UTR |
| 6 | PID1 | chr2 | 229889188 | A | 9 | 3' UTR |
| 6 | PIGN | chr18 | 59712451 | A | 11 | 3' UTR |
| 6 | PIM2 | chrX | 48770831 | A | 20 | 3' UTR |
| 6 | PLAA | chr9 | 26904508 | T | 10 | 3' UTR |
| 6 | PLEKHA6 | chr1 | 204190022 | A | 13 | 3' UTR |
| 6 | PPM1A | chr14 | 60761433 | T | 10 | 3' UTR |
| 6 | PPP1R3D | chr20 | 58513623 | T | 11 | 3' UTR |
| 6 | PRDM1 | chr6 | 106557171 | T | 10 | 3' UTR |
| 6 | PTCD3 | chr2 | 86366926 | A | 11 | 3' UTR |
| 6 | PTGDR | chr14 | 52741746 | A | 11 | 3' UTR |
| 6 | RAB22A | chr20 | 56941068 | T | 10 | 3' UTR |
| 6 | RAB8B | chr15 | 63557574 | T | 13 | 3' UTR |
| 6 | RAD51L1 | chr14 | 68964202 | T | 12 | 3' UTR |
| 6 | RBM12B | chr8 | 94744118 | T | 11 | 3' UTR |
| 6 | RNF10 | chr12 | 121014987 | T | 11 | 3' UTR |
| 6 | RORA | chr15 | 60785852 | T | 11 | 3' UTR |
| 6 | RRAGD | chr6 | 90076341 | A | 13 | 3' UTR |
| 6 | RRM2B | chr8 | 103216874 | A | 9 | 3' UTR |
| 6 | RTF1 | chr15 | 41775015 | T | 10 | 3' UTR |
| 6 | RUFY3 | chr4 | 71655520 | A | 12 | 3' UTR |
| 6 | S100A4 | chr1 | 153516162 | A | 10 | 3' UTR |
| 6 | SBK1 | chr16 | 28334644 | A | 13 | 3' UTR |
| 6 | SERBP1 | chr1 | 67878789 | T | 11 | 3' UTR |
| 6 | SIPA1L3 | chr19 | 38698671 | T | 17 | 3' UTR |
| 6 | SLC16A6 | chr17 | 66265042 | A | 11 | 3' UTR |
| 6 | SLC25A20 | chr3 | 48894565 | A | 12 | 3' UTR |
| 6 | SLC30A5 | chr5 | 68399959 | T | 11 | 3' UTR |
| 6 | SLC35B4 | chr7 | 133977008 | T | 10 | 3' UTR |
| 6 | SLC44A5 | chr1 | 75668544 | A | 11 | 3' UTR |
| 6 | SLMAP | chr3 | 57913669 | T | 13 | 3' UTR |
| 6 | SMAD5 | chr5 | 135515014 | A | 10 | 3' UTR |
| 6 | SMEK1 | chr14 | 91924528 | A | 11 | 3' UTR |
| 6 | SOCS4 | chr14 | 55512747 | T | 10 | 3' UTR |
| 6 | SORCS1 | chr10 | 108333635 | A | 11 | 3' UTR |
| 6 | SOX1 | chr13 | 112724861 | A | 10 | 3' UTR |
| 6 | SOX4 | chr6 | 21597192 | A | 11 | 3' UTR |
| 6 | SPIRE1 | chr18 | 12449300 | T | 11 | 3' UTR |
| 6 | SPTLC2 | chr14 | 77975645 | A | 11 | 3' UTR |
| 6 | SRCIN1 | chr17 | 36687785 | T | 12 | 3' UTR |
| 6 | STEAP3 | chr2 | 120023163 | T | 12 | 3' UTR |
| 6 | STK11 | chr19 | 1228058 | T | 11 | 3' UTR |
| 6 | STX12 | chr1 | 28150575 | T | 10 | 3' UTR |
| 6 | STX3 | chr11 | 59569295 | A | 11 | 3' UTR |
| 6 | SULF2 | chr20 | 46286320 | A | 10 | 3' UTR |
| 6 | SUZ12 | chr17 | 30326763 | T | 12 | 3' UTR |
| 6 | SYNJ2BP | chr14 | 70834868 | A | 10 | 3' UTR |
| 6 | TARDBP | chr1 | 11084333 | T | 11 | 3' UTR |
| 6 | TBC1D1 | chr4 | 38140081 | A | 10 | 3' UTR |
| 6 | TBC1D5 | chr3 | 17201870 | T | 11 | 3' UTR |
| 6 | TCERG1 | chr5 | 145890609 | T | 12 | 3' UTR |
| 6 | TCF20 | chr22 | 42556646 | A | 12 | 3' UTR |
| 6 | TFAP2B | chr6 | 50814900 | A | 10 | 3' UTR |
| 6 | TLCD2 | chr17 | 1608003 | T | 11 | 3' UTR |
| 6 | TMTC3 | chr12 | 88591036 | T | 25 | 3' UTR |
| 6 | TMTC3 | chr12 | 88590177 | T | 12 | 3' UTR |
| 6 | TNIP3 | chr4 | 122052756 | T | 22 | 3' UTR |
| 6 | TNRC6B | chr22 | 40731027 | T | 10 | 3' UTR |
| 6 | TOR1AIP1 | chr1 | 179888400 | A | 12 | 3' UTR |
| 6 | TP53INP1 | chr8 | 95941646 | A | 13 | 3' UTR |

TABLE 1-continued

| Nr of affected samples | Gene | Chromo-some | Start Position | Affected homo-polymer base | Affected homo-polymer length | region |
|---|---|---|---|---|---|---|
| 6 | TRIM66 | chr11 | 8636480 | T | 13 | 3' UTR |
| 6 | TRRAP | chr7 | 98610830 | T | 11 | 3' UTR |
| 6 | TSR2 | chrX | 54471045 | T | 10 | 3' UTR |
| 6 | TTC30B | chr2 | 178415366 | T | 10 | 3' UTR |
| 6 | UBASH3B | chr11 | 122681008 | T | 13 | 3' UTR |
| 6 | VAX1 | chr10 | 118893337 | A | 10 | 3' UTR |
| 6 | WDFY1 | chr2 | 224742022 | T | 12 | 3' UTR |
| 6 | WIF1 | chr12 | 65444595 | T | 13 | 3' UTR |
| 6 | XKR7 | chr20 | 30585884 | G | 10 | 3' UTR |
| 6 | XYLT1 | chr16 | 17199775 | A | 11 | 3' UTR |
| 6 | ZADH2 | chr18 | 72910475 | T | 13 | 3' UTR |
| 6 | ZBTB7A | chr19 | 4046340 | T | 11 | 3' UTR |
| 6 | ZNF238 | chr1 | 244219033 | T | 11 | 3' UTR |
| 6 | ZNF24 | chr18 | 32917176 | T | 12 | 3' UTR |
| 6 | ZNF362 | chr1 | 33764950 | T | 12 | 3' UTR |
| 6 | ZNF407 | chr18 | 72516095 | T | 11 | 3' UTR |
| 6 | ZNF430 | chr19 | 21241252 | A | 14 | 3' UTR |
| 6 | ZNF80 | chr3 | 113954690 | A | 12 | 3' UTR |
| 5 | ABHD2 | chr15 | 89739843 | T | 10 | 3' UTR |
| 5 | ABI2 | chr2 | 204292194 | T | 10 | 3' UTR |
| 5 | ACOX1 | chr17 | 73941869 | A | 10 | 3' UTR |
| 5 | ACTBL2 | chr5 | 56777006 | T | 10 | 3' UTR |
| 5 | AFF2 | chrX | 148080284 | T | 10 | 3' UTR |
| 5 | ANAPC16 | chr10 | 73993363 | T | 10 | 3' UTR |
| 5 | ARF5 | chr7 | 127231635 | T | 10 | 3' UTR |
| 5 | ARL1 | chr12 | 101787092 | T | 11 | 3' UTR |
| 5 | ASAH1 | chr8 | 17914871 | A | 10 | 3' UTR |
| 5 | ATP1B2 | chr17 | 7560698 | A | 10 | 3' UTR |
| 5 | ATXN7 | chr3 | 63985894 | T | 11 | 3' UTR |
| 5 | B3GNT7 | chr2 | 232264806 | T | 26 | 3' UTR |
| 5 | BAG1 | chr9 | 33253979 | T | 12 | 3' UTR |
| 5 | BCL11B | chr14 | 99638830 | A | 9 | 3' UTR |
| 5 | BMP7 | chr20 | 55744815 | T | 10 | 3' UTR |
| 5 | BTBD11 | chr12 | 108052115 | T | 12 | 3' UTR |
| 5 | BTBD7 | chr14 | 93708030 | A | 10 | 3' UTR |
| 5 | C14orf126 | chr14 | 31917025 | A | 10 | 3' UTR |
| 5 | C14orf28 | chr14 | 45376124 | A | 12 | 3' UTR |
| 5 | C18orf56 | chr18 | 649879 | T | 15 | 3' UTR |
| 5 | C20orf12 | chr20 | 18364708 | T | 12 | 3' UTR |
| 5 | C5orf41 | chr5 | 172563230 | A | 11 | 3' UTR |
| 5 | C7orf68 | chr7 | 128097963 | A | 10 | 3' UTR |
| 5 | C9orf66 | chr9 | 214453 | T | 9 | 3' UTR |
| 5 | CABP4 | chr11 | 67226510 | T | 14 | 3' UTR |
| 5 | CACNB4 | chr2 | 152695481 | T | 11 | 3' UTR |
| 5 | CASP2 | chr7 | 143003342 | T | 25 | 3' UTR |
| 5 | CBFB | chr16 | 67133969 | T | 9 | 3' UTR |
| 5 | CBX5 | chr12 | 54630019 | T | 10 | 3' UTR |
| 5 | CCDC102B | chr18 | 66722368 | A | 9 | 3' UTR |
| 5 | CCND1 | chr11 | 69468187 | T | 14 | 3' UTR |
| 5 | CCND2 | chr12 | 4409520 | T | 10 | 3' UTR |
| 5 | CCNL2 | chr1 | 1327869 | T | 9 | 3' UTR |
| 5 | CCR1 | chr3 | 46244273 | G | 10 | 3' UTR |
| 5 | CDH3 | chr16 | 68732679 | T | 11 | 3' UTR |
| 5 | CEP68 | chr2 | 65312945 | A | 12 | 3' UTR |
| 5 | CGGBP1 | chr3 | 88104472 | T | 10 | 3' UTR |
| 5 | CHMP2B | chr3 | 87303064 | A | 14 | 3' UTR |
| 5 | CIB2 | chr15 | 78397249 | T | 12 | 3' UTR |
| 5 | CLEC5A | chr7 | 141627861 | T | 12 | 3' UTR |
| 5 | CNST | chr1 | 246830426 | A | 10 | 3' UTR |
| 5 | COL19A1 | chr6 | 70918737 | T | 12 | 3' UTR |
| 5 | COL8A2 | chr1 | 36561052 | A | 10 | 3' UTR |
| 5 | COX16,SYNJ2BP-COX16 | chr14 | 70793015 | A | 14 | 3' UTR |
| 5 | CPLX4 | chr18 | 56963029 | A | 10 | 3' UTR |
| 5 | CREB3L2 | chr7 | 137563914 | A | 10 | 3' UTR |
| 5 | CSNK1G1 | chr15 | 64461259 | A | 9 | 3' UTR |
| 5 | CTIF | chr18 | 46388423 | T | 10 | 3' UTR |
| 5 | CUL5 | chr11 | 107975795 | T | 13 | 3' UTR |
| 5 | CYP17A1 | chr10 | 104590293 | A | 11 | 3' UTR |
| 5 | DAND5 | chr19 | 13084677 | T | 17 | 3' UTR |
| 5 | DCUN1D5 | chr11 | 102930486 | G | 7 | 3' UTR |
| 5 | DDN | chr12 | 49389156 | A | 11 | 3' UTR |
| 5 | DDX5 | chr17 | 62495664 | A | 10 | 3' UTR |
| 5 | DDX6 | chr11 | 118622141 | A | 10 | 3' UTR |
| 5 | DLX3 | chr17 | 48067712 | T | 14 | 3' UTR |
| 5 | DNAJC15 | chr13 | 43681779 | T | 9 | 3' UTR |

TABLE 1-continued

| Nr of affected samples | Gene | Chromosome | Start Position | Affected homopolymer base | Affected homopolymer length | region |
|---|---|---|---|---|---|---|
| 5 | DNAJC18 | chr5 | 138747976 | T | 11 | 3' UTR |
| 5 | DOPEY2 | chr21 | 37666277 | A | 14 | 3' UTR |
| 5 | DPYSL2 | chr8 | 26515559 | T | 10 | 3' UTR |
| 5 | DSEL | chr18 | 65174583 | A | 26 | 3' UTR |
| 5 | DTNA | chr18 | 32448118 | A | 16 | 3' UTR |
| 5 | DYNC1LI2 | chr16 | 66755235 | T | 11 | 3' UTR |
| 5 | DYRK2 | chr12 | 68055576 | T | 10 | 3' UTR |
| 5 | EBF1 | chr5 | 158125671 | T | 15 | 3' UTR |
| 5 | EFNA5 | chr5 | 106716350 | A | 11 | 3' UTR |
| 5 | EFNA5 | chr5 | 106712689 | T | 12 | 3' UTR |
| 5 | EFR3B | chr2 | 25378726 | T | 13 | 3' UTR |
| 5 | ELAVL1 | chr19 | 8023995 | T | 11 | 3' UTR |
| 5 | ELAVL3 | chr19 | 11562278 | T | 16 | 3' UTR |
| 5 | EPS15 | chr1 | 51822219 | A | 12 | 3' UTR |
| 5 | ESRP1 | chr8 | 95719492 | A | 11 | 3' UTR |
| 5 | EVI5 | chr1 | 92978704 | A | 11 | 3' UTR |
| 5 | EVI5 | chr1 | 92977467 | T | 11 | 3' UTR |
| 5 | EXTL2 | chr1 | 101338118 | A | 10 | 3' UTR |
| 5 | FAF2 | chr5 | 175935960 | T | 10 | 3' UTR |
| 5 | FAM105A | chr5 | 14611814 | T | 10 | 3' UTR |
| 5 | FAM164A | chr8 | 79631105 | T | 10 | 3' UTR |
| 5 | FAM20B | chr1 | 179044326 | A | 13 | 3' UTR |
| 5 | FAM46A | chr6 | 82457992 | T | 10 | 3' UTR |
| 5 | FBN2 | chr5 | 127594063 | A | 10 | 3' UTR |
| 5 | FBRSL1 | chr12 | 133160562 | A | 9 | 3' UTR |
| 5 | FBXL4 | chr6 | 99321799 | T | 10 | 3' UTR |
| 5 | FBXO36 | chr2 | 230876985 | A | 11 | 3' UTR |
| 5 | FBXW2 | chr9 | 123524089 | A | 12 | 3' UTR |
| 5 | FCGR3A | chr1 | 161512430 | T | 9 | 3' UTR |
| 5 | FCHSD2 | chr11 | 72549649 | A | 10 | 3' UTR |
| 5 | FICD | chr12 | 108913292 | A | 11 | 3' UTR |
| 5 | FOXN2 | chr2 | 48604358 | T | 10 | 3' UTR |
| 5 | FOXN3 | chr14 | 89627649 | T | 11 | 3' UTR |
| 5 | GABRB2 | chr5 | 160719907 | A | 9 | 3' UTR |
| 5 | GNA13 | chr17 | 63005677 | A | 10 | 3' UTR |
| 5 | GNAI2 | chr3 | 50296405 | C | 9 | 3' UTR |
| 5 | GNAI2 | chr3 | 50296330 | A | 12 | 3' UTR |
| 5 | GPR12 | chr13 | 27330332 | T | 10 | 3' UTR |
| 5 | GPR137B | chr1 | 236372038 | T | 10 | 3' UTR |
| 5 | GPR37L1 | chr1 | 202098133 | T | 21 | 3' UTR |
| 5 | GRID1 | chr10 | 87359476 | T | 11 | 3' UTR |
| 5 | GRIN3A | chr9 | 104331901 | A | 9 | 3' UTR |
| 5 | GRPEL2 | chr5 | 148731880 | T | 14 | 3' UTR |
| 5 | HAPLN1 | chr5 | 82937251 | A | 10 | 3' UTR |
| 5 | HBS1L | chr6 | 135357535 | A | 10 | 3' UTR |
| 5 | HDAC4 | chr2 | 239974109 | A | 9 | 3' UTR |
| 5 | HEXA | chr15 | 72636197 | T | 10 | 3' UTR |
| 5 | HNRNPK | chr9 | 86583800 | A | 10 | 3' UTR |
| 5 | HOOK3 | chr8 | 42876247 | A | 29 | 3' UTR |
| 5 | HRH1 | chr3 | 11303522 | A | 11 | 3' UTR |
| 5 | HUWE1 | chrX | 53559710 | T | 11 | 3' UTR |
| 5 | IGDCC4 | chr15 | 65674432 | A | 12 | 3' UTR |
| 5 | IGF1 | chr12 | 102790988 | A | 11 | 3' UTR |
| 5 | IGF2BP2 | chr3 | 185361762 | T | 12 | 3' UTR |
| 5 | IGFBP5 | chr2 | 217537240 | A | 11 | 3' UTR |
| 5 | INSR | chr19 | 7116555 | A | 12 | 3' UTR |
| 5 | JAM3 | chr11 | 134020535 | T | 12 | 3' UTR |
| 5 | KCTD1 | chr18 | 24035448 | T | 12 | 3' UTR |
| 5 | KCTD6 | chr3 | 58487415 | T | 11 | 3' UTR |
| 5 | KDM5A | chr12 | 393804 | T | 11 | 3' UTR |
| 5 | KIAA1324 | chr1 | 109749368 | T | 11 | 3' UTR |
| 5 | KIAA1324 | chr1 | 109748644 | T | 11 | 3' UTR |
| 5 | KIAA1737 | chr14 | 77582032 | T | 14 | 3' UTR |
| 5 | KIAA2026 | chr9 | 5919249 | T | 11 | 3' UTR |
| 5 | KLHL20 | chr1 | 173754885 | A | 12 | 3' UTR |
| 5 | KLHL24 | chr3 | 183400567 | T | 10 | 3' UTR |
| 5 | LDHAL6A | chr11 | 18500557 | T | 12 | 3' UTR |
| 5 | LENG8 | chr19 | 54972801 | T | 9 | 3' UTR |
| 5 | LHFP | chr13 | 39917691 | A | 12 | 3' UTR |
| 5 | LMO4 | chr1 | 87811174 | A | 11 | 3' UTR |
| 5 | LPHN3 | chr4 | 62937355 | A | 12 | 3' UTR |
| 5 | LPL | chr8 | 19823634 | A | 11 | 3' UTR |
| 5 | LRRC27 | chr10 | 134193076 | T | 9 | 3' UTR |
| 5 | LRRC4B | chr19 | 51020187 | T | 10 | 3' UTR |
| 5 | LTN1 | chr21 | 30301899 | T | 10 | 3' UTR |

TABLE 1-continued

| Nr of affected samples | Gene | Chromosome | Start Position | Affected homopolymer base | Affected homopolymer length | region |
|---|---|---|---|---|---|---|
| 5 | MAP1B | chr5 | 71505347 | A | 11 | 3' UTR |
| 5 | MAP3K7 | chr6 | 91225524 | A | 9 | 3' UTR |
| 5 | MAPK1 | chr22 | 22114660 | T | 12 | 3' UTR |
| 5 | MAX | chr14 | 65543065 | A | 10 | 3' UTR |
| 5 | MED1 | chr17 | 37562164 | T | 11 | 3' UTR |
| 5 | MED13 | chr17 | 60022040 | A | 11 | 3' UTR |
| 5 | MED28 | chr4 | 17625638 | T | 10 | 3' UTR |
| 5 | MKX | chr10 | 27962805 | A | 10 | 3' UTR |
| 5 | MNT | chr17 | 2287533 | T | 13 | 3' UTR |
| 5 | MOBKL2A | chr19 | 2072745 | A | 13 | 3' UTR |
| 5 | MORC1 | chr3 | 108677146 | A | 10 | 3' UTR |
| 5 | MST4 | chrX | 131208596 | A | 9 | 3' UTR |
| 5 | MTA2 | chr11 | 62360911 | A | 27 | 3' UTR |
| 5 | MTF1 | chr1 | 38278949 | A | 11 | 3' UTR |
| 5 | NAA38 | chr7 | 117832209 | A | 9 | 3' UTR |
| 5 | NAPG | chr18 | 10551001 | T | 11 | 3' UTR |
| 5 | NCOA1 | chr2 | 24991385 | A | 25 | 3' UTR |
| 5 | NCOA3 | chr20 | 46282984 | T | 11 | 3' UTR |
| 5 | NKAIN4 | chr20 | 61872616 | T | 12 | 3' UTR |
| 5 | NLGN4X | chrX | 5808268 | T | 11 | 3' UTR |
| 5 | NMNAT1 | chr1 | 10044969 | T | 8 | 3' UTR |
| 5 | NPLOC4 | chr17 | 79525610 | A | 9 | 3' UTR |
| 5 | NPNT | chr4 | 106890724 | T | 10 | 3' UTR |
| 5 | NR2F2 | chr15 | 96881909 | T | 10 | 3' UTR |
| 5 | NUFIP2 | chr17 | 27585085 | T | 12 | 3' UTR |
| 5 | ODZ4 | chr11 | 78367062 | T | 9 | 3' UTR |
| 5 | OGFOD1 | chr16 | 56510333 | T | 12 | 3' UTR |
| 5 | OPA3 | chr19 | 46049757 | T | 14 | 3' UTR |
| 5 | OSBP | chr11 | 59341900 | T | 12 | 3' UTR |
| 5 | PAPD5 | chr16 | 50264179 | T | 10 | 3' UTR |
| 5 | PAPD5 | chr16 | 50263692 | T | 10 | 3' UTR |
| 5 | PAPD5 | chr16 | 50263454 | A | 8 | 3' UTR |
| 5 | PFN1 | chr17 | 4848972 | A | 10 | 3' UTR |
| 5 | PHKB | chr16 | 47734578 | A | 10 | 3' UTR |
| 5 | PIGM | chr1 | 159998080 | T | 11 | 3' UTR |
| 5 | PIGM | chr1 | 159997525 | A | 10 | 3' UTR |
| 5 | PKP2 | chr12 | 32944046 | A | 11 | 3' UTR |
| 5 | PLAGL2 | chr20 | 30781644 | A | 11 | 3' UTR |
| 5 | PLEKHM3 | chr2 | 208686453 | A | 10 | 3' UTR |
| 5 | POLR3B | chr12 | 106903452 | A | 9 | 3' UTR |
| 5 | PPIC | chr5 | 122359467 | A | 12 | 3' UTR |
| 5 | PPP1R10 | chr6 | 30568234 | A | 11 | 3' UTR |
| 5 | PPP6C | chr9 | 127911821 | A | 11 | 3' UTR |
| 5 | PPPDE1 | chr1 | 244869241 | A | 12 | 3' UTR |
| 5 | PRKX | chrX | 3525721 | T | 9 | 3' UTR |
| 5 | PRRG1 | chrX | 37313537 | T | 10 | 3' UTR |
| 5 | PSMD5 | chr9 | 123578376 | A | 10 | 3' UTR |
| 5 | PTGS2 | chr1 | 186642025 | T | 9 | 3' UTR |
| 5 | RAB11FIP2 | chr10 | 119765266 | T | 11 | 3' UTR |
| 5 | RANBP10 | chr16 | 67757024 | T | 10 | 3' UTR |
| 5 | RASGRP4 | chr19 | 38900377 | A | 11 | 3' UTR |
| 5 | RBL1 | chr20 | 35632028 | A | 13 | 3' UTR |
| 5 | RBM15B | chr3 | 51431679 | T | 11 | 3' UTR |
| 5 | RBMS3 | chr3 | 30046424 | A | 11 | 3' UTR |
| 5 | RC3H1 | chr1 | 173904709 | A | 11 | 3' UTR |
| 5 | RHOBTB3 | chr5 | 95129188 | A | 12 | 3' UTR |
| 5 | RIMBP2 | chr12 | 130882589 | A | 11 | 3' UTR |
| 5 | RNF41 | chr12 | 56599353 | G | 10 | 3' UTR |
| 5 | RRP15 | chr1 | 218506526 | A | 10 | 3' UTR |
| 5 | SAMD12 | chr8 | 119208740 | A | 13 | 3' UTR |
| 5 | SAR1A | chr10 | 71910315 | A | 10 | 3' UTR |
| 5 | SARM1 | chr17 | 26726913 | T | 12 | 3' UTR |
| 5 | SATB2 | chr2 | 200135086 | T | 10 | 3' UTR |
| 5 | SCAI | chr9 | 127706579 | T | 16 | 3' UTR |
| 5 | SCAMP1 | chr5 | 77772627 | A | 10 | 3' UTR |
| 5 | SCUBE3 | chr6 | 35216591 | A | 10 | 3' UTR |
| 5 | SDC4 | chr20 | 43954848 | A | 9 | 3' UTR |
| 5 | SENP5 | chr3 | 196660478 | T | 11 | 3' UTR |
| 5 | SERPINE1 | chr7 | 100781987 | G | 8 | 3' UTR |
| 5 | SFRS18 | chr6 | 99848035 | A | 12 | 3' UTR |
| 5 | SH3KBP1 | chrX | 19553810 | T | 12 | 3' UTR |
| 5 | SIK1 | chr21 | 44835578 | A | 10 | 3' UTR |
| 5 | SKI | chr1 | 2240043 | T | 10 | 3' UTR |
| 5 | SLC16A1 | chr1 | 113455427 | A | 13 | 3' UTR |
| 5 | SLC26A4 | chr7 | 107357810 | A | 25 | 3' UTR |

TABLE 1-continued

| Nr of affected samples | Gene | Chromosome | Start Position | Affected homopolymer base | Affected homopolymer length | region |
|---|---|---|---|---|---|---|
| 5 | SLC2A12 | chr6 | 134312045 | T | 11 | 3' UTR |
| 5 | SLC6A6 | chr3 | 14526824 | T | 11 | 3' UTR |
| 5 | SLC7A11 | chr4 | 139090880 | A | 10 | 3' UTR |
| 5 | SMAD5 | chr5 | 135513612 | A | 11 | 3' UTR |
| 5 | SMG1 | chr16 | 18819070 | T | 11 | 3' UTR |
| 5 | SMS | chrX | 22012649 | T | 10 | 3' UTR |
| 5 | SMURF2 | chr17 | 62541185 | T | 13 | 3' UTR |
| 5 | SNAP23 | chr15 | 42824292 | T | 14 | 3' UTR |
| 5 | SOST | chr17 | 41831361 | T | 11 | 3' UTR |
| 5 | SPCS3 | chr4 | 177250844 | T | 10 | 3' UTR |
| 5 | SPOCK1 | chr5 | 136313113 | A | 11 | 3' UTR |
| 5 | SSR1 | chr6 | 7284948 | T | 13 | 3' UTR |
| 5 | SSR3 | chr3 | 156259169 | T | 10 | 3' UTR |
| 5 | ST3GAL5 | chr2 | 86067101 | A | 9 | 3' UTR |
| 5 | ST7L | chr1 | 113066620 | A | 11 | 3' UTR |
| 5 | STC2 | chr5 | 172744019 | T | 12 | 3' UTR |
| 5 | STX6 | chr1 | 180945093 | A | 9 | 3' UTR |
| 5 | SYNJ2BP | chr14 | 70838863 | T | 10 | 3' UTR |
| 5 | SYT11 | chr1 | 155851834 | T | 12 | 3' UTR |
| 5 | TAF8 | chr6 | 42045495 | T | 11 | 3' UTR |
| 5 | THRAP3 | chr1 | 36770047 | T | 17 | 3' UTR |
| 5 | TLL2 | chr10 | 98124863 | A | 11 | 3' UTR |
| 5 | TMEM119 | chr12 | 108984472 | A | 11 | 3' UTR |
| 5 | TMEM201 | chr1 | 9674449 | T | 10 | 3' UTR |
| 5 | TMOD3 | chr15 | 52201130 | T | 10 | 3' UTR |
| 5 | TMTC1 | chr12 | 29656466 | A | 8 | 3' UTR |
| 5 | TNFAIP1 | chr17 | 26672324 | A | 10 | 3' UTR |
| 5 | TNFAIP3 | chr6 | 138204003 | A | 12 | 3' UTR |
| 5 | TNRC6B | chr22 | 40724536 | T | 10 | 3' UTR |
| 5 | TRIP10 | chr19 | 6751495 | A | 12 | 3' UTR |
| 5 | TRPM1 | chr15 | 31293995 | A | 11 | 3' UTR |
| 5 | TSC22D2 | chr3 | 150177375 | T | 13 | 3' UTR |
| 5 | TTC39C | chr18 | 21715264 | T | 11 | 3' UTR |
| 5 | UBE2G2 | chr21 | 46191155 | A | 12 | 3' UTR |
| 5 | UBLCP1 | chr5 | 158712401 | A | 11 | 3' UTR |
| 5 | UBN2 | chr7 | 138989574 | T | 10 | 3' UTR |
| 5 | UGT8 | chr4 | 115598050 | T | 11 | 3' UTR |
| 5 | UTP15 | chr5 | 72876582 | T | 12 | 3' UTR |
| 5 | WASL | chr7 | 123323428 | A | 12 | 3' UTR |
| 5 | WDFY2 | chr13 | 52334589 | A | 11 | 3' UTR |
| 5 | WDR76 | chr15 | 44158820 | T | 21 | 3' UTR |
| 5 | XYLT1 | chr16 | 17199280 | T | 8 | 3' UTR |
| 5 | ZBTB41 | chr1 | 197124441 | A | 11 | 3' UTR |
| 5 | ZC3H6 | chr2 | 113097277 | T | 13 | 3' UTR |
| 5 | ZDBF2 | chr2 | 207177005 | T | 8 | 3' UTR |
| 5 | ZNF287 | chr17 | 16454419 | T | 9 | 3' UTR |
| 5 | ZNF395 | chr8 | 28205776 | T | 27 | 3' UTR |
| 5 | ZNF451 | chr6 | 57033558 | A | 8 | 3' UTR |
| 5 | ZNF566 | chr19 | 36937171 | T | 18 | 3' UTR |
| 5 | ZNF572 | chr8 | 125990551 | T | 11 | 3' UTR |
| 5 | ZNF780B | chr19 | 40535764 | A | 10 | 3' UTR |
| 5 | ZXDC | chr3 | 126179925 | T | 11 | 3' UTR |
| 5 | ZYG11B | chr1 | 53290310 | A | 13 | 3' UTR |
| 4 | SEPT11 | chr4 | 77957803 | T | 10 | 3' UTR |
| 4 | ACVR1C | chr2 | 158390343 | A | 10 | 3' UTR |
| 4 | ACVR2A | chr2 | 148687300 | A | 10 | 3' UTR |
| 4 | ADAMTS18 | chr16 | 77316279 | T | 11 | 3' UTR |
| 4 | AGPAT5 | chr8 | 6617153 | A | 11 | 3' UTR |
| 4 | AKAP1 | chr17 | 55198578 | A | 14 | 3' UTR |
| 4 | ANKIB1 | chr7 | 92030525 | A | 11 | 3' UTR |
| 4 | ANKRD13B | chr17 | 27941253 | T | 19 | 3' UTR |
| 4 | ANKS1B | chr12 | 99138458 | T | 11 | 3' UTR |
| 4 | ARHGAP12 | chr10 | 32096465 | A | 9 | 3' UTR |
| 4 | ARID5B | chr10 | 63853410 | T | 27 | 3' UTR |
| 4 | ARL2BP | chr16 | 57287376 | T | 12 | 3' UTR |
| 4 | ARMC8 | chr3 | 137964255 | T | 9 | 3' UTR |
| 4 | ARPP19 | chr15 | 52841555 | A | 10 | 3' UTR |
| 4 | ATP6V0D1 | chr16 | 67472221 | G | 9 | 3' UTR |
| 4 | AXIN2 | chr17 | 63525462 | A | 11 | 3' UTR |
| 4 | BAG5 | chr14 | 104023132 | A | 10 | 3' UTR |
| 4 | BARX2 | chr11 | 129321925 | T | 10 | 3' UTR |
| 4 | BCL11A | chr2 | 60685736 | T | 13 | 3' UTR |
| 4 | BCL11A | chr2 | 60684501 | A | 11 | 3' UTR |
| 4 | BCL11B | chr14 | 99637754 | T | 10 | 3' UTR |
| 4 | BCL7A | chr12 | 122498867 | A | 11 | 3' UTR |

TABLE 1-continued

| Nr of affected samples | Gene | Chromosome | Start Position | Affected homopolymer base | Affected homopolymer length | region |
|---|---|---|---|---|---|---|
| 4 | BEND4 | chr4 | 42114856 | A | 10 | 3' UTR |
| 4 | BFAR | chr16 | 14762692 | A | 16 | 3' UTR |
| 4 | BRAF | chr7 | 140434294 | A | 9 | 3' UTR |
| 4 | BTBD7 | chr14 | 93708031 | A | 9 | 3' UTR |
| 4 | BTBD7 | chr14 | 93705796 | T | 13 | 3' UTR |
| 4 | C10orf46 | chr10 | 120445285 | A | 10 | 3' UTR |
| 4 | C10orf84 | chr10 | 120069534 | A | 9 | 3' UTR |
| 4 | C11orf41 | chr11 | 33690228 | T | 8 | 3' UTR |
| 4 | C11orf58 | chr11 | 16777810 | T | 24 | 3' UTR |
| 4 | C11orf58 | chr11 | 16777368 | T | 9 | 3' UTR |
| 4 | C12orf23 | chr12 | 107367018 | A | 10 | 3' UTR |
| 4 | C12orf5 | chr12 | 4463524 | T | 10 | 3' UTR |
| 4 | C12orf66 | chr12 | 64587315 | A | 10 | 3' UTR |
| 4 | C12orf76 | chr12 | 110479725 | A | 11 | 3' UTR |
| 4 | C14orf101 | chr14 | 57116192 | A | 10 | 3' UTR |
| 4 | C14orf43 | chr14 | 74183215 | A | 11 | 3' UTR |
| 4 | C16orf45 | chr16 | 15680717 | C | 9 | 3' UTR |
| 4 | C16orf87 | chr16 | 46836142 | T | 12 | 3' UTR |
| 4 | C17orf78 | chr17 | 35749617 | A | 11 | 3' UTR |
| 4 | C18orf25 | chr18 | 43846502 | A | 9 | 3' UTR |
| 4 | C3orf70 | chr3 | 184795851 | A | 10 | 3' UTR |
| 4 | C6orf170 | chr6 | 121401361 | T | 21 | 3' UTR |
| 4 | C6orf62 | chr6 | 24705738 | A | 10 | 3' UTR |
| 4 | C7orf45 | chr7 | 129856476 | A | 11 | 3' UTR |
| 4 | C7orf69 | chr7 | 47859241 | A | 11 | 3' UTR |
| 4 | C8orf48 | chr8 | 13425580 | T | 9 | 3' UTR |
| 4 | C9 | chr5 | 39285017 | T | 9 | 3' UTR |
| 4 | CA5B | chrX | 15801003 | T | 10 | 3' UTR |
| 4 | CABLES2 | chr20 | 60965113 | A | 10 | 3' UTR |
| 4 | CAPRIN1 | chr11 | 34121880 | T | 8 | 3' UTR |
| 4 | CBFA2T2 | chr20 | 32236969 | T | 11 | 3' UTR |
| 4 | CBL | chr11 | 119172610 | A | 10 | 3' UTR |
| 4 | CBY1 | chr22 | 39069285 | T | 9 | 3' UTR |
| 4 | CC2D1B | chr1 | 52817555 | A | 22 | 3' UTR |
| 4 | CCND1 | chr11 | 69466274 | A | 9 | 3' UTR |
| 4 | CD59 | chr11 | 33730438 | T | 8 | 3' UTR |
| 4 | CD96 | chr3 | 111368930 | A | 9 | 3' UTR |
| 4 | CDH13 | chr16 | 83828683 | A | 11 | 3' UTR |
| 4 | CDH4 | chr20 | 60512276 | A | 19 | 3' UTR |
| 4 | CEP164 | chr11 | 117283967 | T | 11 | 3' UTR |
| 4 | CEP57L1 | chr6 | 109484935 | T | 10 | 3' UTR |
| 4 | CHMP4C | chr8 | 82671242 | A | 12 | 3' UTR |
| 4 | CLCN5 | chrX | 49858223 | A | 9 | 3' UTR |
| 4 | CLDN14 | chr21 | 37833059 | T | 10 | 3' UTR |
| 4 | CLEC3A | chr16 | 78065330 | T | 12 | 3' UTR |
| 4 | CMTM8 | chr3 | 32411483 | A | 9 | 3' UTR |
| 4 | CNNM1 | chr10 | 101153279 | A | 9 | 3' UTR |
| 4 | CNNM3 | chr2 | 97499281 | A | 12 | 3' UTR |
| 4 | CORO2B | chr15 | 69020046 | T | 10 | 3' UTR |
| 4 | CPSF2 | chr14 | 92630061 | T | 9 | 3' UTR |
| 4 | CREBBP | chr16 | 3776240 | G | 10 | 3' UTR |
| 4 | CRTC1 | chr19 | 18890340 | A | 9 | 3' UTR |
| 4 | CSMD3 | chr8 | 113236641 | T | 9 | 3' UTR |
| 4 | CTTN | chr11 | 70281530 | T | 10 | 3' UTR |
| 4 | CYP1B1 | chr2 | 38296985 | T | 10 | 3' UTR |
| 4 | CYP20A1 | chr2 | 204163758 | A | 10 | 3' UTR |
| 4 | CYP2C18 | chr10 | 96495747 | A | 9 | 3' UTR |
| 4 | CYP4F22 | chr19 | 15662704 | C | 9 | 3' UTR |
| 4 | DACH1 | chr13 | 72014288 | T | 11 | 3' UTR |
| 4 | DCUN1D3 | chr16 | 20870892 | A | 10 | 3' UTR |
| 4 | DCUN1D5 | chr11 | 102928449 | A | 11 | 3' UTR |
| 4 | DDHD1 | chr14 | 53513329 | T | 10 | 3' UTR |
| 4 | DDX18 | chr2 | 118589332 | A | 9 | 3' UTR |
| 4 | DDX3X | chrX | 41207099 | T | 10 | 3' UTR |
| 4 | DFFB | chr1 | 3801133 | T | 11 | 3' UTR |
| 4 | DGCR8 | chr22 | 20099229 | C | 16 | 3' UTR |
| 4 | DICER1 | chr14 | 95554259 | T | 10 | 3' UTR |
| 4 | DLGAP4 | chr20 | 35156622 | T | 10 | 3' UTR |
| 4 | DPP8 | chr15 | 65738415 | A | 11 | 3' UTR |
| 4 | DSE | chr6 | 116758558 | A | 11 | 3' UTR |
| 4 | DSTYK | chr1 | 205115701 | T | 16 | 3' UTR |
| 4 | DUT | chr15 | 48634591 | A | 10 | 3' UTR |
| 4 | DUT | chr15 | 48634443 | A | 9 | 3' UTR |
| 4 | EAPP | chr14 | 34985335 | A | 10 | 3' UTR |
| 4 | EDEM1 | chr3 | 5260540 | T | 10 | 3' UTR |

TABLE 1-continued

| Nr of affected samples | Gene | Chromosome | Start Position | Affected homopolymer base | Affected homopolymer length | region |
|---|---|---|---|---|---|---|
| 4 | EEF2K | chr16 | 22299309 | T | 19 | 3' UTR |
| 4 | EIF2B2 | chr14 | 75476004 | A | 10 | 3' UTR |
| 4 | EIF4G3 | chr1 | 21133145 | T | 12 | 3' UTR |
| 4 | ELAVL3 | chr19 | 11564674 | T | 11 | 3' UTR |
| 4 | ERLIN2 | chr8 | 37614867 | T | 10 | 3' UTR |
| 4 | ESRRB | chr14 | 76967818 | G | 8 | 3' UTR |
| 4 | ETNK1 | chr12 | 22839785 | T | 28 | 3' UTR |
| 4 | ETS1 | chr11 | 128329018 | A | 9 | 3' UTR |
| 4 | FADS1 | chr11 | 61567668 | T | 14 | 3' UTR |
| 4 | FAIM3 | chr1 | 207077642 | T | 18 | 3' UTR |
| 4 | FAM101B | chr17 | 292360 | T | 10 | 3' UTR |
| 4 | FAM116A | chr3 | 57612436 | A | 13 | 3' UTR |
| 4 | FAM117B | chr2 | 203633341 | T | 10 | 3' UTR |
| 4 | FAM126B | chr2 | 201845397 | G | 7 | 3' UTR |
| 4 | FAM160B1 | chr10 | 116621715 | A | 9 | 3' UTR |
| 4 | FAM189A1 | chr15 | 29414906 | G | 8 | 3' UTR |
| 4 | FANCD2 | chr3 | 10143061 | T | 25 | 3' UTR |
| 4 | FBN2 | chr5 | 127594650 | A | 8 | 3' UTR |
| 4 | FBXO27 | chr19 | 39515468 | T | 11 | 3' UTR |
| 4 | FGD4 | chr12 | 32798227 | T | 12 | 3' UTR |
| 4 | FGD5 | chr3 | 14976010 | T | 9 | 3' UTR |
| 4 | FGF12 | chr3 | 191859718 | T | 11 | 3' UTR |
| 4 | FGFR1OP2 | chr12 | 27118562 | T | 10 | 3' UTR |
| 4 | FLCN | chr17 | 17115789 | A | 26 | 3' UTR |
| 4 | FMNL3 | chr12 | 50033467 | A | 10 | 3' UTR |
| 4 | FOXN2 | chr2 | 48603079 | T | 10 | 3' UTR |
| 4 | FOXO1 | chr13 | 41132503 | A | 9 | 3' UTR |
| 4 | FOXP1 | chr3 | 71005222 | T | 9 | 3' UTR |
| 4 | FPGT | chr1 | 74672686 | T | 9 | 3' UTR |
| 4 | FTSJD1 | chr16 | 71317151 | A | 10 | 3' UTR |
| 4 | FUT8 | chr14 | 66209673 | T | 13 | 3' UTR |
| 4 | FZD7 | chr2 | 202902385 | A | 11 | 3' UTR |
| 4 | GADL1 | chr3 | 30769514 | T | 11 | 3' UTR |
| 4 | GAL3ST4 | chr7 | 99757342 | A | 13 | 3' UTR |
| 4 | GAN | chr16 | 81413521 | T | 12 | 3' UTR |
| 4 | GAPVD1 | chr9 | 128127210 | T | 10 | 3' UTR |
| 4 | GATAD2A | chr19 | 19617715 | T | 10 | 3' UTR |
| 4 | GATAD2B | chr1 | 153781275 | A | 20 | 3' UTR |
| 4 | GDAP2 | chr1 | 118411744 | T | 10 | 3' UTR |
| 4 | GDAP2 | chr1 | 118408218 | A | 10 | 3' UTR |
| 4 | GFPT1 | chr2 | 69549530 | A | 9 | 3' UTR |
| 4 | GLCCI1 | chr7 | 8127832 | T | 11 | 3' UTR |
| 4 | GLDN | chr15 | 51697574 | T | 21 | 3' UTR |
| 4 | GLYR1 | chr16 | 4853902 | T | 10 | 3' UTR |
| 4 | GOLT1B | chr12 | 21669842 | A | 9 | 3' UTR |
| 4 | GPM6A | chr4 | 176555451 | T | 10 | 3' UTR |
| 4 | GPR124 | chr8 | 37701260 | A | 10 | 3' UTR |
| 4 | GPR155 | chr2 | 175299037 | T | 13 | 3' UTR |
| 4 | GPR161 | chr1 | 168054505 | T | 10 | 3' UTR |
| 4 | GPR180 | chr13 | 95279582 | A | 8 | 3' UTR |
| 4 | GPX8 | chr5 | 54460112 | T | 10 | 3' UTR |
| 4 | GRAMD3 | chr5 | 125829168 | T | 10 | 3' UTR |
| 4 | GSTCD | chr4 | 106767825 | T | 20 | 3' UTR |
| 4 | GXYLT1 | chr12 | 42477780 | A | 10 | 3' UTR |
| 4 | HCCS | chrX | 11140989 | T | 11 | 3' UTR |
| 4 | HCN1 | chr5 | 45260992 | T | 9 | 3' UTR |
| 4 | HDAC4 | chr2 | 239971996 | A | 11 | 3' UTR |
| 4 | HELZ | chr17 | 65067696 | T | 8 | 3' UTR |
| 4 | HEY2 | chr6 | 126081692 | T | 10 | 3' UTR |
| 4 | HIF3A | chr19 | 46843765 | T | 12 | 3' UTR |
| 4 | HNRNPA1L2 | chr13 | 53217847 | T | 11 | 3' UTR |
| 4 | HNRNPK | chr9 | 86584095 | C | 9 | 3' UTR |
| 4 | HOOK1 | chr1 | 60338642 | A | 8 | 3' UTR |
| 4 | HP1BP3 | chr1 | 21070971 | A | 10 | 3' UTR |
| 4 | HS3ST5 | chr6 | 114376959 | A | 10 | 3' UTR |
| 4 | HUWE1 | chrX | 53559518 | A | 12 | 3' UTR |
| 4 | IKZF4 | chr12 | 56431620 | A | 10 | 3' UTR |
| 4 | IL7R | chr5 | 35876844 | A | 10 | 3' UTR |
| 4 | IMPG2 | chr3 | 100945663 | A | 9 | 3' UTR |
| 4 | INSR | chr19 | 7112871 | A | 10 | 3' UTR |
| 4 | IRGQ | chr19 | 44094353 | A | 11 | 3' UTR |
| 4 | IRS1 | chr2 | 227600758 | T | 11 | 3' UTR |
| 4 | ISL1 | chr5 | 50689706 | A | 9 | 3' UTR |
| 4 | ITPRIPL1 | chr2 | 96994050 | A | 10 | 3' UTR |
| 4 | JAKMIP1 | chr4 | 6055625 | A | 11 | 3' UTR |

TABLE 1-continued

| Nr of affected samples | Gene | Chromosome | Start Position | Affected homopolymer base | Affected homopolymer length | region |
|---|---|---|---|---|---|---|
| 4 | KBTBD7 | chr13 | 41766026 | A | 9 | 3' UTR |
| 4 | KBTBD8 | chr3 | 67059954 | T | 10 | 3' UTR |
| 4 | KCNMA1 | chr10 | 78646910 | A | 9 | 3' UTR |
| 4 | KDELR2 | chr7 | 6501817 | A | 10 | 3' UTR |
| 4 | KDM5A | chr12 | 393295 | T | 11 | 3' UTR |
| 4 | KDSR | chr18 | 60998042 | T | 15 | 3' UTR |
| 4 | KIAA0182 | chr16 | 85706942 | A | 10 | 3' UTR |
| 4 | KIAA0494 | chr1 | 47142711 | T | 9 | 3' UTR |
| 4 | KIAA0825 | chr5 | 93487128 | A | 28 | 3' UTR |
| 4 | KIF1B | chr1 | 10438932 | T | 10 | 3' UTR |
| 4 | KIF1B | chr1 | 10437995 | A | 13 | 3' UTR |
| 4 | KLF12 | chr13 | 74261703 | T | 11 | 3' UTR |
| 4 | KLHL4 | chrX | 86922592 | A | 12 | 3' UTR |
| 4 | KPNA6 | chr1 | 32639763 | C | 9 | 3' UTR |
| 4 | KREMEN1 | chr22 | 29539729 | A | 14 | 3' UTR |
| 4 | L1CAM | chrX | 153127125 | T | 9 | 3' UTR |
| 4 | LARP4B | chr10 | 856761 | A | 9 | 3' UTR |
| 4 | LATS2 | chr13 | 21547830 | A | 9 | 3' UTR |
| 4 | LBR | chr1 | 225590887 | A | 10 | 3' UTR |
| 4 | LEF1 | chr4 | 108969352 | A | 9 | 3' UTR |
| 4 | LIAS | chr4 | 39478848 | A | 11 | 3' UTR |
| 4 | LIMS1 | chr2 | 109300693 | A | 10 | 3' UTR |
| 4 | LIN7C | chr11 | 27517538 | A | 10 | 3' UTR |
| 4 | LIX1 | chr5 | 96428100 | A | 10 | 3' UTR |
| 4 | LMTK2 | chr7 | 97837420 | A | 11 | 3' UTR |
| 4 | LRCH2 | chrX | 114346112 | T | 10 | 3' UTR |
| 4 | LRRC8A | chr9 | 131679397 | A | 11 | 3' UTR |
| 4 | LUZP2 | chr11 | 25102964 | A | 12 | 3' UTR |
| 4 | LYRM7 | chr5 | 130540369 | A | 15 | 3' UTR |
| 4 | MAP1B | chr5 | 71502852 | A | 10 | 3' UTR |
| 4 | MAP4 | chr3 | 48016254 | A | 13 | 3' UTR |
| 4 | MAP6 | chr11 | 75316787 | A | 11 | 3' UTR |
| 4 | MAPK1IP1L | chr14 | 55534134 | T | 10 | 3' UTR |
| 4 | MB21D2 | chr3 | 192516152 | A | 10 | 3' UTR |
| 4 | MDM2 | chr12 | 69233886 | T | 11 | 3' UTR |
| 4 | MEF2C | chr5 | 88017643 | A | 7 | 3' UTR |
| 4 | MEGF9 | chr9 | 123366681 | T | 10 | 3' UTR |
| 4 | METAP2 | chr12 | 95908545 | A | 11 | 3' UTR |
| 4 | METTL8 | chr2 | 172174950 | T | 8 | 3' UTR |
| 4 | MEX3A | chr1 | 156044195 | T | 17 | 3' UTR |
| 4 | MFN2 | chr1 | 12073251 | A | 11 | 3' UTR |
| 4 | MGAT4A | chr2 | 99236361 | T | 10 | 3' UTR |
| 4 | MIDN | chr19 | 1258791 | A | 10 | 3' UTR |
| 4 | MKLN1 | chr7 | 131181200 | T | 10 | 3' UTR |
| 4 | MKRN3 | chr15 | 23812682 | T | 8 | 3' UTR |
| 4 | MLL2 | chr12 | 49413198 | A | 10 | 3' UTR |
| 4 | MLLT6 | chr17 | 36883386 | T | 16 | 3' UTR |
| 4 | MMP2 | chr16 | 55539895 | T | 10 | 3' UTR |
| 4 | MOSPD1 | chrX | 134022551 | A | 9 | 3' UTR |
| 4 | MRPL44 | chr2 | 224831951 | T | 11 | 3' UTR |
| 4 | MTMR4 | chr17 | 56567367 | A | 9 | 3' UTR |
| 4 | MTSS1 | chr8 | 125564840 | A | 9 | 3' UTR |
| 4 | MYCL1 | chr1 | 40361307 | A | 10 | 3' UTR |
| 4 | NAPB | chr20 | 23355923 | A | 9 | 3' UTR |
| 4 | NARG2 | chr15 | 60714335 | T | 11 | 3' UTR |
| 4 | NCS1 | chr9 | 132996076 | T | 12 | 3' UTR |
| 4 | NDFIP1 | chr5 | 141533930 | T | 10 | 3' UTR |
| 4 | NEGR1 | chr1 | 71869847 | T | 11 | 3' UTR |
| 4 | NEIL3 | chr4 | 178283942 | T | 10 | 3' UTR |
| 4 | NF2 | chr22 | 30092784 | T | 14 | 3' UTR |
| 4 | NLK | chr17 | 26523190 | T | 10 | 3' UTR |
| 4 | NPC2 | chr14 | 74946724 | A | 10 | 3' UTR |
| 4 | NR2F2 | chr15 | 96882212 | G | 8 | 3' UTR |
| 4 | NRSN1 | chr6 | 24147583 | T | 10 | 3' UTR |
| 4 | OSBP2 | chr22 | 31302451 | T | 10 | 3' UTR |
| 4 | OSBPL3 | chr7 | 24837354 | A | 10 | 3' UTR |
| 4 | OTUD4 | chr4 | 146058513 | T | 8 | 3' UTR |
| 4 | OTUD4 | chr4 | 146057615 | G | 13 | 3' UTR |
| 4 | OXR1 | chr8 | 107764095 | A | 10 | 3' UTR |
| 4 | PABPC5 | chrX | 90691818 | T | 9 | 3' UTR |
| 4 | PAICS | chr4 | 57327144 | A | 10 | 3' UTR |
| 4 | PAK1IP1 | chr6 | 10709747 | T | 12 | 3' UTR |
| 4 | PALM2 | chr9 | 112706843 | A | 11 | 3' UTR |
| 4 | PAPD4 | chr5 | 78982336 | T | 10 | 3' UTR |
| 4 | PAPOLA | chr14 | 97033430 | A | 10 | 3' UTR |

TABLE 1-continued

| Nr of affected samples | Gene | Chromosome | Start Position | Affected homopolymer base | Affected homopolymer length | region |
|---|---|---|---|---|---|---|
| 4 | PCDH17 | chr13 | 58300047 | A | 10 | 3' UTR |
| 4 | PCNP | chr3 | 101312474 | A | 10 | 3' UTR |
| 4 | PDE4C | chr19 | 18320061 | T | 12 | 3' UTR |
| 4 | PDGFA | chr7 | 537622 | A | 11 | 3' UTR |
| 4 | PDGFA | chr7 | 536908 | T | 11 | 3' UTR |
| 4 | PGM2L1 | chr11 | 74047320 | T | 11 | 3' UTR |
| 4 | PIGW | chr17 | 34894609 | T | 11 | 3' UTR |
| 4 | PIK3R1 | chr5 | 67595054 | A | 10 | 3' UTR |
| 4 | PIM1 | chr6 | 37143155 | T | 11 | 3' UTR |
| 4 | PIP5K1A | chr1 | 151220867 | T | 11 | 3' UTR |
| 4 | PKD2 | chr4 | 88998190 | A | 11 | 3' UTR |
| 4 | PKN2 | chr1 | 89301773 | T | 11 | 3' UTR |
| 4 | PLA2G12A | chr4 | 110633665 | T | 10 | 3' UTR |
| 4 | PLAGL2 | chr20 | 30784138 | T | 11 | 3' UTR |
| 4 | PLCB1 | chr20 | 8863118 | A | 10 | 3' UTR |
| 4 | PLCL1 | chr2 | 199013907 | T | 9 | 3' UTR |
| 4 | PLCXD3 | chr5 | 41307606 | A | 9 | 3' UTR |
| 4 | PLK2 | chr5 | 57749858 | A | 9 | 3' UTR |
| 4 | PODNL1 | chr19 | 14042032 | G | 8 | 3' UTR |
| 4 | PODXL | chr7 | 131185943 | A | 11 | 3' UTR |
| 4 | POLH | chr6 | 43584323 | A | 14 | 3' UTR |
| 4 | PPAP2B | chr1 | 56962088 | T | 10 | 3' UTR |
| 4 | PPARA | chr22 | 46633507 | A | 16 | 3' UTR |
| 4 | PPARGC1B | chr5 | 149227267 | A | 14 | 3' UTR |
| 4 | PPM1E | chr17 | 57060351 | A | 10 | 3' UTR |
| 4 | PPP1R3A | chr7 | 113517422 | A | 9 | 3' UTR |
| 4 | PPP3CA | chr4 | 101946069 | T | 10 | 3' UTR |
| 4 | PRDM15 | chr21 | 43220664 | A | 12 | 3' UTR |
| 4 | PROSC | chr8 | 37636576 | A | 10 | 3' UTR |
| 4 | PRTG | chr15 | 55907920 | T | 10 | 3' UTR |
| 4 | PTP4A2 | chr1 | 32374021 | A | 10 | 3' UTR |
| 4 | PTPN22 | chr1 | 114357118 | T | 10 | 3' UTR |
| 4 | PTPRF | chr1 | 44088117 | T | 11 | 3' UTR |
| 4 | PTRF | chr17 | 40554683 | A | 15 | 3' UTR |
| 4 | PUM1 | chr1 | 31405680 | T | 10 | 3' UTR |
| 4 | QRICH1 | chr3 | 49067797 | A | 11 | 3' UTR |
| 4 | RAB39B | chrX | 154488466 | T | 11 | 3' UTR |
| 4 | RAB7L1 | chr1 | 205738564 | T | 10 | 3' UTR |
| 4 | RAB8B | chr15 | 63559206 | T | 12 | 3' UTR |
| 4 | RASAL2 | chr1 | 178447287 | T | 11 | 3' UTR |
| 4 | RBM12B | chr8 | 94745547 | A | 10 | 3' UTR |
| 4 | RBM38 | chr20 | 55983973 | G | 8 | 3' UTR |
| 4 | RBMS3 | chr3 | 30045473 | T | 10 | 3' UTR |
| 4 | RDX | chr11 | 110102325 | A | 10 | 3' UTR |
| 4 | RGS18 | chr1 | 192154126 | T | 8 | 3' UTR |
| 4 | RGS6 | chr14 | 73030606 | A | 11 | 3' UTR |
| 4 | RND2 | chr17 | 41181921 | A | 24 | 3' UTR |
| 4 | RNF122 | chr8 | 33405498 | A | 26 | 3' UTR |
| 4 | RNGTT | chr6 | 89320667 | T | 10 | 3' UTR |
| 4 | ROCK1 | chr18 | 18530891 | A | 10 | 3' UTR |
| 4 | RPRD2 | chr1 | 150447772 | T | 10 | 3' UTR |
| 4 | RPRD2 | chr1 | 150445907 | T | 10 | 3' UTR |
| 4 | RRM2 | chr2 | 10269544 | T | 10 | 3' UTR |
| 4 | RSBN1L | chr7 | 77408705 | A | 9 | 3' UTR |
| 4 | RSL1D1 | chr16 | 11930997 | T | 11 | 3' UTR |
| 4 | SALL3 | chr18 | 76757543 | A | 10 | 3' UTR |
| 4 | SAMD4A | chr14 | 55257700 | A | 10 | 3' UTR |
| 4 | SASH1 | chr6 | 148872287 | T | 10 | 3' UTR |
| 4 | SATB1 | chr3 | 18390227 | T | 12 | 3' UTR |
| 4 | SCN1A | chr2 | 166846936 | T | 10 | 3' UTR |
| 4 | SDC4 | chr20 | 43955023 | A | 24 | 3' UTR |
| 4 | SEC63 | chr6 | 108190403 | A | 10 | 3' UTR |
| 4 | SENP5 | chr3 | 196658083 | A | 10 | 3' UTR |
| 4 | SEPHS1 | chr10 | 13360740 | A | 11 | 3' UTR |
| 4 | SFXN1 | chr5 | 174954918 | T | 22 | 3' UTR |
| 4 | SGK223 | chr8 | 8175297 | T | 12 | 3' UTR |
| 4 | SH2B3 | chr12 | 111887735 | T | 14 | 3' UTR |
| 4 | SHC1 | chr1 | 154935862 | G | 8 | 3' UTR |
| 4 | SHC4 | chr15 | 49117721 | T | 10 | 3' UTR |
| 4 | SHCBP1 | chr16 | 46614658 | T | 14 | 3' UTR |
| 4 | SHOC2 | chr10 | 112773341 | T | 10 | 3' UTR |
| 4 | SIPA1L3 | chr19 | 38698929 | T | 10 | 3' UTR |
| 4 | SIPA1L3 | chr19 | 38698868 | T | 10 | 3' UTR |
| 4 | SIX4 | chr14 | 61178202 | A | 10 | 3' UTR |
| 4 | SLAIN2 | chr4 | 48426160 | T | 9 | 3' UTR |

TABLE 1-continued

| Nr of affected samples | Gene | Chromosome | Start Position | Affected homopolymer base | Affected homopolymer length | region |
|---|---|---|---|---|---|---|
| 4 | SLC17A5 | chr6 | 74303467 | A | 10 | 3' UTR |
| 4 | SLC22A5 | chr5 | 131730903 | T | 17 | 3' UTR |
| 4 | SLC25A36 | chr3 | 140696772 | A | 11 | 3' UTR |
| 4 | SLC2A2 | chr3 | 170715683 | T | 10 | 3' UTR |
| 4 | SLC39A9 | chr14 | 69928356 | T | 10 | 3' UTR |
| 4 | SLC6A15 | chr12 | 85253350 | T | 10 | 3' UTR |
| 4 | SLC9A6 | chrX | 135128103 | T | 11 | 3' UTR |
| 4 | SMAD3 | chr15 | 67485102 | A | 9 | 3' UTR |
| 4 | SMAD4 | chr18 | 48605007 | T | 10 | 3' UTR |
| 4 | SMAD7 | chr18 | 46447623 | A | 10 | 3' UTR |
| 4 | SORL1 | chr11 | 121502077 | T | 11 | 3' UTR |
| 4 | SORL1 | chr11 | 121501334 | T | 9 | 3' UTR |
| 4 | SOST | chr17 | 41831941 | T | 10 | 3' UTR |
| 4 | SOX30 | chr5 | 157053271 | T | 10 | 3' UTR |
| 4 | SPATA13 | chr13 | 24878597 | T | 11 | 3' UTR |
| 4 | SPATS2 | chr12 | 49921053 | T | 10 | 3' UTR |
| 4 | SPINK7 | chr5 | 147695440 | T | 10 | 3' UTR |
| 4 | SPOP | chr17 | 47676672 | A | 13 | 3' UTR |
| 4 | SPRED1 | chr15 | 38648129 | A | 9 | 3' UTR |
| 4 | SPTBN1 | chr2 | 54898095 | T | 10 | 3' UTR |
| 4 | SRRM4 | chr12 | 119599690 | A | 10 | 3' UTR |
| 4 | SRRM4 | chr12 | 119596858 | T | 9 | 3' UTR |
| 4 | STAT2 | chr12 | 56736372 | A | 13 | 3' UTR |
| 4 | STK4 | chr20 | 43708275 | A | 10 | 3' UTR |
| 4 | STMN2 | chr8 | 80577224 | A | 13 | 3' UTR |
| 4 | SUMO2 | chr17 | 73164056 | T | 11 | 3' UTR |
| 4 | SYT13 | chr11 | 45264120 | A | 9 | 3' UTR |
| 4 | TACC1 | chr8 | 38708293 | A | 25 | 3' UTR |
| 4 | TAOK1 | chr17 | 27871502 | A | 11 | 3' UTR |
| 4 | TBL1X | chrX | 9684635 | A | 9 | 3' UTR |
| 4 | TFAP2B | chr6 | 50814917 | T | 9 | 3' UTR |
| 4 | TFCP2L1 | chr2 | 121975868 | T | 11 | 3' UTR |
| 4 | THAP2 | chr12 | 72073229 | T | 10 | 3' UTR |
| 4 | THSD4 | chr15 | 72072880 | A | 10 | 3' UTR |
| 4 | THSD7A | chr7 | 11411520 | T | 10 | 3' UTR |
| 4 | TLCD2 | chr17 | 1606349 | T | 13 | 3' UTR |
| 4 | TM9SF4 | chr20 | 30754878 | T | 11 | 3' UTR |
| 4 | TMEM14C | chr6 | 10731011 | A | 9 | 3' UTR |
| 4 | TMEM169 | chr2 | 216966376 | T | 10 | 3' UTR |
| 4 | TMEM192 | chr4 | 165997961 | T | 10 | 3' UTR |
| 4 | TMEM40 | chr3 | 12775743 | T | 9 | 3' UTR |
| 4 | TNFAIP8 | chr5 | 118729618 | A | 10 | 3' UTR |
| 4 | TNRC6C | chr17 | 76104332 | C | 9 | 3' UTR |
| 4 | TPM4 | chr19 | 16212343 | T | 9 | 3' UTR |
| 4 | TRAK2 | chr2 | 202244537 | T | 11 | 3' UTR |
| 4 | TRIM33 | chr1 | 114940229 | T | 13 | 3' UTR |
| 4 | TRIM56 | chr7 | 100733606 | A | 9 | 3' UTR |
| 4 | TRIM9 | chr14 | 51442832 | T | 10 | 3' UTR |
| 4 | TRPC1 | chr3 | 142525356 | T | 9 | 3' UTR |
| 4 | TRPS1 | chr8 | 116424772 | T | 10 | 3' UTR |
| 4 | TRPS1 | chr8 | 116423510 | A | 12 | 3' UTR |
| 4 | TSPAN31 | chr12 | 58141530 | T | 13 | 3' UTR |
| 4 | TTC14 | chr3 | 180326182 | T | 15 | 3' UTR |
| 4 | TULP4 | chr6 | 158929910 | T | 27 | 3' UTR |
| 4 | TXNDC9 | chr2 | 99936109 | A | 9 | 3' UTR |
| 4 | U2AF1 | chr21 | 44513110 | T | 11 | 3' UTR |
| 4 | UBE2G1 | chr17 | 4173433 | A | 10 | 3' UTR |
| 4 | UBE2K | chr4 | 39780193 | A | 11 | 3' UTR |
| 4 | UBE3C | chr7 | 157060934 | T | 10 | 3' UTR |
| 4 | UBE4B | chr1 | 10240859 | T | 10 | 3' UTR |
| 4 | UBFD1 | chr16 | 23582355 | T | 10 | 3' UTR |
| 4 | UBN2 | chr7 | 138992059 | T | 9 | 3' UTR |
| 4 | USF2 | chr19 | 35770658 | A | 10 | 3' UTR |
| 4 | USP31 | chr16 | 23077020 | T | 11 | 3' UTR |
| 4 | USP43 | chr17 | 9632696 | T | 12 | 3' UTR |
| 4 | USP43 | chr17 | 9632427 | T | 13 | 3' UTR |
| 4 | USP43 | chr17 | 9632418 | A | 9 | 3' UTR |
| 4 | VEZF1 | chr17 | 56051105 | T | 14 | 3' UTR |
| 4 | VGLL3 | chr3 | 86990599 | T | 11 | 3' UTR |
| 4 | VPS53 | chr17 | 422006 | A | 27 | 3' UTR |
| 4 | VTI1A | chr10 | 114575744 | T | 10 | 3' UTR |
| 4 | WDR3 | chr1 | 118502087 | T | 11 | 3' UTR |
| 4 | WDR82 | chr3 | 52288956 | T | 19 | 3' UTR |
| 4 | WHSC1 | chr4 | 1945453 | A | 9 | 3' UTR |
| 4 | XKR6 | chr8 | 10755309 | T | 10 | 3' UTR |

TABLE 1-continued

| Nr of affected samples | Gene | Chromosome | Start Position | Affected homopolymer base | Affected homopolymer length | region |
|---|---|---|---|---|---|---|
| 4 | XKR6 | chr8 | 10755102 | T | 11 | 3' UTR |
| 4 | ZBTB16 | chr11 | 114121371 | A | 11 | 3' UTR |
| 4 | ZBTB4 | chr17 | 7363093 | A | 10 | 3' UTR |
| 4 | ZC3HAV1L | chr7 | 138710878 | A | 11 | 3' UTR |
| 4 | ZCCHC13 | chrX | 73524759 | A | 9 | 3' UTR |
| 4 | ZCCHC2 | chr18 | 60244188 | A | 10 | 3' UTR |
| 4 | ZFHX4 | chr8 | 77778696 | T | 14 | 3' UTR |
| 4 | ZFP36L1 | chr14 | 69255309 | T | 12 | 3' UTR |
| 4 | ZFP36L2 | chr2 | 43450053 | C | 8 | 3' UTR |
| 4 | ZMIZ1 | chr10 | 81075616 | A | 10 | 3' UTR |
| 4 | ZNF498 | chr7 | 99229241 | T | 11 | 3' UTR |
| 4 | ZNF528 | chr19 | 52920874 | T | 12 | 3' UTR |
| 4 | ZNF594 | chr17 | 5084035 | A | 10 | 3' UTR |
| 4 | ZNF618 | chr9 | 116812463 | A | 9 | 3' UTR |
| 4 | ZNF629 | chr16 | 30792783 | T | 10 | 3' UTR |
| 4 | ZNF681 | chr19 | 23925293 | A | 13 | 3' UTR |
| 4 | ZNF737 | chr19 | 20726934 | A | 11 | 3' UTR |
| 4 | ZNF740 | chr12 | 53584463 | T | 14 | 3' UTR |
| 4 | ZSCAN30 | chr18 | 32831761 | T | 12 | 3' UTR |
| 13 | GABRG2 | chr5 | 161494990 | A | 12 | 5' UTR |
| 12 | ARHGEF11 | chr1 | 157014811 | A | 12 | 5' UTR |
| 12 | CCT6B | chr17 | 33288433 | A | 11 | 5' UTR |
| 12 | LRMP | chr12 | 25205380 | A | 11 | 5' UTR |
| 11 | TMEM177 | chr2 | 120437061 | A | 11 | 5' UTR |
| 11 | ZNF781 | chr19 | 38161161 | T | 11 | 5' UTR |
| 10 | EPHB6 | chr7 | 142560576 | A | 13 | 5' UTR |
| 10 | LMOD3 | chr3 | 69171664 | T | 13 | 5' UTR |
| 10 | MBNL1 | chr3 | 152017897 | T | 11 | 5' UTR |
| 9 | ARHGEF9 | chrX | 62974288 | T | 12 | 5' UTR |
| 9 | BDNF | chr11 | 27741184 | A | 10 | 5' UTR |
| 9 | CBLN2 | chr18 | 70211389 | A | 14 | 5' UTR |
| 9 | OIT3 | chr10 | 74653468 | A | 10 | 5' UTR |
| 8 | BMP5 | chr6 | 55739711 | A | 14 | 5' UTR |
| 8 | LOC642587 | chr1 | 209602342 | T | 13 | 5' UTR |
| 8 | OMD | chr9 | 95179844 | T | 11 | 5' UTR |
| 8 | SEMA6A | chr5 | 115910134 | A | 11 | 5' UTR |
| 8 | TCF4 | chr18 | 53255634 | A | 12 | 5' UTR |
| 7 | ASPH | chr8 | 62602295 | A | 11 | 5' UTR |
| 7 | CNTNAP2 | chr7 | 145813627 | T | 11 | 5' UTR |
| 7 | DIO2 | chr14 | 80678323 | T | 14 | 5' UTR |
| 7 | DIO2 | chr14 | 80678077 | T | 25 | 5' UTR |
| 7 | GSDMC | chr8 | 130798567 | A | 14 | 5' UTR |
| 7 | PTP4A2 | chr1 | 32384716 | A | 11 | 5' UTR |
| 7 | ZXDB | chrX | 57618380 | T | 9 | 5' UTR |
| 6 | AMD1 | chr6 | 111196178 | A | 11 | 5' UTR |
| 6 | DDX3X | chrX | 41192964 | A | 10 | 5' UTR |
| 6 | ESCO1 | chr18 | 19164371 | A | 11 | 5' UTR |
| 6 | GEN1 | chr2 | 17935494 | T | 11 | 5' UTR |
| 6 | LPHN1 | chr19 | 14316982 | A | 15 | 5' UTR |
| 6 | LRRC70 | chr5 | 61874619 | A | 18 | 5' UTR |
| 6 | MEIS1 | chr2 | 66662690 | T | 13 | 5' UTR |
| 6 | SATB1 | chr3 | 18465613 | A | 13 | 5' UTR |
| 6 | ST7L | chr1 | 113162029 | C | 10 | 5' UTR |
| 6 | TMEM31 | chrX | 102965989 | T | 10 | 5' UTR |
| 6 | TOX | chr8 | 60031707 | A | 14 | 5' UTR |
| 5 | AAK1 | chr2 | 69870217 | T | 24 | 5' UTR |
| 5 | ARHGEF11 | chr1 | 157014870 | A | 11 | 5' UTR |
| 5 | CBLN2 | chr18 | 70211440 | A | 9 | 5' UTR |
| 5 | CEPT1 | chr1 | 111690319 | A | 9 | 5' UTR |
| 5 | EMP1 | chr12 | 13364426 | A | 10 | 5' UTR |
| 5 | GTF2A1 | chr14 | 81686922 | A | 13 | 5' UTR |
| 5 | L3MBTL3 | chr6 | 130339785 | A | 10 | 5' UTR |
| 5 | LMO7 | chr13 | 76195056 | A | 9 | 5' UTR |
| 5 | LPAR4 | chrX | 78003392 | A | 31 | 5' UTR |
| 5 | LRRC4C | chr11 | 40314470 | A | 10 | 5' UTR |
| 5 | MCF2 | chrX | 138724841 | A | 15 | 5' UTR |
| 5 | NDE1 | chr16 | 15737427 | T | 11 | 5' UTR |
| 5 | PBX1 | chr1 | 164528904 | T | 10 | 5' UTR |
| 5 | PRMT8 | chr12 | 3600691 | T | 11 | 5' UTR |
| 5 | PTPRB | chr12 | 71031210 | A | 10 | 5' UTR |
| 5 | SCN2B | chr11 | 118047234 | A | 9 | 5' UTR |
| 5 | TIGD7 | chr16 | 3350676 | A | 10 | 5' UTR |
| 5 | TSHZ1 | chr18 | 72922942 | T | 10 | 5' UTR |
| 5 | XRRA1 | chr11 | 74656098 | T | 10 | 5' UTR |
| 5 | ZXDA | chrX | 57936946 | A | 9 | 5' UTR |

TABLE 1-continued

| Nr of affected samples | Gene | Chromosome | Start Position | Affected homopolymer base | Affected homopolymer length | region |
|---|---|---|---|---|---|---|
| 4 | ABCC10 | chr6 | 43399532 | T | 10 | 5' UTR |
| 4 | C1QL3 | chr10 | 16563613 | T | 10 | 5' UTR |
| 4 | CPLX4 | chr18 | 56985739 | A | 10 | 5' UTR |
| 4 | DHRS3 | chr1 | 12677525 | A | 21 | 5' UTR |
| 4 | FAM65B | chr6 | 24877343 | A | 8 | 5' UTR |
| 4 | GRIA2 | chr4 | 158142151 | A | 9 | 5' UTR |
| 4 | HEXIM1 | chr17 | 43226461 | T | 10 | 5' UTR |
| 4 | HRH2 | chr5 | 175110094 | A | 21 | 5' UTR |
| 4 | HYLS1 | chr11 | 125753769 | A | 10 | 5' UTR |
| 4 | IL18RAP | chr2 | 103035368 | T | 11 | 5' UTR |
| 4 | MBNL1 | chr3 | 152017452 | A | 10 | 5' UTR |
| 4 | NLRP3 | chr1 | 247581609 | T | 12 | 5' UTR |
| 4 | NR2F2 | chr15 | 96874920 | T | 11 | 5' UTR |
| 4 | NRXN3 | chr14 | 79746442 | T | 10 | 5' UTR |
| 4 | OBFC2A | chr2 | 192543129 | T | 24 | 5' UTR |
| 4 | PDGFB | chr22 | 39640806 | T | 16 | 5' UTR |
| 4 | PIK3R1 | chr5 | 67584512 | T | 12 | 5' UTR |
| 4 | PPP2R5C | chr14 | 102276205 | T | 11 | 5' UTR |
| 4 | RALYL | chr8 | 85095860 | T | 11 | 5' UTR |
| 4 | RFWD2 | chr1 | 176176257 | T | 9 | 5' UTR |
| 4 | RGS4 | chr1 | 163038838 | T | 10 | 5' UTR |
| 4 | SCN2A | chr2 | 166150520 | A | 28 | 5' UTR |
| 4 | SEMA3E | chr7 | 83278198 | A | 16 | 5' UTR |
| 4 | SETBP1 | chr18 | 42260910 | G | 8 | 5' UTR |
| 4 | SIAE,SPA17 | chr11 | 124543762 | T | 15 | 5' UTR |
| 4 | SKIV2L2 | chr5 | 54603686 | A | 13 | 5' UTR |
| 4 | SLC38A5 | chrX | 48327811 | T | 12 | 5' UTR |
| 4 | STIM2 | chr4 | 26862546 | T | 18 | 5' UTR |
| 4 | STK11 | chr19 | 1206796 | T | 10 | 5' UTR |
| 4 | TGFB3 | chr14 | 76447771 | A | 11 | 5' UTR |
| 4 | TRIP6 | chr7 | 100464995 | A | 10 | 5' UTR |
| 4 | ZNF107 | chr7 | 64152284 | A | 8 | 5' UTR |

TABLE 2

| Nr of affected samples | Gene | Chromosome | Start Position | Affected homopolymer base | Affected homopolymer length | Nr of Insertions | Nr of deletions |
|---|---|---|---|---|---|---|---|
| 11 | SETD1B | chr12 | 122242657 | C | 8 | 0 | 11 |
| 10 | OR7E24 | chr19 | 9361740 | T | 11 | 0 | 10 |
| 10 | SEC31A | chr4 | 83785564 | T | 9 | 0 | 10 |
| 9 | ASTE1 | chr3 | 130733046 | T | 11 | 0 | 9 |
| 9 | CASP5 | chr11 | 104879686 | T | 10 | 2 | 7 |
| 9 | MYL1 | chr2 | 211179765 | T | 11 | 0 | 9 |
| 9 | RPL22 | chr1 | 6257784 | T | 8 | 1 | 8 |
| 8 | C15orf40 | chr15 | 83677270 | A | 14 | 3 | 5 |
| 8 | CNOT2 | chr12 | 70747693 | A | 25 | 0 | 8 |
| 8 | LTN1 | chr21 | 30339205 | T | 11 | 0 | 8 |
| 8 | TTK | chr6 | 80751896 | A | 9 | 0 | 8 |
| 7 | CCDC150 | chr2 | 197531518 | A | 11 | 1 | 6 |
| 7 | KIAA2018 | chr3 | 113377481 | T | 11 | 0 | 7 |
| 7 | MBD4 | chr3 | 129155547 | T | 10 | 1 | 6 |
| 7 | MSH6 | chr2 | 48030639 | C | 8 | 4 | 3 |
| 7 | PHF2 | chr9 | 96422611 | A | 8 | 0 | 7 |
| 7 | RNF145 | chr5 | 158630629 | T | 11 | 1 | 6 |
| 7 | RNPC3 | chr1 | 104076466 | A | 12 | 1 | 6 |
| 7 | SLC22A9 | chr11 | 63149670 | A | 11 | 1 | 6 |
| 7 | TMBIM4 | chr12 | 66531936 | A | 10 | 1 | 6 |
| 6 | AIM2 | chr1 | 159032486 | T | 10 | 1 | 5 |
| 6 | ATR | chr3 | 142274739 | T | 10 | 0 | 6 |
| 6 | CASP5 | chr11 | 104878040 | T | 10 | 3 | 3 |
| 6 | CDH26 | chr20 | 58587783 | A | 10 | 1 | 5 |
| 6 | CLOCK | chr4 | 56336953 | A | 9 | 3 | 3 |
| 6 | CTCF | chr16 | 67645338 | A | 7 | 6 | 0 |
| 6 | GRIK2 | chr6 | 102503431 | A | 8 | 1 | 5 |
| 6 | KIAA0182 | chr16 | 85682289 | C | 8 | 6 | 0 |
| 6 | LOC100129387 | chr15 | 50648218 | A | 13 | 1 | 5 |
| 6 | MIS18BP1 | chr14 | 45716018 | T | 11 | 1 | 5 |

TABLE 2-continued

| Nr of affected samples | Gene | Chromo-some | Start Position | Affected homo-polymer base | Affected homo-polymer length | Nr of Inser-tions | Nr of dele-tions |
|---|---|---|---|---|---|---|---|
| 6 | MLL3 | chr7 | 151874147 | T | 9 | 1 | 5 |
| 6 | NDUFC2, NDUFC2-KCTD14 | chr11 | 77784146 | A | 9 | 0 | 6 |
| 6 | RBMXL1 | chr1 | 89449508 | T | 11 | 0 | 6 |
| 6 | SLC35F5 | chr2 | 114500276 | A | 10 | 1 | 5 |
| 6 | TAF1B | chr2 | 9989570 | A | 11 | 0 | 6 |
| 6 | TGFBR2 | chr3 | 30691871 | A | 10 | 0 | 6 |
| 6 | TMEM60 | chr7 | 77423459 | T | 9 | 0 | 6 |
| 5 | ACVR2A | chr2 | 148683685 | A | 8 | 0 | 5 |
| 5 | BRD3 | chr9 | 136918528 | G | 8 | 2 | 3 |
| 5 | C13orf40 | chr13 | 103381995 | A | 9 | 2 | 3 |
| 5 | COBLL1 | chr2 | 165551295 | A | 9 | 1 | 4 |
| 5 | CREBZF | chr11 | 85369692 | A | 13 | 0 | 5 |
| 5 | DDX27 | chr20 | 47858503 | A | 8 | 0 | 5 |
| 5 | DOCK3 | chr3 | 51417603 | C | 7 | 0 | 5 |
| 5 | FAM111B | chr11 | 58892376 | A | 10 | 0 | 5 |
| 5 | FAM18A | chr16 | 10867202 | A | 9 | 1 | 4 |
| 5 | FETUB | chr3 | 186362543 | A | 9 | 1 | 4 |
| 5 | HMGN2P46 | chr15 | 45848230 | T | 16 | 0 | 5 |
| 5 | IGF2R | chr6 | 160485487 | G | 8 | 3 | 2 |
| 5 | KIAA1919 | chr6 | 111587360 | T | 9 | 0 | 5 |
| 5 | MAP3K4 | chr6 | 161469775 | A | 8 | 0 | 5 |
| 5 | MIAT | chr22 | 27066924 | T | 12 | 0 | 5 |
| 5 | MIR100HG | chr11 | 121959910 | A | 15 | 0 | 5 |
| 5 | NRIP1 | chr21 | 16338329 | T | 8 | 0 | 5 |
| 5 | PDGFC | chr4 | 157683777 | A | 17 | 1 | 4 |
| 5 | PRKDC | chr8 | 48866909 | T | 10 | 1 | 4 |
| 5 | PRRG1 | chrX | 37312610 | C | 8 | 1 | 4 |
| 5 | PRRT2 | chr16 | 29825015 | C | 9 | 4 | 1 |
| 5 | RAD51L3-RFFL | chr17 | 33336605 | A | 14 | 1 | 4 |
| 5 | RGS12 | chr4 | 3430398 | A | 9 | 0 | 5 |
| 5 | SLMO2-ATP5E | chr20 | 57603795 | T | 11 | 1 | 4 |
| 5 | SMC6 | chr2 | 17898125 | T | 9 | 2 | 3 |
| 5 | SNAR-G1 | chr19 | 49540383 | A | 14 | 0 | 5 |
| 5 | SRSF3 | chr6 | 36570853 | T | 14 | 0 | 5 |
| 5 | TSIX | chrX | 73039404 | A | 13 | 0 | 5 |
| 5 | TSIX | chrX | 73031598 | A | 14 | 0 | 5 |
| 5 | UBR5 | chr8 | 103289348 | T | 8 | 1 | 4 |
| 5 | UVRAG | chr11 | 75694430 | A | 10 | 0 | 5 |
| 5 | YWHAE | chr17 | 1248583 | A | 18 | 1 | 4 |
| 4 | BRCA1 | chr17 | 41196821 | T | 19 | 0 | 4 |
| 4 | BRD2 | chr6 | 32948951 | T | 11 | 1 | 3 |
| 4 | C14orf39 | chr14 | 60903564 | A | 8 | 0 | 4 |
| 4 | C15orf5 | chr15 | 77516475 | T | 11 | 0 | 4 |
| 4 | CEP164 | chr11 | 117222647 | A | 11 | 0 | 4 |
| 4 | CYHR1 | chr8 | 145689658 | C | 9 | 1 | 3 |
| 4 | DCAF17 | chr2 | 172339178 | T | 11 | 0 | 4 |
| 4 | ELAVL3 | chr19 | 11577604 | C | 9 | 2 | 2 |
| 4 | EXOSC9 | chr4 | 122723893 | T | 8 | 0 | 4 |
| 4 | FAM20A | chr17 | 66531810 | T | 13 | 1 | 3 |
| 4 | FAM92A3 | chr4 | 183960483 | A | 13 | 0 | 4 |
| 4 | FLJ37453 | chr1 | 16160954 | T | 13 | 0 | 4 |
| 4 | FLJ90757 | chr17 | 79005507 | C | 9 | 0 | 4 |
| 4 | FOXO3B | chr17 | 18570304 | T | 16 | 0 | 4 |
| 4 | GBP3 | chr1 | 89473441 | T | 10 | 0 | 4 |
| 4 | GLTSCR1 | chr19 | 48197890 | C | 8 | 0 | 4 |
| 4 | HMGB3P1 | chr20 | 33421796 | T | 11 | 0 | 4 |
| 4 | HPS1 | chr10 | 100186986 | G | 8 | 0 | 4 |
| 4 | INO80E | chr16 | 30016652 | C | 9 | 1 | 3 |
| 4 | INTS2 | chr17 | 59944673 | A | 11 | 0 | 4 |
| 4 | ITPRIPL2 | chr16 | 19132369 | T | 13 | 0 | 4 |
| 4 | JAK1 | chr1 | 65325832 | G | 7 | 2 | 2 |
| 4 | KIAA0664L3 | chr16 | 31718743 | A | 15 | 0 | 4 |
| 4 | LMLN | chr3 | 197766471 | A | 13 | 0 | 4 |
| 4 | LOC283392 | chr12 | 72657140 | A | 12 | 0 | 4 |
| 4 | LOC284023 | chr17 | 7818450 | A | 14 | 0 | 4 |
| 4 | LOC284232 | chr13 | 19444480 | A | 15 | 0 | 4 |
| 4 | LOC541471 | chr2 | 112252632 | A | 12 | 0 | 4 |
| 4 | LOC645431 | chr14 | 65877626 | A | 11 | 0 | 4 |
| 4 | LOC646982 | chr13 | 40922820 | A | 13 | 0 | 4 |
| 4 | LOC647979 | chr20 | 34633827 | A | 15 | 0 | 4 |
| 4 | LOC92659 | chr17 | 79888376 | A | 17 | 0 | 4 |
| 4 | MALAT1 | chr11 | 65271779 | T | 13 | 1 | 3 |
| 4 | MIAT | chr22 | 27067793 | A | 13 | 0 | 4 |
| 4 | MIR567 | chr3 | 111831723 | A | 13 | 1 | 3 |

TABLE 2-continued

| Nr of affected samples | Gene | Chromo-some | Start Position | Affected homo-polymer base | Affected homo-polymer length | Nr of Inser-tions | Nr of dele-tions |
|---|---|---|---|---|---|---|---|
| 4 | MYO10 | chr5 | 16694605 | C | 8 | 2 | 2 |
| 4 | NCRNA00294 | chr11 | 33099777 | A | 14 | 0 | 4 |
| 4 | ODF2 | chr9 | 131262968 | T | 13 | 0 | 4 |
| 4 | OPN5 | chr6 | 47792559 | T | 13 | 0 | 4 |
| 4 | OSBPL2 | chr20 | 60854257 | C | 7 | 3 | 1 |
| 4 | PAR-SN | chr15 | 25227494 | A | 11 | 0 | 4 |
| 4 | PDCD6IP | chr3 | 33868210 | T | 15 | 1 | 3 |
| 4 | PDIK1L | chr1 | 26449667 | T | 15 | 0 | 4 |
| 4 | PMCHL2 | chr5 | 70673206 | A | 14 | 0 | 4 |
| 4 | POGLUT1 | chr3 | 119212650 | T | 21 | 0 | 4 |
| 4 | PRR11 | chr17 | 57247170 | A | 9 | 0 | 4 |
| 4 | RBM27 | chr5 | 145647319 | A | 9 | 1 | 3 |
| 4 | RBM43 | chr2 | 152108087 | T | 10 | 0 | 4 |
| 4 | RFC3 | chr13 | 34398062 | A | 10 | 1 | 3 |
| 4 | RG9MTD1 | chr3 | 101284008 | A | 10 | 1 | 3 |
| 4 | RPL29P2 | chr17 | 7658284 | A | 15 | 0 | 4 |
| 4 | RPS26P11 | chrX | 71264809 | A | 15 | 1 | 3 |
| 4 | SCARF1 | chr17 | 1537682 | A | 17 | 0 | 4 |
| 4 | SEC63 | chr6 | 108214754 | T | 10 | 0 | 4 |
| 4 | SLC23A2 | chr20 | 4850568 | G | 9 | 1 | 3 |
| 4 | SLC5A1 | chr22 | 32506613 | T | 10 | 0 | 4 |
| 4 | SNORD116-10 | chr15 | 25319287 | T | 16 | 0 | 4 |
| 4 | SPECC1 | chr17 | 20108262 | A | 8 | 1 | 3 |
| 4 | SRPR | chr11 | 126137086 | T | 8 | 1 | 3 |
| 4 | SUGT1P3 | chr13 | 41372415 | A | 16 | 0 | 4 |
| 4 | TBC1D15 | chr12 | 72318794 | A | 19 | 0 | 4 |
| 4 | TESC | chr12 | 117476741 | T | 14 | 0 | 4 |
| 4 | TEX11 | chrX | 70127617 | A | 8 | 0 | 4 |
| 4 | TGFBR3 | chr1 | 92147602 | A | 11 | 0 | 4 |
| 4 | TMCC1 | chr3 | 129407106 | A | 13 | 0 | 4 |
| 4 | TRIB2 | chr2 | 12882650 | T | 14 | 0 | 4 |
| 4 | TROVE2 | chr1 | 193054575 | T | 12 | 0 | 4 |
| 4 | TROVE2 | chr1 | 193053996 | A | 12 | 0 | 4 |
| 4 | TSIX | chrX | 73017534 | A | 12 | 1 | 3 |
| 4 | TSIX | chrX | 73016421 | T | 13 | 0 | 4 |
| 4 | TUBA4B | chr2 | 220118076 | G | 10 | 0 | 4 |
| 4 | WDTC1 | chr1 | 27621107 | G | 8 | 2 | 2 |
| 4 | XIST | chrX | 73071940 | A | 13 | 0 | 4 |
| 4 | XPA | chr9 | 100437633 | T | 10 | 0 | 4 |
| 4 | ZBTB20 | chr3 | 114058002 | G | 7 | 0 | 4 |
| 4 | ZDHHC8 | chr22 | 20130521 | C | 6 | 0 | 4 |
| 4 | ZMAT1 | chrX | 101138438 | T | 11 | 4 | 0 |
| 4 | ZNF252 | chr8 | 146201232 | A | 20 | 0 | 4 |
| 4 | ZNF273 | chr7 | 64390205 | T | 13 | 1 | 3 |
| 4 | ZNF831 | chr20 | 57766219 | C | 8 | 1 | 3 |

TABLE 3

| Marker Nr. | Gene | Region | Type | Chromo-some | Position | Reference base | Length of affected homo-polymer |
|---|---|---|---|---|---|---|---|
| 1 | DDX27 | Exonic | Deletion | 20 | 47858504 | A | 8 |
| 2 | EXOSC9 | Exonic | Deletion | 4 | 122723894 | T | 8 |
| 3 | FAM111B | Exonic | Deletion | 11 | 58892377 | A | 10 |
| 4 | GRIK2 | Exonic | Deletion | 6 | 102503432 | A | 8 |
| 5 | KIAA1919 | Exonic | Deletion | 6 | 111587361 | T | 9 |
| 6 | MYL1 | Exonic | Deletion | 2 | 211179766 | T | 11 |
| 7 | PHF2 | Exonic | Deletion | 9 | 96422612 | A | 8 |
| 8 | SEC31A | Exonic | Deletion | 4 | 83785565 | T | 9 |
| 9 | SETD1B | Exonic | Deletion | 12 | 122242658 | C | 8 |
| 10 | TMEM60 | Exonic | Deletion | 7 | 77423460 | T | 9 |
| 11 | TTK | Exonic | Deletion | 6 | 80751897 | A | 9 |
| 12 | ABAT | 3'UTR | Deletion | 16 | 8876793 | T | 11 |
| 13 | AKIRIN1 | 3'UTR | Deletion | 1 | 39471673 | A | 10 |
| 14 | ARFIP1 | 3'UTR | Deletion | 4 | 153832103 | T | 11 |
| 15 | ARL10 | 3'UTR | Deletion | 5 | 175800427 | T | 10 |
| 16 | BMPR2 | 3'UTR | Deletion | 2 | 203426177 | T | 8 |
| 17 | BTBD7 | 3'UTR | Deletion | 14 | 93708031 | A | 12 |
| 18 | C15orf2 | 3'UTR | Deletion | 15 | 24927892 | A | 10 |
| 19 | C17orf96 | 3'UTR | Deletion | 17 | 36829266 | T | 8 |

TABLE 3-continued

| Marker Nr. | Gene | Region | Type | Chromosome | Position | Reference base | Length of affected homopolymer |
|---|---|---|---|---|---|---|---|
| 20 | CCDC89 | 3'UTR | Deletion | 11 | 85395560 | T | 10 |
| 21 | CCND1 | 3'UTR | Deletion | 11 | 69466274 | A | 10 |
| 22 | DIDO1 | 3'UTR | Deletion | 20 | 61536692 | A | 11 |
| 23 | EDEM1 | 3'UTR | Deletion | 3 | 5260541 | T | 10 |
| 24 | ENTPD4 | 3'UTR | Deletion | 8 | 23289681 | A | 11 |
| 25 | FCHSD2 | 3'UTR | Deletion | 11 | 72548510 | A | |
| 26 | FGFBP3 | 3'UTR | Deletion | 10 | 93666831 | A | 11 |
| 27 | FMO2 | 3'UTR | Deletion | 1 | 171178336 | A | 11 |
| 28 | FOXN2 | 3'UTR | Deletion | 2 | 48603080 | T | 10 |
| 29 | HDAC4 | 3'UTR | Deletion | 2 | 239974110 | A | 9 |
| 30 | HUS1B | 3'UTR | Deletion | 6 | 656080 | A | 10 |
| 31 | KDM5A | 3'UTR | Deletion | 12 | 393805 | T | 11 |
| 32 | KIF5C | 3'UTR | Deletion | 2 | 149879666 | T | 10 |
| 33 | LANCL1 | 3'UTR | Deletion | 2 | 211297866 | T | 9 |
| 34 | LRCH1 | 3'UTR | Deletion | 13 | 47325657 | A | 10 |
| 35 | MKLN1 | 3'UTR | Deletion | 7 | 131175981 | A | 10 |
| 36 | PCDHB3 | 3'UTR | Deletion | 5 | 140482944 | T | 10 |
| 37 | PPM1A | 3'UTR | Deletion | 14 | 60761434 | T | 10 |
| 38 | PURB | 3'UTR | Deletion | 7 | 44920831 | A | 9 |
| 39 | RYBP | 3'UTR | Deletion | 3 | 72424550 | T | 9 |
| 40 | RYR3 | 3'UTR | Deletion | 15 | 34157542 | A | 10 |
| 41 | SLC35F1 | 3'UTR | Deletion | 6 | 118638704 | A | 24 |
| 42 | ST7L | 3'UTR | Deletion | 1 | 113067471 | A | 10 |
| 43 | TMC7 | 3'UTR | Deletion | 16 | 19073948 | A | 10 |
| 44 | TMEM65 | 3'UTR | Deletion | 8 | 125325218 | A | 11 |
| 45 | TSR2 | 3'UTR | Deletion | X | 54471046 | T | 10 |
| 46 | UBA6 | 3'UTR | Deletion | 4 | 68481878 | T | 12 |
| 47 | UBE2Z | 3'UTR | Deletion | 17 | 47005702 | A | 11 |
| 48 | USP14 | 3'UTR | Deletion | 18 | 212030 | A | 9 |
| 49 | WHSC1L1 | 3'UTR | Deletion | 8 | 38175280 | A | 11 |
| 50 | ZNF185 | 3'UTR | Deletion | X | 152140996 | C | 10 |
| 51 | ZNF287 | 3'UTR | Deletion | 17 | 16454420 | T | 9 |
| 52 | CEPT1 | 5'UTR | Insertion/Deletion | 1 | 111690319 | A | 9 |
| 53 | ESCO1 | 5'UTR | Deletion | 18 | 19164371 | A | 11 |
| 54 | GRIA2 | 5'UTR | Insertion/Deletion | 4 | 158142151 | A | 9 |
| 55 | SETBP1 | 5'UTR | Insertion/Deletion | 18 | 42260910 | G | 8 |
| 56 | ZXDA | 5'UTR | Deletion | X | 57936947 | A | 9 |

TABLE 4

| Nr of affected samples | Gene | Chromosome | Start Position | Affected homopolymer base | Affected homopolymer length | region |
|---|---|---|---|---|---|---|
| 13 | LRRC8D | chr1 | 90401405 | T | 11 | 3' UTR |
| 13 | NPR3 | chr5 | 32787131 | A | 11 | 3' UTR |
| 12 | AHCYL1 | chr1 | 110566210 | A | 14 | 3' UTR |
| 12 | CD5L | chr1 | 157801230 | A | 13 | 3' UTR |
| 12 | CEP170 | chr1 | 243288181 | T | 11 | 3' UTR |
| 12 | SAMD12 | chr8 | 119209320 | A | 11 | 3' UTR |
| 12 | UBE2Z | chr17 | 47005701 | A | 11 | 3' UTR |
| 11 | SEPT7 | chr7 | 35944036 | T | 11 | 3' UTR |
| 11 | CASK | chrX | 41379131 | A | 13 | 3' UTR |
| 11 | DIDO1 | chr20 | 61536691 | A | 11 | 3' UTR |
| 11 | EIF4G3 | chr1 | 21133286 | A | 13 | 3' UTR |
| 11 | FAM20B | chr1 | 179044906 | A | 12 | 3' UTR |
| 11 | GSK3B | chr3 | 119542766 | A | 11 | 3' UTR |
| 11 | HELZ | chr17 | 65070976 | A | 14 | 3' UTR |
| 11 | KCNK1 | chr1 | 233807667 | A | 11 | 3' UTR |
| 11 | KCNMB4 | chr12 | 70824838 | A | 14 | 3' UTR |
| 11 | LHX9 | chr1 | 197898395 | T | 12 | 3' UTR |
| 11 | LYRM1 | chr16 | 20935842 | T | 11 | 3' UTR |
| 11 | MYO5B | chr18 | 47351784 | A | 12 | 3' UTR |
| 11 | NARG2 | chr15 | 60712503 | T | 13 | 3' UTR |
| 11 | PPP1R12A | chr12 | 80169697 | T | 13 | 3' UTR |
| 11 | PRTG | chr15 | 55903921 | A | 11 | 3' UTR |
| 11 | RAB11FIP1 | chr8 | 37718707 | A | 13 | 3' UTR |
| 11 | RASGRP1 | chr15 | 38781450 | T | 13 | 3' UTR |
| 11 | SH3KBP1 | chrX | 19552231 | T | 13 | 3' UTR |
| 11 | SHROOM3 | chr4 | 77701305 | A | 12 | 3' UTR |
| 11 | TMEM26 | chr10 | 63166725 | A | 12 | 3' UTR |

TABLE 4-continued

| Nr of affected samples | Gene | Chromosome | Start Position | Affected homopolymer base | Affected homopolymer length | region |
|---|---|---|---|---|---|---|
| 11 | TMEM65 | chr8 | 125325217 | A | 11 | 3' UTR |
| 11 | TRIP11 | chr14 | 92435633 | A | 12 | 3' UTR |
| 11 | ZBTB7A | chr19 | 4046571 | T | 11 | 3' UTR |
| 11 | ZKSCAN1 | chr7 | 99633041 | T | 12 | 3' UTR |
| 11 | ZNF217 | chr20 | 52185289 | A | 13 | 3' UTR |
| 11 | ZNF275 | chrX | 152617043 | A | 12 | 3' UTR |
| 10 | ACVR1C | chr2 | 158387581 | T | 14 | 3' UTR |
| 10 | ARAP2 | chr4 | 36068192 | A | 12 | 3' UTR |
| 10 | BCL11A | chr2 | 60685409 | T | 12 | 3' UTR |
| 10 | C14orf101 | chr14 | 57114799 | A | 13 | 3' UTR |
| 10 | C15orf29 | chr15 | 34434105 | T | 12 | 3' UTR |
| 10 | C17orf63 | chr17 | 27083744 | T | 12 | 3' UTR |
| 10 | CBFB | chr16 | 67133068 | T | 11 | 3' UTR |
| 10 | CBX5 | chr12 | 54628041 | T | 13 | 3' UTR |
| 10 | CD36 | chr7 | 80306123 | T | 12 | 3' UTR |
| 10 | EPS15 | chr1 | 51821385 | A | 13 | 3' UTR |
| 10 | ERBB2IP | chr5 | 65375200 | T | 15 | 3' UTR |
| 10 | ERGIC2 | chr12 | 29493722 | T | 11 | 3' UTR |
| 10 | FAM38B | chr18 | 10670849 | T | 14 | 3' UTR |
| 10 | FGF9 | chr13 | 22278024 | T | 13 | 3' UTR |
| 10 | FLRT2 | chr14 | 86090074 | A | 12 | 3' UTR |
| 10 | GABPB1 | chr15 | 50570604 | A | 13 | 3' UTR |
| 10 | GBP1 | chr1 | 89518865 | T | 13 | 3' UTR |
| 10 | HIPK1 | chr1 | 114519857 | T | 14 | 3' UTR |
| 10 | KCNG1 | chr20 | 49620212 | T | 14 | 3' UTR |
| 10 | LPHN3 | chr4 | 62936763 | T | 12 | 3' UTR |
| 10 | MAPK1IP1L | chr14 | 55535728 | T | 13 | 3' UTR |
| 10 | MSR1 | chr8 | 15997800 | A | 11 | 3' UTR |
| 10 | NCEH1 | chr3 | 172348807 | A | 12 | 3' UTR |
| 10 | PEX13 | chr2 | 61276332 | T | 15 | 3' UTR |
| 10 | PTEN | chr10 | 89725293 | T | 11 | 3' UTR |
| 10 | RBMS1 | chr2 | 161128989 | T | 13 | 3' UTR |
| 10 | RSPO2 | chr8 | 108912568 | A | 11 | 3' UTR |
| 10 | SEMA6A | chr5 | 115779928 | A | 13 | 3' UTR |
| 10 | SLAIN2 | chr4 | 48428163 | T | 11 | 3' UTR |
| 10 | SNX31 | chr8 | 101585895 | T | 11 | 3' UTR |
| 10 | TMEM57 | chr1 | 25826052 | T | 12 | 3' UTR |
| 10 | TMTC3 | chr12 | 88591979 | T | 13 | 3' UTR |
| 10 | UST | chr6 | 149398012 | T | 13 | 3' UTR |
| 10 | VEGFA | chr6 | 43754176 | A | 12 | 3' UTR |
| 10 | KLHL4 | chrX | 86922591 | A | 13 | 3' UTR |
| 9 | AEN | chr15 | 89174888 | T | 12 | 3' UTR |
| 9 | ALDH8A1 | chr6 | 135238907 | T | 10 | 3' UTR |
| 9 | ANK2 | chr4 | 114303782 | T | 11 | 3' UTR |
| 9 | ARHGAP17 | chr16 | 24930800 | A | 14 | 3' UTR |
| 9 | ASPN | chr9 | 95218905 | A | 12 | 3' UTR |
| 9 | BCL11B | chr14 | 99637947 | T | 12 | 3' UTR |
| 9 | BCL7A | chr12 | 122498799 | A | 12 | 3' UTR |
| 9 | BRAP | chr12 | 112080129 | T | 12 | 3' UTR |
| 9 | C11orf87 | chr11 | 109296012 | A | 12 | 3' UTR |
| 9 | C15orf2 | chr15 | 24927891 | A | 10 | 3' UTR |
| 9 | CACNB4 | chr2 | 152694131 | T | 11 | 3' UTR |
| 9 | CALN1 | chr7 | 71245682 | A | 12 | 3' UTR |
| 9 | CAMK2A | chr5 | 149600684 | T | 11 | 3' UTR |
| 9 | CBLN4 | chr20 | 54572755 | A | 12 | 3' UTR |
| 9 | CCDC85C | chr14 | 99978765 | A | 12 | 3' UTR |
| 9 | CD1E | chr1 | 158327025 | T | 13 | 3' UTR |
| 9 | CISD1 | chr10 | 60048285 | T | 11 | 3' UTR |
| 9 | CMTM6 | chr3 | 32523862 | A | 12 | 3' UTR |
| 9 | CNR1 | chr6 | 88853530 | A | 11 | 3' UTR |
| 9 | CSNK1E | chr22 | 38686807 | T | 12 | 3' UTR |
| 9 | CYP1B1 | chr2 | 38297055 | T | 12 | 3' UTR |
| 9 | DLGAP2 | chr8 | 1652939 | A | 11 | 3' UTR |
| 9 | DRAM2 | chr1 | 111660181 | A | 11 | 3' UTR |
| 9 | DUSP10 | chr1 | 221875661 | A | 11 | 3' UTR |
| 9 | EHD4 | chr15 | 42191704 | A | 12 | 3' UTR |
| 9 | EPT1 | chr2 | 26617514 | T | 11 | 3' UTR |
| 9 | FAM104A | chr17 | 71204073 | A | 13 | 3' UTR |
| 9 | FAM46A | chr6 | 82458103 | A | 13 | 3' UTR |
| 9 | FMO2 | chr1 | 171178335 | A | 11 | 3' UTR |
| 9 | FOXN3 | chr14 | 89622979 | T | 13 | 3' UTR |
| 9 | FRMD4A | chr10 | 13686797 | A | 12 | 3' UTR |
| 9 | FYN | chr6 | 111982555 | T | 12 | 3' UTR |
| 9 | GLI3 | chr7 | 42001569 | A | 11 | 3' UTR |
| 9 | H3F3C | chr12 | 31944217 | T | 12 | 3' UTR |

TABLE 4-continued

| Nr of affected samples | Gene | Chromosome | Start Position | Affected homopolymer base | Affected homopolymer length | region |
|---|---|---|---|---|---|---|
| 9 | HIPK2 | chr7 | 139249947 | A | 14 | 3' UTR |
| 9 | HNRNPK | chr9 | 86583189 | T | 12 | 3' UTR |
| 9 | IER3IP1 | chr18 | 44682385 | A | 11 | 3' UTR |
| 9 | IFNGR1 | chr6 | 137518966 | A | 14 | 3' UTR |
| 9 | IL33 | chr9 | 6256984 | T | 12 | 3' UTR |
| 9 | KCTD7 | chr7 | 66105589 | T | 11 | 3' UTR |
| 9 | KCTD9 | chr8 | 25286171 | A | 12 | 3' UTR |
| 9 | KIAA1712 | chr4 | 175238738 | T | 13 | 3' UTR |
| 9 | KIAA2018 | chr3 | 113371321 | A | 11 | 3' UTR |
| 9 | KRT8 | chr12 | 53291007 | A | 11 | 3' UTR |
| 9 | LARP4B | chr10 | 856116 | A | 13 | 3' UTR |
| 9 | MED1 | chr17 | 37561712 | T | 13 | 3' UTR |
| 9 | MED28 | chr4 | 17626082 | T | 11 | 3' UTR |
| 9 | METTL9 | chr16 | 21667438 | A | 12 | 3' UTR |
| 9 | MEX3A | chr1 | 156043944 | T | 11 | 3' UTR |
| 9 | MLL2 | chr12 | 49413580 | A | 12 | 3' UTR |
| 9 | NAALAD2 | chr11 | 89925062 | T | 10 | 3' UTR |
| 9 | PCBD2 | chr5 | 134296980 | T | 14 | 3' UTR |
| 9 | PCDH9 | chr13 | 66878392 | A | 26 | 3' UTR |
| 9 | PGK1 | chrX | 77381770 | T | 13 | 3' UTR |
| 9 | PHACTR2 | chr6 | 144151003 | T | 10 | 3' UTR |
| 9 | PI15 | chr8 | 75766071 | T | 10 | 3' UTR |
| 9 | PLEKHA2 | chr8 | 38830288 | T | 13 | 3' UTR |
| 9 | PPP2R3A | chr3 | 135865826 | T | 11 | 3' UTR |
| 9 | PRCC | chr1 | 156770552 | T | 12 | 3' UTR |
| 9 | PRKD3 | chr2 | 37478759 | T | 12 | 3' UTR |
| 9 | PRPF40A | chr2 | 153512044 | T | 15 | 3' UTR |
| 9 | PSEN1 | chr14 | 73688298 | T | 13 | 3' UTR |
| 9 | RCC2 | chr1 | 17735285 | A | 14 | 3' UTR |
| 9 | RELL1 | chr4 | 37613352 | A | 12 | 3' UTR |
| 9 | RGS16 | chr1 | 182569291 | T | 26 | 3' UTR |
| 9 | RUNDC3B | chr7 | 87460421 | T | 12 | 3' UTR |
| 9 | SATB2 | chr2 | 200136194 | T | 12 | 3' UTR |
| 9 | SCML4 | chr6 | 108025850 | T | 13 | 3' UTR |
| 9 | SEC61G | chr7 | 54819993 | A | 11 | 3' UTR |
| 9 | SENP1 | chr12 | 48436768 | T | 11 | 3' UTR |
| 9 | SLC35D1 | chr1 | 67465371 | A | 13 | 3' UTR |
| 9 | SMAD3 | chr15 | 67486032 | T | 13 | 3' UTR |
| 9 | SPIN1 | chr9 | 91090830 | A | 12 | 3' UTR |
| 9 | SRC | chr20 | 36033633 | T | 13 | 3' UTR |
| 9 | TACC1 | chr8 | 38705639 | A | 11 | 3' UTR |
| 9 | TAF4B | chr18 | 23971176 | A | 14 | 3' UTR |
| 9 | TBC1D24 | chr16 | 2553486 | A | 13 | 3' UTR |
| 9 | THAP1 | chr8 | 42692467 | A | 12 | 3' UTR |
| 9 | TMEM106B | chr7 | 12273303 | A | 13 | 3' UTR |
| 9 | TMEM14B | chr6 | 10756863 | A | 11 | 3' UTR |
| 9 | TMEM209 | chr7 | 129805893 | A | 12 | 3' UTR |
| 9 | TMEM33 | chr4 | 41959614 | T | 14 | 3' UTR |
| 9 | TRA2A | chr7 | 23544783 | A | 11 | 3' UTR |
| 9 | TRIM66 | chr11 | 8635430 | A | 9 | 3' UTR |
| 9 | TTBK2 | chr15 | 43037302 | A | 12 | 3' UTR |
| 9 | UBE2M | chr19 | 59067290 | A | 13 | 3' UTR |
| 9 | USP44 | chr12 | 95911789 | A | 11 | 3' UTR |
| 9 | VCPIP1 | chr8 | 67545797 | A | 15 | 3' UTR |
| 9 | VGLL4 | chr3 | 11599949 | T | 13 | 3' UTR |
| 9 | XPO4 | chr13 | 21356029 | A | 10 | 3' UTR |
| 9 | ZBTB3 | chr11 | 62519422 | A | 12 | 3' UTR |
| 9 | ZNF264 | chr19 | 57730525 | A | 14 | 3' UTR |
| 9 | ZNF347 | chr19 | 53643153 | T | 12 | 3' UTR |
| 9 | ZNF704 | chr8 | 81550824 | A | 12 | 3' UTR |
| 9 | ZNF740 | chr12 | 53582896 | T | 11 | 3' UTR |
| 8 | A1CF | chr10 | 52566432 | T | 12 | 3' UTR |
| 8 | ABAT | chr16 | 8876792 | T | 11 | 3' UTR |
| 8 | ABI1 | chr10 | 27037487 | A | 11 | 3' UTR |
| 8 | ACTR2 | chr2 | 65498035 | A | 12 | 3' UTR |
| 8 | AIDA | chr1 | 222841524 | T | 10 | 3' UTR |
| 8 | AKIRIN1 | chr1 | 39471672 | A | 10 | 3' UTR |
| 8 | APH1B | chr15 | 63600287 | T | 12 | 3' UTR |
| 8 | ARHGAP18 | chr6 | 129898731 | A | 11 | 3' UTR |
| 8 | ARHGAP5 | chr14 | 32627034 | T | 11 | 3' UTR |
| 8 | ASB7 | chr15 | 101189293 | T | 10 | 3' UTR |
| 8 | ATRX | chrX | 76763679 | A | 13 | 3' UTR |
| 8 | BACE1 | chr11 | 117159733 | T | 11 | 3' UTR |
| 8 | C4orf49 | chr4 | 140187661 | T | 11 | 3' UTR |
| 8 | CADPS | chr3 | 62384481 | T | 10 | 3' UTR |

TABLE 4-continued

| Nr of affected samples | Gene | Chromosome | Start Position | Affected homopolymer base | Affected homopolymer length | region |
|---|---|---|---|---|---|---|
| 8 | CALML4 | chr15 | 68483096 | A | 12 | 3' UTR |
| 8 | CAMKK2 | chr12 | 121676365 | A | 11 | 3' UTR |
| 8 | CANX | chr5 | 179158477 | A | 12 | 3' UTR |
| 8 | CANX | chr5 | 179155907 | T | 12 | 3' UTR |
| 8 | CAP2 | chr6 | 17556926 | A | 11 | 3' UTR |
| 8 | CCDC43 | chr17 | 42754916 | T | 13 | 3' UTR |
| 8 | CCDC89 | chr11 | 85395559 | T | 10 | 3' UTR |
| 8 | CD47 | chr3 | 107762288 | A | 11 | 3' UTR |
| 8 | CDC23 | chr5 | 137524388 | A | 11 | 3' UTR |
| 8 | CELF2 | chr10 | 11373567 | A | 11 | 3' UTR |
| 8 | CHM | chrX | 85118100 | T | 13 | 3' UTR |
| 8 | COPA | chr1 | 160258927 | T | 15 | 3' UTR |
| 8 | CPEB3 | chr10 | 93809826 | A | 11 | 3' UTR |
| 8 | CPNE3 | chr8 | 87571865 | T | 11 | 3' UTR |
| 8 | CRTAP | chr3 | 33187520 | A | 12 | 3' UTR |
| 8 | CSDA | chr12 | 10851811 | T | 14 | 3' UTR |
| 8 | CSMD2 | chr1 | 33979967 | T | 12 | 3' UTR |
| 8 | DCP2 | chr5 | 112351058 | T | 11 | 3' UTR |
| 8 | DDHD1 | chr14 | 53513439 | A | 12 | 3' UTR |
| 8 | DIEXF | chr1 | 210026704 | T | 15 | 3' UTR |
| 8 | DLG3 | chrX | 69722274 | T | 13 | 3' UTR |
| 8 | DLGAP2 | chr8 | 1653883 | T | 11 | 3' UTR |
| 8 | DSC3 | chr18 | 28573880 | A | 12 | 3' UTR |
| 8 | EFNA5 | chr5 | 106714693 | A | 12 | 3' UTR |
| 8 | EPHA4 | chr2 | 222290623 | T | 11 | 3' UTR |
| 8 | EXOSC2 | chr9 | 133579920 | A | 11 | 3' UTR |
| 8 | FAM107B | chr10 | 14561157 | T | 12 | 3' UTR |
| 8 | FAM116A | chr3 | 57611367 | A | 11 | 3' UTR |
| 8 | FAM8A1 | chr6 | 17609273 | T | 11 | 3' UTR |
| 8 | FAM91A1 | chr8 | 124826583 | T | 12 | 3' UTR |
| 8 | FGFBP3 | chr10 | 93666830 | A | 11 | 3' UTR |
| 8 | GABRG2 | chr5 | 161581834 | A | 11 | 3' UTR |
| 8 | GAL | chr11 | 68458592 | T | 12 | 3' UTR |
| 8 | GLS | chr2 | 191828629 | T | 12 | 3' UTR |
| 8 | GPAM | chr10 | 113910871 | T | 12 | 3' UTR |
| 8 | HCRTR2 | chr6 | 55147361 | T | 12 | 3' UTR |
| 8 | HERPUD2 | chr7 | 35672678 | T | 14 | 3' UTR |
| 8 | HIP1 | chr7 | 75166838 | A | 11 | 3' UTR |
| 8 | HIPK2 | chr7 | 139257355 | T | 11 | 3' UTR |
| 8 | HMGCS1 | chr5 | 43290194 | A | 16 | 3' UTR |
| 8 | HNRNPUL1 | chr19 | 41812943 | A | 12 | 3' UTR |
| 8 | HSPA9 | chr5 | 137891047 | A | 13 | 3' UTR |
| 8 | IFIT2 | chr10 | 91068075 | T | 12 | 3' UTR |
| 8 | IGF2BP1 | chr17 | 47129195 | T | 12 | 3' UTR |
| 8 | KLF9 | chr9 | 73002115 | T | 11 | 3' UTR |
| 8 | LHFPL4 | chr3 | 9543422 | A | 13 | 3' UTR |
| 8 | LRAT | chr4 | 155673737 | A | 10 | 3' UTR |
| 8 | LSM14A | chr19 | 34718607 | T | 12 | 3' UTR |
| 8 | MAP3K5 | chr6 | 136878751 | T | 14 | 3' UTR |
| 8 | MED13 | chr17 | 60023567 | A | 10 | 3' UTR |
| 8 | MESDC1 | chr15 | 81296129 | T | 12 | 3' UTR |
| 8 | METTL21B | chr12 | 58175145 | T | 15 | 3' UTR |
| 8 | MITF | chr3 | 70014804 | A | 11 | 3' UTR |
| 8 | MS4A7 | chr11 | 60161438 | A | 12 | 3' UTR |
| 8 | MTF2 | chr1 | 93602675 | A | 14 | 3' UTR |
| 8 | NAP1L4 | chr11 | 2966276 | A | 15 | 3' UTR |
| 8 | NEDD1 | chr12 | 97346987 | A | 13 | 3' UTR |
| 8 | NEK5 | chr13 | 52639268 | A | 13 | 3' UTR |
| 8 | OXR1 | chr8 | 107763507 | T | 13 | 3' UTR |
| 8 | PAPD5 | chr16 | 50264031 | A | 13 | 3' UTR |
| 8 | PDE9A | chr21 | 44195537 | A | 13 | 3' UTR |
| 8 | PIGM | chr1 | 159998798 | T | 11 | 3' UTR |
| 8 | PM20D2 | chr6 | 89874860 | T | 11 | 3' UTR |
| 8 | POGZ | chr1 | 151377008 | A | 13 | 3' UTR |
| 8 | POMT2 | chr14 | 77741349 | T | 11 | 3' UTR |
| 8 | POU2F2 | chr19 | 42595246 | T | 17 | 3' UTR |
| 8 | RAB11FIP2 | chr10 | 119766958 | A | 12 | 3' UTR |
| 8 | RAP2A | chr13 | 98118463 | A | 14 | 3' UTR |
| 8 | RBM25 | chr14 | 73587904 | T | 14 | 3' UTR |
| 8 | RBM33 | chr7 | 155569742 | T | 13 | 3' UTR |
| 8 | RBM45 | chr2 | 178994205 | T | 11 | 3' UTR |
| 8 | RIMKLB | chr12 | 8926680 | T | 11 | 3' UTR |
| 8 | RNF149 | chr2 | 101893233 | A | 10 | 3' UTR |
| 8 | RNLS | chr10 | 90034667 | A | 11 | 3' UTR |
| 8 | RORA | chr15 | 60788653 | A | 12 | 3' UTR |

TABLE 4-continued

| Nr of affected samples | Gene | Chromosome | Start Position | Affected homopolymer base | Affected homopolymer length | region |
|---|---|---|---|---|---|---|
| 8 | SAMD5 | chr6 | 147887423 | T | 12 | 3' UTR |
| 8 | SAR1A | chr10 | 71911798 | A | 12 | 3' UTR |
| 8 | SEL1L | chr14 | 81942829 | T | 13 | 3' UTR |
| 8 | SEMA4D | chr9 | 91992883 | A | 13 | 3' UTR |
| 8 | SETX | chr9 | 135139195 | T | 11 | 3' UTR |
| 8 | SH3RF1 | chr4 | 170017405 | A | 14 | 3' UTR |
| 8 | SMARCC2 | chr12 | 56556167 | A | 14 | 3' UTR |
| 8 | SNRNP40 | chr1 | 31732677 | A | 11 | 3' UTR |
| 8 | SOX4 | chr6 | 21596500 | A | 12 | 3' UTR |
| 8 | ST7L | chr1 | 113067470 | A | 10 | 3' UTR |
| 8 | STXBP5 | chr6 | 147708451 | A | 10 | 3' UTR |
| 8 | TGIF2 | chr20 | 35220571 | A | 14 | 3' UTR |
| 8 | TLE3 | chr15 | 70340967 | A | 11 | 3' UTR |
| 8 | TMC7 | chr16 | 19073947 | A | 10 | 3' UTR |
| 8 | TMEM57 | chr1 | 25825931 | T | 13 | 3' UTR |
| 8 | TNRC6B | chr22 | 40722031 | A | 10 | 3' UTR |
| 8 | TNRC6B | chr22 | 40720866 | T | 14 | 3' UTR |
| 8 | TNRC6B | chr22 | 40720294 | T | 15 | 3' UTR |
| 8 | TRPS1 | chr8 | 116424407 | A | 12 | 3' UTR |
| 8 | TSGA10 | chr2 | 99614595 | A | 13 | 3' UTR |
| 8 | TSPAN14 | chr10 | 82279557 | T | 14 | 3' UTR |
| 8 | TTL | chr2 | 113289264 | A | 11 | 3' UTR |
| 8 | TTLL5 | chr14 | 76420881 | T | 11 | 3' UTR |
| 8 | UBA6 | chr4 | 68481877 | T | 12 | 3' UTR |
| 8 | UFM1 | chr13 | 38935214 | T | 11 | 3' UTR |
| 8 | VCP | chr9 | 35056078 | T | 12 | 3' UTR |
| 8 | VEZF1 | chr17 | 56049540 | T | 11 | 3' UTR |
| 8 | WHSC1L1 | chr8 | 38175279 | A | 11 | 3' UTR |
| 8 | WSB1 | chr17 | 25640066 | A | 15 | 3' UTR |
| 8 | ZBTB43 | chr9 | 129596297 | A | 11 | 3' UTR |
| 8 | ZNF12 | chr7 | 6730082 | T | 12 | 3' UTR |
| 8 | ZNF238 | chr1 | 244220229 | T | 10 | 3' UTR |
| 8 | ZNF281 | chr1 | 200375822 | T | 12 | 3' UTR |
| 8 | ZNF621 | chr3 | 40575421 | A | 11 | 3' UTR |
| 7 | ADRBK2 | chr22 | 26121915 | A | 11 | 3' UTR |
| 7 | ALG9 | chr11 | 111655441 | A | 11 | 3' UTR |
| 7 | ANKIB1 | chr7 | 92029899 | T | 11 | 3' UTR |
| 7 | ANKRD28 | chr3 | 15709862 | T | 13 | 3' UTR |
| 7 | ARFIP1 | chr4 | 153832102 | T | 11 | 3' UTR |
| 7 | ARID4A | chr14 | 58840119 | T | 10 | 3' UTR |
| 7 | ATP11A | chr13 | 113540850 | T | 12 | 3' UTR |
| 7 | ATP2B1 | chr12 | 89984601 | T | 12 | 3' UTR |
| 7 | ATXN1 | chr6 | 16300902 | T | 11 | 3' UTR |
| 7 | BOD1L | chr4 | 13570453 | A | 11 | 3' UTR |
| 7 | C14orf37 | chr14 | 58471378 | T | 11 | 3' UTR |
| 7 | C2orf29 | chr2 | 101886538 | T | 12 | 3' UTR |
| 7 | C3orf58 | chr3 | 143709141 | T | 11 | 3' UTR |
| 7 | C3orf62 | chr3 | 49308391 | A | 11 | 3' UTR |
| 7 | C3orf72 | chr3 | 138671354 | T | 13 | 3' UTR |
| 7 | C8orf44-SGK3,SGK3 | chr8 | 67772690 | A | 11 | 3' UTR |
| 7 | CALN1 | chr7 | 71249416 | T | 10 | 3' UTR |
| 7 | CASK | chrX | 41377809 | A | 11 | 3' UTR |
| 7 | CD300LB | chr17 | 72518440 | A | 11 | 3' UTR |
| 7 | CDC25A | chr3 | 48199852 | T | 12 | 3' UTR |
| 7 | CDC73 | chr1 | 193220974 | T | 12 | 3' UTR |
| 7 | CDKN2AIPNL | chr5 | 133738313 | A | 11 | 3' UTR |
| 7 | CELSR1 | chr22 | 46756848 | A | 11 | 3' UTR |
| 7 | CMIP | chr16 | 81744987 | A | 10 | 3' UTR |
| 7 | COIL | chr17 | 55016354 | A | 14 | 3' UTR |
| 7 | COPS7B | chr2 | 232673378 | T | 13 | 3' UTR |
| 7 | COX18 | chr4 | 73923142 | A | 12 | 3' UTR |
| 7 | CSNK1E | chr22 | 38686864 | A | 11 | 3' UTR |
| 7 | DCP1A | chr3 | 53321360 | T | 27 | 3' UTR |
| 7 | DNAJC27 | chr2 | 25167221 | T | 14 | 3' UTR |
| 7 | DNMT3B | chr20 | 31395997 | T | 11 | 3' UTR |
| 7 | DTNA | chr18 | 32446839 | T | 12 | 3' UTR |
| 7 | EFNB1 | chrX | 68061978 | A | 12 | 3' UTR |
| 7 | ENTPD1 | chr10 | 97628618 | A | 10 | 3' UTR |
| 7 | ERBB4 | chr2 | 212247967 | A | 18 | 3' UTR |
| 7 | EYA1 | chr8 | 72110673 | A | 12 | 3' UTR |
| 7 | FAM118A | chr22 | 45736689 | T | 11 | 3' UTR |
| 7 | FAM126B | chr2 | 201838933 | A | 13 | 3' UTR |
| 7 | FAM13B | chr5 | 137274915 | A | 11 | 3' UTR |
| 7 | FAM169A | chr5 | 74075446 | T | 12 | 3' UTR |
| 7 | FAM60A | chr12 | 31435556 | A | 10 | 3' UTR |

TABLE 4-continued

| Nr of affected samples | Gene | Chromosome | Start Position | Affected homopolymer base | Affected homopolymer length | region |
|---|---|---|---|---|---|---|
| 7 | FBLN7 | chr2 | 112945284 | T | 11 | 3' UTR |
| 7 | FGF9 | chr13 | 22277774 | T | 10 | 3' UTR |
| 7 | FKBP5 | chr6 | 35554624 | T | 12 | 3' UTR |
| 7 | FOXO3 | chr6 | 109005013 | A | 11 | 3' UTR |
| 7 | FXR1 | chr3 | 180694863 | T | 14 | 3' UTR |
| 7 | GBP6 | chr1 | 89851722 | A | 13 | 3' UTR |
| 7 | GNB1 | chr1 | 1717242 | T | 12 | 3' UTR |
| 7 | GNRHR | chr4 | 68604166 | A | 12 | 3' UTR |
| 7 | GPC3 | chrX | 132670054 | A | 13 | 3' UTR |
| 7 | GRIK2 | chr6 | 102517011 | T | 11 | 3' UTR |
| 7 | H3F3B | chr17 | 73774199 | T | 13 | 3' UTR |
| 7 | HAS2 | chr8 | 122625936 | A | 12 | 3' UTR |
| 7 | HELZ | chr17 | 65073603 | A | 11 | 3' UTR |
| 7 | HIPK2 | chr7 | 139250450 | T | 11 | 3' UTR |
| 7 | HN1 | chr17 | 73132058 | A | 12 | 3' UTR |
| 7 | HNRNPA3 | chr2 | 178088002 | T | 10 | 3' UTR |
| 7 | HNRNPR | chr1 | 23636874 | T | 11 | 3' UTR |
| 7 | HUS1B | chr6 | 656079 | A | 10 | 3' UTR |
| 7 | KDM5A | chr12 | 389523 | T | 11 | 3' UTR |
| 7 | KHNYN | chr14 | 24908391 | T | 11 | 3' UTR |
| 7 | KIF3A | chr5 | 132029672 | A | 14 | 3' UTR |
| 7 | KIF5C | chr2 | 149879665 | T | 10 | 3' UTR |
| 7 | KLHL28 | chr14 | 45398006 | T | 11 | 3' UTR |
| 7 | LRCH1 | chr13 | 47325657 | A | 10 | 3' UTR |
| 7 | LRIG2 | chr1 | 113667282 | T | 11 | 3' UTR |
| 7 | LRP6 | chr12 | 12272288 | A | 12 | 3' UTR |
| 7 | MAGEB3 | chrX | 30255422 | A | 11 | 3' UTR |
| 7 | MAK | chr6 | 10764372 | T | 9 | 3' UTR |
| 7 | MCTS1 | chrX | 119754487 | A | 14 | 3' UTR |
| 7 | MDM2 | chr12 | 69236873 | T | 13 | 3' UTR |
| 7 | MED19 | chr11 | 57471199 | T | 13 | 3' UTR |
| 7 | MESDC1 | chr15 | 81296262 | T | 9 | 3' UTR |
| 7 | MGAT4A | chr2 | 99235842 | A | 11 | 3' UTR |
| 7 | MLL3 | chr7 | 151832596 | T | 11 | 3' UTR |
| 7 | MTMR9 | chr8 | 11185354 | A | 10 | 3' UTR |
| 7 | NAA35 | chr9 | 88637203 | A | 10 | 3' UTR |
| 7 | NAF1 | chr4 | 164049985 | A | 11 | 3' UTR |
| 7 | NHLH1 | chr1 | 160341680 | A | 11 | 3' UTR |
| 7 | NIPAL3 | chr1 | 24799398 | A | 12 | 3' UTR |
| 7 | NPAS3 | chr14 | 34271068 | A | 12 | 3' UTR |
| 7 | NRF1 | chr7 | 129395138 | T | 11 | 3' UTR |
| 7 | NTRK2 | chr9 | 87487518 | T | 11 | 3' UTR |
| 7 | PALM2 | chr9 | 112708967 | A | 25 | 3' UTR |
| 7 | PAPSS2 | chr10 | 89507276 | A | 11 | 3' UTR |
| 7 | PCDH7 | chr4 | 31146675 | T | 12 | 3' UTR |
| 7 | PCSK2 | chr20 | 17463028 | T | 11 | 3' UTR |
| 7 | PHF6 | chrX | 133561520 | T | 10 | 3' UTR |
| 7 | PKP4 | chr2 | 159537312 | T | 10 | 3' UTR |
| 7 | PLXNA4 | chr7 | 131809795 | A | 13 | 3' UTR |
| 7 | POFUT1 | chr20 | 30826323 | A | 11 | 3' UTR |
| 7 | PPP1CB | chr2 | 29024298 | T | 14 | 3' UTR |
| 7 | PPP2R3A | chr3 | 135865709 | A | 14 | 3' UTR |
| 7 | PRPF4 | chr9 | 116054493 | A | 14 | 3' UTR |
| 7 | PRPF40A | chr2 | 153509691 | A | 11 | 3' UTR |
| 7 | PRR23A | chr3 | 138723892 | A | 9 | 3' UTR |
| 7 | PSMD11 | chr17 | 30807996 | A | 11 | 3' UTR |
| 7 | PTAFR | chr1 | 28475836 | T | 27 | 3' UTR |
| 7 | PTPN11 | chr12 | 112944240 | T | 12 | 3' UTR |
| 7 | PTPN18 | chr2 | 131131908 | T | 14 | 3' UTR |
| 7 | PTPRJ | chr11 | 48189153 | T | 13 | 3' UTR |
| 7 | PURB | chr7 | 44920830 | A | 9 | 3' UTR |
| 7 | RB1CC1 | chr8 | 53536112 | A | 11 | 3' UTR |
| 7 | RBM12B | chr8 | 94745437 | A | 11 | 3' UTR |
| 7 | RC3H1 | chr1 | 173901043 | T | 11 | 3' UTR |
| 7 | RDH10 | chr8 | 74236678 | T | 10 | 3' UTR |
| 7 | RECK | chr9 | 36123172 | T | 11 | 3' UTR |
| 7 | RPS6KA2 | chr6 | 166824706 | T | 13 | 3' UTR |
| 7 | RS1 | chrX | 18659977 | A | 13 | 3' UTR |
| 7 | RUNDC3B | chr7 | 87459581 | A | 13 | 3' UTR |
| 7 | RXRA | chr9 | 137331937 | A | 12 | 3' UTR |
| 7 | RYBP | chr3 | 72424549 | T | 9 | 3' UTR |
| 7 | RYR3 | chr15 | 34157541 | A | 10 | 3' UTR |
| 7 | SAMD10 | chr20 | 62605493 | T | 12 | 3' UTR |
| 7 | SEC31A | chr4 | 83740163 | T | 11 | 3' UTR |
| 7 | SENP1 | chr12 | 48437910 | T | 11 | 3' UTR |

TABLE 4-continued

| Nr of affected samples | Gene | Chromosome | Start Position | Affected homopolymer base | Affected homopolymer length | region |
|---|---|---|---|---|---|---|
| 7 | SGCD | chr5 | 156190730 | A | 12 | 3' UTR |
| 7 | SH3BP5 | chr3 | 15297082 | T | 13 | 3' UTR |
| 7 | SH3RF1 | chr4 | 170016066 | A | 11 | 3' UTR |
| 7 | SLC16A7 | chr12 | 60173983 | A | 11 | 3' UTR |
| 7 | SLC2A3 | chr12 | 8072022 | T | 13 | 3' UTR |
| 7 | SLC30A7 | chr1 | 101446221 | T | 11 | 3' UTR |
| 7 | SLC7A11 | chr4 | 139092374 | A | 11 | 3' UTR |
| 7 | SLC9A2 | chr2 | 103326258 | T | 10 | 3' UTR |
| 7 | SMAD4 | chr18 | 48609102 | T | 12 | 3' UTR |
| 7 | SNAPC1 | chr14 | 62262433 | A | 11 | 3' UTR |
| 7 | SNAPC3 | chr9 | 15461137 | A | 13 | 3' UTR |
| 7 | SNX27 | chr1 | 151666826 | T | 11 | 3' UTR |
| 7 | SPCS3 | chr4 | 177250201 | T | 10 | 3' UTR |
| 7 | STARD7 | chr2 | 96851899 | A | 14 | 3' UTR |
| 7 | TBC1D22B | chr6 | 37299299 | T | 12 | 3' UTR |
| 7 | TBL1XR1 | chr3 | 176741889 | A | 13 | 3' UTR |
| 7 | TFAP2C | chr20 | 55213320 | T | 11 | 3' UTR |
| 7 | TIGD6 | chr5 | 149373143 | T | 13 | 3' UTR |
| 7 | TMEM108 | chr3 | 133116233 | A | 14 | 3' UTR |
| 7 | TMEM161B | chr5 | 87491917 | T | 10 | 3' UTR |
| 7 | TMEM47 | chrX | 34646666 | T | 12 | 3' UTR |
| 7 | TMEM64 | chr8 | 91637753 | A | 12 | 3' UTR |
| 7 | TNRC6B | chr22 | 40719790 | A | 14 | 3' UTR |
| 7 | TNRC6C | chr17 | 76101834 | T | 9 | 3' UTR |
| 7 | TOMM20 | chr1 | 235275027 | T | 12 | 3' UTR |
| 7 | TPH1 | chr11 | 18042321 | A | 11 | 3' UTR |
| 7 | UACA | chr15 | 70946988 | A | 12 | 3' UTR |
| 7 | UBXN7 | chr3 | 196080741 | T | 11 | 3' UTR |
| 7 | UGT2B28 | chr4 | 70160632 | A | 11 | 3' UTR |
| 7 | USP28 | chr11 | 113669136 | A | 11 | 3' UTR |
| 7 | WDR82 | chr3 | 52289627 | A | 11 | 3' UTR |
| 7 | ZBTB34 | chr9 | 129646763 | T | 11 | 3' UTR |
| 7 | ZBTB44 | chr11 | 130102910 | A | 11 | 3' UTR |
| 7 | ZDHHC13 | chr11 | 19197719 | A | 10 | 3' UTR |
| 7 | ZNF136 | chr19 | 12299608 | A | 13 | 3' UTR |
| 7 | ZNF238 | chr1 | 244219573 | A | 9 | 3' UTR |
| 7 | ZNF563 | chr19 | 12428823 | T | 15 | 3' UTR |
| 7 | ZNF652 | chr17 | 47369576 | T | 11 | 3' UTR |
| 7 | ZNF716 | chr7 | 57529811 | A | 10 | 3' UTR |
| 7 | ZNF737 | chr19 | 20723566 | A | 11 | 3' UTR |
| 7 | ZNF737 | chr19 | 20722094 | A | 14 | 3' UTR |
| 6 | MARCH1 | chr4 | 164446860 | T | 9 | 3' UTR |
| 6 | ADRA1D | chr20 | 4201344 | T | 10 | 3' UTR |
| 6 | AJAP1 | chr1 | 4843660 | T | 11 | 3' UTR |
| 6 | AK4 | chr1 | 65692499 | T | 11 | 3' UTR |
| 6 | ANKH | chr5 | 14705393 | A | 13 | 3' UTR |
| 6 | ANKRD13C | chr1 | 70727638 | A | 12 | 3' UTR |
| 6 | ANKRD40 | chr17 | 48770711 | A | 10 | 3' UTR |
| 6 | AP1AR | chr4 | 113190822 | A | 11 | 3' UTR |
| 6 | APOL1 | chr22 | 36662141 | T | 12 | 3' UTR |
| 6 | ARHGAP28 | chr18 | 6914974 | A | 10 | 3' UTR |
| 6 | ARID1B | chr6 | 157530262 | A | 14 | 3' UTR |
| 6 | ARIH1 | chr15 | 72877867 | A | 12 | 3' UTR |
| 6 | ARL10 | chr5 | 175800426 | T | 10 | 3' UTR |
| 6 | ATF2 | chr2 | 175939223 | A | 12 | 3' UTR |
| 6 | ATP11C | chrX | 138809822 | A | 10 | 3' UTR |
| 6 | ATXN1 | chr6 | 16301824 | A | 13 | 3' UTR |
| 6 | BCLAF1 | chr6 | 136581674 | T | 11 | 3' UTR |
| 6 | BIN1 | chr2 | 127805622 | T | 10 | 3' UTR |
| 6 | BNIP3L | chr8 | 26268445 | A | 10 | 3' UTR |
| 6 | BOD1L | chr4 | 13571144 | A | 10 | 3' UTR |
| 6 | C1orf9 | chr1 | 172580460 | T | 9 | 3' UTR |
| 6 | C5orf43 | chr5 | 60453908 | A | 9 | 3' UTR |
| 6 | C6orf145 | chr6 | 3723315 | A | 11 | 3' UTR |
| 6 | C9orf167 | chr9 | 140176659 | T | 10 | 3' UTR |
| 6 | CAMLG | chr5 | 134086670 | A | 13 | 3' UTR |
| 6 | CBL | chr11 | 119175340 | T | 14 | 3' UTR |
| 6 | CCND2 | chr12 | 4411110 | T | 12 | 3' UTR |
| 6 | CCNE2 | chr8 | 95892992 | A | 11 | 3' UTR |
| 6 | CHD7 | chr8 | 61778758 | T | 11 | 3' UTR |
| 6 | CHP | chr15 | 41572703 | T | 27 | 3' UTR |
| 6 | CIT | chr12 | 120123939 | T | 11 | 3' UTR |
| 6 | CLCN5 | chrX | 49862213 | A | 12 | 3' UTR |
| 6 | CLN8 | chr8 | 1729701 | T | 14 | 3' UTR |
| 6 | CLSPN | chr1 | 36201819 | A | 17 | 3' UTR |

TABLE 4-continued

| Nr of affected samples | Gene | Chromosome | Start Position | Affected homopolymer base | Affected homopolymer length | region |
|---|---|---|---|---|---|---|
| 6 | CRTC1 | chr19 | 18890267 | T | 14 | 3' UTR |
| 6 | DAG1 | chr3 | 49571620 | T | 11 | 3' UTR |
| 6 | DNAJB7 | chr22 | 41256660 | T | 14 | 3' UTR |
| 6 | DNAJC17 | chr15 | 41060070 | A | 14 | 3' UTR |
| 6 | DSTYK | chr1 | 205112278 | T | 14 | 3' UTR |
| 6 | DYRK2 | chr12 | 68054141 | A | 11 | 3' UTR |
| 6 | EBF1 | chr5 | 158125829 | A | 12 | 3' UTR |
| 6 | ECE1 | chr1 | 21546032 | A | 10 | 3' UTR |
| 6 | EGR3 | chr8 | 22545637 | T | 11 | 3' UTR |
| 6 | EIF4EBP2 | chr10 | 72188037 | A | 11 | 3' UTR |
| 6 | EIF5A2 | chr3 | 170607962 | A | 11 | 3' UTR |
| 6 | ELTD1 | chr1 | 79356149 | T | 11 | 3' UTR |
| 6 | ENTPD4 | chr8 | 23289680 | A | 11 | 3' UTR |
| 6 | EPM2AIP1 | chr3 | 37030780 | T | 11 | 3' UTR |
| 6 | ERBB2IP | chr5 | 65376306 | A | 11 | 3' UTR |
| 6 | ERBB4 | chr2 | 212243952 | T | 11 | 3' UTR |
| 6 | FAM120C | chrX | 54098998 | A | 12 | 3' UTR |
| 6 | FAM122A | chr9 | 71396662 | T | 11 | 3' UTR |
| 6 | FAM168B | chr2 | 131805979 | G | 9 | 3' UTR |
| 6 | FBLIM1 | chr1 | 16112130 | A | 10 | 3' UTR |
| 6 | FBXO21 | chr12 | 117582899 | T | 11 | 3' UTR |
| 6 | FBXO27 | chr19 | 39514872 | T | 12 | 3' UTR |
| 6 | FGFR1OP2 | chr12 | 27118594 | A | 11 | 3' UTR |
| 6 | FOXP1 | chr3 | 71007140 | T | 11 | 3' UTR |
| 6 | G3BP1 | chr5 | 151184779 | T | 11 | 3' UTR |
| 6 | GABRB2 | chr5 | 160717254 | T | 12 | 3' UTR |
| 6 | GDA | chr9 | 74866560 | T | 12 | 3' UTR |
| 6 | GIT1 | chr17 | 27901146 | A | 12 | 3' UTR |
| 6 | GJC1 | chr17 | 42878975 | T | 13 | 3' UTR |
| 6 | GPR4 | chr19 | 46093443 | A | 11 | 3' UTR |
| 6 | GSK3B | chr3 | 119544323 | A | 9 | 3' UTR |
| 6 | GSR | chr8 | 30536666 | A | 19 | 3' UTR |
| 6 | GTF3C1 | chr16 | 27471985 | T | 11 | 3' UTR |
| 6 | HAS2 | chr8 | 122625490 | T | 10 | 3' UTR |
| 6 | HMGN2 | chr1 | 26801737 | T | 15 | 3' UTR |
| 6 | HNRNPA3 | chr2 | 178088125 | A | 12 | 3' UTR |
| 6 | HNRNPH2, RPL36A-HNRNPH2 | chrX | 100668932 | T | 13 | 3' UTR |
| 6 | HNRNPU | chr1 | 245014280 | T | 11 | 3' UTR |
| 6 | HOMEZ | chr14 | 23744114 | A | 14 | 3' UTR |
| 6 | ICA1L | chr2 | 203642599 | T | 22 | 3' UTR |
| 6 | IGF2BP3 | chr7 | 23350733 | T | 12 | 3' UTR |
| 6 | IGFBP5 | chr2 | 217537045 | T | 14 | 3' UTR |
| 6 | ILF3 | chr19 | 10796313 | T | 10 | 3' UTR |
| 6 | INSR | chr19 | 7112347 | A | 9 | 3' UTR |
| 6 | IPCEF1 | chr6 | 154476149 | A | 12 | 3' UTR |
| 6 | KCNJ2 | chr17 | 68175917 | A | 10 | 3' UTR |
| 6 | KDM5A | chr12 | 393489 | T | 12 | 3' UTR |
| 6 | KHSRP | chr19 | 6413651 | T | 10 | 3' UTR |
| 6 | KIAA0825 | chr5 | 93489194 | T | 8 | 3' UTR |
| 6 | KIAA1671 | chr22 | 25592399 | T | 12 | 3' UTR |
| 6 | LANCL1 | chr2 | 211297865 | T | 9 | 3' UTR |
| 6 | LCORL | chr4 | 17882781 | T | 11 | 3' UTR |
| 6 | LIN7C | chr11 | 27517703 | A | 14 | 3' UTR |
| 6 | LMO4 | chr1 | 87813143 | A | 11 | 3' UTR |
| 6 | LRRC4 | chr7 | 127668232 | T | 9 | 3' UTR |
| 6 | LYRM7 | chr5 | 130537006 | A | 12 | 3' UTR |
| 6 | MAGI1 | chr3 | 65340577 | T | 11 | 3' UTR |
| 6 | MAL | chr2 | 95719330 | A | 10 | 3' UTR |
| 6 | MEIS2 | chr15 | 37183446 | T | 10 | 3' UTR |
| 6 | MKL1 | chr22 | 40806781 | C | 9 | 3' UTR |
| 6 | MKLN1 | chr7 | 131175980 | A | 10 | 3' UTR |
| 6 | MTDH | chr8 | 98740104 | A | 10 | 3' UTR |
| 6 | NANP | chr20 | 25595618 | A | 11 | 3' UTR |
| 6 | NAPEPLD | chr7 | 102742595 | A | 10 | 3' UTR |
| 6 | NCEH1 | chr3 | 172349171 | T | 12 | 3' UTR |
| 6 | NCOA5 | chr20 | 44689693 | A | 10 | 3' UTR |
| 6 | NKAIN2 | chr6 | 125146684 | T | 9 | 3' UTR |
| 6 | NPNT | chr4 | 106892254 | T | 13 | 3' UTR |
| 6 | NPR3 | chr5 | 32786465 | T | 11 | 3' UTR |
| 6 | NR2F2 | chr15 | 96881216 | T | 10 | 3' UTR |
| 6 | NR3C1 | chr5 | 142657694 | T | 9 | 3' UTR |
| 6 | NUFIP2 | chr17 | 27584536 | T | 12 | 3' UTR |
| 6 | OPA3 | chr19 | 46052745 | T | 12 | 3' UTR |
| 6 | ORAI3 | chr16 | 30965549 | T | 15 | 3' UTR |

TABLE 4-continued

| Nr of affected samples | Gene | Chromosome | Start Position | Affected homopolymer base | Affected homopolymer length | region |
|---|---|---|---|---|---|---|
| 6 | OTUB2 | chr14 | 94512841 | A | 11 | 3' UTR |
| 6 | OXR1 | chr8 | 107764239 | A | 10 | 3' UTR |
| 6 | PAQR7 | chr1 | 26188503 | A | 31 | 3' UTR |
| 6 | PCDHB3 | chr5 | 140482943 | T | 10 | 3' UTR |
| 6 | PDP2 | chr16 | 66920308 | T | 10 | 3' UTR |
| 6 | PEBP1 | chr12 | 118582973 | A | 21 | 3' UTR |
| 6 | PELI2 | chr14 | 56764487 | T | 13 | 3' UTR |
| 6 | PGPEP1 | chr19 | 18477965 | A | 20 | 3' UTR |
| 6 | PGR | chr11 | 100902321 | T | 15 | 3' UTR |
| 6 | PHLDA1 | chr12 | 76421757 | T | 12 | 3' UTR |
| 6 | PID1 | chr2 | 229889188 | A | 9 | 3' UTR |
| 6 | PIGN | chr18 | 59712451 | A | 11 | 3' UTR |
| 6 | PIM2 | chrX | 48770831 | A | 20 | 3' UTR |
| 6 | PLAA | chr9 | 26904508 | T | 10 | 3' UTR |
| 6 | PLEKHA6 | chr1 | 204190022 | A | 13 | 3' UTR |
| 6 | PPM1A | chr14 | 60761433 | T | 10 | 3' UTR |
| 6 | PPP1R3D | chr20 | 58513623 | T | 11 | 3' UTR |
| 6 | PRDM1 | chr6 | 106557171 | T | 10 | 3' UTR |
| 6 | PTCD3 | chr2 | 86366926 | A | 11 | 3' UTR |
| 6 | PTGDR | chr14 | 52741746 | A | 11 | 3' UTR |
| 6 | RAB22A | chr20 | 56941068 | T | 10 | 3' UTR |
| 6 | RAB8B | chr15 | 63557574 | T | 13 | 3' UTR |
| 6 | RAD51L1 | chr14 | 68964202 | T | 12 | 3' UTR |
| 6 | RBM12B | chr8 | 94744118 | T | 11 | 3' UTR |
| 6 | RNF10 | chr12 | 121014987 | T | 11 | 3' UTR |
| 6 | RORA | chr15 | 60785852 | T | 11 | 3' UTR |
| 6 | RRAGD | chr6 | 90076341 | A | 13 | 3' UTR |
| 6 | RRM2B | chr8 | 103216874 | A | 9 | 3' UTR |
| 6 | RTF1 | chr15 | 41775015 | T | 10 | 3' UTR |
| 6 | RUFY3 | chr4 | 71655520 | A | 12 | 3' UTR |
| 6 | S100A4 | chr1 | 153516162 | A | 10 | 3' UTR |
| 6 | SBK1 | chr16 | 28334644 | A | 13 | 3' UTR |
| 6 | SERBP1 | chr1 | 67878789 | T | 11 | 3' UTR |
| 6 | SIPA1L3 | chr19 | 38698671 | T | 17 | 3' UTR |
| 6 | SLC16A6 | chr17 | 66265042 | A | 11 | 3' UTR |
| 6 | SLC25A20 | chr3 | 48894565 | A | 12 | 3' UTR |
| 6 | SLC30A5 | chr5 | 68399959 | T | 11 | 3' UTR |
| 6 | SLC35B4 | chr7 | 133977008 | T | 10 | 3' UTR |
| 6 | SLC44A5 | chr1 | 75668544 | A | 11 | 3' UTR |
| 6 | SLMAP | chr3 | 57913669 | T | 13 | 3' UTR |
| 6 | SMAD5 | chr5 | 135515014 | A | 10 | 3' UTR |
| 6 | SMEK1 | chr14 | 91924528 | A | 11 | 3' UTR |
| 6 | SOCS4 | chr14 | 55512747 | T | 10 | 3' UTR |
| 6 | SORCS1 | chr10 | 108333635 | A | 11 | 3' UTR |
| 6 | SOX1 | chr13 | 112724861 | A | 10 | 3' UTR |
| 6 | SOX4 | chr6 | 21597192 | A | 11 | 3' UTR |
| 6 | SPIRE1 | chr18 | 12449300 | T | 11 | 3' UTR |
| 6 | SPTLC2 | chr14 | 77975645 | A | 11 | 3' UTR |
| 6 | SRCIN1 | chr17 | 36687785 | T | 12 | 3' UTR |
| 6 | STEAP3 | chr2 | 120023163 | T | 12 | 3' UTR |
| 6 | STK11 | chr19 | 1228058 | T | 11 | 3' UTR |
| 6 | STX12 | chr1 | 28150575 | T | 10 | 3' UTR |
| 6 | STX3 | chr11 | 59569295 | A | 11 | 3' UTR |
| 6 | SULF2 | chr20 | 46286320 | A | 10 | 3' UTR |
| 6 | SUZ12 | chr17 | 30326763 | T | 12 | 3' UTR |
| 6 | SYNJ2BP | chr14 | 70834868 | A | 10 | 3' UTR |
| 6 | TARDBP | chr1 | 11084333 | T | 11 | 3' UTR |
| 6 | TBC1D1 | chr4 | 38140081 | A | 10 | 3' UTR |
| 6 | TBC1D5 | chr3 | 17201870 | T | 11 | 3' UTR |
| 6 | TCERG1 | chr5 | 145890609 | T | 12 | 3' UTR |
| 6 | TCF20 | chr22 | 42556646 | A | 12 | 3' UTR |
| 6 | TFAP2B | chr6 | 50814900 | A | 10 | 3' UTR |
| 6 | TLCD2 | chr17 | 1608003 | T | 11 | 3' UTR |
| 6 | TMTC3 | chr12 | 88591036 | T | 25 | 3' UTR |
| 6 | TMTC3 | chr12 | 88590177 | T | 12 | 3' UTR |
| 6 | TNIP3 | chr4 | 122052756 | T | 22 | 3' UTR |
| 6 | TNRC6B | chr22 | 40731027 | T | 10 | 3' UTR |
| 6 | TOR1AIP1 | chr1 | 179888400 | A | 12 | 3' UTR |
| 6 | TP53INP1 | chr8 | 95941646 | A | 13 | 3' UTR |
| 6 | TRIM66 | chr11 | 8636480 | T | 13 | 3' UTR |
| 6 | TRRAP | chr7 | 98610830 | T | 11 | 3' UTR |
| 6 | TSR2 | chrX | 54471045 | T | 10 | 3' UTR |
| 6 | TTC30B | chr2 | 178415366 | T | 10 | 3' UTR |
| 6 | UBASH3B | chr11 | 122681008 | T | 13 | 3' UTR |
| 6 | VAX1 | chr10 | 118893337 | A | 10 | 3' UTR |

TABLE 4-continued

| Nr of affected samples | Gene | Chromosome | Start Position | Affected homopolymer base | Affected homopolymer length | region |
|---|---|---|---|---|---|---|
| 6 | WDFY1 | chr2 | 224742022 | T | 12 | 3' UTR |
| 6 | WIF1 | chr12 | 65444595 | T | 13 | 3' UTR |
| 6 | XKR7 | chr20 | 30585884 | G | 10 | 3' UTR |
| 6 | XYLT1 | chr16 | 17199775 | A | 11 | 3' UTR |
| 6 | ZADH2 | chr18 | 72910475 | T | 13 | 3' UTR |
| 6 | ZBTB7A | chr19 | 4046340 | T | 11 | 3' UTR |
| 6 | ZNF238 | chr1 | 244219033 | T | 11 | 3' UTR |
| 6 | ZNF24 | chr18 | 32917176 | T | 12 | 3' UTR |
| 6 | ZNF362 | chr1 | 33764950 | T | 12 | 3' UTR |
| 6 | ZNF407 | chr18 | 72516095 | T | 11 | 3' UTR |
| 6 | ZNF430 | chr19 | 21241252 | A | 14 | 3' UTR |
| 6 | ZNF80 | chr3 | 113954690 | A | 12 | 3' UTR |
| 5 | ABHD2 | chr15 | 89739843 | T | 10 | 3' UTR |
| 5 | ABI2 | chr2 | 204292194 | T | 10 | 3' UTR |
| 5 | ACOX1 | chr17 | 73941869 | A | 10 | 3' UTR |
| 5 | ACTBL2 | chr5 | 56777006 | T | 10 | 3' UTR |
| 5 | AFF2 | chrX | 148080284 | T | 10 | 3' UTR |
| 5 | ANAPC16 | chr10 | 73993363 | T | 10 | 3' UTR |
| 5 | ARF5 | chr7 | 127231635 | T | 10 | 3' UTR |
| 5 | ARL1 | chr12 | 101787092 | T | 11 | 3' UTR |
| 5 | ASAH1 | chr8 | 17914871 | A | 10 | 3' UTR |
| 5 | ATP1B2 | chr17 | 7560698 | A | 10 | 3' UTR |
| 5 | ATXN7 | chr3 | 63985894 | T | 11 | 3' UTR |
| 5 | B3GNT7 | chr2 | 232264806 | T | 26 | 3' UTR |
| 5 | BAG1 | chr9 | 33253979 | T | 12 | 3' UTR |
| 5 | BCL11B | chr14 | 99638830 | A | 9 | 3' UTR |
| 5 | BMP7 | chr20 | 55744815 | T | 10 | 3' UTR |
| 5 | BTBD11 | chr12 | 108052115 | T | 12 | 3' UTR |
| 5 | BTBD7 | chr14 | 93708030 | A | 10 | 3' UTR |
| 5 | C14orf126 | chr14 | 31917025 | A | 10 | 3' UTR |
| 5 | C14orf28 | chr14 | 45376124 | A | 12 | 3' UTR |
| 5 | C18orf56 | chr18 | 649879 | T | 15 | 3' UTR |
| 5 | C20orf12 | chr20 | 18364708 | T | 12 | 3' UTR |
| 5 | C5orf41 | chr5 | 172563230 | A | 11 | 3' UTR |
| 5 | C7orf68 | chr7 | 128097963 | A | 10 | 3' UTR |
| 5 | C9orf66 | chr9 | 214453 | T | 9 | 3' UTR |
| 5 | CABP4 | chr11 | 67226510 | T | 14 | 3' UTR |
| 5 | CACNB4 | chr2 | 152695481 | T | 11 | 3' UTR |
| 5 | CASP2 | chr7 | 143003342 | T | 25 | 3' UTR |
| 5 | CBFB | chr16 | 67133969 | T | 9 | 3' UTR |
| 5 | CBX5 | chr12 | 54630019 | T | 10 | 3' UTR |
| 5 | CCDC102B | chr18 | 66722368 | A | 9 | 3' UTR |
| 5 | CCND1 | chr11 | 69468187 | T | 14 | 3' UTR |
| 5 | CCND2 | chr12 | 4409520 | T | 10 | 3' UTR |
| 5 | CCNL2 | chr1 | 1327869 | T | 9 | 3' UTR |
| 5 | CCR1 | chr3 | 46244273 | G | 10 | 3' UTR |
| 5 | CDH3 | chr16 | 68732679 | T | 11 | 3' UTR |
| 5 | CEP68 | chr2 | 65312945 | A | 12 | 3' UTR |
| 5 | CGGBP1 | chr3 | 88104472 | T | 10 | 3' UTR |
| 5 | CHMP2B | chr3 | 87303064 | A | 14 | 3' UTR |
| 5 | CIB2 | chr15 | 78397249 | T | 12 | 3' UTR |
| 5 | CLEC5A | chr7 | 141627861 | T | 12 | 3' UTR |
| 5 | CNST | chr1 | 246830426 | A | 10 | 3' UTR |
| 5 | COL19A1 | chr6 | 70918737 | T | 12 | 3' UTR |
| 5 | COL8A2 | chr1 | 36561052 | A | 10 | 3' UTR |
| 5 | COX16,SYNJ2BP-COX16 | chr14 | 70793015 | A | 14 | 3' UTR |
| 5 | CPLX4 | chr18 | 56963029 | A | 10 | 3' UTR |
| 5 | CREB3L2 | chr7 | 137563914 | A | 10 | 3' UTR |
| 5 | CSNK1G1 | chr15 | 64461259 | A | 9 | 3' UTR |
| 5 | CTIF | chr18 | 46388423 | T | 10 | 3' UTR |
| 5 | CUL5 | chr11 | 107975795 | T | 13 | 3' UTR |
| 5 | CYP17A1 | chr10 | 104590293 | A | 11 | 3' UTR |
| 5 | DAND5 | chr19 | 13084677 | T | 17 | 3' UTR |
| 5 | DCUN1D5 | chr11 | 102930486 | G | 7 | 3' UTR |
| 5 | DDN | chr12 | 49389156 | A | 11 | 3' UTR |
| 5 | DDX5 | chr17 | 62495664 | A | 10 | 3' UTR |
| 5 | DDX6 | chr11 | 118622141 | A | 10 | 3' UTR |
| 5 | DLX3 | chr17 | 48067712 | T | 14 | 3' UTR |
| 5 | DNAJC15 | chr13 | 43681779 | T | 9 | 3' UTR |
| 5 | DNAJC18 | chr5 | 138747976 | T | 11 | 3' UTR |
| 5 | DOPEY2 | chr21 | 37666277 | A | 14 | 3' UTR |
| 5 | DPYSL2 | chr8 | 26515559 | T | 10 | 3' UTR |
| 5 | DSEL | chr18 | 65174583 | A | 26 | 3' UTR |
| 5 | DTNA | chr18 | 32448118 | A | 16 | 3' UTR |
| 5 | DYNC1LI2 | chr16 | 66755235 | T | 11 | 3' UTR |

TABLE 4-continued

| Nr of affected samples | Gene | Chromosome | Start Position | Affected homopolymer base | Affected homopolymer length | region |
|---|---|---|---|---|---|---|
| 5 | DYRK2 | chr12 | 68055576 | T | 10 | 3' UTR |
| 5 | EBF1 | chr5 | 158125671 | T | 15 | 3' UTR |
| 5 | EFNA5 | chr5 | 106716350 | A | 11 | 3' UTR |
| 5 | EFNA5 | chr5 | 106712689 | T | 12 | 3' UTR |
| 5 | EFR3B | chr2 | 25378726 | T | 13 | 3' UTR |
| 5 | ELAVL1 | chr19 | 8023995 | T | 11 | 3' UTR |
| 5 | ELAVL3 | chr19 | 11562278 | T | 16 | 3' UTR |
| 5 | EPS15 | chr1 | 51822219 | A | 12 | 3' UTR |
| 5 | ESRP1 | chr8 | 95719492 | A | 11 | 3' UTR |
| 5 | EVI5 | chr1 | 92978704 | A | 11 | 3' UTR |
| 5 | EVI5 | chr1 | 92977467 | T | 11 | 3' UTR |
| 5 | EXTL2 | chr1 | 101338118 | A | 10 | 3' UTR |
| 5 | FAF2 | chr5 | 175935960 | T | 10 | 3' UTR |
| 5 | FAM105A | chr5 | 14611814 | T | 10 | 3' UTR |
| 5 | FAM164A | chr8 | 79631105 | T | 10 | 3' UTR |
| 5 | FAM20B | chr1 | 179044326 | A | 13 | 3' UTR |
| 5 | FAM46A | chr6 | 82457992 | T | 10 | 3' UTR |
| 5 | FBN2 | chr5 | 127594063 | A | 10 | 3' UTR |
| 5 | FBRSL1 | chr12 | 133160562 | A | 9 | 3' UTR |
| 5 | FBXL4 | chr6 | 99321799 | T | 10 | 3' UTR |
| 5 | FBXO36 | chr2 | 230876985 | A | 11 | 3' UTR |
| 5 | FBXW2 | chr9 | 123524089 | A | 12 | 3' UTR |
| 5 | FCGR3A | chr1 | 161512430 | T | 9 | 3' UTR |
| 5 | FCHSD2 | chr11 | 72549649 | A | 10 | 3' UTR |
| 5 | FICD | chr12 | 108913292 | A | 11 | 3' UTR |
| 5 | FOXN2 | chr2 | 48604358 | T | 10 | 3' UTR |
| 5 | FOXN3 | chr14 | 89627649 | T | 11 | 3' UTR |
| 5 | GABRB2 | chr5 | 160719907 | A | 9 | 3' UTR |
| 5 | GNA13 | chr17 | 63005677 | A | 10 | 3' UTR |
| 5 | GNAI2 | chr3 | 50296405 | C | 9 | 3' UTR |
| 5 | GNAI2 | chr3 | 50296330 | A | 12 | 3' UTR |
| 5 | GPR12 | chr13 | 27330332 | T | 10 | 3' UTR |
| 5 | GPR137B | chr1 | 236372038 | T | 10 | 3' UTR |
| 5 | GPR37L1 | chr1 | 202098133 | T | 21 | 3' UTR |
| 5 | GRID1 | chr10 | 87359476 | T | 11 | 3' UTR |
| 5 | GRIN3A | chr9 | 104331901 | A | 9 | 3' UTR |
| 5 | GRPEL2 | chr5 | 148731880 | T | 14 | 3' UTR |
| 5 | HAPLN1 | chr5 | 82937251 | A | 10 | 3' UTR |
| 5 | HBS1L | chr6 | 135357535 | A | 10 | 3' UTR |
| 5 | HDAC4 | chr2 | 239974109 | A | 9 | 3' UTR |
| 5 | HEXA | chr15 | 72636197 | T | 10 | 3' UTR |
| 5 | HNRNPK | chr9 | 86583800 | A | 10 | 3' UTR |
| 5 | HOOK3 | chr8 | 42876247 | A | 29 | 3' UTR |
| 5 | HRH1 | chr3 | 11303522 | A | 11 | 3' UTR |
| 5 | HUWE1 | chrX | 53559710 | T | 11 | 3' UTR |
| 5 | IGDCC4 | chr15 | 65674432 | A | 12 | 3' UTR |
| 5 | IGF1 | chr12 | 102790988 | A | 11 | 3' UTR |
| 5 | IGF2BP2 | chr3 | 185361762 | T | 12 | 3' UTR |
| 5 | IGFBP5 | chr2 | 217537240 | A | 11 | 3' UTR |
| 5 | INSR | chr19 | 7116555 | A | 12 | 3' UTR |
| 5 | JAM3 | chr11 | 134020535 | T | 12 | 3' UTR |
| 5 | KCTD1 | chr18 | 24035448 | T | 12 | 3' UTR |
| 5 | KCTD6 | chr3 | 58487415 | T | 11 | 3' UTR |
| 5 | KDM5A | chr12 | 393804 | T | 11 | 3' UTR |
| 5 | KIAA1324 | chr1 | 109749368 | T | 11 | 3' UTR |
| 5 | KIAA1324 | chr1 | 109748644 | T | 11 | 3' UTR |
| 5 | KIAA1737 | chr14 | 77582032 | T | 14 | 3' UTR |
| 5 | KIAA2026 | chr9 | 5919249 | T | 11 | 3' UTR |
| 5 | KLHL20 | chr1 | 173754885 | A | 12 | 3' UTR |
| 5 | KLHL24 | chr3 | 183400567 | T | 10 | 3' UTR |
| 5 | LDHAL6A | chr11 | 18500557 | T | 12 | 3' UTR |
| 5 | LENG8 | chr19 | 54972801 | T | 9 | 3' UTR |
| 5 | LHFP | chr13 | 39917691 | A | 12 | 3' UTR |
| 5 | LMO4 | chr1 | 87811174 | A | 11 | 3' UTR |
| 5 | LPHN3 | chr4 | 62937355 | A | 12 | 3' UTR |
| 5 | LPL | chr8 | 19823634 | A | 11 | 3' UTR |
| 5 | LRRC27 | chr10 | 134193076 | T | 9 | 3' UTR |
| 5 | LRRC4B | chr19 | 51020187 | T | 10 | 3' UTR |
| 5 | LTN1 | chr21 | 30301899 | T | 10 | 3' UTR |
| 5 | MAP1B | chr5 | 71505347 | A | 11 | 3' UTR |
| 5 | MAP3K7 | chr6 | 91225524 | A | 9 | 3' UTR |
| 5 | MAPK1 | chr22 | 22114660 | T | 12 | 3' UTR |
| 5 | MAX | chr14 | 65543065 | A | 10 | 3' UTR |
| 5 | MED1 | chr17 | 37562164 | T | 11 | 3' UTR |
| 5 | MED13 | chr17 | 60022040 | A | 11 | 3' UTR |

TABLE 4-continued

| Nr of affected samples | Gene | Chromosome | Start Position | Affected homopolymer base | Affected homopolymer length | region |
|---|---|---|---|---|---|---|
| 5 | MED28 | chr4 | 17625638 | T | 10 | 3' UTR |
| 5 | MKX | chr10 | 27962805 | A | 10 | 3' UTR |
| 5 | MNT | chr17 | 2287533 | T | 13 | 3' UTR |
| 5 | MOBKL2A | chr19 | 2072745 | A | 13 | 3' UTR |
| 5 | MORC1 | chr3 | 108677146 | A | 10 | 3' UTR |
| 5 | MST4 | chrX | 131208596 | A | 9 | 3' UTR |
| 5 | MTA2 | chr11 | 62360911 | A | 27 | 3' UTR |
| 5 | MTF1 | chr1 | 38278949 | A | 11 | 3' UTR |
| 5 | NAA38 | chr7 | 117832209 | A | 9 | 3' UTR |
| 5 | NAPG | chr18 | 10551001 | T | 11 | 3' UTR |
| 5 | NCOA1 | chr2 | 24991385 | A | 25 | 3' UTR |
| 5 | NCOA3 | chr20 | 46282984 | T | 11 | 3' UTR |
| 5 | NKAIN4 | chr20 | 61872616 | T | 12 | 3' UTR |
| 5 | NLGN4X | chrX | 5808268 | T | 11 | 3' UTR |
| 5 | NMNAT1 | chr1 | 10044969 | T | 8 | 3' UTR |
| 5 | NPLOC4 | chr17 | 79525610 | A | 9 | 3' UTR |
| 5 | NPNT | chr4 | 106890724 | T | 10 | 3' UTR |
| 5 | NR2F2 | chr15 | 96881909 | T | 10 | 3' UTR |
| 5 | NUFIP2 | chr17 | 27585085 | T | 12 | 3' UTR |
| 5 | ODZ4 | chr11 | 78367062 | T | 9 | 3' UTR |
| 5 | OGFOD1 | chr16 | 56510333 | T | 12 | 3' UTR |
| 5 | OPA3 | chr19 | 46049757 | T | 14 | 3' UTR |
| 5 | OSBP | chr11 | 59341900 | T | 12 | 3' UTR |
| 5 | PAPD5 | chr16 | 50264179 | T | 10 | 3' UTR |
| 5 | PAPD5 | chr16 | 50263692 | T | 10 | 3' UTR |
| 5 | PAPD5 | chr16 | 50263454 | A | 8 | 3' UTR |
| 5 | PFN1 | chr17 | 4848972 | A | 10 | 3' UTR |
| 5 | PHKB | chr16 | 47734578 | A | 10 | 3' UTR |
| 5 | PIGM | chr1 | 159998080 | T | 11 | 3' UTR |
| 5 | PIGM | chr1 | 159997525 | A | 10 | 3' UTR |
| 5 | PKP2 | chr12 | 32944046 | A | 11 | 3' UTR |
| 5 | PLAGL2 | chr20 | 30781644 | A | 11 | 3' UTR |
| 5 | PLEKHM3 | chr2 | 208686453 | A | 10 | 3' UTR |
| 5 | POLR3B | chr12 | 106903452 | A | 9 | 3' UTR |
| 5 | PPIC | chr5 | 122359467 | A | 12 | 3' UTR |
| 5 | PPP1R10 | chr6 | 30568234 | A | 11 | 3' UTR |
| 5 | PPP6C | chr9 | 127911821 | A | 11 | 3' UTR |
| 5 | PPPDE1 | chr1 | 244869241 | A | 12 | 3' UTR |
| 5 | PRKX | chrX | 3525721 | T | 9 | 3' UTR |
| 5 | PRRG1 | chrX | 37313537 | T | 10 | 3' UTR |
| 5 | PSMD5 | chr9 | 123578376 | A | 10 | 3' UTR |
| 5 | PTGS2 | chr1 | 186642025 | T | 9 | 3' UTR |
| 5 | RAB11FIP2 | chr10 | 119765266 | T | 11 | 3' UTR |
| 5 | RANBP10 | chr16 | 67757024 | T | 10 | 3' UTR |
| 5 | RASGRP4 | chr19 | 38900377 | A | 11 | 3' UTR |
| 5 | RBL1 | chr20 | 35632028 | A | 13 | 3' UTR |
| 5 | RBM15B | chr3 | 51431679 | T | 11 | 3' UTR |
| 5 | RBMS3 | chr3 | 30046424 | A | 11 | 3' UTR |
| 5 | RC3H1 | chr1 | 173904709 | A | 11 | 3' UTR |
| 5 | RHOBTB3 | chr5 | 95129188 | A | 12 | 3' UTR |
| 5 | RIMBP2 | chr12 | 130882589 | A | 11 | 3' UTR |
| 5 | RNF41 | chr12 | 56599353 | G | 10 | 3' UTR |
| 5 | RRP15 | chr1 | 218506526 | A | 10 | 3' UTR |
| 5 | SAMD12 | chr8 | 119208740 | A | 13 | 3' UTR |
| 5 | SAR1A | chr10 | 71910315 | A | 10 | 3' UTR |
| 5 | SARM1 | chr17 | 26726913 | T | 12 | 3' UTR |
| 5 | SATB2 | chr2 | 200135086 | T | 10 | 3' UTR |
| 5 | SCAI | chr9 | 127706579 | T | 16 | 3' UTR |
| 5 | SCAMP1 | chr5 | 77772627 | A | 10 | 3' UTR |
| 5 | SCUBE3 | chr6 | 35216591 | A | 10 | 3' UTR |
| 5 | SDC4 | chr20 | 43954848 | A | 9 | 3' UTR |
| 5 | SENP5 | chr3 | 196660478 | T | 11 | 3' UTR |
| 5 | SERPINE1 | chr7 | 100781987 | G | 8 | 3' UTR |
| 5 | SFRS18 | chr6 | 99848035 | A | 12 | 3' UTR |
| 5 | SH3KBP1 | chrX | 19553810 | T | 12 | 3' UTR |
| 5 | SIK1 | chr21 | 44835578 | A | 10 | 3' UTR |
| 5 | SKI | chr1 | 2240043 | T | 10 | 3' UTR |
| 5 | SLC16A1 | chr1 | 113455427 | A | 13 | 3' UTR |
| 5 | SLC26A4 | chr7 | 107357810 | A | 25 | 3' UTR |
| 5 | SLC2A12 | chr6 | 134312045 | T | 11 | 3' UTR |
| 5 | SLC6A6 | chr3 | 14526824 | T | 11 | 3' UTR |
| 5 | SLC7A11 | chr4 | 139090880 | A | 10 | 3' UTR |
| 5 | SMAD5 | chr5 | 135513612 | A | 11 | 3' UTR |
| 5 | SMG1 | chr16 | 18819070 | T | 11 | 3' UTR |
| 5 | SMS | chrX | 22012649 | T | 10 | 3' UTR |

TABLE 4-continued

| Nr of affected samples | Gene | Chromosome | Start Position | Affected homopolymer base | Affected homopolymer length | region |
|---|---|---|---|---|---|---|
| 5 | SMURF2 | chr17 | 62541185 | T | 13 | 3' UTR |
| 5 | SNAP23 | chr15 | 42824292 | T | 14 | 3' UTR |
| 5 | SOST | chr17 | 41831361 | T | 11 | 3' UTR |
| 5 | SPCS3 | chr4 | 177250844 | T | 10 | 3' UTR |
| 5 | SPOCK1 | chr5 | 136313113 | A | 11 | 3' UTR |
| 5 | SSR1 | chr6 | 7284948 | T | 13 | 3' UTR |
| 5 | SSR3 | chr3 | 156259169 | T | 10 | 3' UTR |
| 5 | ST3GAL5 | chr2 | 86067101 | A | 9 | 3' UTR |
| 5 | ST7L | chr1 | 113066620 | A | 11 | 3' UTR |
| 5 | STC2 | chr5 | 172744019 | T | 12 | 3' UTR |
| 5 | STX6 | chr1 | 180945093 | A | 9 | 3' UTR |
| 5 | SYNJ2BP | chr14 | 70838863 | T | 10 | 3' UTR |
| 5 | SYT11 | chr1 | 155851834 | T | 12 | 3' UTR |
| 5 | TAF8 | chr6 | 42045495 | T | 11 | 3' UTR |
| 5 | THRAP3 | chr1 | 36770047 | T | 17 | 3' UTR |
| 5 | TLL2 | chr10 | 98124863 | A | 11 | 3' UTR |
| 5 | TMEM119 | chr12 | 108984472 | A | 11 | 3' UTR |
| 5 | TMEM201 | chr1 | 9674449 | T | 10 | 3' UTR |
| 5 | TMOD3 | chr15 | 52201130 | T | 10 | 3' UTR |
| 5 | TMTC1 | chr12 | 29656466 | A | 8 | 3' UTR |
| 5 | TNFAIP1 | chr17 | 26672324 | A | 10 | 3' UTR |
| 5 | TNFAIP3 | chr6 | 138204003 | A | 12 | 3' UTR |
| 5 | TNRC6B | chr22 | 40724536 | T | 10 | 3' UTR |
| 5 | TRIP10 | chr19 | 6751495 | A | 12 | 3' UTR |
| 5 | TRPM1 | chr15 | 31293995 | A | 11 | 3' UTR |
| 5 | TSC22D2 | chr3 | 150177375 | T | 13 | 3' UTR |
| 5 | TTC39C | chr18 | 21715264 | T | 11 | 3' UTR |
| 5 | UBE2G2 | chr21 | 46191155 | A | 12 | 3' UTR |
| 5 | UBLCP1 | chr5 | 158712401 | A | 11 | 3' UTR |
| 5 | UBN2 | chr7 | 138989574 | T | 10 | 3' UTR |
| 5 | UGT8 | chr4 | 115598050 | T | 11 | 3' UTR |
| 5 | UTP15 | chr5 | 72876582 | T | 12 | 3' UTR |
| 5 | WASL | chr7 | 123323428 | A | 12 | 3' UTR |
| 5 | WDFY2 | chr13 | 52334589 | A | 11 | 3' UTR |
| 5 | WDR76 | chr15 | 44158820 | T | 21 | 3' UTR |
| 5 | XYLT1 | chr16 | 17199280 | T | 8 | 3' UTR |
| 5 | ZBTB41 | chr1 | 197124441 | A | 11 | 3' UTR |
| 5 | ZC3H6 | chr2 | 113097277 | T | 13 | 3' UTR |
| 5 | ZDBF2 | chr2 | 207177005 | T | 8 | 3' UTR |
| 5 | ZNF287 | chr17 | 16454419 | T | 9 | 3' UTR |
| 5 | ZNF395 | chr8 | 28205776 | T | 27 | 3' UTR |
| 5 | ZNF451 | chr6 | 57033558 | A | 8 | 3' UTR |
| 5 | ZNF566 | chr19 | 36937171 | T | 18 | 3' UTR |
| 5 | ZNF572 | chr8 | 125990551 | T | 11 | 3' UTR |
| 5 | ZNF780B | chr19 | 40535764 | A | 10 | 3' UTR |
| 5 | ZXDC | chr3 | 126179925 | T | 11 | 3' UTR |
| 5 | ZYG11B | chr1 | 53290310 | A | 13 | 3' UTR |
| 4 | SEPT11 | chr4 | 77957803 | T | 10 | 3' UTR |
| 4 | ACVR1C | chr2 | 158390343 | A | 10 | 3' UTR |
| 4 | ACVR2A | chr2 | 148687300 | A | 10 | 3' UTR |
| 4 | ADAMTS18 | chr16 | 77316279 | T | 11 | 3' UTR |
| 4 | AGPAT5 | chr8 | 6617153 | A | 11 | 3' UTR |
| 4 | AKAP1 | chr17 | 55198578 | A | 14 | 3' UTR |
| 4 | ANKIB1 | chr7 | 92030525 | A | 11 | 3' UTR |
| 4 | ANKRD13B | chr17 | 27941253 | T | 19 | 3' UTR |
| 4 | ANKS1B | chr12 | 99138458 | T | 11 | 3' UTR |
| 4 | ARHGAP12 | chr10 | 32096465 | A | 9 | 3' UTR |
| 4 | ARID5B | chr10 | 63853410 | T | 27 | 3' UTR |
| 4 | ARL2BP | chr16 | 57287376 | T | 12 | 3' UTR |
| 4 | ARMC8 | chr3 | 137964255 | T | 9 | 3' UTR |
| 4 | ARPP19 | chr15 | 52841555 | A | 10 | 3' UTR |
| 4 | ATP6V0D1 | chr16 | 67472221 | G | 9 | 3' UTR |
| 4 | AXIN2 | chr17 | 63525462 | A | 11 | 3' UTR |
| 4 | BAG5 | chr14 | 104023132 | A | 10 | 3' UTR |
| 4 | BARX2 | chr11 | 129321925 | T | 10 | 3' UTR |
| 4 | BCL11A | chr2 | 60685736 | T | 13 | 3' UTR |
| 4 | BCL11A | chr2 | 60684501 | A | 11 | 3' UTR |
| 4 | BCL11B | chr14 | 99637754 | T | 10 | 3' UTR |
| 4 | BCL7A | chr12 | 122498867 | A | 11 | 3' UTR |
| 4 | BEND4 | chr4 | 42114856 | A | 10 | 3' UTR |
| 4 | BFAR | chr16 | 14762692 | A | 16 | 3' UTR |
| 4 | BRAF | chr7 | 140434294 | A | 9 | 3' UTR |
| 4 | BTBD7 | chr14 | 93708031 | A | 9 | 3' UTR |
| 4 | BTBD7 | chr14 | 93705796 | T | 13 | 3' UTR |
| 4 | C10orf46 | chr10 | 120445285 | A | 10 | 3' UTR |

TABLE 4-continued

| Nr of affected samples | Gene | Chromosome | Start Position | Affected homopolymer base | Affected homopolymer length | region |
|---|---|---|---|---|---|---|
| 4 | C10orf84 | chr10 | 120069534 | A | 9 | 3' UTR |
| 4 | C11orf41 | chr11 | 33690228 | T | 8 | 3' UTR |
| 4 | C11orf58 | chr11 | 16777810 | T | 24 | 3' UTR |
| 4 | C11orf58 | chr11 | 16777368 | T | 9 | 3' UTR |
| 4 | C12orf23 | chr12 | 107367018 | A | 10 | 3' UTR |
| 4 | C12orf5 | chr12 | 4463524 | T | 10 | 3' UTR |
| 4 | C12orf66 | chr12 | 64587315 | A | 10 | 3' UTR |
| 4 | C12orf76 | chr12 | 110479725 | A | 11 | 3' UTR |
| 4 | C14orf101 | chr14 | 57116192 | A | 10 | 3' UTR |
| 4 | C14orf43 | chr14 | 74183215 | A | 11 | 3' UTR |
| 4 | C16orf45 | chr16 | 15680717 | C | 9 | 3' UTR |
| 4 | C16orf87 | chr16 | 46836142 | T | 12 | 3' UTR |
| 4 | C17orf78 | chr17 | 35749617 | A | 11 | 3' UTR |
| 4 | C18orf25 | chr18 | 43846502 | A | 9 | 3' UTR |
| 4 | C3orf70 | chr3 | 184795851 | A | 10 | 3' UTR |
| 4 | C6orf170 | chr6 | 121401361 | T | 21 | 3' UTR |
| 4 | C6orf62 | chr6 | 24705738 | A | 10 | 3' UTR |
| 4 | C7orf45 | chr7 | 129856476 | A | 11 | 3' UTR |
| 4 | C7orf69 | chr7 | 47859241 | A | 11 | 3' UTR |
| 4 | C8orf48 | chr8 | 13425580 | T | 9 | 3' UTR |
| 4 | C9 | chr5 | 39285017 | T | 9 | 3' UTR |
| 4 | CA5B | chrX | 15801003 | T | 10 | 3' UTR |
| 4 | CABLES2 | chr20 | 60965113 | A | 10 | 3' UTR |
| 4 | CAPRIN1 | chr11 | 34121880 | T | 8 | 3' UTR |
| 4 | CBFA2T2 | chr20 | 32236969 | T | 11 | 3' UTR |
| 4 | CBL | chr11 | 119172610 | A | 10 | 3' UTR |
| 4 | CBY1 | chr22 | 39069285 | T | 9 | 3' UTR |
| 4 | CC2D1B | chr1 | 52817555 | A | 22 | 3' UTR |
| 4 | CCND1 | chr11 | 69466274 | A | 9 | 3' UTR |
| 4 | CD59 | chr11 | 33730438 | T | 8 | 3' UTR |
| 4 | CD96 | chr3 | 111368930 | A | 9 | 3' UTR |
| 4 | CDH13 | chr16 | 83828683 | A | 11 | 3' UTR |
| 4 | CDH4 | chr20 | 60512276 | A | 19 | 3' UTR |
| 4 | CEP164 | chr11 | 117283967 | T | 11 | 3' UTR |
| 4 | CEP57L1 | chr6 | 109484935 | T | 10 | 3' UTR |
| 4 | CHMP4C | chr8 | 82671242 | A | 12 | 3' UTR |
| 4 | CLCN5 | chrX | 49858223 | A | 9 | 3' UTR |
| 4 | CLDN14 | chr21 | 37833059 | T | 10 | 3' UTR |
| 4 | CLEC3A | chr16 | 78065330 | T | 12 | 3' UTR |
| 4 | CMTM8 | chr3 | 32411483 | A | 9 | 3' UTR |
| 4 | CNNM1 | chr10 | 101153279 | A | 9 | 3' UTR |
| 4 | CNNM3 | chr2 | 97499281 | A | 12 | 3' UTR |
| 4 | CORO2B | chr15 | 69020046 | T | 10 | 3' UTR |
| 4 | CPSF2 | chr14 | 92630061 | T | 9 | 3' UTR |
| 4 | CREBBP | chr16 | 3776240 | G | 10 | 3' UTR |
| 4 | CRTC1 | chr19 | 18890340 | A | 9 | 3' UTR |
| 4 | CSMD3 | chr8 | 113236641 | T | 9 | 3' UTR |
| 4 | CTTN | chr11 | 70281530 | T | 10 | 3' UTR |
| 4 | CYP1B1 | chr2 | 38296985 | T | 10 | 3' UTR |
| 4 | CYP20A1 | chr2 | 204163758 | A | 10 | 3' UTR |
| 4 | CYP2C18 | chr10 | 96495747 | A | 9 | 3' UTR |
| 4 | CYP4F22 | chr19 | 15662704 | C | 9 | 3' UTR |
| 4 | DACH1 | chr13 | 72014288 | T | 11 | 3' UTR |
| 4 | DCUN1D3 | chr16 | 20870892 | A | 10 | 3' UTR |
| 4 | DCUN1D5 | chr11 | 102928449 | A | 11 | 3' UTR |
| 4 | DDHD1 | chr14 | 53513329 | T | 10 | 3' UTR |
| 4 | DDX18 | chr2 | 118589332 | A | 9 | 3' UTR |
| 4 | DDX3X | chrX | 41207099 | T | 10 | 3' UTR |
| 4 | DFFB | chr1 | 3801133 | T | 11 | 3' UTR |
| 4 | DGCR8 | chr22 | 20099229 | C | 16 | 3' UTR |
| 4 | DICER1 | chr14 | 95554259 | T | 10 | 3' UTR |
| 4 | DLGAP4 | chr20 | 35156622 | T | 10 | 3' UTR |
| 4 | DPP8 | chr15 | 65738415 | A | 11 | 3' UTR |
| 4 | DSE | chr6 | 116758558 | A | 11 | 3' UTR |
| 4 | DSTYK | chr1 | 205115701 | T | 16 | 3' UTR |
| 4 | DUT | chr15 | 48634591 | A | 10 | 3' UTR |
| 4 | DUT | chr15 | 48634443 | A | 9 | 3' UTR |
| 4 | EAPP | chr14 | 34985335 | A | 10 | 3' UTR |
| 4 | EDEM1 | chr3 | 5260540 | T | 10 | 3' UTR |
| 4 | EEF2K | chr16 | 22299309 | T | 19 | 3' UTR |
| 4 | EIF2B2 | chr14 | 75476004 | A | 10 | 3' UTR |
| 4 | EIF4G3 | chr1 | 21133145 | T | 12 | 3' UTR |
| 4 | ELAVL3 | chr19 | 11564674 | T | 11 | 3' UTR |
| 4 | ERLIN2 | chr8 | 37614867 | T | 10 | 3' UTR |
| 4 | ESRRB | chr14 | 76967818 | G | 8 | 3' UTR |

TABLE 4-continued

| Nr of affected samples | Gene | Chromosome | Start Position | Affected homopolymer base | Affected homopolymer length | region |
|---|---|---|---|---|---|---|
| 4 | ETNK1 | chr12 | 22839785 | T | 28 | 3' UTR |
| 4 | ETS1 | chr11 | 128329018 | A | 9 | 3' UTR |
| 4 | FADS1 | chr11 | 61567668 | T | 14 | 3' UTR |
| 4 | FAIM3 | chr1 | 207077642 | T | 18 | 3' UTR |
| 4 | FAM101B | chr17 | 292360 | T | 10 | 3' UTR |
| 4 | FAM116A | chr3 | 57612436 | A | 13 | 3' UTR |
| 4 | FAM117B | chr2 | 203633341 | T | 10 | 3' UTR |
| 4 | FAM126B | chr2 | 201845397 | G | 7 | 3' UTR |
| 4 | FAM160B1 | chr10 | 116621715 | A | 9 | 3' UTR |
| 4 | FAM189A1 | chr15 | 29414906 | G | 8 | 3' UTR |
| 4 | FANCD2 | chr3 | 10143061 | T | 25 | 3' UTR |
| 4 | FBN2 | chr5 | 127594650 | A | 8 | 3' UTR |
| 4 | FBXO27 | chr19 | 39515468 | T | 11 | 3' UTR |
| 4 | FGD4 | chr12 | 32798227 | T | 12 | 3' UTR |
| 4 | FGD5 | chr3 | 14976010 | T | 9 | 3' UTR |
| 4 | FGF12 | chr3 | 191859718 | T | 11 | 3' UTR |
| 4 | FGFR1OP2 | chr12 | 27118562 | T | 10 | 3' UTR |
| 4 | FLCN | chr17 | 17115789 | A | 26 | 3' UTR |
| 4 | FMNL3 | chr12 | 50033467 | A | 10 | 3' UTR |
| 4 | FOXN2 | chr2 | 48603079 | T | 10 | 3' UTR |
| 4 | FOXO1 | chr13 | 41132503 | A | 9 | 3' UTR |
| 4 | FOXP1 | chr3 | 71005222 | T | 9 | 3' UTR |
| 4 | FPGT | chr1 | 74672686 | T | 9 | 3' UTR |
| 4 | FTSJD1 | chr16 | 71317151 | A | 10 | 3' UTR |
| 4 | FUT8 | chr14 | 66209673 | T | 13 | 3' UTR |
| 4 | FZD7 | chr2 | 202902385 | A | 11 | 3' UTR |
| 4 | GADL1 | chr3 | 30769514 | T | 11 | 3' UTR |
| 4 | GAL3ST4 | chr7 | 99757342 | A | 13 | 3' UTR |
| 4 | GAN | chr16 | 81413521 | T | 12 | 3' UTR |
| 4 | GAPVD1 | chr9 | 128127210 | T | 10 | 3' UTR |
| 4 | GATAD2A | chr19 | 19617715 | T | 10 | 3' UTR |
| 4 | GATAD2B | chr1 | 153781275 | A | 20 | 3' UTR |
| 4 | GDAP2 | chr1 | 118411744 | T | 10 | 3' UTR |
| 4 | GDAP2 | chr1 | 118408218 | A | 10 | 3' UTR |
| 4 | GFPT1 | chr2 | 69549530 | A | 9 | 3' UTR |
| 4 | GLCCI1 | chr7 | 8127832 | T | 11 | 3' UTR |
| 4 | GLDN | chr15 | 51697574 | T | 21 | 3' UTR |
| 4 | GLYR1 | chr16 | 4853902 | T | 10 | 3' UTR |
| 4 | GOLT1B | chr12 | 21669842 | A | 9 | 3' UTR |
| 4 | GPM6A | chr4 | 176555451 | T | 10 | 3' UTR |
| 4 | GPR124 | chr8 | 37701260 | A | 10 | 3' UTR |
| 4 | GPR155 | chr2 | 175299037 | T | 13 | 3' UTR |
| 4 | GPR161 | chr1 | 168054505 | T | 10 | 3' UTR |
| 4 | GPR180 | chr13 | 95279582 | A | 8 | 3' UTR |
| 4 | GPX8 | chr5 | 54460112 | T | 10 | 3' UTR |
| 4 | GRAMD3 | chr5 | 125829168 | T | 10 | 3' UTR |
| 4 | GSTCD | chr4 | 106767825 | T | 20 | 3' UTR |
| 4 | GXYLT1 | chr12 | 42477780 | A | 10 | 3' UTR |
| 4 | HCCS | chrX | 11140989 | T | 11 | 3' UTR |
| 4 | HCN1 | chr5 | 45260992 | T | 9 | 3' UTR |
| 4 | HDAC4 | chr2 | 239971996 | A | 11 | 3' UTR |
| 4 | HELZ | chr17 | 65067696 | T | 8 | 3' UTR |
| 4 | HEY2 | chr6 | 126081692 | T | 10 | 3' UTR |
| 4 | HIF3A | chr19 | 46843765 | T | 12 | 3' UTR |
| 4 | HNRNPA1L2 | chr13 | 53217847 | T | 11 | 3' UTR |
| 4 | HNRNPK | chr9 | 86584095 | C | 9 | 3' UTR |
| 4 | HOOK1 | chr1 | 60338642 | A | 8 | 3' UTR |
| 4 | HP1BP3 | chr1 | 21070971 | A | 10 | 3' UTR |
| 4 | HS3ST5 | chr6 | 114376959 | A | 10 | 3' UTR |
| 4 | HUWE1 | chrX | 53559518 | A | 12 | 3' UTR |
| 4 | IKZF4 | chr12 | 56431620 | A | 10 | 3' UTR |
| 4 | IL7R | chr5 | 35876844 | A | 10 | 3' UTR |
| 4 | IMPG2 | chr3 | 100945663 | A | 9 | 3' UTR |
| 4 | INSR | chr19 | 7112871 | A | 10 | 3' UTR |
| 4 | IRGQ | chr19 | 44094353 | A | 11 | 3' UTR |
| 4 | IRS1 | chr2 | 227600758 | T | 11 | 3' UTR |
| 4 | ISL1 | chr5 | 50689706 | A | 9 | 3' UTR |
| 4 | ITPRIPL1 | chr2 | 96994050 | A | 10 | 3' UTR |
| 4 | JAKMIP1 | chr4 | 6055625 | A | 11 | 3' UTR |
| 4 | KBTBD7 | chr13 | 41766026 | A | 9 | 3' UTR |
| 4 | KBTBD8 | chr3 | 67059954 | T | 10 | 3' UTR |
| 4 | KCNMA1 | chr10 | 78646910 | A | 9 | 3' UTR |
| 4 | KDELR2 | chr7 | 6501817 | A | 10 | 3' UTR |
| 4 | KDM5A | chr12 | 393295 | T | 11 | 3' UTR |
| 4 | KDSR | chr18 | 60998042 | T | 15 | 3' UTR |

TABLE 4-continued

| Nr of affected samples | Gene | Chromosome | Start Position | Affected homopolymer base | Affected homopolymer length | region |
|---|---|---|---|---|---|---|
| 4 | KIAA0182 | chr16 | 85706942 | A | 10 | 3' UTR |
| 4 | KIAA0494 | chr1 | 47142711 | T | 9 | 3' UTR |
| 4 | KIAA0825 | chr5 | 93487128 | A | 28 | 3' UTR |
| 4 | KIF1B | chr1 | 10438932 | T | 10 | 3' UTR |
| 4 | KIF1B | chr1 | 10437995 | A | 13 | 3' UTR |
| 4 | KLF12 | chr13 | 74261703 | T | 11 | 3' UTR |
| 4 | KLHL4 | chrX | 86922592 | A | 12 | 3' UTR |
| 4 | KPNA6 | chr1 | 32639763 | C | 9 | 3' UTR |
| 4 | KREMEN1 | chr22 | 29539729 | A | 14 | 3' UTR |
| 4 | L1CAM | chrX | 153127125 | T | 9 | 3' UTR |
| 4 | LARP4B | chr10 | 856761 | A | 9 | 3' UTR |
| 4 | LATS2 | chr13 | 21547830 | A | 9 | 3' UTR |
| 4 | LBR | chr1 | 225590887 | A | 10 | 3' UTR |
| 4 | LEF1 | chr4 | 108969352 | A | 9 | 3' UTR |
| 4 | LIAS | chr4 | 39478848 | A | 11 | 3' UTR |
| 4 | LIMS1 | chr2 | 109300693 | A | 10 | 3' UTR |
| 4 | LIN7C | chr11 | 27517538 | A | 10 | 3' UTR |
| 4 | LIX1 | chr5 | 96428100 | A | 10 | 3' UTR |
| 4 | LMTK2 | chr7 | 97837420 | A | 11 | 3' UTR |
| 4 | LRCH2 | chrX | 114346112 | T | 10 | 3' UTR |
| 4 | LRRC8A | chr9 | 131679397 | A | 11 | 3' UTR |
| 4 | LUZP2 | chr11 | 25102964 | A | 12 | 3' UTR |
| 4 | LYRM7 | chr5 | 130540369 | A | 15 | 3' UTR |
| 4 | MAP1B | chr5 | 71502852 | A | 10 | 3' UTR |
| 4 | MAP4 | chr3 | 48016254 | A | 13 | 3' UTR |
| 4 | MAP6 | chr11 | 75316787 | A | 11 | 3' UTR |
| 4 | MAPK1IP1L | chr14 | 55534134 | T | 10 | 3' UTR |
| 4 | MB21D2 | chr3 | 192516152 | A | 10 | 3' UTR |
| 4 | MDM2 | chr12 | 69233886 | T | 11 | 3' UTR |
| 4 | MEF2C | chr5 | 88017643 | A | 7 | 3' UTR |
| 4 | MEGF9 | chr9 | 123366681 | T | 10 | 3' UTR |
| 4 | METAP2 | chr12 | 95908545 | A | 11 | 3' UTR |
| 4 | METTL8 | chr2 | 172174950 | T | 8 | 3' UTR |
| 4 | MEX3A | chr1 | 156044195 | T | 17 | 3' UTR |
| 4 | MFN2 | chr1 | 12073251 | A | 11 | 3' UTR |
| 4 | MGAT4A | chr2 | 99236361 | T | 10 | 3' UTR |
| 4 | MIDN | chr19 | 1258791 | A | 10 | 3' UTR |
| 4 | MKLN1 | chr7 | 131181200 | T | 10 | 3' UTR |
| 4 | MKRN3 | chr15 | 23812682 | T | 8 | 3' UTR |
| 4 | MLL2 | chr12 | 49413198 | A | 10 | 3' UTR |
| 4 | MLLT6 | chr17 | 36883386 | T | 16 | 3' UTR |
| 4 | MMP2 | chr16 | 55539895 | T | 10 | 3' UTR |
| 4 | MOSPD1 | chrX | 134022551 | A | 9 | 3' UTR |
| 4 | MRPL44 | chr2 | 224831951 | T | 11 | 3' UTR |
| 4 | MTMR4 | chr17 | 56567367 | A | 9 | 3' UTR |
| 4 | MTSS1 | chr8 | 125564840 | A | 9 | 3' UTR |
| 4 | MYCL1 | chr1 | 40361307 | A | 10 | 3' UTR |
| 4 | NAPB | chr20 | 23355923 | A | 9 | 3' UTR |
| 4 | NARG2 | chr15 | 60714335 | T | 11 | 3' UTR |
| 4 | NCS1 | chr9 | 132996076 | T | 12 | 3' UTR |
| 4 | NDFIP1 | chr5 | 141533930 | T | 10 | 3' UTR |
| 4 | NEGR1 | chr1 | 71869847 | T | 11 | 3' UTR |
| 4 | NEIL3 | chr4 | 178283942 | T | 10 | 3' UTR |
| 4 | NF2 | chr22 | 30092784 | T | 14 | 3' UTR |
| 4 | NLK | chr17 | 26523190 | T | 10 | 3' UTR |
| 4 | NPC2 | chr14 | 74946724 | A | 10 | 3' UTR |
| 4 | NR2F2 | chr15 | 96882212 | G | 8 | 3' UTR |
| 4 | NRSN1 | chr6 | 24147583 | T | 10 | 3' UTR |
| 4 | OSBP2 | chr22 | 31302451 | T | 10 | 3' UTR |
| 4 | OSBPL3 | chr7 | 24837354 | A | 10 | 3' UTR |
| 4 | OTUD4 | chr4 | 146058513 | T | 8 | 3' UTR |
| 4 | OTUD4 | chr4 | 146057615 | G | 13 | 3' UTR |
| 4 | OXR1 | chr8 | 107764095 | A | 10 | 3' UTR |
| 4 | PABPC5 | chrX | 90691818 | T | 9 | 3' UTR |
| 4 | PAICS | chr4 | 57327144 | A | 10 | 3' UTR |
| 4 | PAK1IP1 | chr6 | 10709747 | T | 12 | 3' UTR |
| 4 | PALM2 | chr9 | 112706843 | A | 11 | 3' UTR |
| 4 | PAPD4 | chr5 | 78982336 | T | 10 | 3' UTR |
| 4 | PAPOLA | chr14 | 97033430 | A | 10 | 3' UTR |
| 4 | PCDH17 | chr13 | 58300047 | A | 10 | 3' UTR |
| 4 | PCNP | chr3 | 101312474 | A | 10 | 3' UTR |
| 4 | PDE4C | chr19 | 18320061 | T | 12 | 3' UTR |
| 4 | PDGFA | chr7 | 537622 | A | 11 | 3' UTR |
| 4 | PDGFA | chr7 | 536908 | T | 11 | 3' UTR |
| 4 | PGM2L1 | chr11 | 74047320 | T | 11 | 3' UTR |

TABLE 4-continued

| Nr of affected samples | Gene | Chromosome | Start Position | Affected homopolymer base | Affected homopolymer length | region |
|---|---|---|---|---|---|---|
| 4 | PIGW | chr17 | 34894609 | T | 11 | 3' UTR |
| 4 | PIK3R1 | chr5 | 67595054 | A | 10 | 3' UTR |
| 4 | PIM1 | chr6 | 37143155 | T | 11 | 3' UTR |
| 4 | PIP5K1A | chr1 | 151220867 | T | 11 | 3' UTR |
| 4 | PKD2 | chr4 | 88998190 | A | 11 | 3' UTR |
| 4 | PKN2 | chr1 | 89301773 | T | 11 | 3' UTR |
| 4 | PLA2G12A | chr4 | 110633665 | T | 10 | 3' UTR |
| 4 | PLAGL2 | chr20 | 30784138 | T | 11 | 3' UTR |
| 4 | PLCB1 | chr20 | 8863118 | A | 10 | 3' UTR |
| 4 | PLCL1 | chr2 | 199013907 | T | 9 | 3' UTR |
| 4 | PLCXD3 | chr5 | 41307606 | A | 9 | 3' UTR |
| 4 | PLK2 | chr5 | 57749858 | A | 9 | 3' UTR |
| 4 | PODNL1 | chr19 | 14042032 | G | 8 | 3' UTR |
| 4 | PODXL | chr7 | 131185943 | A | 11 | 3' UTR |
| 4 | POLH | chr6 | 43584323 | A | 14 | 3' UTR |
| 4 | PPAP2B | chr1 | 56962088 | T | 10 | 3' UTR |
| 4 | PPARA | chr22 | 46633507 | A | 16 | 3' UTR |
| 4 | PPARGC1B | chr5 | 149227267 | A | 14 | 3' UTR |
| 4 | PPM1E | chr17 | 57060351 | A | 10 | 3' UTR |
| 4 | PPP1R3A | chr7 | 113517422 | A | 9 | 3' UTR |
| 4 | PPP3CA | chr4 | 101946069 | T | 10 | 3' UTR |
| 4 | PRDM15 | chr21 | 43220664 | A | 12 | 3' UTR |
| 4 | PROSC | chr8 | 37636576 | A | 10 | 3' UTR |
| 4 | PRTG | chr15 | 55907920 | T | 10 | 3' UTR |
| 4 | PTP4A2 | chr1 | 32374021 | A | 10 | 3' UTR |
| 4 | PTPN22 | chr1 | 114357118 | T | 10 | 3' UTR |
| 4 | PTPRF | chr1 | 44088117 | T | 11 | 3' UTR |
| 4 | PTRF | chr17 | 40554683 | A | 15 | 3' UTR |
| 4 | PUM1 | chr1 | 31405680 | T | 10 | 3' UTR |
| 4 | QRICH1 | chr3 | 49067797 | A | 11 | 3' UTR |
| 4 | RAB39B | chrX | 154488466 | T | 11 | 3' UTR |
| 4 | RAB7L1 | chr1 | 205738564 | T | 10 | 3' UTR |
| 4 | RAB8B | chr15 | 63559206 | T | 12 | 3' UTR |
| 4 | RASAL2 | chr1 | 178447287 | T | 11 | 3' UTR |
| 4 | RBM12B | chr8 | 94745547 | A | 10 | 3' UTR |
| 4 | RBM38 | chr20 | 55983973 | G | 8 | 3' UTR |
| 4 | RBMS3 | chr3 | 30045473 | T | 10 | 3' UTR |
| 4 | RDX | chr11 | 110102325 | A | 10 | 3' UTR |
| 4 | RGS18 | chr1 | 192154126 | T | 8 | 3' UTR |
| 4 | RGS6 | chr14 | 73030606 | A | 11 | 3' UTR |
| 4 | RND2 | chr17 | 41181921 | A | 24 | 3' UTR |
| 4 | RNF122 | chr8 | 33405498 | A | 26 | 3' UTR |
| 4 | RNGTT | chr6 | 89320667 | T | 10 | 3' UTR |
| 4 | ROCK1 | chr18 | 18530891 | A | 10 | 3' UTR |
| 4 | RPRD2 | chr1 | 150447772 | T | 10 | 3' UTR |
| 4 | RPRD2 | chr1 | 150445907 | T | 10 | 3' UTR |
| 4 | RRM2 | chr2 | 10269544 | T | 10 | 3' UTR |
| 4 | RSBN1L | chr7 | 77408705 | A | 9 | 3' UTR |
| 4 | RSL1D1 | chr16 | 11930997 | T | 11 | 3' UTR |
| 4 | SALL3 | chr18 | 76757543 | A | 10 | 3' UTR |
| 4 | SAMD4A | chr14 | 55257700 | A | 10 | 3' UTR |
| 4 | SASH1 | chr6 | 148872287 | T | 10 | 3' UTR |
| 4 | SATB1 | chr3 | 18390227 | T | 12 | 3' UTR |
| 4 | SCN1A | chr2 | 166846936 | T | 10 | 3' UTR |
| 4 | SDC4 | chr20 | 43955023 | A | 24 | 3' UTR |
| 4 | SEC63 | chr6 | 108190403 | A | 10 | 3' UTR |
| 4 | SENP5 | chr3 | 196658083 | A | 10 | 3' UTR |
| 4 | SEPHS1 | chr10 | 13360740 | A | 11 | 3' UTR |
| 4 | SFXN1 | chr5 | 174954918 | T | 22 | 3' UTR |
| 4 | SGK223 | chr8 | 8175297 | T | 12 | 3' UTR |
| 4 | SH2B3 | chr12 | 111887735 | T | 14 | 3' UTR |
| 4 | SHC1 | chr1 | 154935862 | G | 8 | 3' UTR |
| 4 | SHC4 | chr15 | 49117721 | T | 10 | 3' UTR |
| 4 | SHCBP1 | chr16 | 46614658 | T | 14 | 3' UTR |
| 4 | SHOC2 | chr10 | 112773341 | T | 10 | 3' UTR |
| 4 | SIPA1L3 | chr19 | 38698929 | T | 10 | 3' UTR |
| 4 | SIPA1L3 | chr19 | 38698868 | T | 10 | 3' UTR |
| 4 | SIX4 | chr14 | 61178202 | A | 10 | 3' UTR |
| 4 | SLAIN2 | chr4 | 48426160 | T | 9 | 3' UTR |
| 4 | SLC17A5 | chr6 | 74303467 | A | 10 | 3' UTR |
| 4 | SLC22A5 | chr5 | 131730903 | T | 17 | 3' UTR |
| 4 | SLC25A36 | chr3 | 140696772 | A | 11 | 3' UTR |
| 4 | SLC2A2 | chr3 | 170715683 | T | 10 | 3' UTR |
| 4 | SLC39A9 | chr14 | 69928356 | T | 10 | 3' UTR |
| 4 | SLC6A15 | chr12 | 85253350 | T | 10 | 3' UTR |

TABLE 4-continued

| Nr of affected samples | Gene | Chromosome | Start Position | Affected homopolymer base | Affected homopolymer length | region |
|---|---|---|---|---|---|---|
| 4 | SLC9A6 | chrX | 135128103 | T | 11 | 3' UTR |
| 4 | SMAD3 | chr15 | 67485102 | A | 9 | 3' UTR |
| 4 | SMAD4 | chr18 | 48605007 | T | 10 | 3' UTR |
| 4 | SMAD7 | chr18 | 46447623 | A | 10 | 3' UTR |
| 4 | SORL1 | chr11 | 121502077 | T | 11 | 3' UTR |
| 4 | SORL1 | chr11 | 121501334 | T | 9 | 3' UTR |
| 4 | SOST | chr17 | 41831941 | T | 10 | 3' UTR |
| 4 | SOX30 | chr5 | 157053271 | T | 10 | 3' UTR |
| 4 | SPATA13 | chr13 | 24878597 | T | 11 | 3' UTR |
| 4 | SPATS2 | chr12 | 49921053 | T | 10 | 3' UTR |
| 4 | SPINK7 | chr5 | 147695440 | T | 10 | 3' UTR |
| 4 | SPOP | chr17 | 47676672 | A | 13 | 3' UTR |
| 4 | SPRED1 | chr15 | 38648129 | A | 9 | 3' UTR |
| 4 | SPTBN1 | chr2 | 54898095 | T | 10 | 3' UTR |
| 4 | SRRM4 | chr12 | 119599690 | A | 10 | 3' UTR |
| 4 | SRRM4 | chr12 | 119596858 | T | 9 | 3' UTR |
| 4 | STAT2 | chr12 | 56736372 | A | 13 | 3' UTR |
| 4 | STK4 | chr20 | 43708275 | A | 10 | 3' UTR |
| 4 | STMN2 | chr8 | 80577224 | A | 13 | 3' UTR |
| 4 | SUMO2 | chr17 | 73164056 | T | 11 | 3' UTR |
| 4 | SYT13 | chr11 | 45264120 | A | 9 | 3' UTR |
| 4 | TACC1 | chr8 | 38708293 | A | 25 | 3' UTR |
| 4 | TAOK1 | chr17 | 27871502 | A | 11 | 3' UTR |
| 4 | TBL1X | chrX | 9684635 | A | 9 | 3' UTR |
| 4 | TFAP2B | chr6 | 50814917 | T | 9 | 3' UTR |
| 4 | TFCP2L1 | chr2 | 121975868 | T | 11 | 3' UTR |
| 4 | THAP2 | chr12 | 72073229 | T | 10 | 3' UTR |
| 4 | THSD4 | chr15 | 72072880 | A | 10 | 3' UTR |
| 4 | THSD7A | chr7 | 11411520 | T | 10 | 3' UTR |
| 4 | TLCD2 | chr17 | 1606349 | T | 13 | 3' UTR |
| 4 | TM9SF4 | chr20 | 30754878 | T | 11 | 3' UTR |
| 4 | TMEM14C | chr6 | 10731011 | A | 9 | 3' UTR |
| 4 | TMEM169 | chr2 | 216966376 | T | 10 | 3' UTR |
| 4 | TMEM192 | chr4 | 165997961 | T | 10 | 3' UTR |
| 4 | TMEM40 | chr3 | 12775743 | T | 9 | 3' UTR |
| 4 | TNFAIP8 | chr5 | 118729618 | A | 10 | 3' UTR |
| 4 | TNRC6C | chr17 | 76104332 | C | 9 | 3' UTR |
| 4 | TPM4 | chr19 | 16212343 | T | 9 | 3' UTR |
| 4 | TRAK2 | chr2 | 202244537 | T | 11 | 3' UTR |
| 4 | TRIM33 | chr1 | 114940229 | T | 13 | 3' UTR |
| 4 | TRIM56 | chr7 | 100733606 | A | 9 | 3' UTR |
| 4 | TRIM9 | chr14 | 51442832 | T | 10 | 3' UTR |
| 4 | TRPC1 | chr3 | 142525356 | T | 9 | 3' UTR |
| 4 | TRPS1 | chr8 | 116424772 | T | 10 | 3' UTR |
| 4 | TRPS1 | chr8 | 116423510 | A | 12 | 3' UTR |
| 4 | TSPAN31 | chr12 | 58141530 | T | 13 | 3' UTR |
| 4 | TTC14 | chr3 | 180326182 | T | 15 | 3' UTR |
| 4 | TULP4 | chr6 | 158929910 | T | 27 | 3' UTR |
| 4 | TXNDC9 | chr2 | 99936109 | A | 9 | 3' UTR |
| 4 | U2AF1 | chr21 | 44513110 | T | 11 | 3' UTR |
| 4 | UBE2G1 | chr17 | 4173433 | A | 10 | 3' UTR |
| 4 | UBE2K | chr4 | 39780193 | A | 11 | 3' UTR |
| 4 | UBE3C | chr7 | 157060934 | T | 10 | 3' UTR |
| 4 | UBE4B | chr1 | 10240859 | T | 10 | 3' UTR |
| 4 | UBFD1 | chr16 | 23582355 | T | 10 | 3' UTR |
| 4 | UBN2 | chr7 | 138992059 | T | 9 | 3' UTR |
| 4 | USF2 | chr19 | 35770658 | A | 10 | 3' UTR |
| 4 | USP31 | chr16 | 23077020 | T | 11 | 3' UTR |
| 4 | USP43 | chr17 | 9632696 | T | 12 | 3' UTR |
| 4 | USP43 | chr17 | 9632427 | T | 13 | 3' UTR |
| 4 | USP43 | chr17 | 9632418 | A | 9 | 3' UTR |
| 4 | VEZF1 | chr17 | 56051105 | T | 14 | 3' UTR |
| 4 | VGLL3 | chr3 | 86990599 | T | 11 | 3' UTR |
| 4 | VPS53 | chr17 | 422006 | A | 27 | 3' UTR |
| 4 | VTI1A | chr10 | 114575744 | T | 10 | 3' UTR |
| 4 | WDR3 | chr1 | 118502087 | T | 11 | 3' UTR |
| 4 | WDR82 | chr3 | 52288956 | T | 19 | 3' UTR |
| 4 | WHSC1 | chr4 | 1945453 | A | 9 | 3' UTR |
| 4 | XKR6 | chr8 | 10755309 | T | 10 | 3' UTR |
| 4 | XKR6 | chr8 | 10755102 | T | 11 | 3' UTR |
| 4 | ZBTB16 | chr11 | 114121371 | A | 11 | 3' UTR |
| 4 | ZBTB4 | chr17 | 7363093 | A | 10 | 3' UTR |
| 4 | ZC3HAV1L | chr7 | 138710878 | A | 11 | 3' UTR |
| 4 | ZCCHC13 | chrX | 73524759 | A | 9 | 3' UTR |
| 4 | ZCCHC2 | chr18 | 60244188 | A | 10 | 3' UTR |

TABLE 4-continued

| Nr of affected samples | Gene | Chromosome | Start Position | Affected homopolymer base | Affected homopolymer length | region |
|---|---|---|---|---|---|---|
| 4 | ZFHX4 | chr8 | 77778696 | T | 14 | 3' UTR |
| 4 | ZFP36L1 | chr14 | 69255309 | T | 12 | 3' UTR |
| 4 | ZFP36L2 | chr2 | 43450053 | C | 8 | 3' UTR |
| 4 | ZMIZ1 | chr10 | 81075616 | A | 10 | 3' UTR |
| 4 | ZNF498 | chr7 | 99229241 | T | 11 | 3' UTR |
| 4 | ZNF528 | chr19 | 52920874 | T | 12 | 3' UTR |
| 4 | ZNF594 | chr17 | 5084035 | A | 10 | 3' UTR |
| 4 | ZNF618 | chr9 | 116812463 | A | 9 | 3' UTR |
| 4 | ZNF629 | chr16 | 30792783 | T | 10 | 3' UTR |
| 4 | ZNF681 | chr19 | 23925293 | A | 13 | 3' UTR |
| 4 | ZNF737 | chr19 | 20726934 | A | 11 | 3' UTR |
| 4 | ZNF740 | chr12 | 53584463 | T | 14 | 3' UTR |
| 4 | ZSCAN30 | chr18 | 32831761 | T | 12 | 3' UTR |
| 13 | GABRG2 | chr5 | 161494990 | A | 12 | 5' UTR |
| 12 | ARHGEF11 | chr1 | 157014811 | A | 12 | 5' UTR |
| 12 | CCT6B | chr17 | 33288433 | A | 11 | 5' UTR |
| 12 | LRMP | chr12 | 25205380 | A | 11 | 5' UTR |
| 11 | TMEM177 | chr2 | 120437061 | A | 11 | 5' UTR |
| 11 | ZNF781 | chr19 | 38161161 | T | 11 | 5' UTR |
| 10 | EPHB6 | chr7 | 142560576 | A | 13 | 5' UTR |
| 10 | LMOD3 | chr3 | 69171664 | T | 13 | 5' UTR |
| 10 | MBNL1 | chr3 | 152017897 | T | 11 | 5' UTR |
| 9 | ARHGEF9 | chrX | 62974288 | T | 12 | 5' UTR |
| 9 | BDNF | chr11 | 27741184 | A | 10 | 5' UTR |
| 9 | CBLN2 | chr18 | 70211389 | A | 14 | 5' UTR |
| 9 | OIT3 | chr10 | 74653468 | A | 10 | 5' UTR |
| 8 | BMP5 | chr6 | 55739711 | A | 14 | 5' UTR |
| 8 | LOC642587 | chr1 | 209602342 | T | 13 | 5' UTR |
| 8 | OMD | chr9 | 95179844 | T | 11 | 5' UTR |
| 8 | SEMA6A | chr5 | 115910134 | A | 11 | 5' UTR |
| 8 | TCF4 | chr18 | 53255634 | A | 12 | 5' UTR |
| 7 | ASPH | chr8 | 62602295 | A | 11 | 5' UTR |
| 7 | CNTNAP2 | chr7 | 145813627 | T | 11 | 5' UTR |
| 7 | DIO2 | chr14 | 80678323 | T | 14 | 5' UTR |
| 7 | DIO2 | chr14 | 80678077 | T | 25 | 5' UTR |
| 7 | GSDMC | chr8 | 130798567 | A | 14 | 5' UTR |
| 7 | PTP4A2 | chr1 | 32384716 | A | 11 | 5' UTR |
| 7 | ZXDB | chrX | 57618380 | T | 9 | 5' UTR |
| 6 | AMD1 | chr6 | 111196178 | A | 11 | 5' UTR |
| 6 | DDX3X | chrX | 41192964 | A | 10 | 5' UTR |
| 6 | ESCO1 | chr18 | 19164371 | A | 11 | 5' UTR |
| 6 | GEN1 | chr2 | 17935494 | T | 11 | 5' UTR |
| 6 | LPHN1 | chr19 | 14316982 | A | 15 | 5' UTR |
| 6 | LRRC70 | chr5 | 61874619 | A | 18 | 5' UTR |
| 6 | MEIS1 | chr2 | 66662690 | T | 13 | 5' UTR |
| 6 | SATB1 | chr3 | 18465613 | A | 13 | 5' UTR |
| 6 | ST7L | chr1 | 113162029 | C | 10 | 5' UTR |
| 6 | TMEM31 | chrX | 102965989 | T | 10 | 5' UTR |
| 6 | TOX | chr8 | 60031707 | A | 14 | 5' UTR |
| 5 | AAK1 | chr2 | 69870217 | T | 24 | 5' UTR |
| 5 | ARHGEF11 | chr1 | 157014870 | A | 11 | 5' UTR |
| 5 | CBLN2 | chr18 | 70211440 | A | 9 | 5' UTR |
| 5 | CEPT1 | chr1 | 111690319 | A | 9 | 5' UTR |
| 5 | EMP1 | chr12 | 13364426 | A | 10 | 5' UTR |
| 5 | GTF2A1 | chr14 | 81686922 | A | 13 | 5' UTR |
| 5 | L3MBTL3 | chr6 | 130339785 | A | 10 | 5' UTR |
| 5 | LMO7 | chr13 | 76195056 | A | 9 | 5' UTR |
| 5 | LPAR4 | chrX | 78003392 | A | 31 | 5' UTR |
| 5 | LRRC4C | chr11 | 40314470 | A | 10 | 5' UTR |
| 5 | MCF2 | chrX | 138724841 | A | 15 | 5' UTR |
| 5 | NDE1 | chr16 | 15737427 | T | 11 | 5' UTR |
| 5 | PBX1 | chr1 | 164528904 | T | 10 | 5' UTR |
| 5 | PRMT8 | chr12 | 3600691 | T | 11 | 5' UTR |
| 5 | PTPRB | chr12 | 71031210 | A | 10 | 5' UTR |
| 5 | SCN2B | chr11 | 118047234 | A | 9 | 5' UTR |
| 5 | TIGD7 | chr16 | 3350676 | A | 10 | 5' UTR |
| 5 | TSHZ1 | chr18 | 72922942 | T | 10 | 5' UTR |
| 5 | XRRA1 | chr11 | 74656098 | T | 10 | 5' UTR |
| 5 | ZXDA | chrX | 57936946 | A | 9 | 5' UTR |
| 4 | ABCC10 | chr6 | 43399532 | T | 10 | 5' UTR |
| 4 | C1QL3 | chr10 | 16563613 | T | 10 | 5' UTR |
| 4 | CPLX4 | chr18 | 56985739 | A | 10 | 5' UTR |
| 4 | DHRS3 | chr1 | 12677525 | A | 21 | 5' UTR |
| 4 | FAM65B | chr6 | 24877343 | A | 8 | 5' UTR |
| 4 | GRIA2 | chr4 | 158142151 | A | 9 | 5' UTR |

TABLE 4-continued

| Nr of affected samples | Gene | Chromosome | Start Position | Affected homopolymer base | Affected homopolymer length | region |
|---|---|---|---|---|---|---|
| 4 | HEXIM1 | chr17 | 43226461 | T | 10 | 5' UTR |
| 4 | HRH2 | chr5 | 175110094 | A | 21 | 5' UTR |
| 4 | HYLS1 | chr11 | 125753769 | A | 10 | 5' UTR |
| 4 | IL18RAP | chr2 | 103035368 | T | 11 | 5' UTR |
| 4 | MBNL1 | chr3 | 152017452 | A | 10 | 5' UTR |
| 4 | NLRP3 | chr1 | 247581609 | T | 12 | 5' UTR |
| 4 | NR2F2 | chr15 | 96874920 | T | 11 | 5' UTR |
| 4 | NRXN3 | chr14 | 79746442 | T | 10 | 5' UTR |
| 4 | OBFC2A | chr2 | 192543129 | T | 24 | 5' UTR |
| 4 | PDGFB | chr22 | 39640806 | T | 16 | 5' UTR |
| 4 | PIK3R1 | chr5 | 67584512 | T | 12 | 5' UTR |
| 4 | PPP2R5C | chr14 | 102276205 | T | 11 | 5' UTR |
| 4 | RALYL | chr8 | 85095860 | T | 11 | 5' UTR |
| 4 | RFWD2 | chr1 | 176176257 | T | 9 | 5' UTR |
| 4 | RGS4 | chr1 | 163038838 | T | 10 | 5' UTR |
| 4 | SCN2A | chr2 | 166150520 | A | 28 | 5' UTR |
| 4 | SEMA3E | chr7 | 83278198 | A | 16 | 5' UTR |
| 4 | SETBP1 | chr18 | 42260910 | G | 8 | 5' UTR |
| 4 | SIAE,SPA17 | chr11 | 124543762 | T | 15 | 5' UTR |
| 4 | SKIV2L2 | chr5 | 54603686 | A | 13 | 5' UTR |
| 4 | SLC38A5 | chrX | 48327811 | T | 12 | 5' UTR |
| 4 | STIM2 | chr4 | 26862546 | T | 18 | 5' UTR |
| 4 | STK11 | chr19 | 1206796 | T | 10 | 5' UTR |
| 4 | TGFB3 | chr14 | 76447771 | A | 11 | 5' UTR |
| 4 | TRIP6 | chr7 | 100464995 | A | 10 | 5' UTR |
| 4 | ZNF107 | chr7 | 64152284 | A | 8 | 5' UTR |

TABLE 5

| Nr of affected samples | Gene | Chromosome | Start Position | Affected homopolymer base | Affected homopolymer length |
|---|---|---|---|---|---|
| 11 | SETD1B | chr12 | 122242657 | C | 8 |
| 10 | OR7E24 | chr19 | 9361740 | T | 11 |
| 10 | SEC31A | chr4 | 83785564 | T | 9 |
| 9 | ASTE1 | chr3 | 130733046 | T | 11 |
| 9 | CASP5 | chr11 | 104879686 | T | 10 |
| 9 | RPL22 | chr1 | 6257784 | T | 8 |
| 8 | CNOT2 | chr12 | 70747693 | A | 25 |
| 8 | LTN1 | chr21 | 30339205 | T | 11 |
| 8 | TTK | chr6 | 80751896 | A | 9 |
| 7 | CCDC150 | chr2 | 197531518 | A | 11 |
| 7 | KIAA2018 | chr3 | 113377481 | T | 11 |
| 7 | MBD4 | chr3 | 129155547 | T | 10 |
| 7 | MSH6 | chr2 | 48030639 | C | 8 |
| 7 | PHF2 | chr9 | 96422611 | A | 8 |
| 7 | RNF145 | chr5 | 158630629 | T | 11 |
| 7 | RNPC3 | chr1 | 104076466 | A | 12 |
| 7 | SLC22A9 | chr11 | 63149670 | A | 11 |
| 7 | TMBIM4 | chr12 | 66531936 | A | 10 |
| 6 | AIM2 | chr1 | 159032486 | T | 10 |
| 6 | ATR | chr3 | 142274739 | T | 10 |
| 6 | CASP5 | chr11 | 104878040 | T | 10 |
| 6 | CDH26 | chr20 | 58587783 | A | 10 |
| 6 | CLOCK | chr4 | 56336953 | A | 9 |
| 6 | CTCF | chr16 | 67645338 | A | 7 |
| 6 | GRIK2 | chr6 | 102503431 | A | 8 |
| 6 | KIAA0182 | chr16 | 85682289 | C | 8 |
| 6 | MIS18BP1 | chr14 | 45716018 | T | 11 |
| 6 | MLL3 | chr7 | 151874147 | A | 9 |
| 6 | NDUFC2 | chr11 | 77784146 | A | 9 |
| 6 | RBMXL1 | chr1 | 89449508 | T | 11 |
| 6 | SLC35F5 | chr2 | 114500276 | A | 10 |
| 6 | TAF1B | chr2 | 9989570 | A | 11 |
| 6 | TGFBR2 | chr3 | 30691871 | A | 10 |
| 6 | TMEM60 | chr7 | 77423459 | T | 9 |
| 5 | ACVR2A | chr2 | 148683685 | A | 8 |
| 5 | BRD3 | chr9 | 136918528 | G | 8 |
| 5 | C13orf40 | chr13 | 103381995 | A | 9 |
| 5 | COBLL1 | chr2 | 165551295 | A | 9 |
| 5 | DDX27 | chr20 | 47858503 | A | 8 |
| 5 | DOCK3 | chr3 | 51417603 | C | 7 |
| 5 | FAM111B | chr11 | 58892376 | A | 10 |
| 5 | FAM18A | chr16 | 10867202 | A | 9 |
| 5 | FETUB | chr3 | 186362543 | A | 9 |
| 5 | IGF2R | chr6 | 160485487 | G | 8 |
| 5 | KIAA1919 | chr6 | 111587360 | T | 9 |
| 5 | MAP3K4 | chr6 | 161469775 | A | 8 |
| 5 | NRIP1 | chr21 | 16338329 | T | 8 |
| 5 | PRKDC | chr8 | 48866909 | T | 10 |
| 5 | PRRG1 | chrX | 37312610 | C | 8 |
| 5 | PRRT2 | chr16 | 29825015 | C | 9 |
| 5 | RFFL | chr17 | 33336605 | A | 14 |
| 5 | RGS12 | chr4 | 3430398 | A | 9 |
| 5 | SLMO2-ATP5E | chr20 | 57603795 | T | 11 |
| 5 | SMC6 | chr2 | 17898125 | T | 9 |
| 5 | SNAR-G1 | chr19 | 49540383 | A | 14 |
| 5 | SRSF3 | chr6 | 36570853 | A | 14 |
| 5 | TSIX | chrX | 73039404 | A | 13 |
| 5 | UBR5 | chr8 | 103289348 | T | 8 |
| 5 | UVRAG | chr11 | 75694430 | A | 10 |
| 4 | C14orf39 | chr14 | 60903564 | A | 8 |
| 4 | C15orf5 | chr15 | 77516475 | T | 11 |
| 4 | CEP164 | chr11 | 117222647 | A | 11 |
| 4 | CYHR1 | chr8 | 145689658 | C | 9 |
| 4 | DCAF17 | chr2 | 172339178 | T | 11 |
| 4 | ELAVL3 | chr19 | 11577604 | C | 9 |
| 4 | EXOSC9 | chr4 | 122723893 | T | 8 |
| 4 | FAM20A | chr17 | 66531810 | T | 13 |
| 4 | FLJ90757 | chr17 | 79005507 | C | 9 |
| 4 | FOXO3B | chr17 | 18570304 | T | 16 |
| 4 | GBP3 | chr1 | 89473441 | T | 10 |
| 4 | GLTSCR1 | chr19 | 48197890 | C | 8 |
| 4 | HPS1 | chr10 | 100186986 | G | 8 |
| 4 | INO80E | chr16 | 30016652 | C | 9 |
| 4 | INTS2 | chr17 | 59944673 | A | 11 |
| 4 | JAK1 | chr1 | 65325832 | G | 7 |

TABLE 5-continued

| Nr of affected samples | Gene | Chromosome | Start Position | Affected homopolymer base | Affected homopolymer length |
|---|---|---|---|---|---|
| 4 | KIAA0664L3 | chr16 | 31718743 | A | 15 |
| 4 | LOC284023 | chr17 | 7818450 | A | 14 |
| 4 | LOC645431 | chr14 | 65877626 | A | 11 |
| 4 | MIAT | chr22 | 27067793 | A | 13 |
| 4 | MYO10 | chr5 | 16694605 | C | 8 |
| 4 | OSBPL2 | chr20 | 60854257 | C | 7 |
| 4 | PAR-SN | chr15 | 25227494 | A | 11 |
| 4 | PRR11 | chr17 | 57247170 | A | 9 |
| 4 | RBM27 | chr5 | 145647319 | A | 9 |
| 4 | RBM43 | chr2 | 152108087 | T | 10 |
| 4 | RFC3 | chr13 | 34398062 | A | 10 |
| 4 | RG9MTD1 | chr3 | 101284008 | A | 10 |
| 4 | RPS26P11 | chrX | 71264809 | A | 15 |
| 4 | SEC63 | chr6 | 108214754 | T | 10 |
| 4 | SLC23A2 | chr20 | 4850568 | G | 9 |
| 4 | SPECC1 | chr17 | 20108262 | A | 8 |
| 4 | SRPR | chr11 | 126137086 | T | 8 |
| 4 | TESC | chr12 | 117476741 | T | 14 |
| 4 | TEX11 | chrX | 70127617 | A | 8 |
| 4 | TMCC1 | chr3 | 129407106 | A | 13 |
| 4 | TSIX | chrX | 73017534 | A | 12 |
| 4 | WDTC1 | chr1 | 27621107 | G | 8 |
| 4 | XPA | chr9 | 100437633 | T | 10 |
| 4 | ZBTB20 | chr3 | 114058002 | G | 7 |
| 4 | ZDHHC8 | chr22 | 20130521 | C | 6 |
| 4 | ZMAT1 | chrX | 101138438 | T | 11 |
| 4 | ZNF273 | chr7 | 64390205 | T | 13 |
| 4 | ZNF831 | chr20 | 57766219 | C | 8 |

TABLE 6

| Nr of affected samples | Gene | Chromosome | Start Position | Affected homopolymer base | Affected homopolymer length | region |
|---|---|---|---|---|---|---|
| 9 | ARHGEF11 | chr1 | 157014811 | A | 12 | 5' UTR |
| 9 | LRMP | chr12 | 25205380 | A | 11 | 5' UTR |
| 8 | GABRG2 | chr5 | 161494990 | A | 12 | 5' UTR |
| 8 | MBNL1 | chr3 | 152017897 | T | 11 | 5' UTR |
| 7 | ARHGEF9 | chrX | 62974288 | T | 12 | 5' UTR |
| 7 | CCT6B | chr17 | 33288433 | A | 11 | 5' UTR |
| 7 | GRIA2 | chr4 | 158142151 | A | 9 | 5' UTR |
| 7 | TRPS1 | chr8 | 116681041 | A | 14 | 5' UTR |
| 7 | ZNF781 | chr19 | 38161161 | T | 11 | 5' UTR |
| 6 | AMD1 | chr6 | 111196178 | A | 11 | 5' UTR |
| 6 | ASPH | chr8 | 62602295 | A | 11 | 5' UTR |
| 6 | EPHB6 | chr7 | 142560576 | A | 13 | 5' UTR |
| 6 | LMOD3 | chr3 | 69171664 | T | 13 | 5' UTR |
| 6 | OMD | chr9 | 95179844 | T | 11 | 5' UTR |
| 6 | SEMA6A | chr5 | 115910134 | A | 11 | 5' UTR |
| 6 | TMEM177 | chr2 | 120437061 | A | 11 | 5' UTR |
| 5 | BMP5 | chr6 | 55739711 | A | 14 | 5' UTR |
| 5 | CBLN2 | chr18 | 70211389 | A | 14 | 5' UTR |
| 5 | CEPT1 | chr1 | 111690319 | A | 9 | 5' UTR |
| 5 | LRRC70 | chr5 | 61874619 | A | 18 | 5' UTR |
| 5 | MCF2 | chrX | 138724841 | A | 15 | 5' UTR |
| 5 | MEIS1 | chr2 | 66662690 | T | 13 | 5' UTR |
| 5 | NDE1 | chr16 | 15737427 | T | 11 | 5' UTR |
| 5 | OIT3 | chr10 | 74653468 | A | 10 | 5' UTR |
| 5 | RCC2 | chr1 | 17766108 | T | 10 | 5' UTR |
| 5 | RUFY3 | chr4 | 71588131 | T | 14 | 5' UTR |
| 5 | ZXDA | chrX | 57936946 | A | 9 | 5' UTR |
| 4 | BDNF | chr11 | 27741184 | A | 10 | 5' UTR |
| 4 | EBF1 | chr5 | 158526596 | T | 11 | 5' UTR |
| 4 | EIF4E | chr4 | 99851375 | T | 11 | 5' UTR |
| 4 | ESCO1 | chr18 | 19164371 | A | 11 | 5' UTR |
| 4 | GEN1 | chr2 | 17935494 | T | 11 | 5' UTR |
| 4 | HEMGN | chr9 | 100700505 | A | 11 | 5' UTR |
| 4 | HRH2 | chr5 | 175110094 | A | 21 | 5' UTR |
| 4 | L3MBTL3 | chr6 | 130339785 | A | 10 | 5' UTR |
| 4 | LMO7 | chr13 | 76195056 | A | 9 | 5' UTR |
| 4 | LOC642587 | chr1 | 209602342 | T | 13 | 5' UTR |
| 4 | LRRC4C | chr11 | 40314470 | A | 10 | 5' UTR |
| 4 | NR3C1 | chr5 | 142814523 | T | 12 | 5' UTR |
| 4 | PTP4A2 | chr1 | 32384716 | A | 11 | 5' UTR |
| 4 | RAPGEF2 | chr4 | 160189200 | T | 11 | 5' UTR |
| 4 | RGS4 | chr1 | 163038838 | T | 10 | 5' UTR |
| 4 | SATB1 | chr3 | 18465613 | A | 13 | 5' UTR |
| 4 | SETBP1 | chr18 | 42260910 | G | 8 | 5' UTR |
| 4 | ST7L | chr1 | 113162029 | C | 10 | 5' UTR |
| 4 | TCF4 | chr18 | 53255634 | A | 12 | 5' UTR |
| 4 | TCF7L2 | chr10 | 114710208 | T | 14 | 5' UTR |
| 4 | TSHZ1 | chr18 | 72922942 | T | 10 | 5' UTR |
| 4 | USP53 | chr4 | 120135275 | A | 18 | 5' UTR |
| 4 | ZNF107 | chr7 | 64152284 | A | 8 | 5' UTR |

TABLE 6-continued

| Nr of affected samples | Gene | Chromosome | Start Position | Affected homopolymer base | Affected homopolymer length | region |
|---|---|---|---|---|---|---|
| 3 | AAK1 | chr2 | 69870217 | T | 24 | 5' UTR |
| 3 | ABCC10 | chr6 | 43399532 | T | 10 | 5' UTR |
| 3 | C10orf140 | chr10 | 21806928 | G | 10 | 5' UTR |
| 3 | C1QL3 | chr10 | 16563613 | T | 10 | 5' UTR |
| 3 | CCDC126 | chr7 | 23650854 | T | 10 | 5' UTR |
| 3 | CCDC99 | chr5 | 169015403 | A | 8 | 5' UTR |
| 3 | CNTNAP2 | chr7 | 145813627 | T | 11 | 5' UTR |
| 3 | CPLX4 | chr18 | 56985739 | A | 10 | 5' UTR |
| 3 | DDX3X | chrX | 41192964 | A | 10 | 5' UTR |
| 3 | DIO2 | chr14 | 80678323 | T | 14 | 5' UTR |
| 3 | DIO2 | chr14 | 80678077 | T | 25 | 5' UTR |
| 3 | EBP | chrX | 48382099 | T | 18 | 5' UTR |
| 3 | EMP1 | chr12 | 13364426 | A | 10 | 5' UTR |
| 3 | FAM65B | chr6 | 24877343 | A | 8 | 5' UTR |
| 3 | FLRT2 | chr14 | 86087801 | T | 10 | 5' UTR |
| 3 | GSDMC | chr8 | 130798567 | A | 14 | 5' UTR |
| 3 | HOXD3 | chr2 | 177028841 | A | 10 | 5' UTR |
| 3 | HYLS1 | chr11 | 125753769 | A | 10 | 5' UTR |
| 3 | JAKMIP2 | chr5 | 147162132 | T | 10 | 5' UTR |
| 3 | LPAR4 | chrX | 78003392 | A | 31 | 5' UTR |
| 3 | LPHN1 | chr19 | 14316982 | A | 15 | 5' UTR |
| 3 | MARCKS | chr6 | 114178627 | T | 9 | 5' UTR |
| 3 | MRGPRF | chr11 | 68780847 | C | 8 | 5' UTR |
| 3 | NCAM1 | chr11 | 112832276 | G | 10 | 5' UTR |
| 3 | NR2F2 | chr15 | 96874920 | T | 11 | 5' UTR |
| 3 | P2RY14 | chr3 | 150937331 | T | 8 | 5' UTR |
| 3 | PBX1 | chr1 | 164528904 | T | 10 | 5' UTR |
| 3 | PKN2 | chr1 | 89150150 | T | 13 | 5' UTR |
| 3 | PPP2R5C | chr14 | 102276205 | T | 11 | 5' UTR |
| 3 | PTPRB | chr12 | 71031210 | A | 10 | 5' UTR |
| 3 | RFWD2 | chr1 | 176176257 | T | 9 | 5' UTR |
| 3 | SCN2B | chr11 | 118047234 | A | 9 | 5' UTR |
| 3 | SLC38A5 | chrX | 48327811 | T | 12 | 5' UTR |
| 3 | TBC1D5 | chr3 | 17781827 | A | 14 | 5' UTR |
| 3 | TMEM31 | chrX | 102965989 | T | 10 | 5' UTR |
| 3 | TOX | chr8 | 60031707 | A | 14 | 5' UTR |
| 3 | TRIP6 | chr7 | 100464995 | A | 10 | 5' UTR |
| 3 | XRRA1 | chr11 | 74656098 | T | 10 | 5' UTR |
| 3 | ZXDB | chrX | 57618380 | T | 9 | 5' UTR |
| 11 | WIPF2 | chr17 | 38436904 | T | 13 | 3' UTR |
| 10 | NARG2 | chr15 | 60712503 | T | 13 | 3' UTR |
| 9 | AHCYL1 | chr1 | 110566210 | A | 14 | 3' UTR |
| 9 | C17orf63 | chr17 | 27083744 | T | 12 | 3' UTR |
| 9 | CD5L | chr1 | 157801230 | A | 13 | 3' UTR |
| 9 | CEP170 | chr1 | 243288181 | T | 11 | 3' UTR |
| 9 | COL5A2 | chr2 | 189898205 | T | 13 | 3' UTR |
| 9 | CSNK1G3 | chr5 | 122950254 | T | 13 | 3' UTR |
| 9 | DIDO1 | chr20 | 61536691 | A | 11 | 3' UTR |
| 9 | EIF4G3 | chr1 | 21133496 | T | 13 | 3' UTR |
| 9 | GSK3B | chr3 | 119542766 | A | 11 | 3' UTR |
| 9 | KCNMB4 | chr12 | 70824838 | A | 14 | 3' UTR |
| 9 | MAPK1IP1L | chr14 | 55535728 | T | 13 | 3' UTR |
| 9 | NPR3 | chr5 | 32787131 | A | 11 | 3' UTR |
| 9 | PI15 | chr8 | 75766071 | T | 10 | 3' UTR |
| 9 | PRTG | chr15 | 55903921 | A | 11 | 3' UTR |
| 9 | RASGRP1 | chr15 | 38781450 | T | 13 | 3' UTR |
| 9 | SH3KBP1 | chrX | 19552231 | T | 13 | 3' UTR |
| 9 | SHROOM3 | chr4 | 77701305 | A | 12 | 3' UTR |
| 9 | SLC5A3 | chr21 | 35470291 | T | 11 | 3' UTR |
| 9 | UBE2Z | chr17 | 47005701 | A | 11 | 3' UTR |
| 9 | ZBTB33 | chrX | 119390643 | T | 14 | 3' UTR |
| 9 | ZNF275 | chrX | 152617043 | A | 12 | 3' UTR |
| 8 | AGPAT3 | chr21 | 45405278 | A | 15 | 3' UTR |
| 8 | APH1B | chr15 | 63600287 | T | 12 | 3' UTR |
| 8 | BCL11A | chr2 | 60685409 | T | 12 | 3' UTR |
| 8 | BMPR1B | chr4 | 96076113 | T | 13 | 3' UTR |
| 8 | CALN1 | chr7 | 71245682 | A | 12 | 3' UTR |
| 8 | CASK | chrX | 41379131 | A | 13 | 3' UTR |
| 8 | CBFB | chr16 | 67133068 | T | 11 | 3' UTR |
| 8 | CBX5 | chr12 | 54628041 | T | 13 | 3' UTR |
| 8 | CCDC85C | chr14 | 99978765 | A | 12 | 3' UTR |
| 8 | CNOT7 | chr8 | 17088039 | T | 11 | 3' UTR |
| 8 | CYP1B1 | chr2 | 38297055 | T | 12 | 3' UTR |
| 8 | DRAM2 | chr1 | 111660181 | A | 11 | 3' UTR |
| 8 | EDA2R | chrX | 65815929 | T | 12 | 3' UTR |

TABLE 6-continued

| Nr of affected samples | Gene | Chromosome | Start Position | Affected homopolymer base | Affected homopolymer length | region |
|---|---|---|---|---|---|---|
| 8 | EDEM3 | chr1 | 184660755 | A | 14 | 3' UTR |
| 8 | EGR1 | chr5 | 137804274 | A | 12 | 3' UTR |
| 8 | EIF4G3 | chr1 | 21133286 | A | 13 | 3' UTR |
| 8 | FAM20B | chr1 | 179044906 | A | 12 | 3' UTR |
| 8 | FCHSD2 | chr11 | 72549649 | A | 10 | 3' UTR |
| 8 | FLT1 | chr13 | 28877146 | A | 12 | 3' UTR |
| 8 | FMO2 | chr1 | 171178335 | A | 11 | 3' UTR |
| 8 | G3BP2 | chr4 | 76568663 | A | 12 | 3' UTR |
| 8 | HELZ | chr17 | 65070976 | A | 14 | 3' UTR |
| 8 | HRNR | chr1 | 152184856 | T | 11 | 3' UTR |
| 8 | IER3IP1 | chr18 | 44682385 | A | 11 | 3' UTR |
| 8 | KCNG1 | chr20 | 49620212 | T | 14 | 3' UTR |
| 8 | KCNK1 | chr1 | 233807667 | A | 11 | 3' UTR |
| 8 | KLF3 | chr4 | 38699104 | T | 14 | 3' UTR |
| 8 | LHX9 | chr1 | 197898395 | T | 12 | 3' UTR |
| 8 | LRRC8D | chr1 | 90401405 | T | 11 | 3' UTR |
| 8 | LYRM1 | chr16 | 20935842 | T | 11 | 3' UTR |
| 8 | MED13 | chr17 | 60023567 | A | 10 | 3' UTR |
| 8 | MYO5B | chr18 | 47351784 | A | 12 | 3' UTR |
| 8 | NCEH1 | chr3 | 172348807 | A | 12 | 3' UTR |
| 8 | PPP1R12A | chr12 | 80169697 | T | 13 | 3' UTR |
| 8 | PPP1R3D | chr20 | 58512721 | T | 13 | 3' UTR |
| 8 | RAB11FIP1 | chr8 | 37718707 | A | 13 | 3' UTR |
| 8 | RAB6C | chr2 | 130739712 | T | 13 | 3' UTR |
| 8 | SAMD12 | chr8 | 119209320 | A | 11 | 3' UTR |
| 8 | SEMA6A | chr5 | 115779928 | A | 13 | 3' UTR |
| 8 | SLAIN2 | chr4 | 48428163 | T | 11 | 3' UTR |
| 8 | SMAD4 | chr18 | 48609831 | T | 11 | 3' UTR |
| 8 | TMED7 | chr5 | 114950622 | A | 14 | 3' UTR |
| 8 | TMEM57 | chr1 | 25826052 | T | 12 | 3' UTR |
| 8 | TMEM65 | chr8 | 125325217 | A | 11 | 3' UTR |
| 8 | TNPO1 | chr5 | 72204773 | A | 13 | 3' UTR |
| 8 | TOR1AIP2 | chr1 | 179814857 | A | 12 | 3' UTR |
| 8 | TRAK2 | chr2 | 202242603 | A | 12 | 3' UTR |
| 8 | TRIP11 | chr14 | 92435633 | A | 12 | 3' UTR |
| 8 | UST | chr6 | 149398012 | T | 13 | 3' UTR |
| 8 | VEGFA | chr6 | 43754176 | A | 12 | 3' UTR |
| 8 | ZBTB7A | chr19 | 4046571 | T | 11 | 3' UTR |
| 8 | ZKSCAN1 | chr7 | 99633041 | T | 12 | 3' UTR |
| 8 | ZNF12 | chr7 | 6730082 | T | 12 | 3' UTR |
| 8 | ZNF169 | chr9 | 97063725 | A | 11 | 3' UTR |
| 7 | ABAT | chr16 | 8876792 | T | 11 | 3' UTR |
| 7 | AEN | chr15 | 89174888 | T | 12 | 3' UTR |
| 7 | AIDA | chr1 | 222841524 | T | 10 | 3' UTR |
| 7 | ALG9 | chr11 | 111655441 | A | 11 | 3' UTR |
| 7 | ANK2 | chr4 | 114303782 | T | 11 | 3' UTR |
| 7 | ANKS1B | chr12 | 99138457 | T | 12 | 3' UTR |
| 7 | ARFIP1 | chr4 | 153832102 | T | 11 | 3' UTR |
| 7 | ARHGAP18 | chr6 | 129898731 | A | 11 | 3' UTR |
| 7 | ARID1A | chr1 | 27107950 | A | 12 | 3' UTR |
| 7 | ASPN | chr9 | 95218905 | A | 12 | 3' UTR |
| 7 | ATP11A | chr13 | 113540850 | T | 12 | 3' UTR |
| 7 | BCL11B | chr14 | 99637947 | T | 12 | 3' UTR |
| 7 | BTBD7 | chr14 | 93708030 | A | 10 | 3' UTR |
| 7 | C11orf87 | chr11 | 109296012 | A | 12 | 3' UTR |
| 7 | C14orf101 | chr14 | 57114799 | A | 13 | 3' UTR |
| 7 | C15orf2 | chr15 | 24927891 | A | 10 | 3' UTR |
| 7 | C15orf29 | chr15 | 34434105 | T | 12 | 3' UTR |
| 7 | C5orf33 | chr5 | 36194227 | A | 11 | 3' UTR |
| 7 | C5orf51 | chr5 | 41921535 | T | 13 | 3' UTR |
| 7 | CAMK2A | chr5 | 149600684 | T | 11 | 3' UTR |
| 7 | CANX | chr5 | 179158477 | A | 12 | 3' UTR |
| 7 | CBLN4 | chr20 | 54572755 | A | 12 | 3' UTR |
| 7 | CD1E | chr1 | 158327025 | T | 13 | 3' UTR |
| 7 | CD47 | chr3 | 107762288 | A | 11 | 3' UTR |
| 7 | CDC23 | chr5 | 137524388 | A | 11 | 3' UTR |
| 7 | CDKN2AIPNL | chr5 | 133738313 | A | 11 | 3' UTR |
| 7 | CEP44 | chr4 | 175238738 | T | 13 | 3' UTR |
| 7 | CMIP | chr16 | 81744987 | A | 10 | 3' UTR |
| 7 | CMTM6 | chr3 | 32523862 | A | 12 | 3' UTR |
| 7 | CNR1 | chr6 | 88853530 | A | 11 | 3' UTR |
| 7 | CPNE3 | chr8 | 87571865 | T | 11 | 3' UTR |
| 7 | CREB3L2 | chr7 | 137561927 | A | 11 | 3' UTR |
| 7 | CRTAP | chr3 | 33187520 | A | 12 | 3' UTR |
| 7 | CSDA | chr12 | 10851811 | T | 14 | 3' UTR |

TABLE 6-continued

| Nr of affected samples | Gene | Chromosome | Start Position | Affected homopolymer base | Affected homopolymer length | region |
|---|---|---|---|---|---|---|
| 7 | DLGAP2 | chr8 | 1652939 | A | 11 | 3' UTR |
| 7 | DLGAP4 | chr20 | 35156539 | T | 11 | 3' UTR |
| 7 | EBF1 | chr5 | 158123905 | T | 13 | 3' UTR |
| 7 | ENAM | chr4 | 71511776 | T | 15 | 3' UTR |
| 7 | EPS15 | chr1 | 51821385 | A | 13 | 3' UTR |
| 7 | EPT1 | chr2 | 26617514 | T | 11 | 3' UTR |
| 7 | ERBB2IP | chr5 | 65375200 | T | 15 | 3' UTR |
| 7 | FAM104A | chr17 | 71204073 | A | 13 | 3' UTR |
| 7 | FAM126B | chr2 | 201844251 | A | 11 | 3' UTR |
| 7 | FAM126B | chr2 | 201838933 | A | 13 | 3' UTR |
| 7 | FGF9 | chr13 | 22278024 | T | 13 | 3' UTR |
| 7 | FGFBP3 | chr10 | 93666830 | A | 11 | 3' UTR |
| 7 | FLRT2 | chr14 | 86090074 | A | 12 | 3' UTR |
| 7 | FLRT3 | chr20 | 14305760 | T | 12 | 3' UTR |
| 7 | FLT1 | chr13 | 28875309 | A | 14 | 3' UTR |
| 7 | FYN | chr6 | 111982555 | T | 12 | 3' UTR |
| 7 | GABPB1 | chr15 | 50570604 | A | 13 | 3' UTR |
| 7 | GABRG2 | chr5 | 161581834 | A | 11 | 3' UTR |
| 7 | GBP1 | chr1 | 89518865 | T | 13 | 3' UTR |
| 7 | GLUD1 | chr10 | 88810337 | A | 15 | 3' UTR |
| 7 | HCRTR2 | chr6 | 55147361 | T | 12 | 3' UTR |
| 7 | HIPK2 | chr7 | 139249947 | A | 14 | 3' UTR |
| 7 | INSR | chr19 | 7116555 | A | 12 | 3' UTR |
| 7 | KIAA2018 | chr3 | 113371321 | A | 11 | 3' UTR |
| 7 | KLHL4 | chrX | 86922591 | A | 13 | 3' UTR |
| 7 | KRT8 | chr12 | 53291007 | A | 11 | 3' UTR |
| 7 | LARP4B | chr10 | 856116 | A | 13 | 3' UTR |
| 7 | LRAT | chr4 | 155673737 | A | 10 | 3' UTR |
| 7 | MAT2A | chr2 | 85772061 | T | 12 | 3' UTR |
| 7 | MED28 | chr4 | 17626082 | T | 11 | 3' UTR |
| 7 | METTL9 | chr16 | 21667438 | A | 12 | 3' UTR |
| 7 | MEX3A | chr1 | 156043944 | T | 11 | 3' UTR |
| 7 | MITF | chr3 | 70014804 | A | 11 | 3' UTR |
| 7 | MLL3 | chr7 | 151832596 | T | 11 | 3' UTR |
| 7 | MSR1 | chr8 | 15997800 | A | 11 | 3' UTR |
| 7 | NEK5 | chr13 | 52639268 | A | 13 | 3' UTR |
| 7 | NFIX | chr19 | 13208001 | T | 13 | 3' UTR |
| 7 | NRXN3 | chr14 | 80328831 | A | 11 | 3' UTR |
| 7 | OXR1 | chr8 | 107763507 | T | 13 | 3' UTR |
| 7 | PEX13 | chr2 | 61276332 | T | 15 | 3' UTR |
| 7 | PGK1 | chrX | 77381770 | T | 13 | 3' UTR |
| 7 | PHACTR2 | chr6 | 144151003 | T | 10 | 3' UTR |
| 7 | PLEKHA2 | chr8 | 38830288 | T | 13 | 3' UTR |
| 7 | POFUT1 | chr20 | 30826323 | A | 11 | 3' UTR |
| 7 | PPP2R3A | chr3 | 135865826 | T | 11 | 3' UTR |
| 7 | PRKD3 | chr2 | 37479023 | A | 11 | 3' UTR |
| 7 | PRKD3 | chr2 | 37478759 | T | 12 | 3' UTR |
| 7 | PSEN1 | chr14 | 73688298 | T | 13 | 3' UTR |
| 7 | PTEN | chr10 | 89725293 | T | 11 | 3' UTR |
| 7 | RAB6A | chr11 | 73387527 | A | 12 | 3' UTR |
| 7 | RBM25 | chr14 | 73587904 | T | 14 | 3' UTR |
| 7 | RBM45 | chr2 | 178994205 | T | 11 | 3' UTR |
| 7 | RBMS1 | chr2 | 161128989 | T | 13 | 3' UTR |
| 7 | RCC2 | chr1 | 17735285 | A | 14 | 3' UTR |
| 7 | RELL1 | chr4 | 37613352 | A | 12 | 3' UTR |
| 7 | RORA | chr15 | 60788653 | A | 12 | 3' UTR |
| 7 | RSPO2 | chr8 | 108912568 | A | 11 | 3' UTR |
| 7 | SEC61G | chr7 | 54819993 | A | 11 | 3' UTR |
| 7 | SEPT7 | chr7 | 35944036 | T | 11 | 3' UTR |
| 7 | SLC35D1 | chr1 | 67465371 | A | 13 | 3' UTR |
| 7 | SMAD3 | chr15 | 67486032 | T | 13 | 3' UTR |
| 7 | SNAPC1 | chr14 | 62262575 | T | 12 | 3' UTR |
| 7 | SNRNP40 | chr1 | 31732677 | A | 11 | 3' UTR |
| 7 | SNX31 | chr8 | 101585895 | T | 11 | 3' UTR |
| 7 | SPIN1 | chr9 | 91090830 | A | 12 | 3' UTR |
| 7 | STX11 | chr6 | 144511720 | T | 12 | 3' UTR |
| 7 | SUCNR1 | chr3 | 151599651 | A | 14 | 3' UTR |
| 7 | SUMO2 | chr17 | 73164055 | T | 12 | 3' UTR |
| 7 | TACC1 | chr8 | 38705639 | A | 11 | 3' UTR |
| 7 | TAF4B | chr18 | 23971326 | A | 13 | 3' UTR |
| 7 | TBC1D24 | chr16 | 2553486 | A | 13 | 3' UTR |
| 7 | TMC1 | chr9 | 75451136 | T | 15 | 3' UTR |
| 7 | TMTC3 | chr12 | 88591979 | T | 13 | 3' UTR |
| 7 | TOB2 | chr22 | 41832049 | A | 12 | 3' UTR |
| 7 | TRA2A | chr7 | 23544783 | A | 11 | 3' UTR |

TABLE 6-continued

| Nr of affected samples | Gene | Chromosome | Start Position | Affected homopolymer base | Affected homopolymer length | region |
|---|---|---|---|---|---|---|
| 7 | TRIM66 | chr11 | 8637072 | T | 13 | 3' UTR |
| 7 | TRIM66 | chr11 | 8635430 | A | 9 | 3' UTR |
| 7 | TTBK2 | chr15 | 43037302 | A | 12 | 3' UTR |
| 7 | UBA6 | chr4 | 68481877 | T | 12 | 3' UTR |
| 7 | UBE2W | chr8 | 74703502 | A | 14 | 3' UTR |
| 7 | USP44 | chr12 | 95911789 | A | 11 | 3' UTR |
| 7 | USP9X | chrX | 41093298 | T | 15 | 3' UTR |
| 7 | VGLL4 | chr3 | 11599949 | T | 13 | 3' UTR |
| 7 | VPS26A | chr10 | 70931260 | T | 11 | 3' UTR |
| 7 | WHSC1L1 | chr8 | 38175279 | A | 11 | 3' UTR |
| 7 | WSB1 | chr17 | 25640280 | T | 15 | 3' UTR |
| 7 | WWP1 | chr8 | 87479625 | A | 13 | 3' UTR |
| 7 | ZBTB3 | chr11 | 62519422 | A | 12 | 3' UTR |
| 7 | ZDHHC9 | chrX | 128939304 | T | 13 | 3' UTR |
| 7 | ZNF185 | chrX | 152140995 | C | 10 | 3' UTR |
| 7 | ZNF217 | chr20 | 52185289 | A | 13 | 3' UTR |
| 7 | ZNF238 | chr1 | 244220229 | T | 10 | 3' UTR |
| 7 | ZNF264 | chr19 | 57730525 | A | 14 | 3' UTR |
| 7 | ZNF281 | chr1 | 200375822 | T | 12 | 3' UTR |
| 7 | ZNF549 | chr19 | 58050715 | T | 14 | 3' UTR |
| 7 | ZNF740 | chr12 | 53582896 | T | 11 | 3' UTR |
| 6 | ACTR2 | chr2 | 65498035 | A | 12 | 3' UTR |
| 6 | ACVR1C | chr2 | 158387581 | T | 14 | 3' UTR |
| 6 | AES | chr19 | 3053066 | T | 13 | 3' UTR |
| 6 | AJAP1 | chr1 | 4843660 | T | 11 | 3' UTR |
| 6 | ALDH8A1 | chr6 | 135238907 | T | 10 | 3' UTR |
| 6 | ANKRD28 | chr3 | 15709862 | T | 13 | 3' UTR |
| 6 | ANP32B | chr9 | 100777784 | A | 14 | 3' UTR |
| 6 | APPBP2 | chr17 | 58524281 | A | 12 | 3' UTR |
| 6 | ARAP2 | chr4 | 36068192 | A | 12 | 3' UTR |
| 6 | ARHGAP17 | chr16 | 24930800 | A | 14 | 3' UTR |
| 6 | ARHGAP5 | chr14 | 32627034 | T | 11 | 3' UTR |
| 6 | ARID4A | chr14 | 58840119 | T | 10 | 3' UTR |
| 6 | ARL4C | chr2 | 235403511 | A | 11 | 3' UTR |
| 6 | ARL5B | chr10 | 18964315 | T | 11 | 3' UTR |
| 6 | ATRX | chrX | 76763679 | A | 13 | 3' UTR |
| 6 | ATXN7 | chr3 | 63987679 | A | 15 | 3' UTR |
| 6 | BCL7A | chr12 | 122498799 | A | 12 | 3' UTR |
| 6 | BMPR1B | chr4 | 96077805 | A | 12 | 3' UTR |
| 6 | BRAP | chr12 | 112080129 | T | 12 | 3' UTR |
| 6 | C14orf104 | chr14 | 50092077 | A | 13 | 3' UTR |
| 6 | C3orf62 | chr3 | 49308391 | A | 11 | 3' UTR |
| 6 | C3orf72 | chr3 | 138671354 | T | 13 | 3' UTR |
| 6 | C4orf49 | chr4 | 140187661 | T | 11 | 3' UTR |
| 6 | C5orf42 | chr5 | 37107311 | T | 11 | 3' UTR |
| 6 | C6orf145 | chr6 | 3723315 | A | 11 | 3' UTR |
| 6 | CACNB4 | chr2 | 152694131 | T | 11 | 3' UTR |
| 6 | CADPS | chr3 | 62384481 | T | 10 | 3' UTR |
| 6 | CALN1 | chr7 | 71249416 | T | 10 | 3' UTR |
| 6 | CAMKK2 | chr12 | 121676365 | A | 11 | 3' UTR |
| 6 | CANX | chr5 | 179155907 | T | 12 | 3' UTR |
| 6 | CCDC89 | chr11 | 85395559 | T | 10 | 3' UTR |
| 6 | CCDC93 | chr2 | 118675891 | A | 11 | 3' UTR |
| 6 | CCND2 | chr12 | 4411082 | T | 11 | 3' UTR |
| 6 | CCND2 | chr12 | 4410638 | T | 16 | 3' UTR |
| 6 | CD36 | chr7 | 80306123 | T | 12 | 3' UTR |
| 6 | CDC73 | chr1 | 193220974 | T | 12 | 3' UTR |
| 6 | CDK2 | chr12 | 56366445 | A | 11 | 3' UTR |
| 6 | CDK4 | chr12 | 58142004 | A | 14 | 3' UTR |
| 6 | CHMP2B | chr3 | 87303064 | A | 14 | 3' UTR |
| 6 | CISD1 | chr10 | 60048285 | T | 11 | 3' UTR |
| 6 | COIL | chr17 | 55016354 | A | 14 | 3' UTR |
| 6 | COPS7A | chr12 | 6840953 | A | 11 | 3' UTR |
| 6 | COX18 | chr4 | 73923142 | A | 12 | 3' UTR |
| 6 | CSMD2 | chr1 | 33979967 | T | 12 | 3' UTR |
| 6 | CSNK1E | chr22 | 38686864 | A | 11 | 3' UTR |
| 6 | CSNK1E | chr22 | 38686807 | T | 12 | 3' UTR |
| 6 | DCBLD2 | chr3 | 98516119 | A | 13 | 3' UTR |
| 6 | DCP2 | chr5 | 112351058 | T | 11 | 3' UTR |
| 6 | DENND5B | chr12 | 31535650 | T | 12 | 3' UTR |
| 6 | DIEXF | chr1 | 210026704 | T | 15 | 3' UTR |
| 6 | DNAJA2 | chr16 | 46989766 | T | 10 | 3' UTR |
| 6 | DSC3 | chr18 | 28573880 | A | 12 | 3' UTR |
| 6 | DTNA | chr18 | 32446839 | T | 12 | 3' UTR |
| 6 | DUSP9 | chrX | 152916312 | T | 12 | 3' UTR |

TABLE 6-continued

| Nr of affected samples | Gene | Chromosome | Start Position | Affected homopolymer base | Affected homopolymer length | region |
|---|---|---|---|---|---|---|
| 6 | DUT | chr15 | 48634319 | A | 15 | 3' UTR |
| 6 | EDA2R | chrX | 65815870 | A | 13 | 3' UTR |
| 6 | EFNA5 | chr5 | 106714693 | A | 12 | 3' UTR |
| 6 | EHD4 | chr15 | 42191704 | A | 12 | 3' UTR |
| 6 | ELTD1 | chr1 | 79356149 | T | 11 | 3' UTR |
| 6 | EMCN | chr4 | 101318099 | T | 12 | 3' UTR |
| 6 | EPB41L1 | chr20 | 34818694 | T | 14 | 3' UTR |
| 6 | EPHA4 | chr2 | 222290623 | T | 11 | 3' UTR |
| 6 | ERBB4 | chr2 | 212247967 | A | 18 | 3' UTR |
| 6 | ERGIC2 | chr12 | 29493722 | T | 11 | 3' UTR |
| 6 | ESRP1 | chr8 | 95719492 | A | 11 | 3' UTR |
| 6 | FAM103A1 | chr15 | 83659295 | T | 14 | 3' UTR |
| 6 | FAM116A | chr3 | 57611367 | A | 11 | 3' UTR |
| 6 | FAM120A | chr9 | 96327976 | A | 13 | 3' UTR |
| 6 | FAM46A | chr6 | 82458103 | A | 13 | 3' UTR |
| 6 | FAM46C | chr1 | 118167727 | T | 12 | 3' UTR |
| 6 | FAM60A | chr12 | 31435608 | T | 11 | 3' UTR |
| 6 | FAM60A | chr12 | 31435556 | A | 10 | 3' UTR |
| 6 | FBLN7 | chr2 | 112945284 | T | 11 | 3' UTR |
| 6 | FGF9 | chr13 | 22277774 | T | 10 | 3' UTR |
| 6 | FOXL2 | chr3 | 138663653 | T | 13 | 3' UTR |
| 6 | FOXN3 | chr14 | 89622979 | T | 13 | 3' UTR |
| 6 | GLI3 | chr7 | 42001569 | A | 11 | 3' UTR |
| 6 | GNRHR | chr4 | 68604166 | A | 12 | 3' UTR |
| 6 | GOLGA7B | chr10 | 99627458 | T | 14 | 3' UTR |
| 6 | GPAM | chr10 | 113910871 | T | 12 | 3' UTR |
| 6 | GRIN2A | chr16 | 9849712 | A | 11 | 3' UTR |
| 6 | H3F3C | chr12 | 31944217 | T | 12 | 3' UTR |
| 6 | HAS2 | chr8 | 122625936 | A | 12 | 3' UTR |
| 6 | HIP1 | chr7 | 75166838 | A | 11 | 3' UTR |
| 6 | HMGCS1 | chr5 | 43290194 | A | 16 | 3' UTR |
| 6 | HN1L | chr16 | 1751589 | T | 11 | 3' UTR |
| 6 | HNRNPA3 | chr2 | 178088002 | T | 10 | 3' UTR |
| 6 | HNRNPK | chr9 | 86583189 | T | 12 | 3' UTR |
| 6 | HS3ST1 | chr4 | 11400430 | T | 13 | 3' UTR |
| 6 | HSPC159 | chr2 | 64687147 | T | 16 | 3' UTR |
| 6 | HUS1B | chr6 | 656079 | A | 10 | 3' UTR |
| 6 | IGF2BP1 | chr17 | 47129195 | T | 12 | 3' UTR |
| 6 | IL33 | chr9 | 6256984 | T | 12 | 3' UTR |
| 6 | IQGAP1 | chr15 | 91044621 | A | 14 | 3' UTR |
| 6 | IRF2BP2 | chr1 | 234742204 | A | 13 | 3' UTR |
| 6 | KCNJ2 | chr17 | 68175917 | A | 10 | 3' UTR |
| 6 | KCTD9 | chr8 | 25286171 | A | 12 | 3' UTR |
| 6 | KDM5A | chr12 | 389523 | T | 11 | 3' UTR |
| 6 | KHDRBS1 | chr1 | 32508883 | A | 11 | 3' UTR |
| 6 | KIAA1671 | chr22 | 25592399 | T | 12 | 3' UTR |
| 6 | KIF3A | chr5 | 132029672 | A | 14 | 3' UTR |
| 6 | KLF9 | chr9 | 73002115 | T | 11 | 3' UTR |
| 6 | LACE1 | chr6 | 108844116 | T | 11 | 3' UTR |
| 6 | LANCL1 | chr2 | 211297865 | T | 9 | 3' UTR |
| 6 | LDB3 | chr10 | 88495759 | T | 11 | 3' UTR |
| 6 | LHFPL4 | chr3 | 9543422 | A | 13 | 3' UTR |
| 6 | LPHN3 | chr4 | 62936763 | T | 12 | 3' UTR |
| 6 | LRCH1 | chr13 | 47325657 | A | 10 | 3' UTR |
| 6 | LRIG2 | chr1 | 113667282 | T | 11 | 3' UTR |
| 6 | LRRC4 | chr7 | 127668232 | T | 9 | 3' UTR |
| 6 | LRRN3 | chr7 | 110764988 | A | 13 | 3' UTR |
| 6 | LSM14A | chr19 | 34718607 | T | 12 | 3' UTR |
| 6 | LYPLA1 | chr8 | 54959960 | T | 12 | 3' UTR |
| 6 | MAGEB3 | chrX | 30255422 | A | 11 | 3' UTR |
| 6 | MAK16 | chr8 | 33357516 | T | 11 | 3' UTR |
| 6 | MAP3K5 | chr6 | 136878751 | T | 14 | 3' UTR |
| 6 | MDM2 | chr12 | 69236873 | T | 13 | 3' UTR |
| 6 | MED1 | chr17 | 37561712 | T | 13 | 3' UTR |
| 6 | MESDC1 | chr15 | 81296262 | T | 9 | 3' UTR |
| 6 | MESDC1 | chr15 | 81296129 | T | 12 | 3' UTR |
| 6 | METTL21B | chr12 | 58175145 | T | 15 | 3' UTR |
| 6 | MKLN1 | chr7 | 131175980 | A | 10 | 3' UTR |
| 6 | MLL5 | chr7 | 104754047 | T | 14 | 3' UTR |
| 6 | MRE11A | chr11 | 94151547 | T | 13 | 3' UTR |
| 6 | MTF2 | chr1 | 93602675 | A | 14 | 3' UTR |
| 6 | MTMR9 | chr8 | 11185354 | A | 10 | 3' UTR |
| 6 | NAA35 | chr9 | 88637203 | A | 10 | 3' UTR |
| 6 | NAALAD2 | chr11 | 89925062 | T | 10 | 3' UTR |
| 6 | NAF1 | chr4 | 164049985 | A | 11 | 3' UTR |

TABLE 6-continued

| Nr of affected samples | Gene | Chromosome | Start Position | Affected homopolymer base | Affected homopolymer length | region |
|---|---|---|---|---|---|---|
| 6 | NANP | chr20 | 25595951 | A | 13 | 3' UTR |
| 6 | NANP | chr20 | 25595618 | A | 11 | 3' UTR |
| 6 | NEDD1 | chr12 | 97346987 | A | 13 | 3' UTR |
| 6 | NHLH1 | chr1 | 160341680 | A | 11 | 3' UTR |
| 6 | NPAS3 | chr14 | 34271068 | A | 12 | 3' UTR |
| 6 | NUS1 | chr6 | 118029805 | T | 11 | 3' UTR |
| 6 | OXSR1 | chr3 | 38296209 | T | 12 | 3' UTR |
| 6 | PAPD5 | chr16 | 50264031 | A | 13 | 3' UTR |
| 6 | PCDH9 | chr13 | 66878392 | A | 26 | 3' UTR |
| 6 | PCGF3 | chr4 | 761102 | T | 11 | 3' UTR |
| 6 | PCGF5 | chr10 | 93043932 | T | 11 | 3' UTR |
| 6 | PEG3 | chr19 | 57323786 | T | 13 | 3' UTR |
| 6 | PHF6 | chrX | 133561520 | T | 10 | 3' UTR |
| 6 | PLCH1 | chr3 | 155197737 | A | 12 | 3' UTR |
| 6 | PM20D2 | chr6 | 89874860 | T | 11 | 3' UTR |
| 6 | PMEPA1 | chr20 | 56226891 | T | 11 | 3' UTR |
| 6 | POGZ | chr1 | 151377008 | A | 13 | 3' UTR |
| 6 | POLR2D | chr2 | 128604217 | A | 15 | 3' UTR |
| 6 | POMT2 | chr14 | 77741349 | T | 11 | 3' UTR |
| 6 | POU2F2 | chr19 | 42595246 | T | 17 | 3' UTR |
| 6 | POU2F2 | chr19 | 42594356 | T | 13 | 3' UTR |
| 6 | PPM1A | chr14 | 60761433 | T | 10 | 3' UTR |
| 6 | PPP2R3A | chr3 | 135865709 | A | 14 | 3' UTR |
| 6 | PRCC | chr1 | 156770552 | T | 12 | 3' UTR |
| 6 | PROK2 | chr3 | 71821522 | A | 14 | 3' UTR |
| 6 | PRPF40A | chr2 | 153512044 | T | 15 | 3' UTR |
| 6 | PTP4A1 | chr6 | 64290633 | T | 15 | 3' UTR |
| 6 | PURB | chr7 | 44920830 | A | 9 | 3' UTR |
| 6 | RAP2A | chr13 | 98118463 | A | 14 | 3' UTR |
| 6 | RASSF3 | chr12 | 65088985 | T | 11 | 3' UTR |
| 6 | RBM12B | chr8 | 94745437 | A | 11 | 3' UTR |
| 6 | RBM24 | chr6 | 17292448 | A | 11 | 3' UTR |
| 6 | RBM33 | chr7 | 155569742 | T | 13 | 3' UTR |
| 6 | RGS16 | chr1 | 182569291 | T | 26 | 3' UTR |
| 6 | RIMKLB | chr12 | 8926680 | T | 11 | 3' UTR |
| 6 | RPIA | chr2 | 89049874 | A | 12 | 3' UTR |
| 6 | RSPO2 | chr8 | 108911856 | A | 10 | 3' UTR |
| 6 | RUNDC3B | chr7 | 87460421 | T | 12 | 3' UTR |
| 6 | RUNX1T1 | chr8 | 92972022 | T | 12 | 3' UTR |
| 6 | RYR3 | chr15 | 34157541 | A | 10 | 3' UTR |
| 6 | SAMD5 | chr6 | 147887423 | T | 12 | 3' UTR |
| 6 | SATB2 | chr2 | 200136194 | T | 12 | 3' UTR |
| 6 | SCD5 | chr4 | 83552278 | A | 11 | 3' UTR |
| 6 | SCML4 | chr6 | 108025850 | T | 13 | 3' UTR |
| 6 | SEC24A | chr5 | 134063499 | A | 14 | 3' UTR |
| 6 | SEMA4D | chr9 | 91992883 | A | 13 | 3' UTR |
| 6 | SEMA6A | chr5 | 115781801 | T | 10 | 3' UTR |
| 6 | SENP1 | chr12 | 48436768 | T | 11 | 3' UTR |
| 6 | SETX | chr9 | 135139195 | T | 11 | 3' UTR |
| 6 | SFXN2 | chr10 | 104498056 | T | 14 | 3' UTR |
| 6 | SGK196 | chr8 | 42978200 | T | 13 | 3' UTR |
| 6 | SH3BP5 | chr3 | 15297082 | T | 13 | 3' UTR |
| 6 | SH3RF1 | chr4 | 170017405 | A | 14 | 3' UTR |
| 6 | SH3RF1 | chr4 | 170016066 | A | 11 | 3' UTR |
| 6 | SLAIN2 | chr4 | 48426783 | A | 11 | 3' UTR |
| 6 | SLC16A7 | chr12 | 60173983 | A | 11 | 3' UTR |
| 6 | SLC2A3 | chr12 | 8072022 | T | 13 | 3' UTR |
| 6 | SLC30A7 | chr1 | 101446221 | T | 11 | 3' UTR |
| 6 | SLITRK3 | chr3 | 164905648 | A | 11 | 3' UTR |
| 6 | SNX27 | chr1 | 151666826 | T | 11 | 3' UTR |
| 6 | SOCS4 | chr14 | 55512747 | T | 10 | 3' UTR |
| 6 | SOX4 | chr6 | 21597192 | A | 11 | 3' UTR |
| 6 | SOX6 | chr11 | 15988219 | A | 11 | 3' UTR |
| 6 | SPTB | chr14 | 65213610 | A | 13 | 3' UTR |
| 6 | SRC | chr20 | 36033633 | T | 13 | 3' UTR |
| 6 | ST7L | chr1 | 113067470 | A | 10 | 3' UTR |
| 6 | STARD7 | chr2 | 96851899 | A | 14 | 3' UTR |
| 6 | STXBP5 | chr6 | 147708451 | A | 10 | 3' UTR |
| 6 | SULF2 | chr20 | 46286320 | A | 10 | 3' UTR |
| 6 | SYK | chr9 | 93658485 | A | 12 | 3' UTR |
| 6 | TAF4B | chr18 | 23971176 | A | 14 | 3' UTR |
| 6 | TBC1D22B | chr6 | 37299299 | T | 12 | 3' UTR |
| 6 | TFAP2C | chr20 | 55213320 | T | 11 | 3' UTR |
| 6 | TGIF2 | chr20 | 35220571 | A | 14 | 3' UTR |
| 6 | THAP1 | chr8 | 42692467 | A | 12 | 3' UTR |

TABLE 6-continued

| Nr of affected samples | Gene | Chromo-some | Start Position | Affected homo-polymer base | Affected homo-polymer length | region |
|---|---|---|---|---|---|---|
| 6 | TIGD6 | chr5 | 149373143 | T | 13 | 3' UTR |
| 6 | TMC7 | chr16 | 19073947 | A | 10 | 3' UTR |
| 6 | TMEM106B | chr7 | 12273303 | A | 13 | 3' UTR |
| 6 | TMEM14B | chr6 | 10756863 | A | 11 | 3' UTR |
| 6 | TMEM33 | chr4 | 41959614 | T | 14 | 3' UTR |
| 6 | TMEM57 | chr1 | 25825931 | T | 13 | 3' UTR |
| 6 | TNFAIP3 | chr6 | 138204003 | A | 12 | 3' UTR |
| 6 | TNRC6B | chr22 | 40723852 | T | 12 | 3' UTR |
| 6 | TNRC6B | chr22 | 40722031 | A | 10 | 3' UTR |
| 6 | TNRC6B | chr22 | 40719790 | A | 14 | 3' UTR |
| 6 | TSGA10 | chr2 | 99614595 | A | 13 | 3' UTR |
| 6 | TTL | chr2 | 113289264 | A | 11 | 3' UTR |
| 6 | TTLL5 | chr14 | 76420881 | T | 11 | 3' UTR |
| 6 | UBE2M | chr19 | 59067290 | A | 13 | 3' UTR |
| 6 | UBXN7 | chr3 | 196080741 | T | 11 | 3' UTR |
| 6 | UFM1 | chr13 | 38935214 | T | 11 | 3' UTR |
| 6 | USP14 | chr18 | 212029 | A | 9 | 3' UTR |
| 6 | VCP | chr9 | 35056078 | T | 12 | 3' UTR |
| 6 | VEZF1 | chr17 | 56049540 | T | 11 | 3' UTR |
| 6 | WDR82 | chr3 | 52289627 | A | 11 | 3' UTR |
| 6 | XPO4 | chr13 | 21356029 | A | 10 | 3' UTR |
| 6 | ZBTB43 | chr9 | 129596297 | A | 11 | 3' UTR |
| 6 | ZBTB44 | chr11 | 130102910 | A | 11 | 3' UTR |
| 6 | ZCCHC5 | chrX | 77911813 | A | 12 | 3' UTR |
| 6 | ZFHX3 | chr16 | 72820314 | T | 15 | 3' UTR |
| 6 | ZIC5 | chr13 | 100616014 | A | 11 | 3' UTR |
| 6 | ZNF136 | chr19 | 12299608 | A | 13 | 3' UTR |
| 6 | ZNF2 | chr2 | 95848209 | T | 11 | 3' UTR |
| 6 | ZNF347 | chr19 | 53643153 | T | 12 | 3' UTR |
| 6 | ZNF407 | chr18 | 72516095 | T | 11 | 3' UTR |
| 6 | ZNF563 | chr19 | 12428823 | T | 15 | 3' UTR |
| 6 | ZNF621 | chr3 | 40575421 | A | 11 | 3' UTR |
| 6 | ZNF704 | chr8 | 81550824 | A | 12 | 3' UTR |
| 6 | ZNF716 | chr7 | 57529811 | A | 10 | 3' UTR |
| 6 | ZNF737 | chr19 | 20722094 | A | 14 | 3' UTR |
| 5 | A1CF | chr10 | 52566432 | T | 12 | 3' UTR |
| 5 | ABHD2 | chr15 | 89739843 | T | 10 | 3' UTR |
| 5 | ABI1 | chr10 | 27037487 | A | 11 | 3' UTR |
| 5 | ADAP2 | chr17 | 29285905 | A | 14 | 3' UTR |
| 5 | ADCY9 | chr16 | 4013843 | A | 11 | 3' UTR |
| 5 | ADRBK2 | chr22 | 26121915 | A | 11 | 3' UTR |
| 5 | AKIRIN1 | chr1 | 39471672 | A | 10 | 3' UTR |
| 5 | ANAPC16 | chr10 | 73993363 | T | 10 | 3' UTR |
| 5 | ARID1B | chr6 | 157530262 | A | 14 | 3' UTR |
| 5 | ARL1 | chr12 | 101787092 | T | 11 | 3' UTR |
| 5 | ARL10 | chr5 | 175800426 | T | 10 | 3' UTR |
| 5 | ASB7 | chr15 | 101191402 | T | 13 | 3' UTR |
| 5 | ASB7 | chr15 | 101189293 | T | 10 | 3' UTR |
| 5 | ATF2 | chr2 | 175939223 | A | 12 | 3' UTR |
| 5 | ATP7A | chrX | 77302385 | A | 11 | 3' UTR |
| 5 | ATXN1 | chr6 | 16300902 | T | 11 | 3' UTR |
| 5 | BACE1 | chr11 | 117159733 | T | 11 | 3' UTR |
| 5 | BEND2 | chrX | 18183097 | A | 15 | 3' UTR |
| 5 | BOD1L | chr4 | 13570453 | A | 11 | 3' UTR |
| 5 | C1orf9 | chr1 | 172580460 | T | 9 | 3' UTR |
| 5 | C2orf3 | chr2 | 75890030 | A | 16 | 3' UTR |
| 5 | C3orf58 | chr3 | 143709141 | T | 11 | 3' UTR |
| 5 | C5orf43 | chr5 | 60453908 | A | 9 | 3' UTR |
| 5 | C6orf47 | chr6 | 31626580 | A | 14 | 3' UTR |
| 5 | CACNB4 | chr2 | 152695481 | T | 11 | 3' UTR |
| 5 | CACNB4 | chr2 | 152695178 | T | 12 | 3' UTR |
| 5 | CALML4 | chr15 | 68483096 | A | 12 | 3' UTR |
| 5 | CAMTA1 | chr1 | 7827963 | A | 10 | 3' UTR |
| 5 | CASK | chrX | 41377809 | A | 11 | 3' UTR |
| 5 | CCDC43 | chr17 | 42754916 | T | 13 | 3' UTR |
| 5 | CCND1 | chr11 | 69466273 | A | 10 | 3' UTR |
| 5 | CCND2 | chr12 | 4409520 | T | 10 | 3' UTR |
| 5 | CD300LB | chr17 | 72518440 | A | 11 | 3' UTR |
| 5 | CDC25A | chr3 | 48199852 | T | 12 | 3' UTR |
| 5 | CDK19 | chr6 | 110932988 | A | 12 | 3' UTR |
| 5 | CELF2 | chr10 | 11373567 | A | 11 | 3' UTR |
| 5 | CELSR1 | chr22 | 46756848 | A | 11 | 3' UTR |
| 5 | CFL1 | chr11 | 65622295 | T | 12 | 3' UTR |
| 5 | CHM | chrX | 85118100 | T | 13 | 3' UTR |
| 5 | CLEC3A | chr16 | 78065330 | T | 12 | 3' UTR |

TABLE 6-continued

| Nr of affected samples | Gene | Chromosome | Start Position | Affected homopolymer base | Affected homopolymer length | region |
|---|---|---|---|---|---|---|
| 5 | CLN8 | chr8 | 1729701 | T | 14 | 3' UTR |
| 5 | COPS7B | chr2 | 232673378 | T | 13 | 3' UTR |
| 5 | COQ7 | chr16 | 19089610 | T | 13 | 3' UTR |
| 5 | CPEB3 | chr10 | 93809826 | A | 11 | 3' UTR |
| 5 | CREB3L2 | chr7 | 137563914 | A | 10 | 3' UTR |
| 5 | CREB3L2 | chr7 | 137559830 | T | 14 | 3' UTR |
| 5 | CRTC1 | chr19 | 18890267 | T | 14 | 3' UTR |
| 5 | CTNND2 | chr5 | 10972888 | T | 14 | 3' UTR |
| 5 | DAG1 | chr3 | 49571620 | T | 11 | 3' UTR |
| 5 | DCUN1D5 | chr11 | 102930486 | G | 7 | 3' UTR |
| 5 | DDHD1 | chr14 | 53513439 | A | 12 | 3' UTR |
| 5 | DIXDC1 | chr11 | 111892703 | A | 18 | 3' UTR |
| 5 | DLG3 | chrX | 69722274 | T | 13 | 3' UTR |
| 5 | DLGAP2 | chr8 | 1653883 | T | 11 | 3' UTR |
| 5 | DNAJC27 | chr2 | 25167221 | T | 14 | 3' UTR |
| 5 | DNMT3B | chr20 | 31395997 | T | 11 | 3' UTR |
| 5 | DPP8 | chr15 | 65738042 | A | 11 | 3' UTR |
| 5 | DSEL | chr18 | 65174583 | A | 26 | 3' UTR |
| 5 | DUSP10 | chr1 | 221875661 | A | 11 | 3' UTR |
| 5 | DUSP10 | chr1 | 221874929 | A | 16 | 3' UTR |
| 5 | EGR1 | chr5 | 137804475 | T | 15 | 3' UTR |
| 5 | EGR3 | chr8 | 22545637 | T | 11 | 3' UTR |
| 5 | EIF2S1 | chr14 | 67851084 | T | 13 | 3' UTR |
| 5 | EIF5A2 | chr3 | 170607962 | A | 11 | 3' UTR |
| 5 | ENTPD1 | chr10 | 97628618 | A | 10 | 3' UTR |
| 5 | ENTPD4 | chr8 | 23289680 | A | 11 | 3' UTR |
| 5 | EP300 | chr22 | 41575537 | A | 15 | 3' UTR |
| 5 | EPM2AIP1 | chr3 | 37030780 | T | 11 | 3' UTR |
| 5 | ERBB2IP | chr5 | 65376306 | A | 11 | 3' UTR |
| 5 | EVI5 | chr1 | 92977467 | T | 11 | 3' UTR |
| 5 | EXOSC2 | chr9 | 133579920 | A | 11 | 3' UTR |
| 5 | EYA1 | chr8 | 72110673 | A | 12 | 3' UTR |
| 5 | FAM118A | chr22 | 45736689 | T | 11 | 3' UTR |
| 5 | FAM122A | chr9 | 71396662 | T | 11 | 3' UTR |
| 5 | FAM168B | chr2 | 131805979 | G | 9 | 3' UTR |
| 5 | FAM169A | chr5 | 74075446 | T | 12 | 3' UTR |
| 5 | FAM178A | chr10 | 102724795 | T | 14 | 3' UTR |
| 5 | FAM91A1 | chr8 | 124826583 | T | 12 | 3' UTR |
| 5 | FBRSL1 | chr12 | 133160562 | A | 9 | 3' UTR |
| 5 | FBXO21 | chr12 | 117582872 | T | 15 | 3' UTR |
| 5 | FGF12 | chr3 | 191861010 | A | 16 | 3' UTR |
| 5 | FOXC1 | chr6 | 1612419 | A | 12 | 3' UTR |
| 5 | FOXN2 | chr2 | 48604358 | T | 10 | 3' UTR |
| 5 | FOXO3 | chr6 | 109005013 | A | 11 | 3' UTR |
| 5 | FOXP1 | chr3 | 71007140 | T | 11 | 3' UTR |
| 5 | FRMD4A | chr10 | 13686797 | A | 12 | 3' UTR |
| 5 | FRYL | chr4 | 48500088 | T | 15 | 3' UTR |
| 5 | FXR1 | chr3 | 180694863 | T | 14 | 3' UTR |
| 5 | GABRB2 | chr5 | 160717254 | T | 12 | 3' UTR |
| 5 | GAL | chr11 | 68458592 | T | 12 | 3' UTR |
| 5 | GALNT7 | chr4 | 174244278 | A | 13 | 3' UTR |
| 5 | GBP6 | chr1 | 89851722 | A | 13 | 3' UTR |
| 5 | GDA | chr9 | 74866560 | T | 12 | 3' UTR |
| 5 | GLS | chr2 | 191828629 | T | 12 | 3' UTR |
| 5 | GNAI2 | chr3 | 50296405 | C | 9 | 3' UTR |
| 5 | GNB1 | chr1 | 1717242 | T | 12 | 3' UTR |
| 5 | GPC3 | chrX | 132670054 | A | 13 | 3' UTR |
| 5 | GPR137B | chr1 | 236372038 | T | 10 | 3' UTR |
| 5 | GPR4 | chr19 | 46093443 | A | 11 | 3' UTR |
| 5 | GRSF1 | chr4 | 71686216 | A | 11 | 3' UTR |
| 5 | GSR | chr8 | 30536666 | A | 19 | 3' UTR |
| 5 | GTF3C1 | chr16 | 27471985 | T | 11 | 3' UTR |
| 5 | H3F3B | chr17 | 73774199 | T | 13 | 3' UTR |
| 5 | HAS2 | chr8 | 122625490 | T | 10 | 3' UTR |
| 5 | HDAC4 | chr2 | 239974109 | A | 9 | 3' UTR |
| 5 | HELZ | chr17 | 65073603 | A | 11 | 3' UTR |
| 5 | HERPUD2 | chr7 | 35672678 | T | 14 | 3' UTR |
| 5 | HEXA | chr15 | 72636197 | T | 10 | 3' UTR |
| 5 | HIATL1 | chr9 | 97221877 | T | 11 | 3' UTR |
| 5 | HIPK1 | chr1 | 114519857 | T | 14 | 3' UTR |
| 5 | HIPK2 | chr7 | 139257355 | T | 11 | 3' UTR |
| 5 | HIPK2 | chr7 | 139250450 | T | 11 | 3' UTR |
| 5 | HNRNPUL1 | chr19 | 41812943 | A | 12 | 3' UTR |
| 5 | HS3ST5 | chr6 | 114378233 | T | 12 | 3' UTR |
| 5 | HYOU1 | chr11 | 118915072 | A | 16 | 3' UTR |

TABLE 6-continued

| Nr of affected samples | Gene | Chromosome | Start Position | Affected homopolymer base | Affected homopolymer length | region |
|---|---|---|---|---|---|---|
| 5 | IFNGR1 | chr6 | 137518966 | A | 14 | 3' UTR |
| 5 | IGF1 | chr12 | 102790566 | T | 13 | 3' UTR |
| 5 | ILF3 | chr19 | 10796313 | T | 10 | 3' UTR |
| 5 | IPCEF1 | chr6 | 154476149 | A | 12 | 3' UTR |
| 5 | KCTD6 | chr3 | 58487415 | T | 11 | 3' UTR |
| 5 | KCTD7 | chr7 | 66105589 | T | 11 | 3' UTR |
| 5 | KDM5A | chr12 | 393804 | T | 11 | 3' UTR |
| 5 | KHNYN | chr14 | 24908391 | T | 11 | 3' UTR |
| 5 | KHSRP | chr19 | 6413217 | A | 13 | 3' UTR |
| 5 | KIAA0825 | chr5 | 93489194 | T | 8 | 3' UTR |
| 5 | KIAA1267 | chr17 | 44107956 | A | 14 | 3' UTR |
| 5 | KIF5C | chr2 | 149879665 | T | 10 | 3' UTR |
| 5 | KLHDC5 | chr12 | 27954136 | T | 13 | 3' UTR |
| 5 | KLHL24 | chr3 | 183400567 | T | 10 | 3' UTR |
| 5 | KLHL28 | chr14 | 45398006 | T | 11 | 3' UTR |
| 5 | LDHAL6A | chr11 | 18500557 | T | 12 | 3' UTR |
| 5 | LENG8 | chr19 | 54972801 | T | 9 | 3' UTR |
| 5 | LILRB3 | chr19 | 54720558 | T | 11 | 3' UTR |
| 5 | LMO4 | chr1 | 87813143 | A | 11 | 3' UTR |
| 5 | LONRF2 | chr2 | 100898347 | T | 12 | 3' UTR |
| 5 | LRP6 | chr12 | 12272288 | A | 12 | 3' UTR |
| 5 | MAGI1 | chr3 | 65340577 | T | 11 | 3' UTR |
| 5 | MAK | chr6 | 10764372 | T | 9 | 3' UTR |
| 5 | MAL | chr2 | 95719330 | A | 10 | 3' UTR |
| 5 | MAL2 | chr8 | 120256100 | A | 8 | 3' UTR |
| 5 | MAP1B | chr5 | 71504719 | T | 11 | 3' UTR |
| 5 | MAP3K13 | chr3 | 185200599 | A | 11 | 3' UTR |
| 5 | MAPK1 | chr22 | 22114660 | T | 12 | 3' UTR |
| 5 | MAPK1IP1L | chr14 | 55532698 | A | 11 | 3' UTR |
| 5 | MED1 | chr17 | 37562164 | T | 11 | 3' UTR |
| 5 | MED13 | chr17 | 60022040 | A | 11 | 3' UTR |
| 5 | MEIS2 | chr15 | 37183446 | T | 10 | 3' UTR |
| 5 | MGAT4A | chr2 | 99235842 | A | 11 | 3' UTR |
| 5 | MID1IP1 | chrX | 38664817 | T | 13 | 3' UTR |
| 5 | MLL2 | chr12 | 49413580 | A | 12 | 3' UTR |
| 5 | MS4A7 | chr11 | 60161438 | A | 12 | 3' UTR |
| 5 | MTDH | chr8 | 98740104 | A | 10 | 3' UTR |
| 5 | NAP1L4 | chr11 | 2966276 | A | 15 | 3' UTR |
| 5 | NEGR1 | chr1 | 71869847 | T | 11 | 3' UTR |
| 5 | NFIB | chr9 | 14082667 | T | 12 | 3' UTR |
| 5 | NIPAL3 | chr1 | 24799398 | A | 12 | 3' UTR |
| 5 | NPNT | chr4 | 106892254 | T | 13 | 3' UTR |
| 5 | NR2F2 | chr15 | 96881909 | T | 10 | 3' UTR |
| 5 | NR2F2 | chr15 | 96881216 | T | 10 | 3' UTR |
| 5 | NRXN1 | chr2 | 50146697 | A | 11 | 3' UTR |
| 5 | NTM | chr11 | 132205623 | T | 14 | 3' UTR |
| 5 | NTRK2 | chr9 | 87487518 | T | 11 | 3' UTR |
| 5 | NUCKS1 | chr1 | 205683626 | A | 10 | 3' UTR |
| 5 | ORAI3 | chr16 | 30965549 | T | 15 | 3' UTR |
| 5 | OTUD1 | chr10 | 23730496 | T | 10 | 3' UTR |
| 5 | PALM2 | chr9 | 112708967 | A | 25 | 3' UTR |
| 5 | PAPSS2 | chr10 | 89507276 | A | 11 | 3' UTR |
| 5 | PDP2 | chr16 | 66920308 | T | 10 | 3' UTR |
| 5 | PHF17 | chr4 | 129783593 | T | 13 | 3' UTR |
| 5 | PID1 | chr2 | 229889188 | A | 9 | 3' UTR |
| 5 | PIGM | chr1 | 159998798 | T | 11 | 3' UTR |
| 5 | PIGN | chr18 | 59712451 | A | 11 | 3' UTR |
| 5 | PIK3R1 | chr5 | 67594399 | A | 12 | 3' UTR |
| 5 | PLAA | chr9 | 26904508 | T | 10 | 3' UTR |
| 5 | PLAGL2 | chr20 | 30781644 | A | 11 | 3' UTR |
| 5 | PLXNA4 | chr7 | 131809795 | T | 13 | 3' UTR |
| 5 | PNPLA3 | chr22 | 44342941 | A | 13 | 3' UTR |
| 5 | POLR3B | chr12 | 106903452 | A | 9 | 3' UTR |
| 5 | PRKCQ | chr10 | 6469109 | T | 13 | 3' UTR |
| 5 | PRKDC | chr8 | 48685753 | A | 11 | 3' UTR |
| 5 | PRKX | chrX | 3525721 | T | 9 | 3' UTR |
| 5 | PRPF4 | chr9 | 116054493 | A | 14 | 3' UTR |
| 5 | PRR23A | chr3 | 138723892 | A | 9 | 3' UTR |
| 5 | PRR3 | chr6 | 30531427 | T | 16 | 3' UTR |
| 5 | PSMD11 | chr17 | 30807996 | A | 11 | 3' UTR |
| 5 | PTAFR | chr1 | 28475836 | T | 27 | 3' UTR |
| 5 | PTPN11 | chr12 | 112944240 | T | 12 | 3' UTR |
| 5 | RAB11FIP2 | chr10 | 119766958 | A | 12 | 3' UTR |
| 5 | RAD51L1 | chr14 | 68964202 | T | 12 | 3' UTR |
| 5 | RB1CC1 | chr8 | 53536112 | A | 11 | 3' UTR |

TABLE 6-continued

| Nr of affected samples | Gene | Chromosome | Start Position | Affected homopolymer base | Affected homopolymer length | region |
|---|---|---|---|---|---|---|
| 5 | RBM25 | chr14 | 73586613 | T | 12 | 3' UTR |
| 5 | RBMS3 | chr3 | 30046424 | A | 11 | 3' UTR |
| 5 | RC3H1 | chr1 | 173901043 | T | 11 | 3' UTR |
| 5 | RDH10 | chr8 | 74236678 | T | 10 | 3' UTR |
| 5 | RECK | chr9 | 36123172 | T | 11 | 3' UTR |
| 5 | REPS2 | chrX | 17169995 | T | 13 | 3' UTR |
| 5 | RHOQ | chr2 | 46809063 | T | 12 | 3' UTR |
| 5 | RNF10 | chr12 | 121014987 | T | 11 | 3' UTR |
| 5 | RNF149 | chr2 | 101893233 | A | 10 | 3' UTR |
| 5 | RNF2 | chr1 | 185070964 | T | 22 | 3' UTR |
| 5 | RNLS | chr10 | 90034667 | A | 11 | 3' UTR |
| 5 | RRM2B | chr8 | 103216874 | A | 9 | 3' UTR |
| 5 | RS1 | chrX | 18659977 | A | 13 | 3' UTR |
| 5 | RXRA | chr9 | 137331937 | A | 12 | 3' UTR |
| 5 | RYBP | chr3 | 72424549 | T | 9 | 3' UTR |
| 5 | SAMD10 | chr20 | 62605493 | T | 12 | 3' UTR |
| 5 | SAR1A | chr10 | 71911798 | A | 12 | 3' UTR |
| 5 | SASS6 | chr1 | 100549698 | A | 16 | 3' UTR |
| 5 | SCAF11 | chr12 | 46314390 | A | 13 | 3' UTR |
| 5 | SEC31A | chr4 | 83740163 | T | 11 | 3' UTR |
| 5 | SENP1 | chr12 | 48437910 | T | 11 | 3' UTR |
| 5 | SENP5 | chr3 | 196658083 | A | 10 | 3' UTR |
| 5 | SERBP1 | chr1 | 67878789 | T | 11 | 3' UTR |
| 5 | SFPQ | chr1 | 35649754 | A | 13 | 3' UTR |
| 5 | SGCD | chr5 | 156190730 | A | 12 | 3' UTR |
| 5 | SGK223 | chr8 | 8175297 | T | 12 | 3' UTR |
| 5 | SLC12A2 | chr5 | 127523981 | T | 24 | 3' UTR |
| 5 | SLC16A6 | chr17 | 66265042 | A | 11 | 3' UTR |
| 5 | SLC30A5 | chr5 | 68399959 | T | 11 | 3' UTR |
| 5 | SLC35B4 | chr7 | 133977008 | T | 10 | 3' UTR |
| 5 | SLC44A5 | chr1 | 75668544 | A | 11 | 3' UTR |
| 5 | SLC7A11 | chr4 | 139092374 | A | 11 | 3' UTR |
| 5 | SLC9A2 | chr2 | 103326258 | T | 10 | 3' UTR |
| 5 | SLMAP | chr3 | 57913669 | T | 13 | 3' UTR |
| 5 | SMAD4 | chr18 | 48609102 | T | 12 | 3' UTR |
| 5 | SMAD4 | chr18 | 48606335 | T | 14 | 3' UTR |
| 5 | SMARCC2 | chr12 | 56556167 | A | 14 | 3' UTR |
| 5 | SMEK1 | chr14 | 91924528 | A | 11 | 3' UTR |
| 5 | SMG1 | chr16 | 18819070 | T | 11 | 3' UTR |
| 5 | SMU1 | chr9 | 33047210 | A | 14 | 3' UTR |
| 5 | SMU1 | chr9 | 33046890 | A | 15 | 3' UTR |
| 5 | SNAPC1 | chr14 | 62262433 | A | 11 | 3' UTR |
| 5 | SORCS1 | chr10 | 108333635 | A | 11 | 3' UTR |
| 5 | SOX4 | chr6 | 21596500 | A | 12 | 3' UTR |
| 5 | SPOCK1 | chr5 | 136313113 | A | 11 | 3' UTR |
| 5 | SSBP3 | chr1 | 54692319 | T | 12 | 3' UTR |
| 5 | STX1B | chr16 | 31000674 | G | 8 | 3' UTR |
| 5 | TARDBP | chr1 | 11084333 | T | 11 | 3' UTR |
| 5 | TBC1D1 | chr4 | 38140081 | A | 10 | 3' UTR |
| 5 | TBC1D5 | chr3 | 17201870 | T | 11 | 3' UTR |
| 5 | TBL1XR1 | chr3 | 176741889 | A | 13 | 3' UTR |
| 5 | TBP | chr6 | 170881389 | T | 13 | 3' UTR |
| 5 | TCERG1 | chr5 | 145890609 | T | 12 | 3' UTR |
| 5 | TFAP2A | chr6 | 10397893 | A | 11 | 3' UTR |
| 5 | TLE3 | chr15 | 70340967 | A | 11 | 3' UTR |
| 5 | TMEM108 | chr3 | 133116233 | A | 14 | 3' UTR |
| 5 | TMEM161B | chr5 | 87491917 | T | 10 | 3' UTR |
| 5 | TMEM178 | chr2 | 39944921 | T | 13 | 3' UTR |
| 5 | TMEM209 | chr7 | 129805893 | A | 12 | 3' UTR |
| 5 | TMEM26 | chr10 | 63166725 | A | 12 | 3' UTR |
| 5 | TMEM47 | chrX | 34646666 | T | 12 | 3' UTR |
| 5 | TMTC3 | chr12 | 88590177 | T | 12 | 3' UTR |
| 5 | TNFAIP1 | chr17 | 26672324 | A | 10 | 3' UTR |
| 5 | TNRC6B | chr22 | 40731027 | T | 10 | 3' UTR |
| 5 | TNRC6B | chr22 | 40720294 | T | 15 | 3' UTR |
| 5 | TNRC6C | chr17 | 76101834 | T | 9 | 3' UTR |
| 5 | TOB1 | chr17 | 48940256 | A | 11 | 3' UTR |
| 5 | TOMM20 | chr1 | 235275027 | T | 12 | 3' UTR |
| 5 | TPH1 | chr11 | 18042321 | A | 11 | 3' UTR |
| 5 | TRPS1 | chr8 | 116424407 | A | 12 | 3' UTR |
| 5 | TRPS1 | chr8 | 116423510 | A | 12 | 3' UTR |
| 5 | TSPAN14 | chr10 | 82279557 | T | 14 | 3' UTR |
| 5 | TSR2 | chrX | 54471045 | T | 10 | 3' UTR |
| 5 | UACA | chr15 | 70946988 | A | 12 | 3' UTR |
| 5 | UGT2B28 | chr4 | 70160632 | A | 11 | 3' UTR |

TABLE 6-continued

| Nr of affected samples | Gene | Chromosome | Start Position | Affected homopolymer base | Affected homopolymer length | region |
|---|---|---|---|---|---|---|
| 5 | USP28 | chr11 | 113669136 | A | 11 | 3' UTR |
| 5 | WASL | chr7 | 123323428 | A | 12 | 3' UTR |
| 5 | WDFY1 | chr2 | 224742022 | T | 12 | 3' UTR |
| 5 | WIF1 | chr12 | 65444595 | T | 13 | 3' UTR |
| 5 | XYLT1 | chr16 | 17199775 | A | 11 | 3' UTR |
| 5 | ZNF238 | chr1 | 244219573 | A | 9 | 3' UTR |
| 5 | ZNF430 | chr19 | 21241252 | A | 14 | 3' UTR |
| 5 | ZNF521 | chr18 | 22642386 | T | 13 | 3' UTR |
| 5 | ZNF536 | chr19 | 31048941 | A | 11 | 3' UTR |
| 5 | ZNF652 | chr17 | 47369576 | T | 11 | 3' UTR |
| 5 | ZNF737 | chr19 | 20723566 | A | 11 | 3' UTR |
| 5 | ZNF80 | chr3 | 113954690 | A | 12 | 3' UTR |
| 4 | ACLY | chr17 | 40023617 | A | 13 | 3' UTR |
| 4 | ACOX1 | chr17 | 73941869 | A | 10 | 3' UTR |
| 4 | ADSS | chr1 | 244571936 | T | 10 | 3' UTR |
| 4 | AFTPH | chr2 | 64819249 | A | 20 | 3' UTR |
| 4 | AICDA | chr12 | 8755425 | T | 16 | 3' UTR |
| 4 | AK4 | chr1 | 65692499 | T | 11 | 3' UTR |
| 4 | ANKIB1 | chr7 | 92028647 | A | 15 | 3' UTR |
| 4 | ANKRD40 | chr17 | 48770711 | A | 10 | 3' UTR |
| 4 | ANXA11 | chr10 | 81915055 | T | 9 | 3' UTR |
| 4 | AP1AR | chr4 | 113190822 | A | 11 | 3' UTR |
| 4 | APOL1 | chr22 | 36662141 | T | 12 | 3' UTR |
| 4 | ARF5 | chr7 | 127231635 | T | 10 | 3' UTR |
| 4 | ARHGAP28 | chr18 | 6914974 | A | 10 | 3' UTR |
| 4 | ARID1B | chr6 | 157529243 | T | 10 | 3' UTR |
| 4 | ARPP19 | chr15 | 52841555 | A | 10 | 3' UTR |
| 4 | ATP2B1 | chr12 | 89984601 | T | 12 | 3' UTR |
| 4 | ATP9A | chr20 | 50214427 | A | 10 | 3' UTR |
| 4 | ATXN1 | chr6 | 16301824 | A | 13 | 3' UTR |
| 4 | ATXN7 | chr3 | 63985894 | T | 11 | 3' UTR |
| 4 | B3GNT7 | chr2 | 232264806 | T | 26 | 3' UTR |
| 4 | BAG1 | chr9 | 33253979 | T | 12 | 3' UTR |
| 4 | BBX | chr3 | 107529758 | T | 12 | 3' UTR |
| 4 | BCL11A | chr2 | 60685736 | T | 13 | 3' UTR |
| 4 | BCL7A | chr12 | 122499827 | T | 14 | 3' UTR |
| 4 | BCL7A | chr12 | 122498867 | A | 11 | 3' UTR |
| 4 | BCLAF1 | chr6 | 136581674 | T | 11 | 3' UTR |
| 4 | BIN1 | chr2 | 127805622 | T | 10 | 3' UTR |
| 4 | BMPR2 | chr2 | 203426176 | T | 8 | 3' UTR |
| 4 | BNIP3L | chr8 | 26268445 | A | 10 | 3' UTR |
| 4 | BTBD11 | chr12 | 108052115 | T | 12 | 3' UTR |
| 4 | BTBD7 | chr14 | 93708432 | A | 12 | 3' UTR |
| 4 | C12orf12 | chr12 | 91346439 | A | 11 | 3' UTR |
| 4 | C12orf5 | chr12 | 4463524 | T | 10 | 3' UTR |
| 4 | C14orf37 | chr14 | 58471378 | T | 11 | 3' UTR |
| 4 | C16orf53 | chr16 | 29833642 | A | 13 | 3' UTR |
| 4 | C17orf96 | chr17 | 36829265 | T | 8 | 3' UTR |
| 4 | C20orf12 | chr20 | 18364708 | T | 12 | 3' UTR |
| 4 | C2orf29 | chr2 | 101886538 | T | 12 | 3' UTR |
| 4 | C2orf67 | chr2 | 210886727 | T | 14 | 3' UTR |
| 4 | C6orf47 | chr6 | 31626545 | T | 14 | 3' UTR |
| 4 | C7orf46 | chr7 | 23741876 | T | 11 | 3' UTR |
| 4 | C9orf123 | chr9 | 7797700 | T | 12 | 3' UTR |
| 4 | CAMLG | chr5 | 134086670 | A | 13 | 3' UTR |
| 4 | CBFA2T2 | chr20 | 32236969 | T | 11 | 3' UTR |
| 4 | CBFB | chr16 | 67133969 | T | 9 | 3' UTR |
| 4 | CBL | chr11 | 119175340 | T | 14 | 3' UTR |
| 4 | CBLN1 | chr16 | 49312880 | A | 10 | 3' UTR |
| 4 | CCDC102B | chr18 | 66722368 | A | 9 | 3' UTR |
| 4 | CCND2 | chr12 | 4411110 | T | 12 | 3' UTR |
| 4 | CCNE2 | chr8 | 95892992 | A | 11 | 3' UTR |
| 4 | CDH1 | chr16 | 68867611 | T | 12 | 3' UTR |
| 4 | CELF2 | chr10 | 11375889 | A | 10 | 3' UTR |
| 4 | CEP68 | chr2 | 65312945 | A | 12 | 3' UTR |
| 4 | CGGBP1 | chr3 | 88104472 | T | 10 | 3' UTR |
| 4 | CHD7 | chr8 | 61778758 | T | 11 | 3' UTR |
| 4 | CIT | chr12 | 120123939 | T | 11 | 3' UTR |
| 4 | CLCN5 | chrX | 49862213 | A | 12 | 3' UTR |
| 4 | CLIC5 | chr6 | 45869504 | T | 10 | 3' UTR |
| 4 | CLSPN | chr1 | 36201819 | A | 17 | 3' UTR |
| 4 | CNTN3 | chr3 | 74312679 | T | 11 | 3' UTR |
| 4 | COL19A1 | chr6 | 70918737 | T | 12 | 3' UTR |
| 4 | COPG | chr3 | 128996444 | T | 19 | 3' UTR |
| 4 | CORO2B | chr15 | 69020046 | T | 10 | 3' UTR |

TABLE 6-continued

| Nr of affected samples | Gene | Chromosome | Start Position | Affected homopolymer base | Affected homopolymer length | region |
|---|---|---|---|---|---|---|
| 4 | CPLX4 | chr18 | 56963029 | A | 10 | 3' UTR |
| 4 | CPSF2 | chr14 | 92630061 | T | 9 | 3' UTR |
| 4 | CTDSPL | chr3 | 38025453 | A | 11 | 3' UTR |
| 4 | CTNNB1 | chr3 | 41281477 | T | 25 | 3' UTR |
| 4 | CUL5 | chr11 | 107975795 | T | 13 | 3' UTR |
| 4 | CYB5B | chr16 | 69499981 | T | 9 | 3' UTR |
| 4 | DACH1 | chr13 | 72014288 | T | 11 | 3' UTR |
| 4 | DCAF10 | chr9 | 37865073 | T | 12 | 3' UTR |
| 4 | DCAF16 | chr4 | 17804263 | A | 15 | 3' UTR |
| 4 | DCP1A | chr3 | 53321360 | T | 27 | 3' UTR |
| 4 | DCUN1D1 | chr3 | 182662347 | A | 12 | 3' UTR |
| 4 | DCUN1D5 | chr11 | 102928449 | A | 11 | 3' UTR |
| 4 | DDAH1 | chr1 | 85786201 | A | 12 | 3' UTR |
| 4 | DDN | chr12 | 49389156 | A | 11 | 3' UTR |
| 4 | DDX5 | chr17 | 62495664 | A | 10 | 3' UTR |
| 4 | DDX52 | chr17 | 35974148 | A | 10 | 3' UTR |
| 4 | DDX6 | chr11 | 118622141 | A | 10 | 3' UTR |
| 4 | DLGAP4 | chr20 | 35156622 | T | 10 | 3' UTR |
| 4 | DNAJB7 | chr22 | 41256660 | T | 14 | 3' UTR |
| 4 | DNAJB9 | chr7 | 108213938 | T | 12 | 3' UTR |
| 4 | DNAJC15 | chr13 | 43681779 | T | 9 | 3' UTR |
| 4 | DOPEY2 | chr21 | 37666277 | A | 14 | 3' UTR |
| 4 | DUSP4 | chr8 | 29193728 | T | 10 | 3' UTR |
| 4 | DYRK2 | chr12 | 68055576 | T | 10 | 3' UTR |
| 4 | DYRK2 | chr12 | 68054141 | A | 11 | 3' UTR |
| 4 | EBF1 | chr5 | 158125829 | A | 12 | 3' UTR |
| 4 | EDEM1 | chr3 | 5260540 | T | 10 | 3' UTR |
| 4 | EFNA5 | chr5 | 106716350 | A | 11 | 3' UTR |
| 4 | EFNA5 | chr5 | 106716281 | A | 12 | 3' UTR |
| 4 | EFNB1 | chrX | 68061978 | A | 12 | 3' UTR |
| 4 | EGFR | chr7 | 55273591 | A | 13 | 3' UTR |
| 4 | EIF2B2 | chr14 | 75476004 | A | 10 | 3' UTR |
| 4 | EIF4B | chr12 | 53434572 | T | 12 | 3' UTR |
| 4 | EIF4EBP2 | chr10 | 72188037 | A | 11 | 3' UTR |
| 4 | ELAVL3 | chr19 | 11563289 | T | 12 | 3' UTR |
| 4 | ENC1 | chr5 | 73923281 | A | 13 | 3' UTR |
| 4 | EPB41L5 | chr2 | 120932994 | T | 14 | 3' UTR |
| 4 | EPM2AIP1 | chr3 | 37032033 | A | 10 | 3' UTR |
| 4 | EPS15 | chr1 | 51822219 | A | 12 | 3' UTR |
| 4 | ERCC6 | chr10 | 50666628 | A | 13 | 3' UTR |
| 4 | EVI5 | chr1 | 92975050 | T | 14 | 3' UTR |
| 4 | EXTL2 | chr1 | 101338118 | A | 10 | 3' UTR |
| 4 | FADS1 | chr11 | 61569354 | T | 16 | 3' UTR |
| 4 | FAF2 | chr5 | 175935960 | T | 10 | 3' UTR |
| 4 | FAM105A | chr5 | 14611814 | T | 10 | 3' UTR |
| 4 | FAM120C | chrX | 54098998 | A | 12 | 3' UTR |
| 4 | FAM13B | chr5 | 137274915 | A | 11 | 3' UTR |
| 4 | FAM164A | chr8 | 79631105 | T | 10 | 3' UTR |
| 4 | FAM189A1 | chr15 | 29414906 | G | 8 | 3' UTR |
| 4 | FAM46A | chr6 | 82457992 | T | 10 | 3' UTR |
| 4 | FAM76A | chr1 | 28087457 | T | 17 | 3' UTR |
| 4 | FAM8A1 | chr6 | 17609273 | T | 11 | 3' UTR |
| 4 | FANCD2 | chr3 | 10143061 | T | 25 | 3' UTR |
| 4 | FBXO21 | chr12 | 117582899 | T | 11 | 3' UTR |
| 4 | FBXO27 | chr19 | 39514872 | T | 12 | 3' UTR |
| 4 | FBXO36 | chr2 | 230876985 | A | 11 | 3' UTR |
| 4 | FCGR3A | chr1 | 161512430 | T | 9 | 3' UTR |
| 4 | FGD5 | chr3 | 14976010 | T | 9 | 3' UTR |
| 4 | FGF12 | chr3 | 191859718 | T | 11 | 3' UTR |
| 4 | FGFBP3 | chr10 | 93667293 | A | 15 | 3' UTR |
| 4 | FGFR1OP2 | chr12 | 27118594 | A | 11 | 3' UTR |
| 4 | FICD | chr12 | 108913292 | A | 11 | 3' UTR |
| 4 | FKBP2 | chr11 | 64011554 | A | 10 | 3' UTR |
| 4 | FKBP5 | chr6 | 35554624 | T | 12 | 3' UTR |
| 4 | FOXN2 | chr2 | 48603079 | T | 10 | 3' UTR |
| 4 | FOXO3 | chr6 | 109004889 | A | 16 | 3' UTR |
| 4 | FPGT | chr1 | 74672686 | T | 9 | 3' UTR |
| 4 | G3BP1 | chr5 | 151184779 | T | 11 | 3' UTR |
| 4 | GABRA4 | chr4 | 46923150 | T | 11 | 3' UTR |
| 4 | GABRB1 | chr4 | 47428211 | A | 10 | 3' UTR |
| 4 | GABRB2 | chr5 | 160719907 | A | 9 | 3' UTR |
| 4 | GADL1 | chr3 | 30769514 | T | 11 | 3' UTR |
| 4 | GAL3ST4 | chr7 | 99757342 | A | 13 | 3' UTR |
| 4 | GALNT1 | chr18 | 33290437 | A | 9 | 3' UTR |
| 4 | GDAP2 | chr1 | 118420019 | T | 11 | 3' UTR |

TABLE 6-continued

| Nr of affected samples | Gene | Chromosome | Start Position | Affected homopolymer base | Affected homopolymer length | region |
|---|---|---|---|---|---|---|
| 4 | GDAP2 | chr1 | 118411744 | T | 10 | 3' UTR |
| 4 | GJC1 | chr17 | 42876925 | A | 14 | 3' UTR |
| 4 | GNAI2 | chr3 | 50296330 | A | 12 | 3' UTR |
| 4 | GPR12 | chr13 | 27330332 | T | 10 | 3' UTR |
| 4 | GRAMD2 | chr15 | 72452633 | A | 10 | 3' UTR |
| 4 | GRIA4 | chr11 | 105783203 | A | 11 | 3' UTR |
| 4 | GRIK2 | chr6 | 102517011 | T | 11 | 3' UTR |
| 4 | GRIN2A | chr16 | 9851215 | T | 15 | 3' UTR |
| 4 | GRIN3A | chr9 | 104331901 | A | 9 | 3' UTR |
| 4 | GXYLT1 | chr12 | 42477780 | A | 10 | 3' UTR |
| 4 | HBEGF | chr5 | 139713520 | T | 11 | 3' UTR |
| 4 | HBS1L | chr6 | 135357535 | A | 10 | 3' UTR |
| 4 | HCCS | chrX | 11140989 | T | 11 | 3' UTR |
| 4 | HIF3A | chr19 | 46843765 | T | 12 | 3' UTR |
| 4 | HLCS | chr21 | 38123320 | A | 11 | 3' UTR |
| 4 | HNRNPA3 | chr2 | 178088125 | A | 12 | 3' UTR |
| 4 | HNRNPH2 | chrX | 100668932 | T | 13 | 3' UTR |
| 4 | HNRNPR | chr1 | 23636874 | T | 11 | 3' UTR |
| 4 | HNRNPU | chr1 | 245014280 | T | 11 | 3' UTR |
| 4 | HOOK3 | chr8 | 42876247 | A | 29 | 3' UTR |
| 4 | HSDL1 | chr16 | 84155968 | T | 13 | 3' UTR |
| 4 | HSPA9 | chr5 | 137891047 | A | 13 | 3' UTR |
| 4 | HTR2A | chr13 | 47408902 | T | 11 | 3' UTR |
| 4 | IGDCC4 | chr15 | 65674432 | A | 12 | 3' UTR |
| 4 | IGF1 | chr12 | 102790988 | A | 11 | 3' UTR |
| 4 | IKZF2 | chr2 | 213869993 | A | 11 | 3' UTR |
| 4 | IPO9 | chr1 | 201847055 | A | 12 | 3' UTR |
| 4 | IRGQ | chr19 | 44094353 | A | 11 | 3' UTR |
| 4 | KBTBD7 | chr13 | 41766026 | A | 9 | 3' UTR |
| 4 | KCNH3 | chr12 | 49952059 | A | 12 | 3' UTR |
| 4 | KCNK2 | chr1 | 215408898 | T | 10 | 3' UTR |
| 4 | KDELR2 | chr7 | 6501817 | A | 10 | 3' UTR |
| 4 | KDM5A | chr12 | 393489 | T | 12 | 3' UTR |
| 4 | KDM5A | chr12 | 393295 | T | 11 | 3' UTR |
| 4 | KDSR | chr18 | 60998042 | T | 15 | 3' UTR |
| 4 | KHSRP | chr19 | 6413651 | T | 10 | 3' UTR |
| 4 | KIAA0494 | chr1 | 47142711 | T | 9 | 3' UTR |
| 4 | KIAA1267 | chr17 | 44107738 | A | 9 | 3' UTR |
| 4 | KIAA1324 | chr1 | 109749368 | T | 11 | 3' UTR |
| 4 | KIAA1324 | chr1 | 109748644 | T | 11 | 3' UTR |
| 4 | KIAA1586 | chr6 | 56919727 | T | 12 | 3' UTR |
| 4 | KIAA1737 | chr14 | 77582032 | T | 14 | 3' UTR |
| 4 | KIAA2026 | chr9 | 5919249 | T | 11 | 3' UTR |
| 4 | KIF1B | chr1 | 10438932 | T | 10 | 3' UTR |
| 4 | LATS2 | chr13 | 21548562 | T | 13 | 3' UTR |
| 4 | LATS2 | chr13 | 21547830 | A | 9 | 3' UTR |
| 4 | LBR | chr1 | 225590887 | A | 10 | 3' UTR |
| 4 | LCOR | chr10 | 98715988 | T | 9 | 3' UTR |
| 4 | LCORL | chr4 | 17882781 | T | 11 | 3' UTR |
| 4 | LHFP | chr13 | 39917691 | A | 12 | 3' UTR |
| 4 | LIN7C | chr11 | 27517703 | A | 14 | 3' UTR |
| 4 | LLGL1 | chr17 | 18147555 | T | 14 | 3' UTR |
| 4 | LMNB2 | chr19 | 2428236 | A | 10 | 3' UTR |
| 4 | LMO4 | chr1 | 87811174 | A | 11 | 3' UTR |
| 4 | LRRC27 | chr10 | 134193076 | T | 9 | 3' UTR |
| 4 | LTN1 | chr21 | 30301899 | T | 10 | 3' UTR |
| 4 | MAGEB18 | chrX | 26158459 | T | 10 | 3' UTR |
| 4 | MAP3K7 | chr6 | 91225524 | A | 9 | 3' UTR |
| 4 | MAP6 | chr11 | 75316787 | A | 11 | 3' UTR |
| 4 | MAP6 | chr11 | 75315642 | T | 10 | 3' UTR |
| 4 | 1/mrt | chr4 | 164446860 | T | 9 | 3' UTR |
| 4 | MAX | chr14 | 65543065 | A | 10 | 3' UTR |
| 4 | MCTS1 | chrX | 119754487 | A | 14 | 3' UTR |
| 4 | MDM2 | chr12 | 69233886 | T | 11 | 3' UTR |
| 4 | MED19 | chr11 | 57471199 | T | 13 | 3' UTR |
| 4 | METAP2 | chr12 | 95908545 | A | 11 | 3' UTR |
| 4 | MIER3 | chr5 | 56216451 | A | 10 | 3' UTR |
| 4 | MKL1 | chr22 | 40806781 | C | 9 | 3' UTR |
| 4 | MKLN1 | chr7 | 131181200 | T | 10 | 3' UTR |
| 4 | MKX | chr10 | 27962805 | A | 10 | 3' UTR |
| 4 | MMAA | chr4 | 146578529 | T | 9 | 3' UTR |
| 4 | MNT | chr17 | 2287533 | T | 13 | 3' UTR |
| 4 | MOBKL1A | chr4 | 71853812 | T | 13 | 3' UTR |
| 4 | MORC1 | chr3 | 108677146 | A | 10 | 3' UTR |
| 4 | MOSPD1 | chrX | 134022551 | A | 9 | 3' UTR |

TABLE 6-continued

| Nr of affected samples | Gene | Chromosome | Start Position | Affected homopolymer base | Affected homopolymer length | region |
|---|---|---|---|---|---|---|
| 4 | MSI1 | chr12 | 120779455 | A | 14 | 3' UTR |
| 4 | MTF1 | chr1 | 38278949 | A | 11 | 3' UTR |
| 4 | NCEH1 | chr3 | 172349171 | T | 12 | 3' UTR |
| 4 | NCOA3 | chr20 | 46282984 | T | 11 | 3' UTR |
| 4 | NCOA5 | chr20 | 44689693 | A | 10 | 3' UTR |
| 4 | NFIB | chr9 | 14082769 | A | 14 | 3' UTR |
| 4 | NKAIN2 | chr6 | 125146684 | T | 9 | 3' UTR |
| 4 | NMNAT1 | chr1 | 10044969 | T | 8 | 3' UTR |
| 4 | NPC2 | chr14 | 74946724 | A | 10 | 3' UTR |
| 4 | NPNT | chr4 | 106890724 | T | 10 | 3' UTR |
| 4 | NPR3 | chr5 | 32786465 | T | 11 | 3' UTR |
| 4 | NR2F2 | chr15 | 96882212 | G | 8 | 3' UTR |
| 4 | NUFIP2 | chr17 | 27584536 | T | 12 | 3' UTR |
| 4 | OGFOD1 | chr16 | 56510333 | T | 12 | 3' UTR |
| 4 | ONECUT2 | chr18 | 55144549 | A | 11 | 3' UTR |
| 4 | OSBP | chr11 | 59341900 | T | 12 | 3' UTR |
| 4 | OSBP2 | chr22 | 31302451 | T | 10 | 3' UTR |
| 4 | OTUB2 | chr14 | 94512841 | A | 11 | 3' UTR |
| 4 | PABPC5 | chrX | 90691818 | T | 9 | 3' UTR |
| 4 | PAPOLA | chr14 | 97033430 | A | 10 | 3' UTR |
| 4 | PAPSS2 | chr10 | 89506162 | A | 11 | 3' UTR |
| 4 | PAQR7 | chr1 | 26188503 | A | 31 | 3' UTR |
| 4 | PCDHB3 | chr5 | 140482943 | T | 10 | 3' UTR |
| 4 | PCM1 | chr8 | 17886665 | A | 26 | 3' UTR |
| 4 | PCSK2 | chr20 | 17463028 | T | 11 | 3' UTR |
| 4 | PDE4D | chr5 | 58266735 | A | 15 | 3' UTR |
| 4 | PDPK1 | chr16 | 2653089 | T | 11 | 3' UTR |
| 4 | PELI2 | chr14 | 56764821 | T | 11 | 3' UTR |
| 4 | PGR | chr11 | 100902321 | T | 15 | 3' UTR |
| 4 | PHKB | chr16 | 47734578 | A | 10 | 3' UTR |
| 4 | PHLDA1 | chr12 | 76421757 | T | 12 | 3' UTR |
| 4 | PIGM | chr1 | 159997525 | A | 10 | 3' UTR |
| 4 | PIM1 | chr6 | 37143155 | T | 11 | 3' UTR |
| 4 | PIM2 | chrX | 48770831 | A | 20 | 3' UTR |
| 4 | PKD2 | chr4 | 88998190 | A | 11 | 3' UTR |
| 4 | PKP4 | chr2 | 159537312 | T | 10 | 3' UTR |
| 4 | PLCB1 | chr20 | 8863118 | A | 10 | 3' UTR |
| 4 | PLEKHA6 | chr1 | 204190022 | A | 13 | 3' UTR |
| 4 | PNPT1 | chr2 | 55861395 | T | 16 | 3' UTR |
| 4 | POLH | chr6 | 43586698 | G | 10 | 3' UTR |
| 4 | POP1 | chr8 | 99172000 | A | 12 | 3' UTR |
| 4 | PPARGC1B | chr5 | 149227267 | A | 14 | 3' UTR |
| 4 | PPIC | chr5 | 122359467 | A | 12 | 3' UTR |
| 4 | PPP1R10 | chr6 | 30568234 | A | 11 | 3' UTR |
| 4 | PRDM1 | chr6 | 106557171 | T | 10 | 3' UTR |
| 4 | PRPF40A | chr2 | 153509691 | A | 11 | 3' UTR |
| 4 | PSMD5 | chr9 | 123578376 | A | 10 | 3' UTR |
| 4 | PTCD3 | chr2 | 86366926 | A | 11 | 3' UTR |
| 4 | PTPN18 | chr2 | 131131908 | T | 14 | 3' UTR |
| 4 | PTPRJ | chr11 | 48189153 | T | 13 | 3' UTR |
| 4 | RAB11FIP2 | chr10 | 119766677 | A | 16 | 3' UTR |
| 4 | RAB11FIP2 | chr10 | 119765266 | T | 11 | 3' UTR |
| 4 | RAB22A | chr20 | 56941068 | T | 10 | 3' UTR |
| 4 | RAB39B | chrX | 154488466 | T | 11 | 3' UTR |
| 4 | RAB8B | chr15 | 63559206 | T | 12 | 3' UTR |
| 4 | RALYL | chr8 | 85833388 | T | 10 | 3' UTR |
| 4 | RANBP10 | chr16 | 67757024 | T | 10 | 3' UTR |
| 4 | RAP2B | chr3 | 152883481 | T | 10 | 3' UTR |
| 4 | RAP2B | chr3 | 152883395 | T | 12 | 3' UTR |
| 4 | RAPH1 | chr2 | 204300244 | A | 12 | 3' UTR |
| 4 | RBM12B | chr8 | 94744118 | T | 11 | 3' UTR |
| 4 | RBM15B | chr3 | 51431679 | T | 11 | 3' UTR |
| 4 | RBMS3 | chr3 | 30045473 | T | 10 | 3' UTR |
| 4 | RBMXL1 | chr1 | 89446107 | T | 14 | 3' UTR |
| 4 | RCOR3 | chr1 | 211487676 | T | 10 | 3' UTR |
| 4 | RDX | chr11 | 110102325 | A | 10 | 3' UTR |
| 4 | RGS18 | chr1 | 192154126 | T | 8 | 3' UTR |
| 4 | RGS6 | chr14 | 73030606 | A | 11 | 3' UTR |
| 4 | RNF41 | chr12 | 56599353 | G | 10 | 3' UTR |
| 4 | RP1 | chr8 | 55543160 | T | 14 | 3' UTR |
| 4 | RPL27A | chr11 | 8711061 | A | 13 | 3' UTR |
| 4 | RPP14 | chr3 | 58304719 | A | 14 | 3' UTR |
| 4 | RPRD2 | chr1 | 150447772 | T | 10 | 3' UTR |
| 4 | RPRD2 | chr1 | 150446032 | A | 23 | 3' UTR |
| 4 | RPS6KA2 | chr6 | 166824706 | T | 13 | 3' UTR |

TABLE 6-continued

| Nr of affected samples | Gene | Chromosome | Start Position | Affected homopolymer base | Affected homopolymer length | region |
|---|---|---|---|---|---|---|
| 4 | RPS6KB1 | chr17 | 58024908 | A | 10 | 3' UTR |
| 4 | RRAGD | chr6 | 90077647 | T | 12 | 3' UTR |
| 4 | RRM2 | chr2 | 10269544 | T | 10 | 3' UTR |
| 4 | RRP15 | chr1 | 218506526 | A | 10 | 3' UTR |
| 4 | RTF1 | chr15 | 41775015 | T | 10 | 3' UTR |
| 4 | RUFY3 | chr4 | 71655520 | A | 12 | 3' UTR |
| 4 | RUNDC3B | chr7 | 87459581 | A | 13 | 3' UTR |
| 4 | SAR1A | chr10 | 71910315 | A | 10 | 3' UTR |
| 4 | SATB2 | chr2 | 200135086 | T | 10 | 3' UTR |
| 4 | SCAI | chr9 | 127706579 | T | 16 | 3' UTR |
| 4 | SCUBE3 | chr6 | 35216591 | A | 10 | 3' UTR |
| 4 | SDC4 | chr20 | 43955023 | A | 24 | 3' UTR |
| 4 | SDC4 | chr20 | 43954848 | A | 9 | 3' UTR |
| 4 | SELT | chr3 | 150345688 | T | 10 | 3' UTR |
| 4 | SENP5 | chr3 | 196660478 | T | 11 | 3' UTR |
| 4 | SERPINE1 | chr7 | 100781987 | G | 8 | 3' UTR |
| 4 | SFXN1 | chr5 | 174954918 | T | 22 | 3' UTR |
| 4 | SGK3 | chr8 | 67772690 | A | 11 | 3' UTR |
| 4 | SHANK2 | chr11 | 70317369 | A | 12 | 3' UTR |
| 4 | SHCBP1 | chr16 | 46614658 | T | 14 | 3' UTR |
| 4 | SHOX2 | chr3 | 157814199 | A | 11 | 3' UTR |
| 4 | SIX1 | chr14 | 61111921 | A | 11 | 3' UTR |
| 4 | SLC17A5 | chr6 | 74303467 | A | 10 | 3' UTR |
| 4 | SLC25A20 | chr3 | 48894565 | A | 12 | 3' UTR |
| 4 | SLC2A12 | chr6 | 134312045 | T | 11 | 3' UTR |
| 4 | SLC2A2 | chr3 | 170715683 | T | 10 | 3' UTR |
| 4 | SLC35F1 | chr6 | 118636596 | T | 24 | 3' UTR |
| 4 | SLC36A4 | chr11 | 92881233 | T | 12 | 3' UTR |
| 4 | SLC6A17 | chr1 | 110743671 | A | 10 | 3' UTR |
| 4 | SLC6A4 | chr17 | 28523382 | T | 12 | 3' UTR |
| 4 | SLC6A6 | chr3 | 14530419 | T | 12 | 3' UTR |
| 4 | SLC6A6 | chr3 | 14526824 | T | 11 | 3' UTR |
| 4 | SMAD5 | chr5 | 135517921 | A | 14 | 3' UTR |
| 4 | SMAD5 | chr5 | 135515014 | A | 10 | 3' UTR |
| 4 | SMAD7 | chr18 | 46447623 | A | 10 | 3' UTR |
| 4 | SMEK1 | chr14 | 91924425 | A | 10 | 3' UTR |
| 4 | SMS | chrX | 22012649 | T | 10 | 3' UTR |
| 4 | SORL1 | chr11 | 121500400 | A | 14 | 3' UTR |
| 4 | SOST | chr17 | 41831941 | T | 10 | 3' UTR |
| 4 | SOST | chr17 | 41831361 | T | 11 | 3' UTR |
| 4 | SOX1 | chr13 | 112724861 | A | 10 | 3' UTR |
| 4 | SOX11 | chr2 | 5834918 | A | 11 | 3' UTR |
| 4 | SPIRE1 | chr18 | 12449300 | T | 11 | 3' UTR |
| 4 | SPRED1 | chr15 | 38648129 | A | 9 | 3' UTR |
| 4 | SPTLC2 | chr14 | 77975645 | A | 11 | 3' UTR |
| 4 | SRCIN1 | chr17 | 36687785 | T | 12 | 3' UTR |
| 4 | SRGAP1 | chr12 | 64537560 | A | 14 | 3' UTR |
| 4 | SRGAP2 | chr1 | 206636489 | T | 12 | 3' UTR |
| 4 | SS18 | chr18 | 23596687 | A | 11 | 3' UTR |
| 4 | ST3GAL5 | chr2 | 86067101 | A | 9 | 3' UTR |
| 4 | STEAP3 | chr2 | 120023163 | T | 12 | 3' UTR |
| 4 | STK11 | chr19 | 1228058 | T | 11 | 3' UTR |
| 4 | STX12 | chr1 | 28150575 | T | 10 | 3' UTR |
| 4 | STX3 | chr11 | 59569295 | A | 11 | 3' UTR |
| 4 | STX6 | chr1 | 180945093 | A | 9 | 3' UTR |
| 4 | SUZ12 | chr17 | 30326763 | T | 12 | 3' UTR |
| 4 | SYNJ2BP | chr14 | 70834868 | A | 10 | 3' UTR |
| 4 | SYT11 | chr1 | 155851834 | T | 12 | 3' UTR |
| 4 | TAF8 | chr6 | 42045495 | T | 11 | 3' UTR |
| 4 | TCF20 | chr22 | 42556646 | A | 12 | 3' UTR |
| 4 | TCF4 | chr18 | 52894479 | A | 13 | 3' UTR |
| 4 | TCF4 | chr18 | 52891868 | A | 11 | 3' UTR |
| 4 | TCP11L1 | chr11 | 33094799 | T | 11 | 3' UTR |
| 4 | TFAP2B | chr6 | 50814900 | A | 10 | 3' UTR |
| 4 | TMEM119 | chr12 | 108984472 | A | 11 | 3' UTR |
| 4 | TMEM14C | chr6 | 10731011 | A | 9 | 3' UTR |
| 4 | TMEM14E | chr3 | 152058228 | T | 10 | 3' UTR |
| 4 | TMEM201 | chr1 | 9674449 | T | 10 | 3' UTR |
| 4 | TMEM213 | chr7 | 138490613 | T | 13 | 3' UTR |
| 4 | TMEM64 | chr8 | 91637753 | A | 12 | 3' UTR |
| 4 | TMOD3 | chr15 | 52201130 | T | 10 | 3' UTR |
| 4 | TNFAIP8 | chr5 | 118729618 | A | 10 | 3' UTR |
| 4 | TNIP3 | chr4 | 122052756 | T | 22 | 3' UTR |
| 4 | TNRC6B | chr22 | 40724536 | T | 10 | 3' UTR |
| 4 | TOPORS | chr9 | 32541245 | A | 10 | 3' UTR |

TABLE 6-continued

| Nr of affected samples | Gene | Chromosome | Start Position | Affected homopolymer base | Affected homopolymer length | region |
|---|---|---|---|---|---|---|
| 4 | TOR1AIP1 | chr1 | 179888400 | A | 12 | 3' UTR |
| 4 | TP53INP1 | chr8 | 95941646 | A | 13 | 3' UTR |
| 4 | TRIM56 | chr7 | 100733606 | A | 9 | 3' UTR |
| 4 | TRIM66 | chr11 | 8636480 | T | 13 | 3' UTR |
| 4 | TRIP10 | chr19 | 6751495 | A | 12 | 3' UTR |
| 4 | TRPM1 | chr15 | 31293995 | A | 11 | 3' UTR |
| 4 | TRRAP | chr7 | 98610830 | T | 11 | 3' UTR |
| 4 | TSC22D2 | chr3 | 150177375 | T | 13 | 3' UTR |
| 4 | TTC30B | chr2 | 178415366 | T | 10 | 3' UTR |
| 4 | TTC39C | chr18 | 21715264 | T | 11 | 3' UTR |
| 4 | UBASH3B | chr11 | 122681008 | T | 13 | 3' UTR |
| 4 | UBE2G1 | chr17 | 4173433 | A | 10 | 3' UTR |
| 4 | UBLCP1 | chr5 | 158712401 | A | 11 | 3' UTR |
| 4 | UBN2 | chr7 | 138992059 | T | 9 | 3' UTR |
| 4 | UBN2 | chr7 | 138989574 | T | 10 | 3' UTR |
| 4 | UGT8 | chr4 | 115598050 | T | 11 | 3' UTR |
| 4 | UGT8 | chr4 | 115598017 | A | 12 | 3' UTR |
| 4 | USP43 | chr17 | 9632427 | T | 13 | 3' UTR |
| 4 | UTP15 | chr5 | 72876582 | T | 12 | 3' UTR |
| 4 | VAX1 | chr10 | 118893337 | A | 10 | 3' UTR |
| 4 | WDR17 | chr4 | 177100754 | T | 11 | 3' UTR |
| 4 | WDTC1 | chr1 | 27633121 | C | 9 | 3' UTR |
| 4 | WNK3 | chrX | 54224160 | A | 16 | 3' UTR |
| 4 | WSB1 | chr17 | 25640066 | A | 15 | 3' UTR |
| 4 | WSB2 | chr12 | 118470668 | T | 10 | 3' UTR |
| 4 | XKR6 | chr8 | 10755309 | T | 10 | 3' UTR |
| 4 | XKR7 | chr20 | 30585884 | G | 10 | 3' UTR |
| 4 | XYLT1 | chr16 | 17199280 | T | 8 | 3' UTR |
| 4 | ZADH2 | chr18 | 72910475 | T | 13 | 3' UTR |
| 4 | ZBTB34 | chr9 | 129646763 | T | 11 | 3' UTR |
| 4 | ZBTB38 | chr3 | 141164925 | A | 14 | 3' UTR |
| 4 | ZBTB41 | chr1 | 197124441 | A | 11 | 3' UTR |
| 4 | ZBTB7A | chr19 | 4046340 | T | 11 | 3' UTR |
| 4 | ZC3HAV1L | chr7 | 138711008 | A | 11 | 3' UTR |
| 4 | ZCCHC2 | chr18 | 60244188 | A | 10 | 3' UTR |
| 4 | ZDBF2 | chr2 | 207177005 | T | 8 | 3' UTR |
| 4 | ZDHHC13 | chr11 | 19197719 | A | 10 | 3' UTR |
| 4 | ZDHHC7 | chr16 | 85009055 | A | 12 | 3' UTR |
| 4 | ZFP36L2 | chr2 | 43450053 | C | 8 | 3' UTR |
| 4 | ZFP36L2 | chr2 | 43449809 | A | 9 | 3' UTR |
| 4 | ZNF154 | chr19 | 58212530 | A | 12 | 3' UTR |
| 4 | ZNF238 | chr1 | 244219033 | T | 11 | 3' UTR |
| 4 | ZNF24 | chr18 | 32917176 | T | 12 | 3' UTR |
| 4 | ZNF287 | chr17 | 16454419 | T | 9 | 3' UTR |
| 4 | ZNF322A | chr6 | 26636980 | T | 11 | 3' UTR |
| 4 | ZNF395 | chr8 | 28205776 | T | 27 | 3' UTR |
| 4 | ZNF451 | chr6 | 57033558 | A | 8 | 3' UTR |
| 4 | ZNF498 | chr7 | 99229241 | T | 11 | 3' UTR |
| 4 | ZNF518B | chr4 | 10442494 | A | 9 | 3' UTR |
| 4 | ZNF527 | chr19 | 37880936 | T | 12 | 3' UTR |
| 4 | ZNF572 | chr8 | 125990551 | T | 11 | 3' UTR |
| 4 | ZNF578 | chr19 | 53018984 | T | 12 | 3' UTR |
| 4 | ZNF585A | chr19 | 37641928 | T | 11 | 3' UTR |
| 4 | ZNF594 | chr17 | 5084035 | A | 10 | 3' UTR |
| 4 | ZNF658 | chr9 | 40771887 | T | 12 | 3' UTR |
| 4 | ZNF740 | chr12 | 53584463 | T | 14 | 3' UTR |
| 3 | AASDHPPT | chr11 | 105967764 | A | 11 | 3' UTR |
| 3 | ABI2 | chr2 | 204292194 | T | 10 | 3' UTR |
| 3 | ACOX1 | chr17 | 73941980 | T | 9 | 3' UTR |
| 3 | ACTBL2 | chr5 | 56777006 | T | 10 | 3' UTR |
| 3 | ACVR1C | chr2 | 158390343 | A | 10 | 3' UTR |
| 3 | ACVR2A | chr2 | 148687300 | A | 10 | 3' UTR |
| 3 | ADAMTS18 | chr16 | 77316279 | T | 11 | 3' UTR |
| 3 | ADAMTSL5 | chr19 | 1505368 | A | 13 | 3' UTR |
| 3 | ADRA1D | chr20 | 4201344 | T | 10 | 3' UTR |
| 3 | AFF1 | chr4 | 88057269 | T | 11 | 3' UTR |
| 3 | AFF2 | chrX | 148080911 | A | 8 | 3' UTR |
| 3 | AFF2 | chrX | 148080284 | T | 10 | 3' UTR |
| 3 | AGMAT | chr1 | 15899314 | T | 18 | 3' UTR |
| 3 | AGPAT5 | chr8 | 6617153 | A | 11 | 3' UTR |
| 3 | AGR2 | chr7 | 16832295 | T | 11 | 3' UTR |
| 3 | AHCTF1 | chr1 | 247002534 | A | 7 | 3' UTR |
| 3 | AK5 | chr1 | 78025528 | T | 13 | 3' UTR |
| 3 | AKAP11 | chr13 | 42896913 | T | 9 | 3' UTR |
| 3 | AKAP5 | chr14 | 64940497 | A | 9 | 3' UTR |

TABLE 6-continued

| Nr of affected samples | Gene | Chromosome | Start Position | Affected homopolymer base | Affected homopolymer length | region |
|---|---|---|---|---|---|---|
| 3 | AKAP8 | chr19 | 15465362 | A | 11 | 3' UTR |
| 3 | AKAP8 | chr19 | 15465302 | A | 9 | 3' UTR |
| 3 | AKIRIN2 | chr6 | 88384713 | A | 11 | 3' UTR |
| 3 | AKT2 | chr19 | 40736623 | T | 14 | 3' UTR |
| 3 | ALS2CR8 | chr2 | 203849779 | A | 14 | 3' UTR |
| 3 | ANKH | chr5 | 14711208 | A | 8 | 3' UTR |
| 3 | ANKH | chr5 | 14705393 | A | 13 | 3' UTR |
| 3 | ANKRD12 | chr18 | 9282855 | A | 10 | 3' UTR |
| 3 | ANKRD13B | chr17 | 27941253 | T | 19 | 3' UTR |
| 3 | ANKRD13C | chr1 | 70727638 | A | 12 | 3' UTR |
| 3 | ANKS1B | chr12 | 99138573 | T | 13 | 3' UTR |
| 3 | ARCN1 | chr11 | 118473732 | T | 8 | 3' UTR |
| 3 | ARHGAP12 | chr10 | 32096465 | A | 9 | 3' UTR |
| 3 | ARHGAP42 | chr11 | 100859972 | T | 10 | 3' UTR |
| 3 | ARID1B | chr6 | 157530011 | A | 10 | 3' UTR |
| 3 | ARID5B | chr10 | 63855130 | A | 10 | 3' UTR |
| 3 | ARIH1 | chr15 | 72877867 | A | 12 | 3' UTR |
| 3 | ARL2BP | chr16 | 57287376 | T | 12 | 3' UTR |
| 3 | ARL8A | chr1 | 202102526 | C | 8 | 3' UTR |
| 3 | ARMC8 | chr3 | 137964255 | T | 9 | 3' UTR |
| 3 | ARPP21 | chr3 | 35726292 | T | 9 | 3' UTR |
| 3 | ASB8 | chr12 | 48541711 | A | 10 | 3' UTR |
| 3 | ASPHD2 | chr22 | 26840193 | T | 13 | 3' UTR |
| 3 | ASPRV1 | chr2 | 70187727 | C | 8 | 3' UTR |
| 3 | ATP11C | chrX | 138809822 | A | 10 | 3' UTR |
| 3 | ATP1B2 | chr17 | 7560698 | A | 10 | 3' UTR |
| 3 | ATP2A2 | chr12 | 110786506 | A | 9 | 3' UTR |
| 3 | ATP6V0D1 | chr16 | 67472221 | G | 9 | 3' UTR |
| 3 | ATP6V1G1 | chr9 | 117360666 | T | 10 | 3' UTR |
| 3 | ATRX | chrX | 76762662 | A | 10 | 3' UTR |
| 3 | AUTS2 | chr7 | 70257601 | T | 15 | 3' UTR |
| 3 | AXIN1 | chr16 | 337827 | G | 9 | 3' UTR |
| 3 | BAG1 | chr9 | 33254142 | T | 20 | 3' UTR |
| 3 | BCL11A | chr2 | 60685168 | T | 10 | 3' UTR |
| 3 | BCL11B | chr14 | 99638830 | A | 9 | 3' UTR |
| 3 | BCL11B | chr14 | 99637754 | T | 10 | 3' UTR |
| 3 | BEND4 | chr4 | 42114856 | A | 10 | 3' UTR |
| 3 | BFAR | chr16 | 14762692 | A | 16 | 3' UTR |
| 3 | BLOC1S2 | chr10 | 102035182 | A | 10 | 3' UTR |
| 3 | BMP7 | chr20 | 55744815 | T | 10 | 3' UTR |
| 3 | BMPR2 | chr2 | 203426266 | T | 8 | 3' UTR |
| 3 | BOD1L | chr4 | 13571144 | A | 10 | 3' UTR |
| 3 | BRAF | chr7 | 140434294 | A | 9 | 3' UTR |
| 3 | C11orf41 | chr11 | 33690228 | T | 8 | 3' UTR |
| 3 | C11orf58 | chr11 | 16777810 | T | 24 | 3' UTR |
| 3 | C12orf5 | chr12 | 4463524 | T | 10 | 3' UTR |
| 3 | C12orf66 | chr12 | 64587315 | A | 10 | 3' UTR |
| 3 | C12orf76 | chr12 | 110479725 | A | 11 | 3' UTR |
| 3 | C14orf101 | chr14 | 57116192 | A | 10 | 3' UTR |
| 3 | C14orf126 | chr14 | 31917025 | A | 10 | 3' UTR |
| 3 | C14orf28 | chr14 | 45376124 | A | 12 | 3' UTR |
| 3 | C16orf45 | chr16 | 15680717 | C | 9 | 3' UTR |
| 3 | C16orf52 | chr16 | 22092814 | A | 15 | 3' UTR |
| 3 | C18orf25 | chr18 | 43846502 | A | 9 | 3' UTR |
| 3 | C18orf25 | chr18 | 43844098 | A | 9 | 3' UTR |
| 3 | C2orf18 | chr2 | 27001810 | T | 13 | 3' UTR |
| 3 | C2orf29 | chr2 | 101886150 | T | 10 | 3' UTR |
| 3 | C3orf63 | chr3 | 56657045 | A | 9 | 3' UTR |
| 3 | C3orf70 | chr3 | 184795851 | A | 10 | 3' UTR |
| 3 | C5orf41 | chr5 | 172563230 | A | 11 | 3' UTR |
| 3 | C6orf106 | chr6 | 34558017 | T | 7 | 3' UTR |
| 3 | C6orf62 | chr6 | 24705738 | A | 10 | 3' UTR |
| 3 | C7orf68 | chr7 | 128097963 | A | 10 | 3' UTR |
| 3 | C7orf69 | chr7 | 47859241 | A | 11 | 3' UTR |
| 3 | C8orf48 | chr8 | 13425580 | T | 9 | 3' UTR |
| 3 | C8orf85 | chr8 | 117955238 | A | 22 | 3' UTR |
| 3 | C9orf167 | chr9 | 140176659 | T | 10 | 3' UTR |
| 3 | C9orf66 | chr9 | 214453 | T | 9 | 3' UTR |
| 3 | CA12 | chr15 | 63616886 | T | 19 | 3' UTR |
| 3 | CABLES2 | chr20 | 60965113 | A | 10 | 3' UTR |
| 3 | CABP4 | chr11 | 67226510 | T | 14 | 3' UTR |
| 3 | CAMKK2 | chr12 | 121678327 | T | 13 | 3' UTR |
| 3 | CAPRIN1 | chr11 | 34121880 | T | 8 | 3' UTR |
| 3 | CASP2 | chr7 | 143003342 | T | 25 | 3' UTR |
| 3 | CBFB | chr16 | 67133322 | T | 14 | 3' UTR |

TABLE 6-continued

| Nr of affected samples | Gene | Chromosome | Start Position | Affected homopolymer base | Affected homopolymer length | region |
|---|---|---|---|---|---|---|
| 3 | CBL | chr11 | 119172610 | A | 10 | 3' UTR |
| 3 | CBX5 | chr12 | 54630019 | T | 10 | 3' UTR |
| 3 | CBY1 | chr22 | 39069285 | T | 9 | 3' UTR |
| 3 | CCDC67 | chr11 | 93170909 | C | 9 | 3' UTR |
| 3 | CCDC8 | chr19 | 46914112 | T | 12 | 3' UTR |
| 3 | CCNL2 | chr1 | 1327869 | T | 9 | 3' UTR |
| 3 | CD59 | chr11 | 33728097 | A | 21 | 3' UTR |
| 3 | CD96 | chr3 | 111368930 | A | 9 | 3' UTR |
| 3 | CDH13 | chr16 | 83828683 | A | 11 | 3' UTR |
| 3 | CDH2 | chr18 | 25531057 | T | 10 | 3' UTR |
| 3 | CDH2 | chr18 | 25531044 | T | 10 | 3' UTR |
| 3 | CDH3 | chr16 | 68732679 | T | 11 | 3' UTR |
| 3 | CDKN1C | chr11 | 2904845 | T | 10 | 3' UTR |
| 3 | CELF1 | chr11 | 47490243 | A | 9 | 3' UTR |
| 3 | CELSR2 | chr1 | 109816863 | C | 8 | 3' UTR |
| 3 | CEP164 | chr11 | 117283967 | T | 11 | 3' UTR |
| 3 | CHD1 | chr5 | 98191372 | T | 13 | 3' UTR |
| 3 | CHP | chr15 | 41572703 | T | 27 | 3' UTR |
| 3 | CIB2 | chr15 | 78397503 | T | 10 | 3' UTR |
| 3 | CKAP4 | chr12 | 106632374 | A | 10 | 3' UTR |
| 3 | CLCN5 | chrX | 49858223 | A | 9 | 3' UTR |
| 3 | CLDN14 | chr21 | 37833059 | T | 10 | 3' UTR |
| 3 | CLIC5 | chr6 | 45868268 | A | 11 | 3' UTR |
| 3 | CLMN | chr14 | 95650666 | A | 8 | 3' UTR |
| 3 | CMTM8 | chr3 | 32411483 | A | 9 | 3' UTR |
| 3 | CNNM1 | chr10 | 101153279 | A | 9 | 3' UTR |
| 3 | CNNM3 | chr2 | 97499281 | A | 12 | 3' UTR |
| 3 | CNST | chr1 | 246830426 | A | 10 | 3' UTR |
| 3 | COL8A2 | chr1 | 36561052 | A | 10 | 3' UTR |
| 3 | COQ10B | chr2 | 198339541 | T | 17 | 3' UTR |
| 3 | COQ2 | chr4 | 84185003 | A | 8 | 3' UTR |
| 3 | COX16 | chr14 | 70793015 | A | 14 | 3' UTR |
| 3 | CPD | chr17 | 28792026 | A | 9 | 3' UTR |
| 3 | CPEB2 | chr4 | 15070967 | A | 9 | 3' UTR |
| 3 | CPSF2 | chr14 | 92629266 | T | 9 | 3' UTR |
| 3 | CR1 | chr1 | 207813472 | T | 9 | 3' UTR |
| 3 | CREB1 | chr2 | 208464929 | G | 8 | 3' UTR |
| 3 | CREBBP | chr16 | 3776240 | G | 10 | 3' UTR |
| 3 | CRLF3 | chr17 | 29111121 | T | 9 | 3' UTR |
| 3 | CRTC1 | chr19 | 18890340 | A | 9 | 3' UTR |
| 3 | CSMD3 | chr8 | 113236641 | T | 9 | 3' UTR |
| 3 | CSNK1A1 | chr5 | 148875717 | T | 9 | 3' UTR |
| 3 | CSNK1G1 | chr15 | 64461432 | T | 12 | 3' UTR |
| 3 | CSNK1G1 | chr15 | 64461259 | A | 9 | 3' UTR |
| 3 | CTIF | chr18 | 46388423 | T | 10 | 3' UTR |
| 3 | CTNNA2 | chr2 | 80875614 | T | 7 | 3' UTR |
| 3 | CX3CR1 | chr3 | 39305465 | A | 8 | 3' UTR |
| 3 | CYP17A1 | chr10 | 104590293 | A | 11 | 3' UTR |
| 3 | CYP1B1 | chr2 | 38296985 | T | 10 | 3' UTR |
| 3 | DBT | chr1 | 100653256 | T | 17 | 3' UTR |
| 3 | DCAF7 | chr17 | 61668717 | A | 9 | 3' UTR |
| 3 | DCUN1D3 | chr16 | 20870892 | A | 10 | 3' UTR |
| 3 | DDHD1 | chr14 | 53513329 | T | 10 | 3' UTR |
| 3 | DDHD2 | chr8 | 38119445 | T | 7 | 3' UTR |
| 3 | DDX18 | chr2 | 118589332 | A | 9 | 3' UTR |
| 3 | DDX3X | chrX | 41207099 | T | 10 | 3' UTR |
| 3 | DDX6 | chr11 | 118620973 | A | 10 | 3' UTR |
| 3 | DFFA | chr1 | 10521379 | A | 10 | 3' UTR |
| 3 | DFFB | chr1 | 3801133 | T | 11 | 3' UTR |
| 3 | DGKG | chr3 | 185866704 | T | 10 | 3' UTR |
| 3 | DHTKD1 | chr10 | 12163218 | A | 19 | 3' UTR |
| 3 | DLG3 | chrX | 69723685 | C | 8 | 3' UTR |
| 3 | DLG3 | chrX | 69723447 | T | 13 | 3' UTR |
| 3 | DNAJC17 | chr15 | 41060070 | A | 14 | 3' UTR |
| 3 | DNAL1 | chr14 | 74166011 | T | 15 | 3' UTR |
| 3 | DNM3 | chr1 | 172380678 | A | 15 | 3' UTR |
| 3 | DPF3 | chr14 | 73137761 | A | 8 | 3' UTR |
| 3 | DPP4 | chr2 | 162849045 | T | 9 | 3' UTR |
| 3 | DPY19L4 | chr8 | 95802923 | T | 10 | 3' UTR |
| 3 | DPYSL2 | chr8 | 26515559 | T | 10 | 3' UTR |
| 3 | DSTYK | chr1 | 205115701 | T | 16 | 3' UTR |
| 3 | DSTYK | chr1 | 205112278 | T | 14 | 3' UTR |
| 3 | DUT | chr15 | 48634591 | A | 10 | 3' UTR |
| 3 | DYNC1LI2 | chr16 | 66757487 | T | 16 | 3' UTR |
| 3 | DYNC1LI2 | chr16 | 66755235 | T | 11 | 3' UTR |

TABLE 6-continued

| Nr of affected samples | Gene | Chromo-some | Start Position | Affected homo-polymer base | Affected homo-polymer length | region |
|---|---|---|---|---|---|---|
| 3 | E2F2 | chr1 | 23834007 | A | 15 | 3' UTR |
| 3 | EAPP | chr14 | 34985335 | A | 10 | 3' UTR |
| 3 | ECE1 | chr1 | 21546032 | A | 10 | 3' UTR |
| 3 | EFR3B | chr2 | 25378726 | T | 13 | 3' UTR |
| 3 | EIF2A | chr3 | 150302798 | A | 10 | 3' UTR |
| 3 | ELAVL1 | chr19 | 8023995 | T | 11 | 3' UTR |
| 3 | ELOVL6 | chr4 | 110971043 | T | 11 | 3' UTR |
| 3 | ENGASE | chr17 | 77083686 | G | 10 | 3' UTR |
| 3 | EPHA3 | chr3 | 89529769 | A | 11 | 3' UTR |
| 3 | EPHA7 | chr6 | 93951343 | A | 9 | 3' UTR |
| 3 | EPHB1 | chr3 | 134978889 | A | 10 | 3' UTR |
| 3 | ERBB4 | chr2 | 212243952 | T | 11 | 3' UTR |
| 3 | ERGIC2 | chr12 | 29493585 | T | 12 | 3' UTR |
| 3 | ERLIN2 | chr8 | 37614867 | T | 10 | 3' UTR |
| 3 | ESRRB | chr14 | 76967818 | G | 8 | 3' UTR |
| 3 | ETNK1 | chr12 | 22839785 | T | 28 | 3' UTR |
| 3 | FADS1 | chr11 | 61567668 | T | 14 | 3' UTR |
| 3 | FAM101B | chr17 | 292360 | T | 10 | 3' UTR |
| 3 | FAM105B | chr5 | 14695377 | T | 9 | 3' UTR |
| 3 | FAM117B | chr2 | 203633341 | T | 10 | 3' UTR |
| 3 | FAM126B | chr2 | 201845397 | G | 7 | 3' UTR |
| 3 | FAM160B1 | chr10 | 116621715 | A | 9 | 3' UTR |
| 3 | FAM19A4 | chr3 | 68781684 | A | 10 | 3' UTR |
| 3 | FAM20B | chr1 | 179044326 | A | 13 | 3' UTR |
| 3 | FBLIM1 | chr1 | 16112130 | A | 10 | 3' UTR |
| 3 | FBN2 | chr5 | 127594650 | A | 8 | 3' UTR |
| 3 | FBN2 | chr5 | 127594063 | A | 10 | 3' UTR |
| 3 | FBXO27 | chr19 | 39515468 | T | 11 | 3' UTR |
| 3 | FBXW2 | chr9 | 123524089 | A | 12 | 3' UTR |
| 3 | FECH | chr18 | 55215482 | A | 15 | 3' UTR |
| 3 | FERMT1 | chr20 | 6055696 | T | 15 | 3' UTR |
| 3 | FGD1 | chrX | 54471920 | A | 13 | 3' UTR |
| 3 | FGD4 | chr12 | 32798227 | T | 12 | 3' UTR |
| 3 | FGD6 | chr12 | 95470673 | A | 10 | 3' UTR |
| 3 | FGFR1OP2 | chr12 | 27118562 | T | 10 | 3' UTR |
| 3 | FLCN | chr17 | 17116100 | A | 10 | 3' UTR |
| 3 | FLCN | chr17 | 17115789 | A | 26 | 3' UTR |
| 3 | FMNL3 | chr12 | 50038887 | A | 25 | 3' UTR |
| 3 | FMNL3 | chr12 | 50033467 | A | 10 | 3' UTR |
| 3 | FNDC3B | chr3 | 172117183 | A | 10 | 3' UTR |
| 3 | FOXJ2 | chr12 | 8208083 | A | 13 | 3' UTR |
| 3 | FOXK1 | chr7 | 4809074 | T | 13 | 3' UTR |
| 3 | FOXO1 | chr13 | 41132503 | A | 9 | 3' UTR |
| 3 | FOXP1 | chr3 | 71007462 | T | 10 | 3' UTR |
| 3 | FOXP1 | chr3 | 71005883 | T | 41 | 3' UTR |
| 3 | FTSJD1 | chr16 | 71317151 | A | 10 | 3' UTR |
| 3 | FUT8 | chr14 | 66209673 | T | 13 | 3' UTR |
| 3 | FZD7 | chr2 | 202902385 | A | 11 | 3' UTR |
| 3 | GAPVD1 | chr9 | 128127210 | T | 10 | 3' UTR |
| 3 | GATAD2B | chr1 | 153781275 | A | 20 | 3' UTR |
| 3 | GCNT1 | chr9 | 79119829 | T | 11 | 3' UTR |
| 3 | GDAP2 | chr1 | 118408218 | A | 10 | 3' UTR |
| 3 | GFPT1 | chr2 | 69549530 | A | 9 | 3' UTR |
| 3 | GIPC2 | chr1 | 78601920 | T | 9 | 3' UTR |
| 3 | GIT1 | chr17 | 27901146 | A | 12 | 3' UTR |
| 3 | GLCCI1 | chr7 | 8127832 | T | 11 | 3' UTR |
| 3 | GLT25D2 | chr1 | 183905658 | A | 10 | 3' UTR |
| 3 | GNA13 | chr17 | 63005677 | A | 10 | 3' UTR |
| 3 | GNPNAT1 | chr14 | 53242966 | A | 11 | 3' UTR |
| 3 | GOLGA2 | chr9 | 131018793 | T | 14 | 3' UTR |
| 3 | GOLPH3L | chr1 | 150619971 | A | 15 | 3' UTR |
| 3 | GPM6A | chr4 | 176555451 | T | 10 | 3' UTR |
| 3 | GPR155 | chr2 | 175299037 | T | 13 | 3' UTR |
| 3 | GPR180 | chr13 | 95279582 | A | 8 | 3' UTR |
| 3 | GPR37L1 | chr1 | 202098133 | T | 21 | 3' UTR |
| 3 | GPRC5A | chr12 | 13065679 | T | 13 | 3' UTR |
| 3 | GPX8 | chr5 | 54460112 | T | 10 | 3' UTR |
| 3 | GRAMD3 | chr5 | 125829168 | T | 10 | 3' UTR |
| 3 | GRB2 | chr17 | 73314260 | T | 10 | 3' UTR |
| 3 | GRID1 | chr10 | 87359476 | T | 11 | 3' UTR |
| 3 | GSK3B | chr3 | 119544323 | A | 9 | 3' UTR |
| 3 | GTF2A2 | chr15 | 59930716 | T | 7 | 3' UTR |
| 3 | GTF2H5 | chr6 | 158615020 | A | 21 | 3' UTR |
| 3 | GTF2H5 | chr6 | 158614314 | A | 10 | 3' UTR |
| 3 | H2AFX | chr11 | 118964586 | A | 10 | 3' UTR |

TABLE 6-continued

| Nr of affected samples | Gene | Chromo-some | Start Position | Affected homo-polymer base | Affected homo-polymer length | region |
|---|---|---|---|---|---|---|
| 3 | H2AFY | chr5 | 134670602 | T | 10 | 3' UTR |
| 3 | HAPLN1 | chr5 | 82937251 | A | 10 | 3' UTR |
| 3 | HCN1 | chr5 | 45260992 | T | 9 | 3' UTR |
| 3 | HELZ | chr17 | 65067696 | T | 8 | 3' UTR |
| 3 | HEPHL1 | chr11 | 93846820 | T | 9 | 3' UTR |
| 3 | HEY2 | chr6 | 126081692 | T | 10 | 3' UTR |
| 3 | HIAT1 | chr1 | 100548278 | A | 11 | 3' UTR |
| 3 | HIPK1 | chr1 | 114518139 | T | 9 | 3' UTR |
| 3 | HMGN2 | chr1 | 26801737 | T | 15 | 3' UTR |
| 3 | HNRNPA3 | chr2 | 178087793 | A | 11 | 3' UTR |
| 3 | HNRNPK | chr9 | 86584095 | C | 9 | 3' UTR |
| 3 | HNRNPK | chr9 | 86583800 | A | 10 | 3' UTR |
| 3 | HOMEZ | chr14 | 23744114 | A | 14 | 3' UTR |
| 3 | HOOK1 | chr1 | 60338642 | A | 8 | 3' UTR |
| 3 | HOXB3 | chr17 | 46627000 | A | 9 | 3' UTR |
| 3 | HOXC9 | chr12 | 54396883 | A | 12 | 3' UTR |
| 3 | HP1BP3 | chr1 | 21070971 | A | 10 | 3' UTR |
| 3 | HRH1 | chr3 | 11303522 | A | 11 | 3' UTR |
| 3 | HS2ST1 | chr1 | 87575244 | T | 10 | 3' UTR |
| 3 | HS3ST5 | chr6 | 114376959 | A | 10 | 3' UTR |
| 3 | HUNK | chr21 | 33373431 | A | 9 | 3' UTR |
| 3 | HUWE1 | chrX | 53559710 | T | 11 | 3' UTR |
| 3 | HUWE1 | chrX | 53559518 | A | 12 | 3' UTR |
| 3 | IFI6 | chr1 | 27992800 | A | 23 | 3' UTR |
| 3 | IFT81 | chr12 | 110656332 | T | 9 | 3' UTR |
| 3 | IGF2BP3 | chr7 | 23350733 | T | 12 | 3' UTR |
| 3 | IGF2BP3 | chr7 | 23350408 | T | 10 | 3' UTR |
| 3 | IGFBP5 | chr2 | 217537045 | T | 14 | 3' UTR |
| 3 | IKZF2 | chr2 | 213865040 | A | 8 | 3' UTR |
| 3 | IL7R | chr5 | 35876844 | A | 10 | 3' UTR |
| 3 | IMPG2 | chr3 | 100945663 | A | 9 | 3' UTR |
| 3 | INSC | chr11 | 15267955 | T | 10 | 3' UTR |
| 3 | INSR | chr19 | 7112347 | A | 9 | 3' UTR |
| 3 | INTS6 | chr13 | 51937816 | T | 10 | 3' UTR |
| 3 | IRS1 | chr2 | 227600758 | T | 11 | 3' UTR |
| 3 | IRS1 | chr2 | 227596558 | A | 10 | 3' UTR |
| 3 | ISL1 | chr5 | 50690278 | A | 11 | 3' UTR |
| 3 | ITGA4 | chr2 | 182400811 | T | 8 | 3' UTR |
| 3 | ITPRIPL1 | chr2 | 96994050 | A | 10 | 3' UTR |
| 3 | JAKMIP1 | chr4 | 6055625 | A | 11 | 3' UTR |
| 3 | JAM3 | chr11 | 134020535 | T | 12 | 3' UTR |
| 3 | JARID2 | chr6 | 15520768 | T | 9 | 3' UTR |
| 3 | KCTD1 | chr18 | 24035448 | T | 12 | 3' UTR |
| 3 | KIAA0182 | chr16 | 85706942 | A | 10 | 3' UTR |
| 3 | KIAA1456 | chr8 | 12883488 | A | 9 | 3' UTR |
| 3 | KIAA1671 | chr22 | 25588892 | T | 9 | 3' UTR |
| 3 | KIF1B | chr1 | 10437995 | A | 13 | 3' UTR |
| 3 | KLF12 | chr13 | 74261703 | T | 11 | 3' UTR |
| 3 | KLHL20 | chr1 | 173754885 | A | 12 | 3' UTR |
| 3 | KNDC1 | chr10 | 135039706 | T | 8 | 3' UTR |
| 3 | KPNA6 | chr1 | 32639763 | C | 9 | 3' UTR |
| 3 | KPNB1 | chr17 | 45760525 | T | 12 | 3' UTR |
| 3 | LARP4B | chr10 | 856761 | A | 9 | 3' UTR |
| 3 | LCA5 | chr6 | 80194766 | A | 9 | 3' UTR |
| 3 | LEF1 | chr4 | 108969352 | A | 9 | 3' UTR |
| 3 | LHFP | chr13 | 39917881 | T | 8 | 3' UTR |
| 3 | LIAS | chr4 | 39478848 | A | 11 | 3' UTR |
| 3 | LIMS1 | chr2 | 109300693 | A | 10 | 3' UTR |
| 3 | LIN7C | chr11 | 27517538 | A | 10 | 3' UTR |
| 3 | LMAN1 | chr18 | 56995800 | T | 10 | 3' UTR |
| 3 | LMAN1 | chr18 | 56995128 | A | 10 | 3' UTR |
| 3 | LMO4 | chr1 | 87812341 | A | 10 | 3' UTR |
| 3 | LMO4 | chr1 | 87811634 | A | 9 | 3' UTR |
| 3 | LMTK2 | chr7 | 97837420 | A | 11 | 3' UTR |
| 3 | LPL | chr8 | 19823634 | A | 11 | 3' UTR |
| 3 | LRCH2 | chrX | 114346112 | T | 10 | 3' UTR |
| 3 | LRIF1 | chr1 | 111489900 | A | 13 | 3' UTR |
| 3 | LRP12 | chr8 | 105502451 | T | 10 | 3' UTR |
| 3 | LRRC14 | chr8 | 145747418 | T | 9 | 3' UTR |
| 3 | LSM1 | chr8 | 38021012 | A | 10 | 3' UTR |
| 3 | LUZP2 | chr11 | 25102964 | A | 12 | 3' UTR |
| 3 | LYN | chr8 | 56923131 | A | 15 | 3' UTR |
| 3 | LYRM7 | chr5 | 130537006 | A | 12 | 3' UTR |
| 3 | MAFB | chr20 | 39314997 | G | 8 | 3' UTR |
| 3 | MAFG | chr17 | 79879435 | T | 12 | 3' UTR |

TABLE 6-continued

| Nr of affected samples | Gene | Chromosome | Start Position | Affected homopolymer base | Affected homopolymer length | region |
|---|---|---|---|---|---|---|
| 3 | MAGI3 | chr1 | 114227223 | A | 10 | 3' UTR |
| 3 | MAP1B | chr5 | 71505347 | A | 11 | 3' UTR |
| 3 | MAP1B | chr5 | 71502852 | A | 10 | 3' UTR |
| 3 | MAP4 | chr3 | 48016254 | A | 13 | 3' UTR |
| 3 | MARK1 | chr1 | 220837099 | T | 10 | 3' UTR |
| 3 | MCM10 | chr10 | 13252313 | A | 16 | 3' UTR |
| 3 | MED1 | chr17 | 37560884 | A | 9 | 3' UTR |
| 3 | MEF2C | chr5 | 88017643 | A | 7 | 3' UTR |
| 3 | MEF2D | chr1 | 156436092 | A | 9 | 3' UTR |
| 3 | METTL8 | chr2 | 172174950 | T | 8 | 3' UTR |
| 3 | MFN2 | chr1 | 12073251 | A | 11 | 3' UTR |
| 3 | MGAT4A | chr2 | 99236361 | T | 10 | 3' UTR |
| 3 | MIER3 | chr5 | 56216276 | A | 9 | 3' UTR |
| 3 | MKLN1 | chr7 | 131176677 | A | 9 | 3' UTR |
| 3 | MKRN3 | chr15 | 23812682 | T | 8 | 3' UTR |
| 3 | MLEC | chr12 | 121138251 | T | 11 | 3' UTR |
| 3 | MMP2 | chr16 | 55539895 | T | 10 | 3' UTR |
| 3 | MOBKL1A | chr4 | 71851985 | T | 9 | 3' UTR |
| 3 | MPP7 | chr10 | 28341712 | T | 9 | 3' UTR |
| 3 | MRPL2 | chr6 | 43021910 | A | 10 | 3' UTR |
| 3 | MRPL44 | chr2 | 224831951 | T | 11 | 3' UTR |
| 3 | MRPS10 | chr6 | 42175651 | A | 9 | 3' UTR |
| 3 | MTAP | chr9 | 21862262 | A | 9 | 3' UTR |
| 3 | MTHFR | chr1 | 11846483 | T | 10 | 3' UTR |
| 3 | MTMR3 | chr22 | 30422037 | T | 14 | 3' UTR |
| 3 | MTMR6 | chr13 | 25821349 | A | 10 | 3' UTR |
| 3 | MXD1 | chr2 | 70166270 | T | 6 | 3' UTR |
| 3 | MYBL1 | chr8 | 67476407 | A | 10 | 3' UTR |
| 3 | MYCL1 | chr1 | 40361307 | A | 10 | 3' UTR |
| 3 | MYCN | chr2 | 16086264 | T | 10 | 3' UTR |
| 3 | MYEF2 | chr15 | 48434757 | A | 6 | 3' UTR |
| 3 | MYLK | chr3 | 123332875 | T | 16 | 3' UTR |
| 3 | NAA38 | chr7 | 117832209 | A | 9 | 3' UTR |
| 3 | NAP1L1 | chr12 | 76440268 | A | 11 | 3' UTR |
| 3 | NAPEPLD | chr7 | 102742595 | A | 10 | 3' UTR |
| 3 | NAPG | chr18 | 10551001 | T | 11 | 3' UTR |
| 3 | NARG2 | chr15 | 60715037 | A | 14 | 3' UTR |
| 3 | NCCRP1 | chr19 | 39691952 | T | 16 | 3' UTR |
| 3 | NCS1 | chr9 | 132996076 | T | 12 | 3' UTR |
| 3 | NDFIP1 | chr5 | 141533930 | T | 10 | 3' UTR |
| 3 | NEBL | chr10 | 21073429 | A | 9 | 3' UTR |
| 3 | NEBL | chr10 | 21072104 | T | 9 | 3' UTR |
| 3 | NEURL1B | chr5 | 172118507 | A | 7 | 3' UTR |
| 3 | NFAM1 | chr22 | 42776800 | A | 11 | 3' UTR |
| 3 | NFAT5 | chr16 | 69731363 | A | 10 | 3' UTR |
| 3 | NFIB | chr9 | 14087579 | T | 9 | 3' UTR |
| 3 | NIPAL1 | chr4 | 48038330 | T | 7 | 3' UTR |
| 3 | NIPAL3 | chr1 | 24798068 | A | 20 | 3' UTR |
| 3 | NKAIN4 | chr20 | 61872616 | T | 12 | 3' UTR |
| 3 | NLGN4X | chrX | 5808268 | T | 11 | 3' UTR |
| 3 | NPLOC4 | chr17 | 79525610 | A | 9 | 3' UTR |
| 3 | NR3C1 | chr5 | 142657694 | T | 9 | 3' UTR |
| 3 | NSL1 | chr1 | 212911280 | A | 9 | 3' UTR |
| 3 | NT5C1B | chr2 | 18744332 | T | 14 | 3' UTR |
| 3 | NUCKS1 | chr1 | 205687213 | A | 19 | 3' UTR |
| 3 | NUFIP2 | chr17 | 27585085 | T | 12 | 3' UTR |
| 3 | ODZ4 | chr11 | 78367062 | T | 9 | 3' UTR |
| 3 | OGFOD1 | chr16 | 56510316 | A | 11 | 3' UTR |
| 3 | OLFM3 | chr1 | 102269548 | T | 11 | 3' UTR |
| 3 | OMA1 | chr1 | 58946539 | T | 10 | 3' UTR |
| 3 | ONECUT2 | chr18 | 55153928 | T | 7 | 3' UTR |
| 3 | OPA3 | chr19 | 46052745 | T | 12 | 3' UTR |
| 3 | OSBPL3 | chr7 | 24837354 | A | 10 | 3' UTR |
| 3 | OTUD4 | chr4 | 146058513 | T | 8 | 3' UTR |
| 3 | OTUD4 | chr4 | 146057615 | G | 13 | 3' UTR |
| 3 | OTUD7B | chr1 | 149914740 | A | 10 | 3' UTR |
| 3 | OXR1 | chr8 | 107764239 | A | 10 | 3' UTR |
| 3 | OXR1 | chr8 | 107764095 | A | 10 | 3' UTR |
| 3 | PAICS | chr4 | 57327144 | A | 10 | 3' UTR |
| 3 | PAK1IP1 | chr6 | 10709747 | T | 12 | 3' UTR |
| 3 | PALM2 | chr9 | 112706843 | A | 11 | 3' UTR |
| 3 | PAPD5 | chr16 | 50264179 | T | 10 | 3' UTR |
| 3 | PAPD5 | chr16 | 50263692 | T | 10 | 3' UTR |
| 3 | PAPD5 | chr16 | 50263454 | A | 8 | 3' UTR |
| 3 | PBRM1 | chr3 | 52579628 | A | 10 | 3' UTR |

TABLE 6-continued

| Nr of affected samples | Gene | Chromosome | Start Position | Affected homopolymer base | Affected homopolymer length | region |
|---|---|---|---|---|---|---|
| 3 | PCDH7 | chr4 | 31146675 | T | 12 | 3' UTR |
| 3 | PCDH7 | chr4 | 31144759 | A | 9 | 3' UTR |
| 3 | PCLO | chr7 | 82451412 | T | 12 | 3' UTR |
| 3 | PCLO | chr7 | 82383474 | T | 9 | 3' UTR |
| 3 | PCNP | chr3 | 101312474 | A | 10 | 3' UTR |
| 3 | PCNP | chr3 | 101312179 | T | 10 | 3' UTR |
| 3 | PCYOX1L | chr5 | 148748459 | T | 8 | 3' UTR |
| 3 | PDCL | chr9 | 125581889 | A | 10 | 3' UTR |
| 3 | PDCL | chr9 | 125581558 | A | 13 | 3' UTR |
| 3 | PDGFA | chr7 | 537622 | A | 11 | 3' UTR |
| 3 | PDGFA | chr7 | 536908 | T | 11 | 3' UTR |
| 3 | PEX6 | chr6 | 42931666 | C | 7 | 3' UTR |
| 3 | PFN1 | chr17 | 4848972 | A | 10 | 3' UTR |
| 3 | PGPEP1 | chr19 | 18477965 | A | 20 | 3' UTR |
| 3 | PHTF2 | chr7 | 77586547 | T | 11 | 3' UTR |
| 3 | PIGM | chr1 | 159998080 | T | 11 | 3' UTR |
| 3 | PIGW | chr17 | 34894609 | T | 11 | 3' UTR |
| 3 | PIK3R1 | chr5 | 67595054 | A | 10 | 3' UTR |
| 3 | PIP5K1A | chr1 | 151220867 | T | 11 | 3' UTR |
| 3 | PKN2 | chr1 | 89301773 | T | 11 | 3' UTR |
| 3 | PLA2G12A | chr4 | 110633665 | T | 10 | 3' UTR |
| 3 | PLCL1 | chr2 | 199013907 | T | 9 | 3' UTR |
| 3 | PLCXD3 | chr5 | 41307606 | A | 9 | 3' UTR |
| 3 | PLK2 | chr5 | 57749858 | A | 9 | 3' UTR |
| 3 | PLXDC2 | chr10 | 20569078 | A | 10 | 3' UTR |
| 3 | POLH | chr6 | 43584323 | A | 14 | 3' UTR |
| 3 | POU2F2 | chr19 | 42595122 | T | 14 | 3' UTR |
| 3 | PPAP2B | chr1 | 56962088 | T | 10 | 3' UTR |
| 3 | PPAT | chr4 | 57261372 | A | 12 | 3' UTR |
| 3 | PPM1E | chr17 | 57060351 | A | 10 | 3' UTR |
| 3 | PPP1R3A | chr7 | 113517422 | A | 9 | 3' UTR |
| 3 | PPP3CA | chr4 | 101946069 | T | 10 | 3' UTR |
| 3 | PPPDE1 | chr1 | 244869241 | A | 12 | 3' UTR |
| 3 | PRELP | chr1 | 203457654 | A | 10 | 3' UTR |
| 3 | PRKCB | chr16 | 24226979 | A | 9 | 3' UTR |
| 3 | PRKCE | chr2 | 46414854 | A | 12 | 3' UTR |
| 3 | PRKD3 | chr2 | 37477691 | A | 9 | 3' UTR |
| 3 | PRPF40A | chr2 | 153512705 | T | 9 | 3' UTR |
| 3 | PRRC2B | chr9 | 134374365 | T | 9 | 3' UTR |
| 3 | PRRG1 | chrX | 37313537 | T | 10 | 3' UTR |
| 3 | PTCD3 | chr2 | 86365336 | T | 9 | 3' UTR |
| 3 | PTCH1 | chr9 | 98208010 | A | 10 | 3' UTR |
| 3 | PTGS2 | chr1 | 186642025 | T | 9 | 3' UTR |
| 3 | PTP4A1 | chr6 | 64292097 | T | 10 | 3' UTR |
| 3 | PTP4A2 | chr1 | 32374021 | A | 10 | 3' UTR |
| 3 | PTPN22 | chr1 | 114357118 | T | 10 | 3' UTR |
| 3 | PTPRF | chr1 | 44088117 | T | 11 | 3' UTR |
| 3 | PUM1 | chr1 | 31405680 | T | 10 | 3' UTR |
| 3 | QKI | chr6 | 163985925 | T | 8 | 3' UTR |
| 3 | QRICH1 | chr3 | 49067797 | A | 11 | 3' UTR |
| 3 | RAB18 | chr10 | 27827928 | A | 8 | 3' UTR |
| 3 | RAB36 | chr22 | 23505793 | C | 10 | 3' UTR |
| 3 | RAB3GAP2 | chr1 | 220324482 | A | 9 | 3' UTR |
| 3 | RAB3IP | chr12 | 70214638 | A | 17 | 3' UTR |
| 3 | RAB3IP | chr12 | 70211224 | A | 11 | 3' UTR |
| 3 | RAB7L1 | chr1 | 205738564 | T | 10 | 3' UTR |
| 3 | RAB8A | chr19 | 16244263 | T | 13 | 3' UTR |
| 3 | RAB8B | chr15 | 63557574 | T | 13 | 3' UTR |
| 3 | RAD23B | chr9 | 110092642 | T | 10 | 3' UTR |
| 3 | RAP2B | chr3 | 152881852 | T | 12 | 3' UTR |
| 3 | RASGRP4 | chr19 | 38900377 | A | 11 | 3' UTR |
| 3 | RBL1 | chr20 | 35632028 | A | 13 | 3' UTR |
| 3 | RBM12B | chr8 | 94745547 | A | 10 | 3' UTR |
| 3 | RBM12B | chr8 | 94745279 | A | 10 | 3' UTR |
| 3 | RBM38 | chr20 | 55983973 | G | 8 | 3' UTR |
| 3 | RC3H1 | chr1 | 173905652 | A | 25 | 3' UTR |
| 3 | RCC2 | chr1 | 17734207 | A | 10 | 3' UTR |
| 3 | RCN1 | chr11 | 32126284 | T | 10 | 3' UTR |
| 3 | RFT1 | chr3 | 53125729 | C | 8 | 3' UTR |
| 3 | RGS20 | chr8 | 54871209 | A | 11 | 3' UTR |
| 3 | RHOB | chr2 | 20648933 | T | 12 | 3' UTR |
| 3 | RHOBTB3 | chr5 | 95129188 | A | 12 | 3' UTR |
| 3 | RIF1 | chr2 | 152331769 | T | 10 | 3' UTR |
| 3 | RIMBP2 | chr12 | 130882589 | A | 11 | 3' UTR |
| 3 | RIMS1 | chr6 | 73111857 | A | 12 | 3' UTR |

TABLE 6-continued

| Nr of affected samples | Gene | Chromosome | Start Position | Affected homopolymer base | Affected homopolymer length | region |
|---|---|---|---|---|---|---|
| 3 | RIMS2 | chr8 | 105264755 | A | 14 | 3' UTR |
| 3 | RNF152 | chr18 | 59482618 | A | 10 | 3' UTR |
| 3 | RNF2 | chr1 | 185069838 | T | 9 | 3' UTR |
| 3 | RNGTT | chr6 | 89320667 | T | 10 | 3' UTR |
| 3 | RORA | chr15 | 60785852 | T | 11 | 3' UTR |
| 3 | RPE65 | chr1 | 68895273 | T | 10 | 3' UTR |
| 3 | RPRD2 | chr1 | 150445907 | T | 10 | 3' UTR |
| 3 | RRP15 | chr1 | 218506210 | A | 17 | 3' UTR |
| 3 | RSBN1 | chr1 | 114307995 | A | 8 | 3' UTR |
| 3 | RSBN1L | chr7 | 77408705 | A | 9 | 3' UTR |
| 3 | RSL1D1 | chr16 | 11930997 | T | 11 | 3' UTR |
| 3 | S100A4 | chr1 | 153516162 | A | 10 | 3' UTR |
| 3 | SALL3 | chr18 | 76757543 | A | 10 | 3' UTR |
| 3 | SAMD4A | chr14 | 55257700 | A | 10 | 3' UTR |
| 3 | SARM1 | chr17 | 26726913 | T | 12 | 3' UTR |
| 3 | SASH1 | chr6 | 148872287 | T | 10 | 3' UTR |
| 3 | SASH1 | chr6 | 148870950 | T | 12 | 3' UTR |
| 3 | SATB1 | chr3 | 18390227 | T | 12 | 3' UTR |
| 3 | SBK1 | chr16 | 28334644 | A | 13 | 3' UTR |
| 3 | SCAI | chr9 | 127707832 | A | 13 | 3' UTR |
| 3 | SCAMP1 | chr5 | 77772627 | A | 10 | 3' UTR |
| 3 | SCN1A | chr2 | 166846936 | T | 10 | 3' UTR |
| 3 | SCO1 | chr17 | 10583834 | T | 8 | 3' UTR |
| 3 | SDR16C5 | chr8 | 57212734 | T | 12 | 3' UTR |
| 3 | SEH1L | chr18 | 12986726 | T | 14 | 3' UTR |
| 3 | SENP6 | chr6 | 76425956 | A | 10 | 3' UTR |
| 3 | SEPT11 | chr4 | 77957803 | T | 10 | 3' UTR |
| 3 | SETD1B | chr12 | 122269303 | T | 9 | 3' UTR |
| 3 | SFXN1 | chr5 | 174954579 | T | 10 | 3' UTR |
| 3 | SGK494 | chr17 | 26937070 | A | 16 | 3' UTR |
| 3 | SGOL2 | chr2 | 201448283 | T | 10 | 3' UTR |
| 3 | SH2B3 | chr12 | 111887735 | T | 14 | 3' UTR |
| 3 | SH3KBP1 | chrX | 19553810 | T | 12 | 3' UTR |
| 3 | SHANK2 | chr11 | 70315627 | T | 14 | 3' UTR |
| 3 | SHISA2 | chr13 | 26619921 | A | 11 | 3' UTR |
| 3 | SHOC2 | chr10 | 112773341 | T | 10 | 3' UTR |
| 3 | SIK1 | chr21 | 44835578 | A | 10 | 3' UTR |
| 3 | SIPA1L3 | chr19 | 38698868 | T | 10 | 3' UTR |
| 3 | SIPA1L3 | chr19 | 38698671 | T | 17 | 3' UTR |
| 3 | SIX4 | chr14 | 61178202 | A | 10 | 3' UTR |
| 3 | SKI | chr1 | 2240043 | T | 10 | 3' UTR |
| 3 | SLC12A6 | chr15 | 34523172 | A | 10 | 3' UTR |
| 3 | SLC14A1 | chr18 | 43332169 | A | 8 | 3' UTR |
| 3 | SLC15A2 | chr3 | 121660272 | T | 11 | 3' UTR |
| 3 | SLC16A1 | chr1 | 113455427 | A | 13 | 3' UTR |
| 3 | SLC16A10 | chr6 | 111544547 | T | 9 | 3' UTR |
| 3 | SLC16A4 | chr1 | 110906247 | A | 19 | 3' UTR |
| 3 | SLC17A6 | chr11 | 22400904 | A | 10 | 3' UTR |
| 3 | SLC22A5 | chr5 | 131730903 | T | 17 | 3' UTR |
| 3 | SLC25A36 | chr3 | 140696772 | A | 11 | 3' UTR |
| 3 | SLC31A1 | chr9 | 116026594 | A | 14 | 3' UTR |
| 3 | SLC35E1 | chr19 | 16663158 | T | 11 | 3' UTR |
| 3 | SLC35E3 | chr12 | 69158739 | A | 12 | 3' UTR |
| 3 | SLC38A1 | chr12 | 46579255 | T | 9 | 3' UTR |
| 3 | SLC38A1 | chr12 | 46576941 | A | 10 | 3' UTR |
| 3 | SLC39A9 | chr14 | 69928356 | T | 10 | 3' UTR |
| 3 | SLC4A10 | chr2 | 162840706 | T | 10 | 3' UTR |
| 3 | SLC6A15 | chr12 | 85253350 | T | 10 | 3' UTR |
| 3 | SLC6A6 | chr3 | 14530588 | A | 10 | 3' UTR |
| 3 | SLC7A11 | chr4 | 139090880 | A | 10 | 3' UTR |
| 3 | SLC7A14 | chr3 | 170182342 | T | 10 | 3' UTR |
| 3 | SLC7A6 | chr16 | 68335452 | T | 10 | 3' UTR |
| 3 | SLC9A6 | chrX | 135128103 | T | 11 | 3' UTR |
| 3 | SMAD3 | chr15 | 67485102 | A | 9 | 3' UTR |
| 3 | SMAD4 | chr18 | 48605007 | T | 10 | 3' UTR |
| 3 | SMPDL3A | chr6 | 123130673 | T | 11 | 3' UTR |
| 3 | SMURF2 | chr17 | 62541185 | T | 13 | 3' UTR |
| 3 | SNAP23 | chr15 | 42824292 | T | 14 | 3' UTR |
| 3 | SNAPC3 | chr9 | 15461137 | A | 13 | 3' UTR |
| 3 | SNX30 | chr9 | 115632450 | T | 10 | 3' UTR |
| 3 | SOCS3 | chr17 | 76353185 | C | 9 | 3' UTR |
| 3 | SOX1 | chr13 | 112725171 | C | 9 | 3' UTR |
| 3 | SOX1 | chr13 | 112724720 | T | 10 | 3' UTR |
| 3 | SOX11 | chr2 | 5834751 | T | 9 | 3' UTR |
| 3 | SPATS2 | chr12 | 49921053 | T | 10 | 3' UTR |

TABLE 6-continued

| Nr of affected samples | Gene | Chromosome | Start Position | Affected homopolymer base | Affected homopolymer length | region |
|---|---|---|---|---|---|---|
| 3 | SPATS2L | chr2 | 201343614 | T | 12 | 3' UTR |
| 3 | SPCS3 | chr4 | 177250844 | T | 10 | 3' UTR |
| 3 | SPTBN1 | chr2 | 54898095 | T | 10 | 3' UTR |
| 3 | SRRM2 | chr16 | 2821013 | T | 10 | 3' UTR |
| 3 | SRRM4 | chr12 | 119599690 | A | 10 | 3' UTR |
| 3 | SRRM4 | chr12 | 119596858 | T | 9 | 3' UTR |
| 3 | SSBP3 | chr1 | 54692340 | T | 15 | 3' UTR |
| 3 | SSR3 | chr3 | 156259169 | T | 10 | 3' UTR |
| 3 | ST7L | chr1 | 113066620 | A | 11 | 3' UTR |
| 3 | STC2 | chr5 | 172744019 | T | 12 | 3' UTR |
| 3 | STK17B | chr2 | 197000501 | A | 23 | 3' UTR |
| 3 | STK4 | chr20 | 43708275 | A | 10 | 3' UTR |
| 3 | STRN3 | chr14 | 31364300 | A | 11 | 3' UTR |
| 3 | SUSD5 | chr3 | 33193040 | T | 10 | 3' UTR |
| 3 | SYNJ2 | chr6 | 158519568 | A | 14 | 3' UTR |
| 3 | SYNRG | chr17 | 35879008 | A | 10 | 3' UTR |
| 3 | SYT13 | chr11 | 45264120 | A | 9 | 3' UTR |
| 3 | TACC1 | chr8 | 38706479 | T | 15 | 3' UTR |
| 3 | TAF12 | chr1 | 28929961 | A | 11 | 3' UTR |
| 3 | TBC1D8B | chrX | 106118337 | A | 13 | 3' UTR |
| 3 | TBL1X | chrX | 9684635 | A | 9 | 3' UTR |
| 3 | TBX18 | chr6 | 85445736 | A | 11 | 3' UTR |
| 3 | TFAP2B | chr6 | 50814917 | T | 9 | 3' UTR |
| 3 | TFCP2L1 | chr2 | 121975868 | T | 11 | 3' UTR |
| 3 | TGOLN2 | chr2 | 85549225 | T | 9 | 3' UTR |
| 3 | THAP2 | chr12 | 72073229 | T | 10 | 3' UTR |
| 3 | THSD7A | chr7 | 11411520 | T | 10 | 3' UTR |
| 3 | TIA1 | chr2 | 70439448 | T | 11 | 3' UTR |
| 3 | TIAL1 | chr10 | 121335156 | T | 9 | 3' UTR |
| 3 | TIGD5 | chr8 | 144682449 | T | 9 | 3' UTR |
| 3 | TLCD2 | chr17 | 1609267 | T | 12 | 3' UTR |
| 3 | TLCD2 | chr17 | 1608003 | T | 11 | 3' UTR |
| 3 | TLL1 | chr4 | 167022770 | T | 8 | 3' UTR |
| 3 | TLL2 | chr10 | 98124863 | A | 11 | 3' UTR |
| 3 | TMBIM4 | chr12 | 66531178 | T | 16 | 3' UTR |
| 3 | TMEM169 | chr2 | 216966376 | T | 10 | 3' UTR |
| 3 | TMEM192 | chr4 | 165997961 | T | 10 | 3' UTR |
| 3 | TMEM194B | chr2 | 191372383 | A | 10 | 3' UTR |
| 3 | TMEM86A | chr11 | 18725436 | T | 9 | 3' UTR |
| 3 | TMSL3 | chr4 | 91759710 | A | 10 | 3' UTR |
| 3 | TMTC1 | chr12 | 29656466 | A | 8 | 3' UTR |
| 3 | TNFRSF11B | chr8 | 119936330 | T | 12 | 3' UTR |
| 3 | TNFRSF9 | chr1 | 7980708 | A | 15 | 3' UTR |
| 3 | TNRC18 | chr7 | 5346838 | T | 9 | 3' UTR |
| 3 | TNRC6C | chr17 | 76104332 | C | 9 | 3' UTR |
| 3 | TNRC6C | chr17 | 76101194 | T | 16 | 3' UTR |
| 3 | TOMM20 | chr1 | 235274461 | A | 8 | 3' UTR |
| 3 | TOX4 | chr14 | 21965677 | T | 12 | 3' UTR |
| 3 | TPM3 | chr1 | 154134840 | A | 21 | 3' UTR |
| 3 | TPM4 | chr19 | 16212343 | T | 9 | 3' UTR |
| 3 | TRAK2 | chr2 | 202244537 | T | 11 | 3' UTR |
| 3 | TRIM33 | chr1 | 114940229 | T | 13 | 3' UTR |
| 3 | TRIM68 | chr11 | 4620726 | A | 9 | 3' UTR |
| 3 | TRIM9 | chr14 | 51442832 | T | 10 | 3' UTR |
| 3 | TRIOBP | chr22 | 38171794 | A | 9 | 3' UTR |
| 3 | TRPC1 | chr3 | 142525356 | T | 9 | 3' UTR |
| 3 | TRPS1 | chr8 | 116424772 | T | 10 | 3' UTR |
| 3 | TSGA14 | chr7 | 130038411 | A | 9 | 3' UTR |
| 3 | TSHZ1 | chr18 | 73001306 | A | 10 | 3' UTR |
| 3 | TSHZ3 | chr19 | 31766335 | T | 13 | 3' UTR |
| 3 | TSPAN31 | chr12 | 58141530 | T | 13 | 3' UTR |
| 3 | TTC14 | chr3 | 180327407 | T | 8 | 3' UTR |
| 3 | TTLL2 | chr6 | 167755564 | T | 9 | 3' UTR |
| 3 | TXLNA | chr1 | 32663414 | T | 11 | 3' UTR |
| 3 | TXNDC9 | chr2 | 99936109 | A | 9 | 3' UTR |
| 3 | U2AF1 | chr21 | 44513110 | T | 11 | 3' UTR |
| 3 | UBAP2L | chr1 | 154242977 | T | 8 | 3' UTR |
| 3 | UBE2G2 | chr21 | 46191155 | A | 12 | 3' UTR |
| 3 | UBE2O | chr17 | 74385876 | T | 9 | 3' UTR |
| 3 | UBE2W | chr8 | 74704584 | T | 10 | 3' UTR |
| 3 | UBE3C | chr7 | 157060934 | T | 10 | 3' UTR |
| 3 | UGDH | chr4 | 39500884 | A | 10 | 3' UTR |
| 3 | UGT2B7 | chr4 | 69978554 | A | 13 | 3' UTR |
| 3 | UNC5D | chr8 | 35649346 | T | 11 | 3' UTR |
| 3 | UQCRB | chr8 | 97242317 | T | 10 | 3' UTR |

TABLE 6-continued

| Nr of affected samples | Gene | Chromosome | Start Position | Affected homopolymer base | Affected homopolymer length | region |
|---|---|---|---|---|---|---|
| 3 | UQCRC1 | chr3 | 48636506 | G | 9 | 3' UTR |
| 3 | UQCRHL | chr1 | 16133663 | T | 15 | 3' UTR |
| 3 | USP11 | chrX | 47107350 | A | 16 | 3' UTR |
| 3 | USP13 | chr3 | 179501981 | A | 11 | 3' UTR |
| 3 | USP14 | chr18 | 213518 | A | 12 | 3' UTR |
| 3 | USP43 | chr17 | 9632696 | T | 12 | 3' UTR |
| 3 | USP46 | chr4 | 53461199 | T | 10 | 3' UTR |
| 3 | USP53 | chr4 | 120216195 | T | 10 | 3' UTR |
| 3 | USP7 | chr16 | 8986976 | T | 9 | 3' UTR |
| 3 | USP8 | chr15 | 50791892 | A | 11 | 3' UTR |
| 3 | VCPIP1 | chr8 | 67545984 | A | 13 | 3' UTR |
| 3 | VEZF1 | chr17 | 56051105 | T | 14 | 3' UTR |
| 3 | VGLL3 | chr3 | 86995866 | A | 11 | 3' UTR |
| 3 | VGLL3 | chr3 | 86990599 | T | 11 | 3' UTR |
| 3 | VPS33A | chr12 | 122716608 | A | 11 | 3' UTR |
| 3 | VTI1A | chr10 | 114578212 | T | 9 | 3' UTR |
| 3 | VTI1A | chr10 | 114575744 | T | 10 | 3' UTR |
| 3 | WDR1 | chr4 | 10076371 | A | 9 | 3' UTR |
| 3 | WDR3 | chr1 | 118502087 | T | 11 | 3' UTR |
| 3 | WHSC1 | chr4 | 1945453 | A | 9 | 3' UTR |
| 3 | WNK3 | chrX | 54222891 | A | 14 | 3' UTR |
| 3 | WWC3 | chrX | 10111121 | T | 10 | 3' UTR |
| 3 | XKR6 | chr8 | 10755102 | T | 11 | 3' UTR |
| 3 | XPO4 | chr13 | 21353626 | A | 9 | 3' UTR |
| 3 | YTHDC1 | chr4 | 69179759 | A | 10 | 3' UTR |
| 3 | YY1 | chr14 | 100744470 | A | 12 | 3' UTR |
| 3 | ZC3H13 | chr13 | 46537561 | T | 13 | 3' UTR |
| 3 | ZC3HAV1 | chr7 | 138745419 | A | 20 | 3' UTR |
| 3 | ZC3HAV1L | chr7 | 138710878 | A | 11 | 3' UTR |
| 3 | ZC3HAV1L | chr7 | 138710715 | A | 10 | 3' UTR |
| 3 | ZFAND3 | chr6 | 38122149 | G | 8 | 3' UTR |
| 3 | ZFAND5 | chr9 | 74968284 | A | 10 | 3' UTR |
| 3 | ZFHX3 | chr16 | 72820483 | A | 17 | 3' UTR |
| 3 | ZFHX3 | chr16 | 72816794 | T | 10 | 3' UTR |
| 3 | ZHX3 | chr20 | 39808271 | T | 16 | 3' UTR |
| 3 | ZNF264 | chr19 | 57731930 | T | 9 | 3' UTR |
| 3 | ZNF362 | chr1 | 33764950 | T | 12 | 3' UTR |
| 3 | ZNF440 | chr19 | 11944944 | T | 11 | 3' UTR |
| 3 | ZNF503 | chr10 | 77157784 | T | 11 | 3' UTR |
| 3 | ZNF528 | chr19 | 52920874 | T | 12 | 3' UTR |
| 3 | ZNF557 | chr19 | 7086241 | A | 13 | 3' UTR |
| 3 | ZNF618 | chr9 | 116812463 | A | 9 | 3' UTR |
| 3 | ZNF629 | chr16 | 30792783 | T | 10 | 3' UTR |
| 3 | ZNF681 | chr19 | 23925293 | A | 13 | 3' UTR |
| 3 | ZNF770 | chr15 | 35272976 | A | 9 | 3' UTR |
| 3 | ZSCAN30 | chr18 | 32831761 | T | 12 | 3' UTR |
| 3 | ZSWIM2 | chr2 | 187692280 | T | 9 | 3' UTR |
| 3 | ZSWIM4 | chr19 | 13942940 | T | 11 | 3' UTR |
| 3 | ZXDC | chr3 | 126179925 | T | 11 | 3' UTR |
| 3 | ZXDC | chr3 | 126170876 | T | 9 | 3' UTR |
| 3 | ZYG11B | chr1 | 53290310 | A | 13 | 3' UTR |

TABLE 7

| Nr of affected samples | Gene | Chromosome | Start Position | Affected homopolymer base | Affected homopolymer length | Cancer Census Gene | Affected in MMR deficient tumors | Associate with other cancers |
|---|---|---|---|---|---|---|---|---|
| 9 | SETD1B | chr12 | 122242657 | C | 8 | | | |
| 8 | CASP5 | chr11 | 104879686 | T | 10 | | | x |
| 7 | RBMXL1 | chr1 | 89449508 | T | 11 | | | |
| 7 | RPL22 | chr1 | 6257784 | T | 8 | x | | |
| 7 | SEC31A | chr4 | 83785564 | T | 9 | | x | |
| 6 | ASTE1 | chr3 | 130733046 | T | 11 | | x | |
| 6 | CCDC150 | chr2 | 197531518 | A | 11 | | | |
| 6 | MSH6 | chr2 | 48030639 | C | 8 | x | x | |
| 6 | MYL1 | chr2 | 211179765 | T | 11 | | | x |
| 6 | OR7E24 | chr19 | 9361740 | T | 11 | | | |
| 5 | C15orf40 | chr15 | 83677270 | A | 14 | | | |
| 5 | CNOT2 | chr12 | 70747693 | A | 25 | | | |

TABLE 7-continued

| Nr of affected samples | Gene | Chromosome | Start Position | Affected homopolymer base | Affected homopolymer length | Cancer Census Gene | Affected in MMR deficeient tumors | Associate with other cancers |
|---|---|---|---|---|---|---|---|---|
| 5 | KIAA2018 | chr3 | 113377481 | T | 11 | | | |
| 5 | LTN1 | chr21 | 30339205 | T | 11 | | | |
| 5 | PHF2 | chr9 | 96422611 | A | 8 | | | x |
| 5 | RGS12 | chr4 | 3430398 | A | 9 | | x | |
| 5 | RNF145 | chr5 | 158630629 | T | 11 | | | |
| 5 | SLC22A9 | chr11 | 63149670 | A | 11 | | | |
| 4 | ACVR2A | chr2 | 148683685 | A | 8 | | x | |
| 4 | ATR | chr3 | 142274739 | T | 10 | | x | |
| 4 | CASP5 | chr11 | 104878040 | T | 10 | | | |
| 4 | CDH26 | chr20 | 58587783 | A | 10 | | | |
| 4 | COBLL1 | chr2 | 165551295 | A | 9 | | x | |
| 4 | CTCF | chr16 | 67645338 | A | 7 | | | x |
| 4 | DDX27 | chr20 | 47858503 | A | 8 | | | |
| 4 | EXOSC9 | chr4 | 122723893 | T | 8 | | | |
| 4 | FAM111B | chr11 | 58892376 | A | 10 | | | |
| 4 | GRIK2 | chr6 | 102503431 | A | 8 | | | x |
| 4 | KIAA0182 | chr16 | 85682289 | C | 8 | | | |
| 4 | KIAA1919 | chr6 | 111587360 | T | 9 | | | |
| 4 | MAP3K4 | chr6 | 161469775 | A | 8 | | | x |
| 4 | MBD4 | chr3 | 129155547 | T | 10 | | x | |
| 4 | MIS18BP1 | chr14 | 45716018 | T | 11 | | | |
| 4 | NDUFC2 | chr11 | 77784146 | A | 9 | | x | |
| 4 | PRRT2 | chr16 | 29825015 | C | 9 | | | |
| 4 | RNPC3 | chr1 | 104076466 | A | 12 | | | |
| 4 | SLC35F5 | chr2 | 114500276 | A | 10 | | | |
| 4 | SMC6 | chr2 | 17898125 | T | 9 | | | x |
| 4 | TAF1B | chr2 | 9989570 | A | 11 | | x | |
| 4 | TGFBR2 | chr3 | 30691871 | A | 10 | | x | |
| 4 | TMBIM4 | chr12 | 66531936 | A | 10 | | | |
| 4 | TMEM60 | chr7 | 77423459 | T | 9 | | | |
| 4 | TTK | chr6 | 80751896 | A | 9 | | x | |
| 4 | WDTC1 | chr1 | 27621107 | G | 8 | | x | |
| 3 | ADD3 | chr10 | 111893349 | A | 8 | | | x |
| 3 | AQP7 | chr9 | 33385689 | G | 7 | | | |
| 3 | ARV1 | chr1 | 231131566 | A | 9 | | | |
| 3 | BRAF | chr7 | 140482926 | G | 7 | x | | x |
| 3 | CCDC168 | chr13 | 103381995 | A | 9 | | | |
| 3 | CD3G | chr11 | 118220582 | A | 9 | | | |
| 3 | CHD4 | chr12 | 6711545 | T | 7 | | x | |
| 3 | CLOCK | chr4 | 56336953 | A | 9 | | x | |
| 3 | COIL | chr17 | 55028015 | T | 8 | | | x |
| 3 | DOCK3 | chr3 | 51417603 | C | 7 | | | |
| 3 | ELAVL3 | chr19 | 11577604 | C | 9 | | | |
| 3 | F8 | chrX | 154157685 | T | 8 | | | |
| 3 | FETUB | chr3 | 186362543 | A | 9 | | | |
| 3 | GLI1 | chr12 | 57860074 | G | 7 | | x | |
| 3 | HPS1 | chr10 | 100186986 | G | 8 | | | |
| 3 | IGF2R | chr6 | 160485487 | G | 8 | | x | |
| 3 | KCNMA1 | chr10 | 78729785 | T | 9 | | | x |
| 3 | MLL3 | chr7 | 151874147 | T | 9 | x | | |
| 3 | MSH3 | chr5 | 79970914 | A | 8 | | x | |
| 3 | MYO10 | chr5 | 16694605 | C | 8 | | | |
| 3 | MYO1A | chr12 | 57422572 | T | 8 | | x | |
| 3 | NBEAL1 | chr2 | 203922057 | A | 9 | | | |
| 3 | NRIP1 | chr21 | 16338329 | T | 8 | | | x |
| 3 | P4HTM | chr3 | 49043192 | C | 7 | | | |
| 3 | PIGB | chr15 | 55631502 | T | 8 | | | |
| 3 | PRKDC | chr8 | 48866909 | T | 10 | | | x |
| 3 | PRRG1 | chrX | 37312610 | C | 8 | | | |
| 3 | RBM43 | chr2 | 152108087 | T | 10 | | | |
| 3 | RG9MTD1 | chr3 | 101284008 | A | 10 | | | |
| 3 | RNF43 | chr17 | 56435160 | C | 7 | | | x |
| 3 | SENP1 | chr12 | 48458895 | T | 8 | | | x |
| 3 | SPINK5 | chr5 | 147499874 | A | 10 | | | x |
| 3 | SRPR | chr11 | 126137086 | T | 8 | | | |
| 3 | TMEM97 | chr17 | 26653806 | A | 10 | | | |
| 3 | UBR5 | chr8 | 103289348 | T | 8 | | | x |
| 3 | UVRAG | chr11 | 75694430 | A | 10 | | | |
| 3 | WNK1 | chr12 | 970296 | A | 10 | | x | x |
| 3 | ZBTB20 | chr3 | 114058002 | G | 7 | | | x |

TABLE 8

| Gene | Chromosome | Start Position | Affected homopolymer base | Affected homopolymer length | Region |
|---|---|---|---|---|---|
| ARHGEF11 | chr1 | 157014811 | A | 12 | 5' UTR |
| LRMP | chr12 | 25205380 | A | 11 | 5' UTR |
| GABRG2 | chr5 | 161494990 | A | 12 | 5' UTR |
| MBNL1 | chr3 | 152017897 | T | 11 | 5' UTR |
| ARHGEF9 | chrX | 62974288 | T | 12 | 5' UTR |
| CCT6B | chr17 | 33288433 | A | 11 | 5' UTR |
| EPHB6 | chr7 | 142560576 | A | 13 | 5' UTR |
| GRIA2 | chr4 | 158142151 | A | 9 | 5' UTR |
| LMOD3 | chr3 | 69171664 | T | 13 | 5' UTR |
| NDE1 | chr16 | 15737427 | T | 11 | 5' UTR |
| OMD | chr9 | 95179844 | T | 11 | 5' UTR |
| TMEM177 | chr2 | 120437061 | A | 11 | 5' UTR |
| TRPS1 | chr8 | 116681041 | A | 14 | 5' UTR |
| ZNF781 | chr19 | 38161161 | T | 11 | 5' UTR |
| ZXDA | chrX | 57936946 | A | 9 | 5' UTR |
| AMD1 | chr6 | 111196178 | A | 11 | 5' UTR |
| ASPH | chr8 | 62602295 | A | 11 | 5' UTR |
| BMP5 | chr6 | 55739711 | A | 14 | 5' UTR |
| CBLN2 | chr18 | 70211389 | A | 14 | 5' UTR |
| CEPT1 | chr1 | 111690319 | A | 9 | 5' UTR |
| EBF1 | chr5 | 158526596 | T | 11 | 5' UTR |
| ESCO1 | chr18 | 19164371 | A | 11 | 5' UTR |
| KDM2B | chr12 | 122018157 | G | 10 | 5' UTR |
| LRRC70 | chr5 | 61874619 | A | 18 | 5' UTR |
| MCF2 | chrX | 138724841 | A | 15 | 5' UTR |
| MEIS1 | chr2 | 66662690 | T | 13 | 5' UTR |
| MEIS2 | chr15 | 37391752 | T | 12 | 5' UTR |
| SEMA6A | chr5 | 115910134 | A | 11 | 5' UTR |
| SETBP1 | chr18 | 42260910 | G | 8 | 5' UTR |
| ST7L | chr1 | 113162029 | C | 10 | 5' UTR |
| MAPK1IP1L | chr14 | 55535728 | T | 13 | 3' UTR |
| NARG2 | chr15 | 60712503 | T | 13 | 3' UTR |
| PI15 | chr8 | 75766071 | T | 10 | 3' UTR |
| AHCYL1 | chr1 | 110566210 | A | 14 | 3' UTR |
| APH1B | chr15 | 63600287 | T | 12 | 3' UTR |
| C17orf63 | chr17 | 27083744 | T | 12 | 3' UTR |
| CALN1 | chr7 | 71245682 | A | 12 | 3' UTR |
| CCND2 | chr12 | 4410638 | T | 16 | 3' UTR |
| CD5L | chr1 | 157801230 | A | 13 | 3' UTR |
| CEP170 | chr1 | 243288181 | T | 11 | 3' UTR |
| CREB3L2 | chr7 | 137561927 | A | 11 | 3' UTR |
| CSNK1G3 | chr5 | 122950254 | T | 13 | 3' UTR |
| DIDO1 | chr20 | 61536691 | A | 11 | 3' UTR |
| DRAM2 | chr1 | 111660181 | A | 11 | 3' UTR |
| EIF4G3 | chr1 | 21133496 | T | 13 | 3' UTR |
| FAM38B | chr18 | 10670849 | T | 14 | 3' UTR |
| GSK3B | chr3 | 119542766 | A | 11 | 3' UTR |
| KCNMB4 | chr12 | 70824838 | A | 14 | 3' UTR |
| KDM5A | chr12 | 389523 | T | 11 | 3' UTR |
| MYO5B | chr18 | 47351784 | A | 12 | 3' UTR |
| NEK5 | chr13 | 52639268 | A | 13 | 3' UTR |
| NPR3 | chr5 | 32787131 | A | 11 | 3' UTR |
| PPP1R12A | chr12 | 80169697 | T | 13 | 3' UTR |
| PRTG | chr15 | 55903921 | A | 11 | 3' UTR |
| RAB11FIP1 | chr8 | 37718707 | A | 13 | 3' UTR |
| RASGRP1 | chr15 | 38781450 | T | 13 | 3' UTR |
| SH3KBP1 | chrX | 19552231 | T | 13 | 3' UTR |
| SHROOM3 | chr4 | 77701305 | A | 12 | 3' UTR |
| SLC5A3 | chr21 | 35470291 | T | 11 | 3' UTR |
| UBE2Z | chr17 | 47005701 | A | 11 | 3' UTR |
| UST | chr6 | 149398012 | T | 13 | 3' UTR |
| ZNF275 | chrX | 152617043 | A | 12 | 3' UTR |
| EIF4G3 | chr1 | 21133286 | A | 13 | 3' UTR |
| FCHSD2 | chr11 | 72549649 | A | 10 | 3' UTR |
| FMO2 | chr1 | 171178335 | A | 11 | 3' UTR |
| RYR3 | chr15 | 34157541 | A | 10 | 3' UTR |
| TMEM65 | chr8 | 125325217 | A | 11 | 3' UTR |
| WHSC1L1 | chr8 | 38175279 | A | 11 | 3' UTR |
| ABAT | chr16 | 8876793 | T | 11 | 3' UTR |
| ARFIP1 | chr4 | 153832103 | T | 11 | 3' UTR |
| BTBD7 | chr14 | 93708030 | A | 10 | 3' UTR |
| C15orf2 | chr15 | 24927891 | A | 10 | 3' UTR |
| CALN1 | chr7 | 71249416 | T | 10 | 3' UTR |
| CCDC89 | chr11 | 85395559 | T | 10 | 3' UTR |
| CCND1 | chr11 | 69466273 | A | 10 | 3' UTR |
| ENTPD4 | chr8 | 23289680 | A | 11 | 3' UTR |
| FCHSD2 | chr11 | 72548510 | A | 14 | 3' UTR |
| FGFBP3 | chr10 | 93666830 | A | 11 | 3' UTR |
| LANCL1 | chr2 | 211297865 | T | 9 | 3' UTR |
| PPM1A | chr14 | 60761433 | T | 10 | 3' UTR |
| PURB | chr7 | 44920830 | A | 9 | 3' UTR |
| ST7L | chr1 | 113067470 | A | 10 | 3' UTR |
| SULF2 | chr20 | 46286320 | A | 10 | 3' UTR |
| TMC7 | chr16 | 19073947 | A | 10 | 3' UTR |
| TSR2 | chrX | 54471045 | T | 10 | 3' UTR |
| UBA6 | chr4 | 68481877 | T | 12 | 3' UTR |
| USP14 | chr18 | 212029 | A | 9 | 3' UTR |
| ZNF185 | chrX | 152140995 | C | 10 | 3' UTR |
| ZNF287 | chr17 | 16454419 | T | 9 | 3' UTR |
| AKIRIN1 | chr1 | 39471673 | A | 10 | 3' UTR |
| ARL10 | chr5 | 175800427 | T | 10 | 3' UTR |
| BMPR2 | chr2 | 203426176 | T | 8 | 3' UTR |
| C17orf96 | chr17 | 36829265 | T | 8 | 3' UTR |
| CCND2 | chr12 | 4409520 | T | 10 | 3' UTR |
| EDEM1 | chr3 | 5260540 | T | 10 | 3' UTR |
| FOXN2 | chr2 | 48604358 | T | 10 | 3' UTR |
| FOXN2 | chr2 | 48603079 | T | 10 | 3' UTR |
| HDAC4 | chr2 | 239974109 | A | 9 | 3' UTR |
| HUS1B | chr6 | 656079 | A | 10 | 3' UTR |
| KDM5A | chr12 | 393804 | T | 11 | 3' UTR |
| KIF5C | chr2 | 149879665 | T | 10 | 3' UTR |
| LRCH1 | chr13 | 47325657 | A | 10 | 3' UTR |
| MKLN1 | chr7 | 131175980 | A | 10 | 3' UTR |
| PCDHB3 | chr5 | 140482943 | T | 10 | 3' UTR |
| RYBP | chr3 | 72424549 | T | 9 | 3' UTR |
| SH3KBP1 | chrX | 19553810 | T | 12 | 3' UTR |
| SLC35F1 | chr6 | 118638703 | A | 8 | 3' UTR |
| MSH6 | chr2 | 48030639 | C | 8 | exon |
| SETD1B | chr12 | 122242657 | C | 8 | Exon |
| CASP5 | chr11 | 104879686 | T | 10 | Exon |
| RBMXL1 | chr1 | 89449508 | T | 11 | Exon |
| SEC31A | chr4 | 83785564 | T | 9 | Exon |
| CCDC150 | chr2 | 197531518 | A | 11 | Exon |
| PHF2 | chr9 | 96422611 | A | 8 | Exon |
| RPL22 | chr1 | 6257784 | T | 8 | Exon |
| TMEM60 | chr7 | 77423459 | T | 9 | Exon |
| AIM2 | chr1 | 159032486 | T | 10 | Exon |
| ASTE1 | chr3 | 130733046 | T | 11 | Exon |
| CASP5 | chr11 | 104878040 | T | 10 | Exon |
| CTCF | chr16 | 67645338 | A | 7 | Exon |
| DDX27 | chr20 | 47858503 | A | 8 | Exon |
| EXOSC9 | chr4 | 122723893 | T | 8 | Exon |
| FAM111B | chr11 | 58892376 | A | 10 | Exon |
| GRIK2 | chr6 | 102503431 | A | 8 | Exon |
| KIAA0182 | chr16 | 85682289 | C | 8 | Exon |
| KIAA1919 | chr6 | 111587360 | T | 9 | Exon |
| MLL3 | chr7 | 151874147 | T | 9 | Exon |
| MYL1 | chr2 | 211179765 | T | 11 | Exon |
| OR7E24 | chr19 | 9361740 | T | 11 | Exon |
| P4HTM | chr3 | 49043192 | C | 7 | Exon |
| PRKDC | chr8 | 48866909 | T | 10 | Exon |
| PRRT2 | chr16 | 29825015 | C | 9 | Exon |
| RNPC3 | chr1 | 104076466 | A | 12 | Exon |
| SMC6 | chr2 | 17898125 | T | 9 | Exon |
| TAF1B | chr2 | 9989570 | A | 11 | Exon |
| TMEM97 | chr17 | 26653806 | A | 10 | Exon |
| TTK | chr6 | 80751896 | A | 9 | Exon |
| UVRAG | chr11 | 75694430 | A | 10 | Exon |

TABLE 9

| Tumor | Sequencing Technology | Tumor type | IHC MLH1 | IHC MSH2 | IHC MSH6 | MSI | MLH1 hyper-methylation |
|---|---|---|---|---|---|---|---|
| MMR- 1 | CG whole-genome | Endometrial | | | -(*) | + | - |
| MMR+ 1 | CG whole-genome | Endometrial | + | + | + | - | + |
| MMR+ 2 | CG whole-genome | Endometrial | + | + | + | - | - |
| MMR- 2 | Illumina exome | Endometrial | -(*) | + | - | + | + |
| MMR- 3 | Illumina exome | Endometrial | - | + | + | + | + |
| MMR- 4 | Illumina exome | Endometrial | + | - | - | - | - |
| MMR- 5 | Illumina exome | Endometrial | + | - | - | + | - |
| MMR- 6 | Illumina exome | Endometrial | + | + | - | + | - |
| MMR- 7 | Illumina exome | Endometrial | - | - | - | - | + |
| MMR- 8 | Illumina exome | Endometrial | + | - | - | - | - |
| MMR- 9 | Illumina exome | Colorectal | + | - | + | + | NA |
| MMR- 10 | Illumina exome | Colorectal | + | + | - | + | NA |
| MMR- 11 | Illumina exome | Colorectal | - | + | + | + | NA |
| MMR+ 3 | Illumina exome | Endometrial | + | + | + | - | - |
| MMR+ 4 | Illumina exome | Endometrial | + | + | + | - | - |
| MMR+ 5 | Illumina exome | Endometrial | + | + | + | - | - |
| MMR+ 6 | Illumina exome | Endometrial | + | + | + | - | - |

TABLE 10

| Tumor | Tumor | BAT 25 | BAT 26 | D5S346 | D17S250 | D2S123 | TGFB | BAT 40 | D18S58 | D17S787 | D18S69 |
|---|---|---|---|---|---|---|---|---|---|---|---|
| Tumor 1 | MMR- 1 | + | + | + | + | + | N/A | N/A | + | + | - |
| Tumor 2 | MMR+ 1 | - | - | - | - | N/A | N/A | - | - | - | - |
| Tumor 3 | MMR+ 2 | - | - | - | - | N/A | N/A | - | - | - | - |

TABLE 11

| Tumor | Tumor | Type | Histopathology | Grade | Stage |
|---|---|---|---|---|---|
| Tumor 1 | MMR- 1 | Endometrium | Endometrioid carcinoma | 3 | IIIc |
| Tumor 2 | MMR+ 1 | Endometrium | Endometrioid carcinoma | 3 | I |
| Tumor 3 | MMR+ 2 | Endometrium | Serous carcinoma | 3 | Ia |

TABLE 12

| | Somatic mutations using calldiff | | | After removal of common variants | | | After applying quality score threshold | | |
|---|---|---|---|---|---|---|---|---|---|
| Tumor | Substitutions | Indels | Mutations | Substitutions | Indels | Mutations | Substitutions | Indels | Mutations |
| MMR- 1 (hypermutator) | 51,914 | 70,857 | 122,771 | 46,679 | 56,629 | 103,308 | 41,943 | 56,629 | 98,572 |
| MMR+ 1 | 10,053 | 5,935 | 15,988 | 4,857 | 2,078 | 6,935 | 2,625 | 2,078 | 4,703 |
| MMR+ 2 | 10,615 | 4,558 | 15,173 | 6,650 | 1,974 | 8,624 | 3,036 | 1,974 | 5,010 |

TABLE 13

| | Tumor | Type | Histopathology | Grade | Stage |
|---|---|---|---|---|---|
| 1 | MMR- 2 | Endometrium | Endometrioid carcinoma | 3 | IIIa |
| 2 | MMR- 3 | Endometrium | Endometrioid carcinoma | 2 | Ib |
| 3 | MMR- 4 | Endometrium | Endometrioid carcinoma | 3 | II |
| 4 | MMR- 5 | Endometrium | Endometrioid carcinoma | 2 | Ia |
| 5 | MMR- 6 | Endometrium | Serous carcinoma | 3 | Ib |
| 6 | MMR- 7 | Endometrium | Endometrioid/clear cell | 3 | Ia |
| 7 | MMR- 8 | Endometrium | Serous/clear cell | 3 | Ib |
| 8 | MMR- 9 | Colon | Adenocarcinoma | 3 | IIa |
| 9 | MMR- 10 | Colon | Adenocarcinoma | 2 | IIIc |
| 10 | MMR- 11 | Colon | Adenocarcinoma | 2 | IIa |
| 11 | MMR+ 3 | Endometrium | Endometrioid carcinoma | 1 | IIIc |
| 12 | MMR+ 4 | Endometrium | Serous carcinoma | 3 | IIIa |

TABLE 13-continued

| Tumor | Type | Histopathology | Grade | Stage |
|---|---|---|---|---|
| 13 MMR+ 5 | Endometrium | Mucinous carcinoma | 2 | IIIa |
| 14 MMR+ 6 | Endometrium | Endometrioid carcinoma | 1 | Ia |

TABLE 14

| Tumor | IHC MLH1 | IHC MSH2 | IHC MSH6 | MSI (Bethesda) | MLH1 hyper-methylation |
|---|---|---|---|---|---|
| MMR− 2 | −(*) | + | − | + | + |
| MMR− 3 | − | + | + | + | + |
| MMR− 4 | + | − | − | − | − |
| MMR− 5 | + | − | − | + | − |
| MMR− 6 | + | + | − | + | − |
| MMR− 7 | − | − | − | − | + |
| MMR− 8 | + | − | − | + | − |
| MMR− 9 | + | − | + | + | NA |
| MMR− 10 | + | + | − | + | NA |
| MMR− 11 | − | + | + | + | NA |
| MMR+ 3 | + | + | + | − | − |
| MMR+ 4 | + | + | + | − | − |
| MMR+ 5 | + | + | + | − | − |
| MMR+ 6 | + | + | + | − | − |

TABLE 15

| Tumor | BAT 25 | BAT 26 | D5S346 | D17S250 | D2S123 | TGFB | BAT 40 | D18S58 | D17S787 | D18S69 |
|---|---|---|---|---|---|---|---|---|---|---|
| MMR− 2 | + | + | + | N/A | N/A | N/A | − | N/A | − | + |
| MMR− 3 | − | + | − | + | + | + | − | + | − | − |
| MMR− 4 | − | − | − | − | − | − | N/A | − | − | − |
| MMR− 5 | + | − | + | + | + | + | N/A | − | − | − |
| MMR− 6 | + | − | + | + | + | − | + | − | − | + |
| MMR− 7 | − | − | − | − | − | − | − | − | − | − |
| MMR− 8 | − | − | − | − | − | − | − | − | − | − |
| MMR− 9 | + | + | + | + | + | − | + | N/A | + | + |
| MMR− 10 | + | + | + | − | + | − | + | N/A | + | + |
| MMR− 11 | + | + | + | + | − | − | + | N/A | + | + |
| MMR+ 3 | − | − | − | − | − | − | − | − | − | − |
| MMR+ 4 | − | − | − | − | − | − | − | − | − | − |
| MMR+ 5 | − | − | − | − | − | − | − | − | − | − |
| MMR+ 6 | − | − | − | − | − | − | − | − | − | − |

TABLE 16

| Tumor | After quality filtering | | | After removal of common variants | | | After validation | | |
|---|---|---|---|---|---|---|---|---|---|
| | Substi-tutions | Indels | Muta-tion | Substi-tutions | Indels | Muta-tions | Substi-tutions | Indels | Muta-tions |
| MMR− 2 | 922 | 299 | 1,221 | 778 | 295 | 1,073 | 778 | 295 | 1,073 |
| MMR− 3 | 902 | 252 | 1,154 | 655 | 249 | 904 | 655 | 249 | 904 |
| MMR− 4 | 1,675 | 160 | 1,835 | 1,476 | 156 | 1,632 | 1,476 | 156 | 1,632 |
| MMR− 5 | 1,526 | 337 | 1,863 | 1,304 | 335 | 1,639 | 1,304 | 335 | 1,639 |
| MMR− 6 | 987 | 221 | 1,208 | 792 | 217 | 1,009 | 792 | 217 | 1,009 |
| MMR− 7 | 477 | 138 | 615 | 283 | 135 | 418 | 283 | 135 | 418 |
| MMR− 8 | 1,408 | 268 | 1,676 | 1,196 | 261 | 1,457 | 1,196 | 261 | 1,457 |
| MMR− 9 | 1,685 | 534 | 2,219 | 1,525 | 521 | 2,046 | 1,525 | 521 | 2,046 |
| MMR− 10 | 2,444 | 444 | 2,888 | 2,233 | 426 | 2,659 | 2,233 | 426 | 2,659 |
| MMR− 11 | 1,648 | 662 | 2,310 | 1,485 | 644 | 2,129 | 1,485 | 644 | 2,129 |
| MMR+ 3 | 327 | 73 | 400 | 160 | 71 | 231 | 22 | 2 | 24 |
| MMR+ 4 | 300 | 48 | 348 | 169 | 45 | 214 | 41 | 2 | 43 |
| MMR+ 5 | 384 | 78 | 462 | 172 | 73 | 245 | 46 | 2 | 48 |
| MMR+ 6 | 270 | 58 | 328 | 149 | 54 | 203 | 35 | 4 | 39 |

TABLE 17

| | Before filtering | | After filtering | |
|---|---|---|---|---|
| Number of samples | Substitutions | Indels | Substitutions | Indels |
| 3 or more | 33 | 84 | 5 | 82 |
| 4 or more | 8 | 45 | 0 | 44 |

TABLE 18

| Number of tumor affected | Number of affected homopolymer |
|---|---|
| 1 | 1,238 |
| 2 | 173 |
| 3 | 38 |
| 4 | 26 |
| 5 | 8 |
| 6 | 5 |
| 7 | 3 |
| 8 | 1 |
| 9 | 1 |

TABLE 19

| Length of homopolymer | Number of affected homopolymers | Total number of homopolymers (whole-genome) | Observed frequency in the hypermutator whole-genome (fe,genome) |
|---|---|---|---|
| 6 | 4,868 | 4,123,709 | 1.18E-03 |
| 7 | 7,332 | 1,583,507 | 4.63E-03 |
| 8 | 8,729 | 562,325 | 1.55E-02 |
| 9 | 8,100 | 319,266 | 2.54E-02 |
| 10 | 5,861 | 206,595 | 2.84E-02 |
| 11 | 4,602 | 126,018 | 3.65E-02 |

TABLE 20

| Length of homo-polymer | Expected number of affected homo-polymers in the exome | Total number of homopolymers (exome) | Observed frequency in exome (fo,exome) | Fold enrichment |
|---|---|---|---|---|
| 6 | 28.5 | 24,008 | 1.19E-03 | 1.0 |
| 7 | 33.6 | 4,787 | 7.02E-03 | 1.5 |
| 8 | 25.8 | 938 | 2.75E-02 | 1.8 |
| 9 | 10.8 | 205 | 5.24E-02 | 2.1 |
| 10 | 6.5 | 60 | 1.08E-01 | 3.8 |
| 11 | 4. | 24 | 1.72E-01 | 4.7 |

TABLE 21

| Length of homopolymer | Observed number of recurrent indels | Expected number of recurrent indels | Fold increase |
|---|---|---|---|
| 6 | 0 | 6.51E-03 | N/A |
| 7 | 9 | 7.84E-02 | 114.80 |
| 8 | 25 | 5.76E-01 | 43.38 |
| 9 | 18 | 5.54E-01 | 32.47 |
| 10 | 16 | 2.27E-01 | 70.56 |
| 11 | 11 | 1.93E-01 | 57.12 |

TABLE 22

| Length of homopolymer | Observed number of recurrent indels | Expected number of recurrent indels | Fold increase |
|---|---|---|---|
| 6 | 0 | 1.54E-05 | N/A |
| 7 | 1 | 7.26E-04 | 1377.52 |
| 8 | 11 | 1.79E-02 | 615.67 |
| 9 | 9 | 2.82E-02 | 319.62 |
| 10 | 10 | 1.29E-02 | 776.36 |
| 11 | 11 | 1.41E-02 | 782.52 |

TABLE 23

| Number of samples affected | Affected genes* |
|---|---|
| 9 | SETD1B |
| 8 | CASP5 |
| 7 | RPL22, RBMXL1 |
| 6 | SEC31A, OR7E24, MSH6, CCDC150, MYL1, ASTE1 |
| 5 | SLC22A9, CNOT2, C15orf40, LTN1, KIAA2018, RGS12, RNF145, PHF2 |
| 4 | WDTC1, RNPC3, FAM111B, NDUFC2, CASP5, TMBIM4 MIS18BP1, PRRT2, CTCF, KIAA0182, TAF1B, SMC6, SLC35F5, ACVR2A, COBLL1, DDX27, CDH26, TGFBR2, MBD4, ATR, EXOSC9, TTK, GRIK2, KIAA1919, MAP3K4, TMEM60 |
| 3 | ARV1, KCNMA1, HPS1, ADD3, UVRAG, CD3G, SRPR, WNK1, CHD4, SENP1, MYO1A, GLI1, CCDC168, PIGB, TMEM97, COIL, RNF43, ELAVL3, RBM43, NBEAL1, NRIP1, P4HTM, DOCK3, RG9MTD1, ZBTB20, FETUB, CLOCK, MYO10, MSH3, SPINK5, IGF2R, BRAF, MLL3, PRKDC, UBR5, AQP7, PRRG1, F8 |

TABLE 24

| | Exome | 5' UTRs | 3' UTRs |
|---|---|---|---|
| Number of recurrently affected homopolymer | 82 | 89 | 1812 |
| Number of recurrently affected homopolymer with length < 9 | 34 | 3 | 71 |
| Percentage of recurrently affected homopolymer with length < 9 | 41.5% | 3.4% | 3.9% |
| Number of homopolymers with length < 9 | 29,733 | 4,857 | 49,769 |
| Percentage of recurrently affected homopolymer with length < 9 correcting for the number of homopolymers with length < 9 | 39.2% | 19.5% | 2.2% |

TABLE 25

| Dataset | MMR-deficient genes | MMR-proficient genes | Recurrent genes | Recurrent exonic |
|---|---|---|---|---|
| Affected genes | N/A | 7,084 | 380 | 994 | 82 |
| Genes in dataset | 14,664 | 5,303 | 243 | 750 | 65 |
| Overexpressed | 9,021 (61.5%) | 3,411 (64.3%) | 142 (58.4%) | 476 (63.5%) | 57 (87.7%) |
| Underexpressed | 463 (3.2%) | 208 (3.9%) | 5 (2.1%) | 30 (4.0%) | 2 (3.1%) |
| Non-differentially expressed | 5,180 (35.3%) | 1,684 (31.8%) | 96 (39.5%) | 244 (32.5%) | 6 (9.2%) |

TABLE 26

| Data set (n = 4,874 genes) | MMR-deficient genes | MMR-proficient genes | Recurrent genes | Recurrent genes |
|---|---|---|---|---|
| Genes in the data set | 7,084 | 380 | 994 | 82 |
| Differentially expressed in MSI-H | 1,524 (21.5%) | 63 (16.6%) | 211 (21.2%) | 28 (34.1%) |

TABLE 27

| Tumor | Type | Histopathology | Grade | Stage |
|---|---|---|---|---|
| MMR− Ovarian 1 | Ovary | Serous | 3 | IIIc |
| MMR+ Ovarian 1 | Ovary | Clear cell | 3 | IIc |
| MMR+ Ovarian 2 | Ovary | Clear cell | 3 | IIIc |
| DND41 (MMR− Leukemia 1) | Blood; Cell line | Acute lymphoblastic leukemia | / | / |
| CCRF-CEM (MMR− Leukemia 2) | Blood; Cell line | Acute lymphoblastic leukemia | / | / |
| SUPT1 (MMR− Leukemia 3) | Blood; Cell line | Acute lymphoblastic leukemia | / | / |
| RPMI8402 (MMR+ Leukemia 1) | Blood; Cell line | Acute lymphoblastic leukemia | / | / |

TABLE 28

| Tumor | Mutation status of MMR genes |
|---|---|
| MMR− Ovarian 1 | MSH6:T1085fs |
| MMR+ Ovarian 1 | / |
| MMR+ Ovarian 2 | / |
| DND41 (MMR− Leukemia 1) | MSH6:T1085fs; MSH3: K381fs |
| CCRF-CEM (MMR− Leukemia 2) | MLH1: R100X |
| SUPT1 (MMR− Leukemia 3) | MLH1: T495fs; MSH3: K381fs |
| RPMI8402 (MMR+ Leukemia 1) | / |

TABLE 29

| Rank | Pathway | P value |
|---|---|---|
| 1 | Role of BRCA1 in DNA damage response | 1.96E−03 |
| 2 | Cell cycle: G2/M DNA damage checkpoint regulation | 3.08E−03 |
| 3 | P53 signaling | 5.04E−03 |
| 4 | GADD45 signaling | 9.00E−03 |
| 5 | D-myo-inositol-trisphosphate biosynthesis | 9.00E−03 |
| 6 | Protein kinase A signaling | 1.33E−02 |
| 7 | PTEN signaling | 2.00E−02 |
| 8 | Thio-molybdenum cofactor biosynthesis | 2.45E−02 |
| 9 | Lipoate salvage and modification | 2.45E−02 |
| 10 | DNA double-strand break repair by Homologous Recombination | 3.89E−02 |
| 11 | Hereditary breast cancer signaling | 4.21E−02 |
| 12 | Molecular mechanisms of cancer | 4.42E−02 |
| 13 | Lipoate biosynthesis and Incorporation II | 4.83E−02 |

TABLE 30

| Gene | Affected MMR-deficient tumor |
|---|---|
| ATM | MMR− 2, MMR− 3, MMR−6, MMR− 8, MMR− 9, MMR− 10, MMR− 11 |
| ATR | MMR− 2, MMR− 8, MMR− 10, MMR− 9 |
| BLM | MMR− 2, MMR− 6 |
| BRCA1 | MMR− 4, MMR− 5 |
| CHEK1 | MMR− 1, MMR− 9 |
| FANCD2 | MMR− 10 |
| FANCE | MMR− 2 |
| FANCM | MMR− 2, MMR− 11 |
| MRE11 | MMR− 1, MMR− 3, MMR− 8, MMR− 10, MMR− 11 |
| RAD50 | MMR− 9 |
| RAD54 | MMR− 5, MMR− 11 |

TABLE 31

| | Cell culture | Type | Histopathology | Grade | MMR status |
|---|---|---|---|---|---|
| 1 | EMC−1 | Endometrium | Endometrioid carcinoma | 2 | Deficient |
| 2 | EMC−2 | Endometrium | Endometrioid carcinoma | 3 | Deficient |
| 3 | EMC−3 | Endometrium | Endometrioid/serous carcinoma | 3 | Deficient |
| 4 | EMC−4 | Endometrium | Endometrioid carcinoma | 1-3 | Deficient |
| 5 | EMC−5 | Endometrium | Endometrioid carcinoma | 3 | Deficient |
| 6 | OVC−1 | Ovary | Serous carcinoma | 3 | Deficient |
| 7 | OVC−2 | Ovary | Serous carcinoma | 3 | Deficient |
| 8 | EMC+1 | Endometrium | Endometrioid carcinoma | 2 | Proficient |
| 9 | OVC+1 | Ovary | Serous carcinoma | 3 | Proficient |

TABLE 32

| | Cell line | Type | Subtype | BRCA status | Mutations in MMR genes | MMR status |
|---|---|---|---|---|---|---|
| 1 | HEC-1-A | Endometrium | Endometrioid | WT BRCA1/2 | Nonsense mutation in PMS2, Splice site mutation in MSH6 | Deficient |
| 2 | MDA-MB-231 | Breast | TNBC | WT BRCA1/2 | — | Proficient |
| 3 | MCF7 | Breast | ER+ PR+ | WT BRCA1/2 | — | Proficient |

What is claimed is:

1. A method of detecting alterations in 3' UTR homopolymer lengths in a human tumor sample, the method comprising:
    performing a multiplex assay on a sample from the tumor, and detecting lengths of at least two 3' UTR homopolymers that differ from the reference lengths of the at least two 3' UTR homopolymers;
    wherein the at least two 3' UTR homopolymers and the reference lengths are selected from the group consisting of:
    11 consecutive adenines in the gene DIDO1 at position 61536692 of chromosome 20,
    11 consecutive adenines in the gene UBE2Z at position 47005702 of chromosome 17,
    10 consecutive adenines in the gene RYR3 at position 34157542 of chromosome 15,
    11 consecutive adenines in the gene TMEM65 at position 125325218 of chromosome 8,
    12 consecutive adenines in the gene BTBD7 at position 93708031 of chromosome 14,
    11 consecutive thymidines in the gene KDM5A at position 393805 of chromosome 12,
    11 consecutive thymidines in the gene ABAT at position 8876793 of chromosome 16,
    11 consecutive thymidines in the gene PPM1A at position 60761434 of chromosome 14,
    12 consecutive thymidines in the gene UBA6 at position 68481878 of chromosome 4,
    10 consecutive cytidines in the gene ZNF185 at position 152140996 of chromosome X,
    10 consecutive thymidines in the gene ARL10 at position 175800427 of chromosome 5,
    10 consecutive adenines in the gene TMC7 at position 19073948 of chromosome 16, and
    10 consecutive adenines in the gene SULF2 at position 46286320 of chromosome 20.

2. The method of claim 1, wherein the tumor is colorectal cancer, endometrial cancer, ovarian cancer, gastric cancer, or a tumor of Lynch syndrome.

3. The method of claim 1, wherein lengths of at least eight 3' UTR homopolymers that differ from the reference lengths of at the least eight 3' UTR homopolymers are detected.

4. The method of claim 1 wherein the at least two 3' UTR homopolymers include the adenines in the gene DIDO1 at position 61536692 of chromosome 20, and the adenines in the gene UBE2Z at position 47005702 of chromosome 17.

5. The method of claim 1 wherein detecting comprises utilizing an oligonucleotide probe.

6. The method of claim 1 wherein the multiplex assay is a single base pair extension assay, a DNA hybridization assay, and/or a melting curve assay.

7. The method according to claim 1 wherein the difference between a detected length and a reference length is one nucleotide base.

8. The method according to claim 1 wherein the difference between a detected length and a reference length is two nucleotide bases.

9. The method of claim 1 wherein one of the at least two 3' UTR homopolymers is the adenines in the gene DIDO1 at position 61536692 of chromosome 20.

10. The method of claim 1 wherein one of the at least two 3' UTR homopolymers is the adenines in the gene UBE2Z at position 47005702 of chromosome 17.

* * * * *